United States Patent [19]
Klein et al.

[11] Patent Number: 5,777,117
[45] Date of Patent: Jul. 7, 1998

[54] METHOD FOR PREPARING SUBSTITUTED AMINO ALCOHOL COMPOUNDS

[75] Inventors: J. Peter Klein, Vashon; Gail E. Underiner, Brier; Anil M. Kumar, Seattle, all of Wash.

[73] Assignee: Cell Therapeutics, Inc., Seattle, Wash.

[21] Appl. No.: 472,569

[22] Filed: Jun. 7, 1995

Related U.S. Application Data

[60] Division of Ser. No. 303,842, Sep. 8, 1994, which is a continuation-in-part of Ser. No. 152,650, Nov. 12, 1993, and Ser. No. 164,081, Dec. 8, 1993, which is a continuation-in-part of Ser. No. 40,820, Mar. 31, 1993, abandoned, said Ser. No. 152,650, is a continuation-in-part of Ser. No. 40,820.

[51] Int. Cl.$^6$ .................. C07D 473/10; C07D 239/80; C07D 211/94; C07D 209/48
[52] U.S. Cl. .................. 544/267; 544/257; 544/285; 544/286; 544/287; 544/311; 546/141; 546/243; 546/246; 548/477; 548/546
[58] Field of Search .................. 544/267, 257, 544/285, 286, 287, 311; 546/141, 243, 246; 548/477, 546

[56] References Cited

U.S. PATENT DOCUMENTS

| | | |
|---|---|---|
| 3,124,579 | 3/1964 | Yoshida et al. |
| 3,422,107 | 1/1969 | Mohler et al. |
| 3,737,433 | 6/1973 | Mohler et al. |
| 4,247,710 | 1/1981 | Tilley .................. 560/55 |
| 4,515,795 | 5/1985 | Hinze et al. |
| 4,576,947 | 3/1986 | Hinze et al. |
| 4,636,507 | 1/1987 | Kreutzer et al. |
| 4,668,786 | 5/1987 | Thiele et al. |
| 4,833,146 | 5/1989 | Gebert et al. |
| 4,965,271 | 10/1990 | Mandell et al. |
| 5,039,666 | 8/1991 | Novick, Jr. |
| 5,096,906 | 3/1992 | Mandell et al. |

FOREIGN PATENT DOCUMENTS

| | | |
|---|---|---|
| 113102 | 7/1984 | European Pat. Off. |
| 132366 | 1/1985 | European Pat. Off. |
| 335723 | 10/1989 | European Pat. Off. |
| 2000943 | 9/1969 | France |
| 2659241 | 7/1978 | Germany |
| 8096087 | 6/1983 | Japan |
| 256428 | 2/1990 | Japan |
| 1356789 | 6/1974 | United Kingdom |
| 2096606 | 10/1982 | United Kingdom |

OTHER PUBLICATIONS

Bianco et al., *Blood*, 76:Supplement 1 (522), p. 133a, "Pentoxifylline (PTX) and GM–CSF Decrease Tumor Necrosis Factor–ALPHA (TNF–α) Levels in Patients Undergoing Allogeneic Bone Marrow Transplantation (BMT)," 1991.

Davis et al., *Applied Environmental Microbial.*, 48:2, pp. 327–331. "Microbial Models of Mammalian Metabolism: Microbial Reduction and Oxidation of Pentoxifylline," Aug. 1984.

Fuhrer et al., *J. Med. Chem.*, vol. 27, pp. 831–836, "β–Adrenergic Blocking Agents: Substituted Phenylalkanolamines. Effect of Side–Chain Length on β–Blocking Potency in Vitro", 1984.

Golding et al., "Reaction between Vicinal Diols and Hydrogen . . . ." *J. Chem. Soc. Perkin Trans.* 1, 1973, pp. 1214–1220.

Carey et al., *Advanced Organic Chemistry*, 3rd Ed., Part B: Reactions and Synthesis, 1990, pp. 625–626.

Primary Examiner—José G. Dees
Assistant Examiner—Mary C. Cebulak
Attorney, Agent, or Firm—McDermott, Will & Emery

[57] ABSTRACT

Disclosed is a process for preparing compounds having a straight or branched aliphatic hydrocarbon structure of formula I:

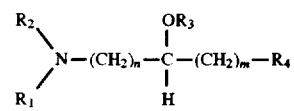

In formula I, n is an integer from one to four and m is an integer from four to twenty. Independently, $R_1$ and $R_2$ are hydrogen, a straight or branched chain alkyl, alkenyl or alkynyl of up to twenty carbon atoms in length or —(CH$_2$)$_w$R$_5$. If $R_1$ or $R_2$ is —(CH$_2$)$_w$R$_5$, w may be an integer from one to twenty and $R_5$ may be an hydroxyl, halo, C$_{1-8}$ alkoxyl group or a substituted or unsubstituted carbocycle or heterocycle. Alternatively, $R_1$ and $R_2$ may jointly form a substituted or unsubstituted, saturated or unsaturated heterocycle having from four to eight carbon atoms, N being a hetero atom of the resulting heterocycle. $R_3$ may be either hydrogen or C$_{1-3}$. In the compounds, a total sum of carbon atoms comprising $R_1$ or $R_2$, (CH$_2$)$_n$ and (CH$_2$)$_m$ does not exceed forty. $R_4$ is a terminal moiety comprising a substituted or unsubstituted, oxidized or reduced ring system, the ring system having a single ring or two to three fused rings, a ring comprising from three to seven ring atoms. The disclosed compounds are effective agents to inhibit undesirable responses to cell stimuli.

22 Claims, 92 Drawing Sheets

Fluorescence Intensity

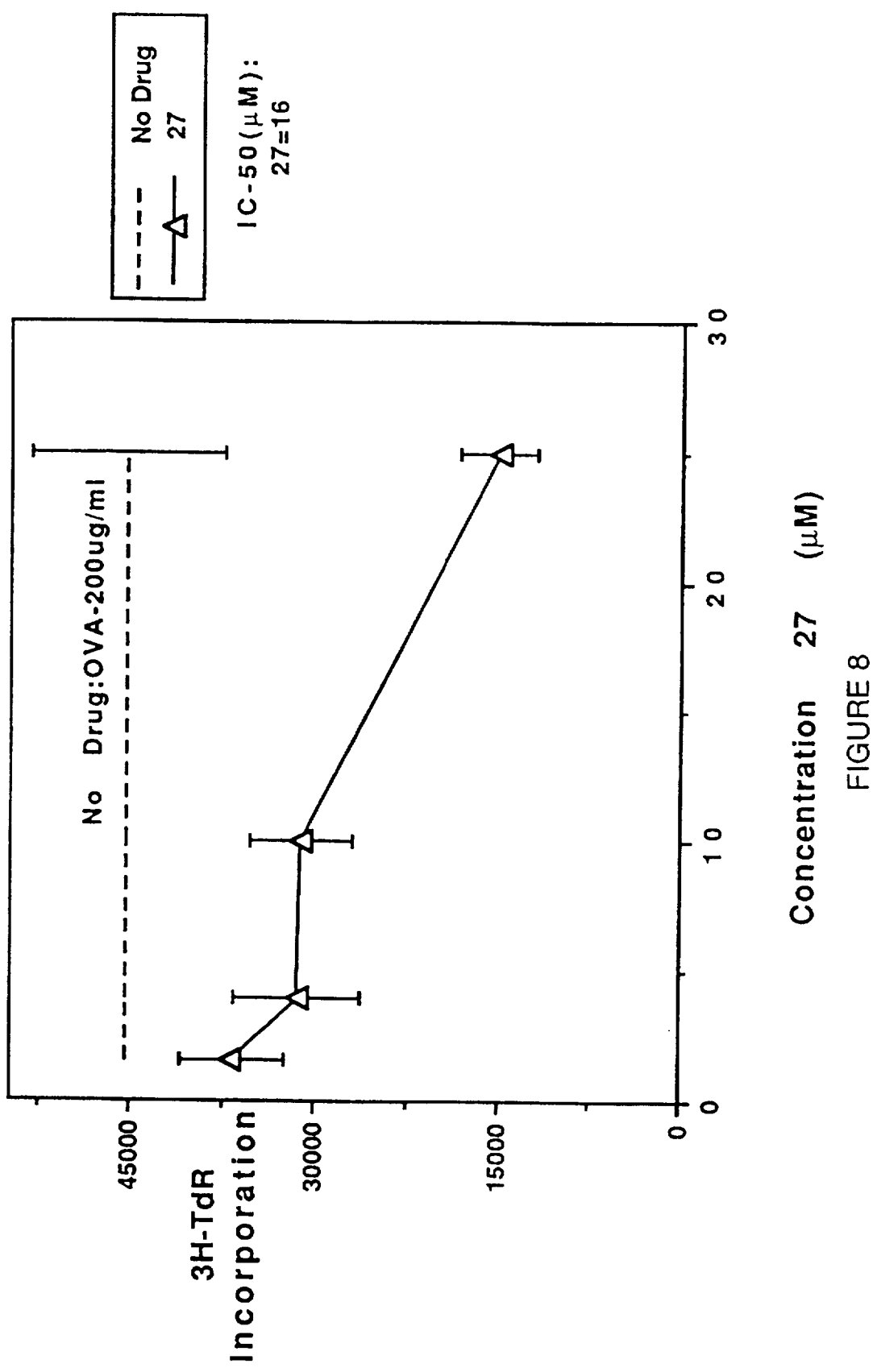

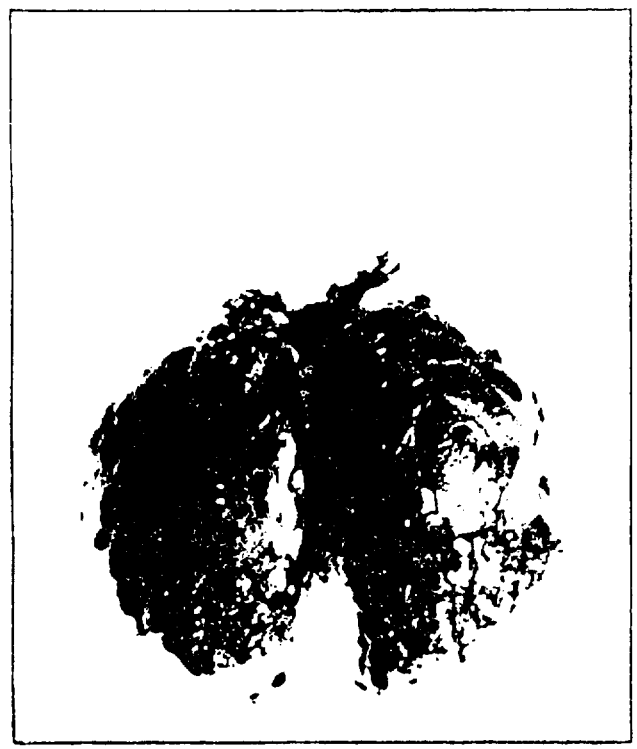
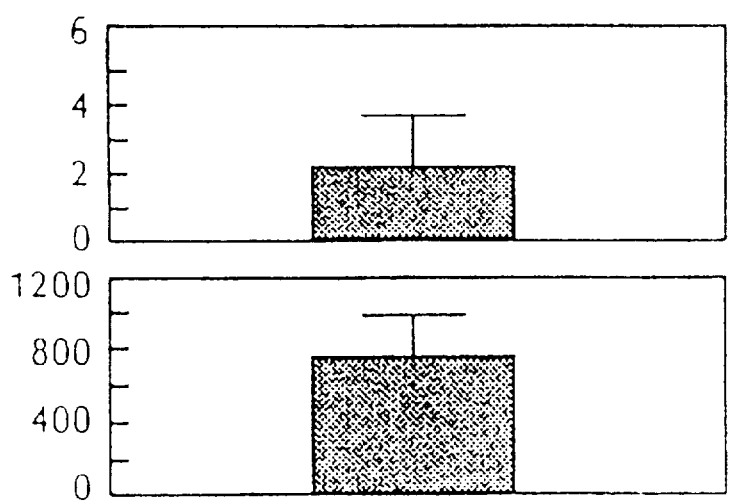
FIGURE 41A

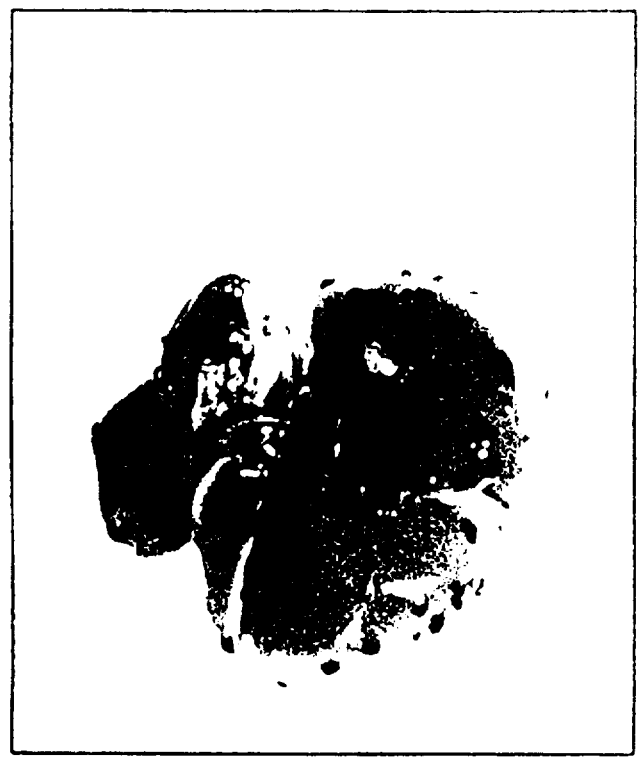
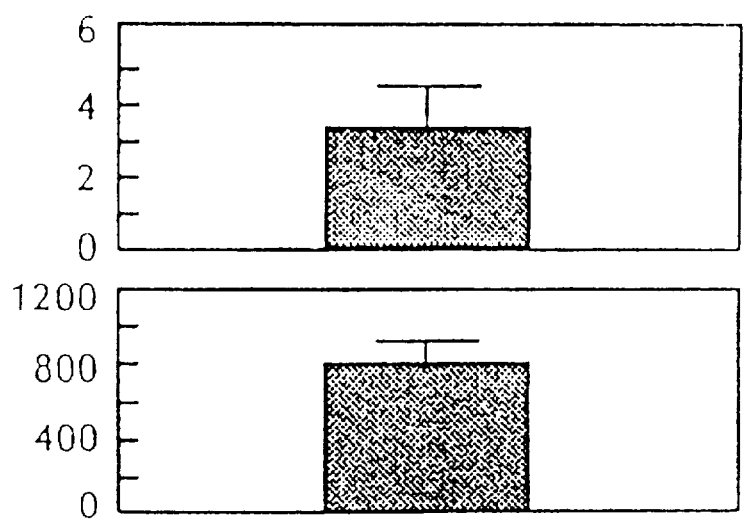
FIGURE 41B

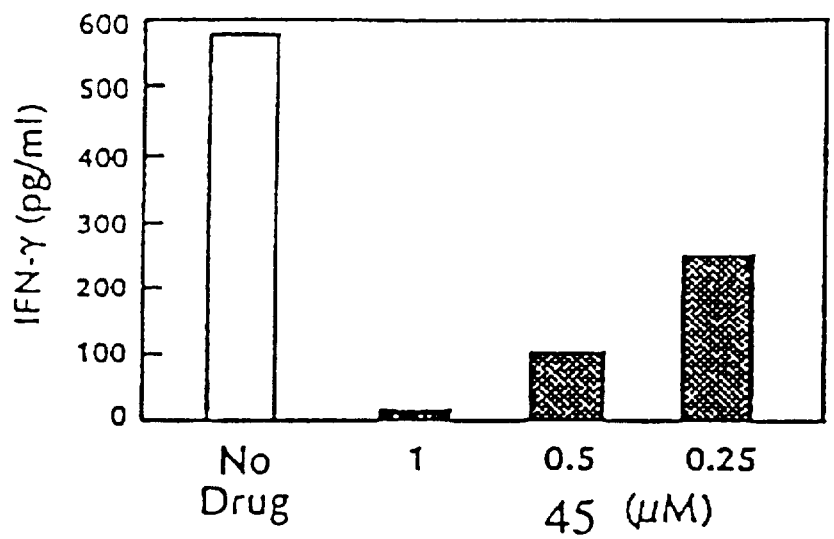
FIGURE 58C
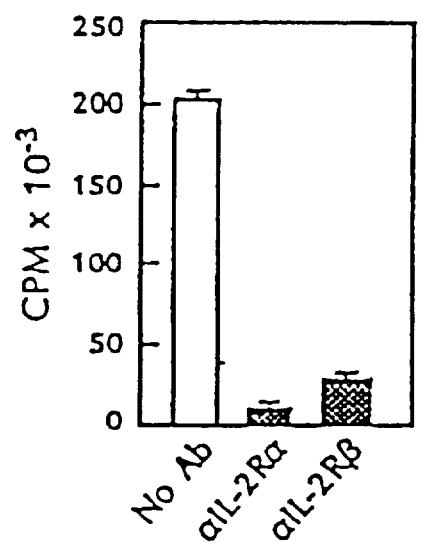 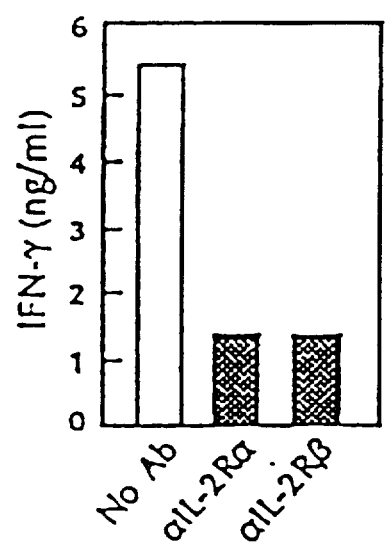
FIGURE 58D          FIGURE 58E

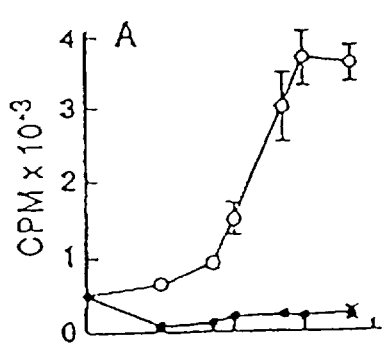
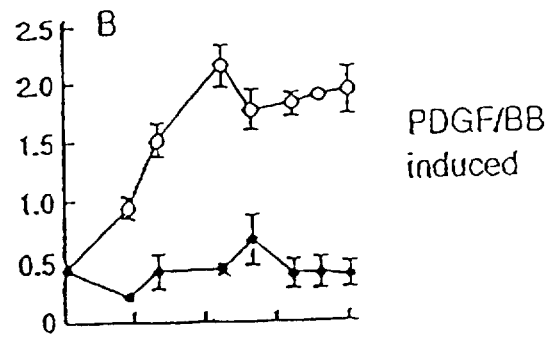
FIGURE 65A  FIGURE 65B  PDGF/BB induced
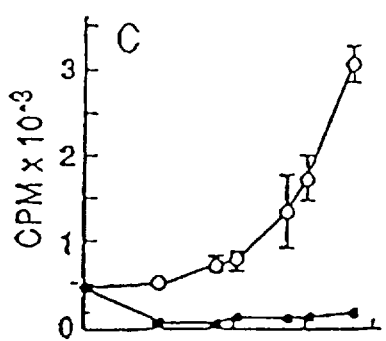
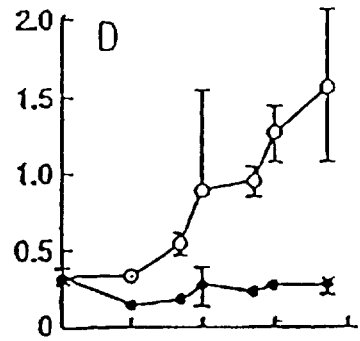
FIGURE 65C  FIGURE 65D  aFGF induced
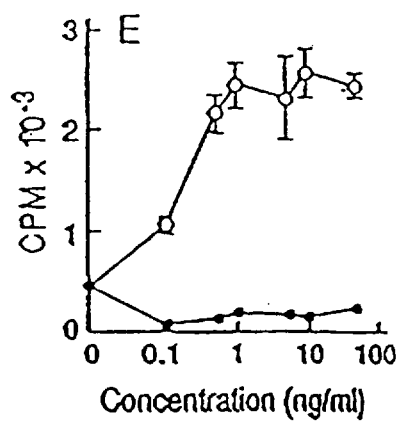
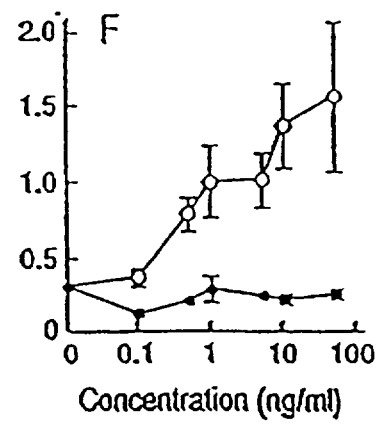
○ No 58
● 58 (5 μM)
FIGURE 65E  FIGURE 65F  bFGF induced

METHOD FOR PREPARING SUBSTITUTED AMINO ALCOHOL COMPOUNDS

This is a Division of U.S. application Ser. No. 08/303,842, filed Sep. 8, 1994, which is a Continuation-in-Part of application Ser. Nos. 08/152,650, filed Nov. 12, 1993 and 08/164,081, filed Dec. 8, 1993, which are Continuation-in-Part Applications of application Ser. No. 08/040,820, filed Mar. 31, 1993, now abandoned.

FIELD OF THE INVENTION

The invention provides a group of compounds that are effective agents to inhibit specific cellular signaling events often induced by inflammatory stimuli, to act as anti-inflammatory or immunosuppressive agents, to act as cytotoxic agents for treatment of cancers, or to be directly or indirectly antimicrobial to yeast or fungal infections. More specifically, the inventive compounds have at least one amino alcohol (or derivative thereof) functional group attached to a terminal moiety via an aliphatic hydrocarbon.

BACKGROUND OF THE INVENTION

Pentoxifylline [1-(5-oxohexyl)-3,7-dimethylxanthine], abbreviated PTX, is widely used medically for increasing blood flow. U.S. Pat. Nos. 3,422,107 and 3,737,433, both to Mohler et al., disclose PTX. Metabolites of PTX were summarized in Davis et al., "Microbial Models of Mammalian Metabolism: Microbial Reduction and oxidation of Pentoxifylline," *Applied and Environmental Microbiology,* Vol. 48, No. 2, pages 327–381, August 1984, and Bryce et al., "Metabolism and Pharmacokinetics of $^{14}$C-Pentoxifylline in Healthy Voluteers," *Arzneim.-Forsch./Drug Res.* Vol. 39, No. 4, pages 512–517, 1989. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947 to Hinze et al. Other metabolites include 1-(5-pentoyl)-3,7-dimethylxanthine carboxylic acid, designated M4, and 1-(4-butyl)-3,7-dimethylxanthine carboxylic acid, designated M5. In addition, U.S. Pat. Nos. 4,833,146 and 5,039,666 to Gebert et al. and Novick, respectively, disclose use of tertiary alcohol analogs of xanthine-containing compounds for enhancing cerebral blood flow.

PTX and its known metabolites thereof have been shown to have in vivo activity in specific biologic systems. U.S. Pat. No. 4,636,507 to Kreutzer et al. describes an ability of PTX and M1 to enhance chemotaxis in polymorphonuclear leukocytes responding to chemotaxis stimulation. In addition, PTX and related tertiary alcohol substituted xanthines inhibit activity of certain cytokines to affect chemotaxis as described in U.S. Pat. Nos. 4,965,271 and 5,096,906 to Mandell et al. Furthermore, by co-administering PTX and GM-CSF, patients undergoing allogeneic bone marrow transplant exhibited decreased levels of tumor necrosis factor, TNFα. Bianco et al., "Pentoxifylline (PTX) and GM-CSF Decrease Tumor Necrosis Factor (TNFα) Levels in patients undergoing allogeneic Bone Marrow Transplantation (MBT)," *Blood,* Vol. 76, No. 1, Suppl. 1 (522), page 133a, 1990. Reduction in assayable levels of TNFα was accompanied by reduced BMT-related complications. However, in normal volunteers, TNFα levels were higher among PTX recipients. Therefore, elevated levels of TNFα are not the primary cause of such complications.

Further research with PTX, its metabolites and their activity relating to various biologic systems spurred investigations with potential therapeutic agents heretofore unknown. These agents were identified as potential therapies for treating or preventing disease by inhibiting secondary cellular response to an external or in situ primary stimuli. These investigations sought efficacious, therapeutic compounds, which would be safe and effective for human or animal administration and would maintain cellular homeostasis in the presence of a variety of deleterious stimuli.

Many diseases are difficult to treat because they have complex mechanisms of action, and multiple, adverse effects on a subject. As an example, cancer has been difficult to treat for this and other reasons. Precise causes of cancer remain unknown. Malignant tumor growth results from many physiologic factors. Cancer cells metastasize (i.e., break through blood vessels and travel to distant body sites) and secrete enzymes called metalloproteases, which "break down" blood vessel walls, allowing the cancer cells to enter the bloodstream and form remote tumors (proteolysis). In addition, tumor cell adhesion receptors (integrins) effect attachment—necessary for tumor residence in organs—of tumor cells to blood vessel walls and normal organs. Cancer cells also secrete certain proteins, such as bFGF, that stimulate new blood vessel development (angiogenesis), these new blood vessels supplying nutrients to promote malignant tumor growth.

Conventional antineoplastic therapies, such as, for example, antimetabolites, alkylating agents and antitumor agents (which target or interfere with DNA and/or synthesis of DNA or its precursors), and biologic therapies (including selective interferons, interleukins and other factors) have significant adverse side effects in patients, not limited to acute toxicity due to effects on rapid-proliferating tissues, such as bone marrow and oral epithelium, myelosuppression and mucositis, renal failure and neurological, hepatic or pulmonary toxicity. Thus, for example, a cancer therapy which effectively prevented, reduced or eliminated malignant tumors without causing deleterious side effects would provide previously unknown treatment.

Compounds disclosed herein and discovered in search of potential disease treatments which would prevent or treat a disease with minimal or no adverse side effects, have biologic activity in multifarious, predictive assays. The inventive compounds exhibit utility in preventing an undesireable cellular response to noxious stimuli. Results from predicitive assays indicate that these inventive compounds have potential as therapies in treating a broad spectrum of clinical indications, acting via a variety of disease mechanisms. However, all these mechanisms appear to affect the second messenger pathway. Results of this research are the subject matter of this disclosure, the compounds discussed herein having novel structures and remarkable and surprising properties heretofore unknown.

SUMMARY OF THE INVENTION

The invention provides compounds useful in a large variety of therapeutic indications for modulating disease by intracellular signaling through specific intracellular signaling pathways. In addition, the compounds and pharmaceutical compositions are suitable for normal routes of therapeutic administration (e.g., parenteral, oral, topical, etc.) for providing effective dosages of a therapeutic compound. The compounds include resolved enantiomers and/or diastereomers, hydrates, salts, solvates and mixtures thereof, the compounds having a straight or branched aliphatic hydrocarbon structure of formula I:

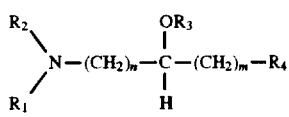

$$\begin{array}{c} R_2 \\ \diagdown \\ \diagup \\ R_1 \end{array} N-(CH_2)_n-\underset{\underset{H}{|}}{\overset{\overset{OR_3}{|}}{C}}-(CH_2)_m-R_4 \qquad I$$

In formula I, n is an integer from one to four and m is an integer from four to twenty. Independently, $R_1$ and $R_2$ are hydrogen, a straight or branched chain alkyl, alkenyl or alkynyl of up to twenty carbon atoms in length or $-(CH_2)_w R_5$. If $R_1$ or $R_2$ is $-(CH_2)_w R_5$, w may be an integer from one to twenty and $R_5$ may be an hydroxyl, halo, $C_{1-8}$ alkoxyl group or a substituted or unsubstituted carbocycle or heterocycle. Alternatively, $R_1$ and $R_2$ may jointly form a substituted or unsubstituted, saturated or unsaturated heterocycle having from four to eight carbon atoms, N being a hetero atom of the resulting heterocycle. $R_3$ may be either hydrogen or $C_{1-3}$. Preferred compounds may have one of $R_1$ or $R_2$ and $R_3$ that form a substituted or unsubstituted linking carbon chain, having from one to four carbon atoms. This $R_1/R_3$ or $R_2/R_3$ linking chain will join the O and N in a cyclic structure, an integer sum equal to n+a number of carbon atoms in the linking carbon chain being less than six.

In the compounds, a total sum of carbon atoms comprising $R_1$ or $R_2$, $(CH_2)_n$ and $(CH_2)_m$ does not exceed forty. $R_4$ is a terminal moiety comprising a substituted or unsubstituted, oxidized or reduced ring system, the ring system having a single ring or two to three fused rings, a ring comprising from three to seven ring atoms. However, if $R_4$ is phthalimide, m of formula I is not less than five.

The compounds may include resolved enantiomers and/or diastereomers, hydrates, salts, solvates and mixtures thereof that have a straight or branched aliphatic hydrocarbon structure of formula II:

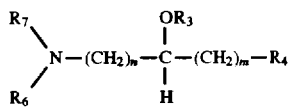

$$\begin{array}{c} R_7 \\ \diagdown \\ \diagup \\ R_6 \end{array} N-(CH_2)_n-\underset{\underset{H}{|}}{\overset{\overset{OR_3}{|}}{C}}-(CH_2)_m-R_4 \qquad II$$

In the above formula II, n, m, $R_3$, and $R_4$ are defined as provided in formula I above. $R_6$ and $R_7$ are hydrogen, a straight or branched chain alkane, alkene or alkyne of up to twenty carbon atoms in length, or $-(CH_2)_x R_8$, at least one of $R_6$ or $R_7$ being $-(CH_2)_x R_8$. In formula II, x is an integer from zero to fourteen and $R_8$ is a moiety having a general structure as provided in formula III

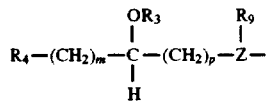

$$R_4-(CH_2)_m-\underset{\underset{H}{|}}{\overset{\overset{OR_3}{|}}{C}}-(CH_2)_p-\overset{R_9}{\overset{|}{Z}}- \qquad III$$

In formula III above, m, $R_3$, and $R_4$ are defined as provided in formula I above. Z is N or CH and p is an integer from zero to four. $R_9$ is H or a straight or branched chain alkane, alkene or alkyne of up to twenty carbon atoms in length.

The invention provides a pharmaceutical composition comprising an compound or a pharmaceutical salt, hydrate or solvate thereof and a pharmaceutically acceptable excipient. The pharmaceutical composition may be formulated for oral, parenteral or topical administration to a patient.

The invention includes a method for treating an individual having a variety of diseases. The disease is characterized by or can be treated by inhibiting an immune response or a cellular response to external or in situ primary stimuli, the cellular response being mediated through a specific phospholipid-based second messenger acting adjacent to a cell membrane inner leaflet. The second messenger pathway is activated in response to various noxious or proliferative stimuli characteristic of a variety of disease states. Biochemistry of this second messenger pathway is described herein. More specifically, the invention includes methods for treating or preventing clinical symptoms of various disease states or reducing toxicity of other treatments by inhibiting cellular signaling through a second messenger pathway involving signaling through phosphatidic acid and through glycan phosphatidylinostinol (Gly PI).

The compounds are of particular significance for inhibiting IL-2-induced proliferative response. IL-2 signaling inhibition is potentially useful in the treatment of numerous disease states involving T-cell activation and hyperproliferation. Exemplary autoimmune diseases treated by inhibiting IL-2 signaling are lupus, scleroderma, rheumatoid arthritis, multiple sclerosis, glomerula nephritis as well as potential malignancies, including but not limited to, chronic myelogenous leukemia as well as others.

BRIEF DESCRIPTION OF THE DRAWINGS

FIGS. 7 and 8 report dose response results from an in vitro assay emphasizing cellular or T-cell immune response.

FIGS. 41A, 41B and 41C illustrate the results from an in vivo study in mice with B16 melanoma cells.

FIGS. 58C, 58D and 58E illustrate that compound no. 45 inhibits IFN-γ release by blocking IL-2 signaling.

FIGS. 65A–65F illustrate inhibition of proliferation in either human aortic or pulmonary smooth muscle cells (SMC) by compound no. 58.

DETAILED DESCRIPTION OF THE INVENTION

Figure 1A:
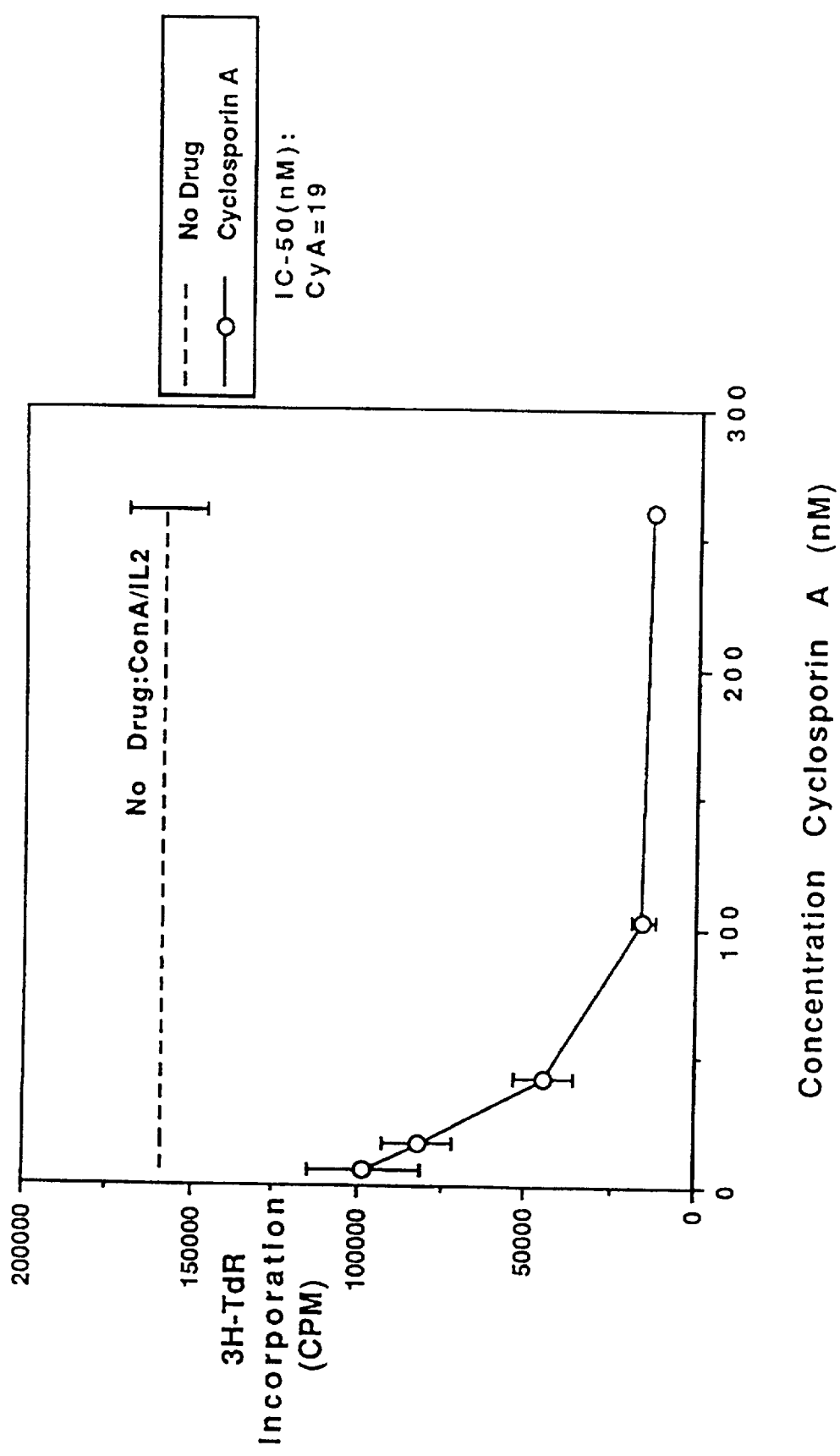
FIGS. 1A and 1B are dose response curves for both cyclosporin A (CsA, FIG. 1A) and various compounds (FIG. 1B) for murine thymocyte proliferation co-stimulated by Concanavalin A (ConA) and interleukin-2 alpha (IL-2).

The invention provides a genus of compounds which can control cellular behavior by a particular phase of a secondary messenger pathway system (Bursten et al., "Interleukin-1 Rapidly Stimulates Lysophosphatidate Acyltransferase and Phosphatidate Phosphohydrolase Activities in Human Mesangial Cells," J. Biol. Chem., Vol. 266, No. 31, pages 20732–20743, Nov. 5, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A2
PLD=phospholipase D
PAA=phosphoarachidonic acid
PC=phosphatidyl choline
PIG-PLD=Glycanphosphotidylinositol phospholipase D
Gly PI=glycanphosphotidylinositol
Gly I=glycan inositol
"remodeled" PA, cyclic pathway=PAA, LPA, PA and DAG intermediates substituted with 1-saturated, 2-linoleoyl or 1,2-dioleoyl, dioleoy/1,2-sn-dilinoleoyl at the indicated sn-1 and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1β, IL-2 or TNFα) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. Each membrane phospholipid subclass (e.g., PA, PI, PE, PC and PS) reaches a-stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. However, it is important to know whether or not each phospholipid species passes through a PA form previous to hydrolysis to DAG. The lyso-PA that is converted to PA and then to DAG may be shown. The complexities of this second messenger pathway can be sorted by suitable analyses by fatty acyl side chain chemistry (i.e., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through the action of PAPH. Several minutes later, DAG is generated from PI through the classical phosphoinositide pathway. In many cells, DAG is derived from both PA that is being remodeled through a cycle whereby PA is sn-2 hydrolyzed by PLA2, followed by sn-2 transacylation by LPAAT, and a PLD-pathway from PA that is generated from either PE or PC or both substrates by PLD.

The present second messenger pathway involves substrates with unsaturated fatty acids in the sn-2 position other than arachidonate and those sub species of PAPH and LPAAT that are not involved in normal cellular housekeeping functions that are part of the classical PI pathway.

The PAPH and LPAAT enzymes involved in the present second messenger pathway are exquisitely stereo specific for different acyl side chains and isomeric forms of substrates. Therefore, the compounds are preferably, substantially enantiomerically pure if a chiral center is present.

An additional signaling pathway associated with inflammatory transduction and cell membrane perturbation generates a separate PA species, enriched in myristate and derived from GlyPI, as described above. Under these signaling conditions, the compounds prevent activation of or directly inhibit the PiG-PLD, hydrolyzing GlyPI to PA and GlyL In some tumor cells and TNFα-activated cells (i.e., Type II receptors), the compounds' efficacy may be dual inhibition of both LPAAT and GlyPI hydrolysis. Experimental results confirm this inhibitive effect. Stimulation of CT-6 cells with IL-2 results in rapid hydrolysis of GlyPI species 15–45 seconds after stimulation, followed by rapid resynthesis of GlyPI. The compounds prevent this hydrolysis and stimulate GlyPI synthesis, resulting in a significant GlyPI increase throughout stimulation without evidence of hydrolysis or formation of GlyPI-derived PA. Stimulation of human umbilical vein endothelial cells with TNFα results in LPAAT-derived and Gly-PI-derived PA species. The compounds inhibit formation of both PA species. Accumulation of lyso-PA and Gly-PI results.

Therapeutic Uses of the Inventive Compounds

The specific activation or inhibition of the second messenger cell signaling pathway, as described above, activated primarily by various stimuli, suggests that the inventive compounds are useful in treating a wide variety of clinical indications. Moreover, in vitro and in vivo data, presented herein, provides predictive data that a wide variety of clinical indications, having similar effects on the specific second messenger pathway, may be treated by the inventive compounds, which specifically inhibit the second messenger pathway mediated through, for example, inflammatory cytokines. In fact, the mechanism of action for the compounds explains why these compounds have multifarious clinical indications.

Activation of the second messenger pathway is a major mediator of response to stimuli and results in intracellular signalling that leads to clinical manifestations of, for example, acute and chronic inflammation, autoimmune diseases and cancer cell growth. However, all inhibitors (i.e., the inventive compounds) do not inhibit all enzymes of this second messenger pathway. Signals mediated by the present second messenger pathway include, for example, those cellular responses of LPS directly, T- and B-cell activation by antigen, cellular responses to first messengers (e.g. inflammatory cytokines), such as, IL-1β and TNFα, growth stimulated by transformations including, but not limited to, activated oncogenes (e.g., ras, abl, her2-neu and the like), smooth muscle cell proliferation stimulated by platelet derived growth factor (PDGF), b-FGF, epidermal growth factor (EGF), vascular endothelial growth factor (VEGF) and IL-1β, T- and B-cell growth stimulation by IL-2, IL-4 or IL-7; and more generally, T cell receptor signaling.

The inventive compounds: (1) block IL-1β signal transduction through the Type I receptor as shown, for example, by preventing IL-1β and IL-1β plus PDGF induction of proliferation of smooth muscle, endothelial and kidney mesangial cells; (2) suppress up-regulation of adhesion molecules as shown, for example, by blocking VCAM in endothelial cells; (3) inhibit TNFα, LPS and IL-1β induced metalloproteases (an inflammation and cancer metasteses model); (4) block LPS, TNFα or IL-1β induced secondary cytokine production (for prevention and treatment of septic shock symptoms); (5) suppress T- and B-cell activation by antigen, for example, IL-2 and IL-4; (6) inhibit mast cell activation by immunoglobulin E (IgE); (7) are cytotoxic for transformed cells and tumor cell lines, yet not for normal cells at equivalent doses; and (8) block signaling by IL-2, IL-4, IL-6 and IL-7 on T- and B-cells.

The foregoing cellular results are the basis for the following pharmacologic effects, including, but not limited to, protection and treatment of endotoxic shock and sepsis induced by gram positive or gram negative bacteria, inhibition and prevention of tumor cell growth and metastatic spread, immunosuppression, treatment of autoimmune diseases, suppression of allograft reactions, stimulation of hair growth (e.g., treatment of baldness or prevention of hair loss due to cytoreductive therapies), and treatment of hyperproliferative skin disorders such as psoriasis through reversal of an apoptotic process. The inventive compounds are most useful to treat acute and chronic inflammatory disease, suppress an immune response, treat cancer by having an apoptotic cytotoxic effect to transformed cells while having minimal toxicity to rapidly proliferating cells at doses cytotoxic to tumor cells, prevent metastatic tumor growth through antiangiogenic and anti-adhesion properties, and treat or prevent an autoimmune disease and stimulate hair growth (when applied topically).

The inventive compounds also are useful as an adjuvant to inhibit toxic side effects of drugs whose side effects are mediated through the present second messenger pathway. Metalloproteases mediate tissue damage such as glomerular diseases of the kidney, joint destruction in arthritis, and lung destruction in emphysema, and play a significant role in tumor metastases. Three examples of metalloproteases include a 92 kD type V gelatinase induced by TNFα, IL-1β and PDGF plus b-FGF, a 72 kD type IV collagenase that is usually constitutively produced and stimulated by TNFα or IL-1β and a stromelysin/PUMP-1 induced by TNFα and IL-1β. The inventive compounds can inhibit TNFα or IL-1β induction of the 92 kD type V gelatinase inducable metalloprotease. Moreover, the inventive compounds can reduce PUMP-1 activity induced by 100 U/ml of IL-1β. Accordingly, the inventive compounds prevent induction of certain metalloproteases induced by IL-1β or TNFα and are not involved with constitutively produced proteases (e.g., 72 kD type IV collagenase) involved in normal tissue remodeling.

The inventive compounds inhibit IL-1 signal transduction, and are therefore considered as IL-1 antagonists. A review article entitled "Mechanisms of Disease: The Role of Interleukin-1 in Disease" (Dinarello et al., *N. Engl. J. Med.*, Vol. 328, No. 2, pages 106–113, 1993) described the role of IL-1 as "an important rapid and direct determinant of disease." "In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds are IL-1 antagonists, the inventive compounds are useful for treating all of the above-mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure, and doses of 300 ng or more per kilogram of body weight may cause severe hypotension. The therapeutic advantage of blocking the action of IL-1 resides in preventing its deleterious biologic effects without interfering with the production of molecules that have a role in homeostasis. The present inventive compounds address the need identified by Dinarello et al. inhibiting IL-1 cellular signaling.

With regard to rheumatoid arthritis, Dinarello et al. state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

Inflammatory bowel disease, ulcerative colitis and Crohn's disease are characterized by infiltrative lesions of the bowel that contain activated neutrophils and macrophages. IL-1β can stimulate production of inflammatory eicosanoids such as prostaglandin $E_2$ ($PGE_2$) and leukotriene $B_4$ ($LTB_4$) and IL-8, an inflammatory cytokine with neutrophil-chemoattractant and neutrophil-stimulating properties. Tissue concentrations of $PGE_2$ and $LTB_4$ correlate with the severity of disease in patients with ulcerative colitis, and tissue concentrations of IL-1β and IL-8 are high in patients with inflammatory bowel disease. Therefore, an IL-1 antagonist, such as the inventive compounds, is effective to treat inflammatory bowel disease.

With regard to acute and chronic myelogenous leukemia, there is increasing evidence that IL-1 acts as a growth factor for such tumor cells. Therefore, the inventive compounds are effective to prevent disease deterioration for acute and chronic myelogenous leukemias.

IDDM is considered to be an autoimmune disease with destruction of beta cells in the islets of Langerhans mediated by immunocompetent cells. Islets of animals with spontaneously occurring IDDM (e.g., BB rats or NOD mice) have inflammatory cells that contain IL-1β. Therefore, the inventive compounds are useful for the prevention of and treatment of IDDM.

IL-1β also plays a role in the development of atherosclerosis. Endothelial cells are a target of IL-1β. IL-1β stimulates proliferation of vascular smooth muscle cells. Foam cells isolated from fatty arterial plaques from hypercholesterolemic rabbits contain IL-1β and IL-1β messenger RNA. The uptake of peripheral blood monocytes results in initiation of IL-1β production by these cells. IL-1β also stimulates production of PDGF. Taken together, IL-1β plays a part in the development of atherosclerotic lesions. Therefore, an IL-1β antagonist, such as the inventive compounds is useful in preventing and treating atherosclerosis.

DAG and PA are up-regulated in oncogenically transformed cells. For example, activating ras mutations result in increased generation of DAG on stimulation with mitogens. In non-transformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells up-regulates serum-stimulated generation of DAG and PA. The specific species of DAG stimulated by serum is dioleoyl and for PA, dilinoleoyl and dioleoyl. This upregulation occurs over 4–12 hours and pretreatment of cells with an compound blocks generation of these phospholipid second messengers. The inhibition occurs either through suppressing the generation of PA de novo from lysoPA, or through inhibition of one or both arms of the Lands cycle. Therefore ras transformation mediates an up-regulation of specific PA species through indirect stimulation of PLA2 and/or LPAAT activity. The inventive compounds inhibit the conversion of the upregulated lysoPA to PA and subsequently block cellular phenotypic changes induced by PA/DAG in the membrane.

The ability of the inventive compounds to inhibit generation of unsaturated phospholipids is mirrored by the ability of compounds to inhibit proliferation and tumorogenicity of ras-transformed cells in vitro and in vivo. This inhibition is reversible and is not associated with significant cytotoxicity.

Excessive or unregulated TNFα production is implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, other viral infections (e.g., CMV, influenza, adenovirus, herpes family), keloid formation, scar tissue formation, Crohn's disease, ulcerative colitis, or pyresis. The compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNFα or IL-1β. With regard to TNFα first messenger signaling, there are several disease states in which excessive or unregulated TNFα production by monocytes/macrophages is implicated in exacerbating or causing the disease. These include, for example, neurodegenerative diseases such as Alzheimers disease, endotoxemia or toxic shock syndrome (Tracey et al., "Anti-cachectin/TNF Monoclonal Antibodies Prevent Septic Shock During Lethal Bacteraemia," *Nature*, Vol. 330, pages 662–664, Dec. 17, 1987 and Hinshaw et al., "Survival of Primates in $LD_{100}$ Septic Shock Following Therapy With Antibody to Tumor Necrosis Factor (TNFα)," *Circ. Shock*, Vol. 30, pages 279–292, 1990); cachexia (Dezube et al., "Pentoxifylline and Wellbeing in Patients with Cancer," *The Lancet*, page 662, Mar. 17, 1990), and adult respiratory distress syndrome (Miller et al., "Tumour Necrosis Factor in Bronchopulmonary Secretions of Patients with Adult Respiratory Distress Syndrome," *The Lancet*, pages 712–713, Sep. 23, 1989). The compounds may be used topically in the treatment of prophylaxis of topical disease states mediated or exacerbated by excessive TNFα or IL-1β, such as viral infections (herpes or viral conjunctivitis), psoriasis, fungal or yeast infections (ringworm, athletes foot, vaginitis, dandruff, etc.) or other dermatologic hyperproliferative disorders. High TNFα levels have been implicated in acute malaria attacks (Grau et al., "Tumor Necrosis Factor and Disease Severity in Children with Falciparum Malaria," *N. Engl. J. Med.*, Vol. 320, No. 24, pages 1586–1591, Jun. 15, 1989), chronic pulmonary inflammatory diseases such as silicosis and asbestosis (Piguet et al., "Requirement of Tumour Necrosis Factor for Development of Silica-induced Pulmonary Fibrosis," *Nature*, Vol. 344, pages 245–247, Mar. 15, 1990, and Bissonnette et al., "Pulmonary Inflammation and Fibrosis in a Murine Model of Asbestosis and Silicosis," *Inflammation*, Vol. 13, No. 3, pages 329–339, 1989), and reperfusion injury (Vedder et al., "Inhibition of Leukocyte Adherence by Anti-CD18 Monoclonal Antibody Attenuates Reperfusion Injury in the Rabbit Ear, *Proc. Natl. Acad. Sci. USA*, Vol. 87, pages 2643–2646, April 1990).

The invention includes methods for treating or preventing clinical symptoms of various disease states or reducing toxicity of other treatments by inhibiting cellular signaling through the second messenger pathway. Disease state or treatment-induced toxicity are selected from the group consisting of proliferation of tumor cells in response to an activated oncogene; hematocytopenia caused by cytoreductive therapies; autoimmune diseases caused by a T-cell response or a B-cell response and antibody production; septic shock; resistance of mesenchymal cells to TNFα; proliferation of smooth muscle cells endothelial cells, fibroblasts and other cell types in response to growth factors, such as PDGF, FGF, EGF and VEGF (i.e., atherosclerosis, restenosis, stroke, and coronary artery disease); human immunodeficiency virus infection (AIDS and AIDS related complex); proliferation of kidney mesangial cells in response to IL-1β, MIP-1α, PDGF or FGF; inflammation; kidney glomerular or tubular toxicity in response to cyclosporin A or amphotericin B treatment; organ toxicity (e.g., gastrointestinal or pulmonary epithelial) in response to a cytoreductive therapy (e.g., cytotoxic drug or radiation); enhancing antitumor effects of non-alkylating antitumor agents; allergies in response to inflammatory stimuli (e.g., TNFα, IL-1β and the like) characterized by production of cell surface metalloproteases or by degranulation of mast cells and basophils in response to IgE, bone diseases caused by overproduction of osteoclast-activating factor (OAF) by osteoclasts. CNS diseases caused by reduced signal transduction of the neurotransmitters epinephrine and acetylcholine, and combinations thereof. The compounds are also useful as antimicrobial agents to directly treat fungal or yeast infections and to indirectly treat bacterial or viral infections through an immune stimulation and pro-hematopoietic effect.

In summary, the compounds and pharmaceutical compositions thereof exhibit some of the following activities: (1) are cytotoxic to tumor cells at doses that are not cytotoxic to normal cells; (2) suppress activation of T-cells by antigen or IL-2 stimulation; (3) suppress activation of monocyte/macrophage cells by endotoxin, TNFα, IL-1β or GM-CSF stimulation; (4) suppress antibody production of B-cells in response to an antigen, IL-4 or CD40 ligand; (5) inhibit the proliferation of smooth muscle cells in response to growth factors capable of stimulating said proliferation (e.g., by inhibiting angiogenesis or preventing atherosclerosis and restenosis or repertusion injury); (6) lower expression of adhesion molecules induced by enhancers thereof; (7) inhibit the proliferation of kidney mesangial cells in response to stimulation by IL-1β and/or MIP-1α and/or PDGF and/or FGF; (8) enhance the resistance of kidney glomerular or tubular cells to cyclosporin A or amphotericin B; (9) prevent the release of MIP-1α by IL-1α, TNFα, or endotoxin stimulated monocytes and macrophages; (10) prevent the release of platelet activating factor by IL-1β, TNFα, or endotoxin treated megakaryocytes, fibroblastic cells, and macrophages; (11) prevent the down-regulation of receptors for cytokines in TNFα -treated hematopoietic progenitor cells; (12) suppress the production of metalloproteases in IL-1β-stimulated or TNFα-stimulated glomerular epithelial cells or synovial cells; (13) enhance the resistance of gastrointestinal or pulmonary epithelial cells to cytotoxic drugs or radiation; (14) enhance the antitumor effect of a non-alkylating antitumor agent; (15) to inhibit the production of osteoclast activating factor in response to IL-1β; (16) inhibit degranulation in response to IgE; (17) enhance the release of adrenergic neural transmitters, dopamine, norepinephrine, or epinephrine, or the neurotransmitter, acetylcholine; (18) modulate the post-synaptic "slow current" effects of the adrenergic neurotransmitters dopamine, epinephrine, or norepinephrine, or the neurotransmitter acetylcholine; (19) suppress signaling by neurotransmitters including acetyl choline, leuenkephalin and seretonin; or (20) increase seizure threshold.

The compounds are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

Compounds of the Invention

The invention provides for a class of compounds that are effective therapeutic agents to inhibit specific inflammatory and proliferative cellular signaling events. The compounds include resolved enantiomers and/or diastereomers, hydrates, salts, solvates and mixtures thereof, the compound having a straight or branched aliphatic hydrocarbon structure of formula I:

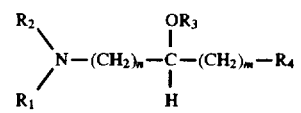

In formula I, n is an integer from one to four and m is an integer from four to twenty. Independently, $R_1$ and $R_2$ are hydrogen, a straight or branched chain alkyl, alkenyl or alkynyl of up to twenty carbon atoms in length or —$(CH_2)_wR_5$. If $R_1$ or $R_2$ is —$(CH_2)_wR_5$, w may be an integer from one to twenty and $R_5$ may be an hydroxyl, halo, $C_{1-8}$ alkoxyl group or a substituted or unsubstituted carbocycle or heterocycle. Alternatively, $R_1$ and $R_2$ may jointly form a substituted or unsubstituted, saturated or unsaturated heterocycle having from four to eight carbon atoms, N being a hetero atom of the resulting heterocycle. $R_3$ may be either hydrogen or $C_{1-3}$. Preferred compounds may have one of $R_1$ or $R_2$ and $R_3$ that form a substituted or unsubstituted linking carbon chain, having from one to four carbon atoms. This $R_1/R_3$ or $R_2/R_3$ linking chain will join the O and N in a cyclic structure, an integer sum equal to n+a number of carbon atoms in the linking carbon chain being less than six.

In the compounds, a total sum of carbon atoms comprising $R_1$ or $R_2$, $(CH_2)_n$ and $(CH_2)_m$ does not exceed forty. $R_4$ is a terminal moiety comprising a substituted or unsubstituted, oxidized or reduced ring system, the ring system having a single ring or two to three fused rings, a ring comprising from three to seven ring atoms. However, if $R_4$ is phthalimide, m of formula I is not less than five.

In preferred compounds of the invention which have a general structure of formula I, $R_5$ may be hydroxy, chloro, fluoro, bromo, or $C_{1-6}$ alkoxy, or a substituted or unsubstituted, saturated or unsaturated heterocycle having from four to seven carbon atoms, more preferably, a mono-, di- or tri-substituted carbocycle or heterocycle. In the compounds, $(CH_2)_m$ may be unsubstituted, or more preferably, $(CH_2)_m$ is substituted by a halogen atom, an hydroxyl group, or substituted or unsubstituted $C_{(1-10)}$ alkoxyl, $C_{(1-10)}$ alkyl, $C_{(2-10)}$ alkenyl or $C_{(1-10)}$ alkynyl group. Substituents of the $R_1/R_3$ or $R_2/R_3$ linking chain may include, without limitation, a $C_{(1-4)}$ alkyl, $C_{(2-4)}$ alkenyl, hydroxyl, carbonyl, amino, thio, thiol, thiocarbonyl and imino group or a single atom, such as, for example, chlorine, bromine, fluorine and oxygen In the compounds comprising a non-cyclic, terminal moiety, the terminal moiety may include, without limitation, an acetamidyl, amidyl, aminyl, amino acid (one or two), carbonyl, carboxyl, alkoxylcarbonyl, halo, hydro, hydroxyl, glutaric acid, alkoxyl, phosphatyl, phosphonatyl, sulfatyl, sulfonatyl, sulfonyl, sulfoxidyl, thio or thiolalkoxylcarbonyl group or a simple ionic functional group. A terminal moiety amino acid may be one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, and are preferably a more hydrophobic amino acid such as leucine or isoleucine. In preferred compounds of the invention, the non-cyclic terminal moiety may be a dipeptide comprising two amino acids selected from the foregoing exemplary list. A preferred halo group may include, but is not limited to bromo, chloro, fluoro or iodo.

In more preferred compounds, the terminal moiety ring system may be saturated, but alternatively, preferred compounds have a ring system terminal moiety having at least one unsaturated carbon-carbon double bond. In more preferred compounds of the invention, ring system substituents may include, but are not intended to be limited to, $C_{(1-4)}$ alkyl, $C_{(2-4)}$ alkenyl, hydroxyl, carbonyl, amino, thio, thiol, thiocarbonyl and imino group or a single atom. Single atoms corresponding to ring substituents may include, but are not intended to be limited to, chlorine, bromine, fluorine and oxygen.

The compounds may have ring systems, in which all ring atoms are carbon atoms. Preferred compounds, in which all ring atoms are carbon atoms, may have ring systems that include, but are not intended to be limited to, one of the following groups: phenyl, cyclopropyl, cyclobutyl, cyclopentyl, cyclopentenyl, cyclohexyl, cyclohexenyl, cycloheptyl, cycloheptenyl, biscyclooctyl, indanyl, indenyl, decalinyl, resorcinolyl, tetralinyl, α-tetralonyl, 1-indanonyl, cyclohexanedionyl or cyclopentanedionyl.

In more preferred compounds of the invention, at least one ring atom of the ring system may be other than carbon. For preferred compounds that have a ring system terminal moiety, having at least one ring atom which is other than carbon, then the total number of non-carbon ring atoms should not exceed a value "X," specified by the equation: X=total number of ring atoms-1. Non-carbon ring atoms may include, for example, atoms such as nitrogen, oxygen, sulfur and phosphorus.

Terminal moiety ring systems which have at least one ring atom that is other than carbon may include, for example, ring systems that have three or four atoms in at least one ring of the system. Preferred ring systems having at least one non-carbon atom and at least one ring which has three or four atoms may include, but are not intended to be limited to: azetidinedionyl; azetidinonyl; azetidinyl; aziridinonyl; aziridinyl; aziriny; diaziridinonyl; diaziridinyl; diazirinyl; dioxetanyl; dioxiranyl; dithietanyl; episulfonyl; lactamyl; lactonyl; oxathietanyl; oxathiiranyl; oxaziranyl; oxaziridinyl; oxetananonyl; oxetanonyl; oxetanyl; oxiranyl; sultamyl; sultinyl; sultonyl; thiazetidinyl; thiaziridinyl; thietanyl or thiiranyl.

Alternatively, preferred compounds may have terminal moieties that have at least one ring having at least five ring atoms, at least one of the at least five ring atoms being other than carbon. In these preferred compounds, the at least five-atom ring system may include, but is not intended to be limited to, one of the following substituted or unsubstituted groups: adeninyl; alloxanyl; alloxazinyl; anthracenyl; anthrenyl; azapinyl; azapurinyl; azinyl; azolyl; barbituric acid; biotinyl; chromylenyl; cinnolinyl; coumarinyl; coumaronyl; depsidinyl; diazepinyl; diazinyl; diazocinyl; dioxadiazinyl; dioxanyl; dioxenyl; dioxepinyl; dioxinonyl; dioxolanyl; dioxolonyl; dioxolyl; dioxanthylenyl; enantholactamyl; flavanyl; flavinyl; flavonyl; fluoranyl; fluorescienyl; furandionyl; faranochromanyl; furanonyl; furanyl; furazanyl; furoxanyl; guaninyl; hydroquinolinyl; imidazolethionyl; imidazolinyl; imidazolonyl; imidazolyl; indolizidinyl; indolizinyl; indolonyl; indolyl; isatinyl; isatogenyl; isoindolinyl; isoquinolinyl; isothiazolyl; isoxazolyl; lactamyl; lactonyl; lumazinyl; naphthacenyl; naphthalenyl; oroticyl; oxadiazinyl; oxadiazolyl; oxathianyl; oxathiazinonyl; oxathiolanyl; oxatriazolyl; oxazinonyl; oxazolidinonyl; oxazolidinyl; oxazolinonyl; oxazolinyl; oxazolonyl; oxazolyl; oxolenyl; pentazinyl; pentazolyl; petrazinyl; phthalimidyl; phthalonyl; piperazindionyl; piperazinodionyl; piperazinyl; piperidinyl; piperidonyl; prolinyl; prylenyl; pteridinyl; pterinyl; purinyl; pyradinyl; pyranoazinyl; pyranoazolyl; pyranonyl; pyranyl; pyrazinyl; pyrazolidinyl; pyrazolidonyl; pyrazolinonyl; pyrazolinyl; pyrazolonyl; pyrazolyl; pyrenyl; pyridazinyl; pyridazonyl; pyridinyl; pyrimidinyl; pyrimidionyl; pyronyl; pyrrolidinyl; pyrrolyl; quinazolidinyl; quinazolinonyl; quinazolinyl; quinolinyl; quinolizinyl; quinonyl; quinoxalinyl; quinuclidinyl; rhodaminyl; spirocoumaranyl; succinimidyl; sulfolanyl; sulfolenyl; sultamyl; sultinyl; sultonyl; sydononyl; tetraoxanyl; tetrazepinyl; tetrazinyl; tetrazolyl; tetronyl; thiazepinyl; thiazinyl; thiazolyl; thiepinyl; thiolanyl; thiolenyl; thiolyl; thiophenyl; thyminyl; triazepinonyl; triazepinyl; triazinyl; triazolinyl; triazolyl; trioxanyl; trithianyl; trixolanyl; trizinyl; tropanyl; uracilyl; xanthenyl; xanthinyl; xanthonyl; xanthydrolyl or xylitolyl.

For compounds having a preferred ring system terminal moiety having at least one ring with one hetero atom, a ring system may include one of the following: acridinyl; acridonyl; alkylpyridinyl; anthraquinonyl; ascorbyl; azaazulenyl; azabenzanthracenyl; azabenzanthrenyl; azabenzophenanthrenyl; azachrysenyl; azacyclazinyl; azaindolyl; azanaphthacenyl; azanaphthalenyl; azapyrenyl; azatriphenylenyl; azepinyl; azinoindolyl; azinopyrrolyl; benzacridinyl; benzazapinyl; benzofuryl; benzonaphthyridinyl; benzopyranonyl; benzopyranyl; benzopyronyl; benzoquinolinyl; benzoquinolizinyl; benzothiepinyl; benzothiophenyl; benzylisoquinolinyl; biotinyl; bipyridinyl; butenolidyl; butyrolactonyl; caprolactamyl; carbazolyl; carbolinyl; catechinyl; chromenopyronyl; chromonopyranyl; coumarinyl; coumaronyl; decahydroquinolinyl; decahydroquinolonyl; diazaanthracenyl; diazaphenanthrenyl; dibenzazepinyl; dibenzofuranyl; dibenzothiophenyl; dichromylenyl; dihydrofuranyl; dihydroisocoumarinyl; dihydroisoquinolinyl; dihydropyranyl; dihydropyridinyl; dihydropyridonyl; dihydropyronyl; dihydrothiopyranyl; diprylenyl; dioxanthylenyl; enantholactamyl; flavanyl; flavonyl; fluoranyl; fluorescienyl; furandionyl; furanochromanyl; furanonyl; furanoquinolinyl; furanyl; furopyranyl; furopyronyl; heteroazulenyl; hexahydropyrazinoisoquinolinyl; hydrofuranyl; hydrofurnanonyl; hydroindolyl; hydropyranyl; hydropyridinyl; hydropyrrolyl; hydroquinolinyl; hydrothiochromenyl; hydrothiophenyl; indolizidinyl; indolizinyl; indolonyl; isatinyl; isatogenyl; isobenzofurandionyl; isobenzofuranyl; isochromanyl; isoflavonyl; isoindolinyl; isoindolobenzazepinyl; isoindolyl; isoquinolinyl; isoquinuclidinyl; lactamyl; lactonyl; maleimidyl; monoazabenzonaphthenyl; naphthalenyl; naphthimidazopyridinedionyl; naphthindolizinedionyl; naphthodihydropyranyl; naphthofuranyl; naphthothiophenyl; naphthyridinyl; oxepinyl; oxindolyl; oxolenyl; perhydroazolopyridinyl; perhydroindolyl; phenanthraquinonyl; phenanthridinyl; phenanthrolinyl; phthalideisoquinolinyl; phthalimnidyl; phthalonyl; piperidinyl; piperidonyl; prolinyl; pyradinyl; pyranoazinyl; pyranoazolyl; pyranopyrandionyl; pyranopyridinyl; pyranoquinolinyl; pyranopyradinyl; pyranyl; pyrazolopyridinyl; pyridinethionyl; pyridinonaphthalenyl; pyridinopyridinyl; pyridinyl; pyridocolinyl; pyridoindolyl; pyridopyridinyl; pyridopyrimidinyl; pyridopyrrolyl; pyridoquinolinyl; pyronyl; pyrrocolinyl; pyrrolidinyl; pyrrolizidinyl; pyrrolizinyl; pyrrolodiazinyl; pyrrolonyl; pyrrolopyrimidinyl; pyrroloquinolonyl; pyrrolyl; quinacridonyl; quinolinyl; quinolizidinyl; quinolizinyl; quinolonyl; quinuclidinyl; rhodaminyl; spirocoumaranyl; succinimidyl; sulfolanyl; sulfolenyl; tetrahydrofuranyl; tetrahydroisoquinolinyl; tetrahydropyranyl; tetrahydropyridinyl; tetrahydrothiapyranyl; tetrahydrothiophenyl; tetrahydrothiopyranonyl; tetrahydrothiopyranyl; tetronyl; thiabenzenyl; thiachromanyl; thiadecalinyl; thianaphthenyl; thiapyranyl; thiapyronyl; thiazolopyridinyl; thienopryidinyl; thienopyrrolyl; thienothiophenyl; thiepinyl; thiochromenyl; thiocoumarinyl; thiophenyl; thiopyranyl; triazaanthracenyl; triazinoindolyl; triazolopyridinyl; tropanyl; xanthenyl; xanthonyl or xanthydrolyl.

In addition, compounds that have a preferred ring system terminal moiety having at least one ring with two hetero atoms, the ring system may include: adeninyl; alloxanyl; alloxazinyl; anthranilyl; azabenzanthrenyl; azabenzonaphthenyl; azanaphthacenyl; azaphenoxazinyl; azapurinyl; azinyl; azoloazinyl; azolyl; barbituric acid; benzazinyl; benzimidazolethionyl; benzimidazolonyl; benzimidazolyl; benzisothiazolyl; benzisoxazolyl; benzocinnolinyl; benzodiazocinyl; benzodioxanyl; benzodioxolanyl; benzodioxolyl; benzopyridazinyl; benzothiazepinyl; benzothiazinyl; benzothiazolyl; benzoxazinyl; benzoxazolinonyl; benzoxazolyl; cinnolinyl; depsidinyl; diazaphenanthrenyl; diazepinyl; diazinyl; dibenzoxazepinyl; dihydrobenzimidazolyl; dihydrobenzothiazinyl; dihydrooxazolyl; dihydropyridazinyl; dihydropyrimidinyl; dihydrothiazinyl; dioxanyl; dioxenyl; dioxepinyl; dioxinonyl; dioxolanyl; dioxolonyl; dioxopiperazinyl; dipyrimidopyrazinyl; dithiolanyl; dithiolenyl; dithiolyl; flavinyl; furopyrimidinyl; glycocyamidinyl; guaninyl; hexahydropyrazinoisoquinolinyl; hexahydropyridazinyl; hydantoinyl; hydroimidazolyl; hydropyrazinyl; hydropyrazolyl; hydropyridazinyl; hydropyrimidinyl; imidazolinyl; imidazolyl; imidazoquinazolinyl; imidazothiazolyl; indazolebenzopyrazolyl; indoxazenyl; inosinyl; isoalloxazinyl; isothiazolyl; isoxazolidinyl; isoxazolinonyl; isoxazolinyl; isoxazolonyl; isoxazolyl; lumazinyl; methylthyminyl; methyluracilyl; morpholinyl; naphthimidazolyl; oroticyl; oxathianyl; oxathiolanyl; oxazinonyl; oxazolidinonyl; oxazolidinyl; oxazolidonyl; oxazolinonyl; oxazolinyl; oxazolonyl; oxazolopyrimidinyl oxazolyl; perhydrocinnolinyl; perhydropyrroloazinyl; perhydropyrrolooxazinyl; perhydropyrrolothiazinyl; perhydrothiazinonyl; perimidinyl; phenazinyl; phenothiazinyl; phenoxathiinyl; phenoxazinyl; phenoxazonyl; phthalazinyl; piperazindionyl; piperazinodionyl; polyquinoxalinyl; pteridinyl; pterinyl; purinyl; pyrazinyl; pyrazolidinyl; pyrazolidonyl; pyrazolinonyl; pyrazolinyl; pyrazolobenzodiazepinyl; pyrazolonyl; pyrazolopyridinyl; pyrazolopyrimidinyl; pyrazolotriazinyl; pyrazolyl; pyridazinyl; pyridazonyl; pyridopyrazinyl; pyridopyrimidinyl; pyrimidinethionyl; pyrimidinyl; pyrimidionyl; pyrimidoazepinyl; pyrimidopteridinyl; pyrrolobenzodiazepinyl; pyrrolodiazinyl; pyrrolopyrimidinyl; quinazolidinyl; quinazolinonyl; quinazolinyl; quinoxalinyl; sultamyl; sultinyl; sultonyl; tetrahydrooxazolyl; tetrahydropyrazinyl; tetrahydropyridazinyl; tetrahydroquinoxalinyl; tetrahydrothiazolyl; thiazepinyl; thiazinyl; thiazolidinonyl; thiazolidinyl; thiazolinonyl; thiazolinyl; thiazolobenzimidazolyl; thiazolyl; thienopyrimidinyl; thiazolidinonyl; thyminyl; triazolopyrimidinyl; uracilyl; xanthinyl; or xylitolyl.

Terminal ring systems having at least one ring having three hetero atoms may include, but are not intended to be limited to, one of the following ring systems: azabenzonaphthenyl; benzofuroxanyl; benzothiadiazinyl; benzotriazepinonyl; benzotriazolyl; benzoxadizinyl; dioxadiazinyl; dithiadazolyl; dithiazolyl; furazanyl; furoxanyl; hydrotriazolyl; hydroxytrizinyl; oxadiazinyl; oxadiazolyl; oxathiazinonyl; oxatriazolyl; pentazinyl; pentazolyl; petrazinyl; polyoxadiazolyl; sydononyl; tetraoxanyl; tetrazepinyl; tetrazinyl; tetrazolyl; thiadiazinyl; thiadiazolinyl; thiadiazolyl; thiadioxazinyl; thiatriazinyl; thiatriazolyl; thiatriazolyl; triazepinyl; triazinoindolyl; triazinyl; triazolinedionyl; triazolinyl; triazolyl; trioxanyl; triphenodioxazinyl; triphenodithiazinyl; trithiadiazepinyl; trithianyl; or trixolanyl.

In these compounds, the most preferred ring systems include, for example, dimethylxanthinyl, methylxanthinyl, phthalimidyl, homophthalimidyl, methylbenzoyleneureayl, quinazolinonyl, octylcarboxamidobenzenyl, methylbenzamidyl, methyldioxotetrahydropteridinyl, glutarimidyl, piperidonyl, succinimidyl, dimethoxybenzenyl, methyldihydrouracilyl, methyluracilyl, methylthyminyl, piperidinyl, dihydroxybenzenyl, or methylpurinyl, even more preferably, methylxanthinyl, dimethylxanthinyl or a derivative thereof. The most preferred compounds may also have a ring-system terminal moiety that has at least one substituent bonded to at least one ring of the ring system, the at least one substituent being bonded to a carbon ring atom of the at least one ring by an sp bond, in which the carbon ring atom is adjacent to a hetero atom of the ring. Also, in the most preferred embodiments of the compounds, ring-system terminal moieties, having at least one hetero atom, may be linked to —(CH$_2$)$_m$ of formula I by a bond between the at least one hetero atom and —(CH$_2$)$_m$.

The compounds may include resolved enantiomers and/or diastereomers, hydrates, salts, solvates and mixtures thereof of compounds that have a straight or branched aliphatic hydrocarbon structure of formula II:

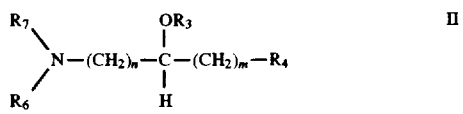

In the above formula II, n, m, R$_3$, and R$_4$ are defined as provided in formula I above. R$_6$ and R$_7$ are hydrogen, a straight or branched chain alkane, alkene or alkyne of up to twenty carbon atoms in length, or —(CH$_2$)$_x$R$_8$, at least one of R$_6$ or R$_7$ being —(CH$_2$)$_x$R$_8$. In formula II, x is an integer from zero to fourteen and R$_8$ is a moiety having a general structure as provided in formula III

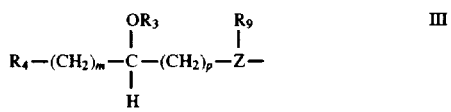

In formula III above, m, R$_3$, and R$_4$ are defined as provided in formula I above. Z is N or CH and p is an integer from zero to four. R$_9$ is H or a straight or branched chain alkane, alkene or alkyne of up to twenty carbon atoms in length.

The invention provides a pharmaceutical composition comprising an compound and a pharmaceutically acceptable excipient. The pharmaceutical composition may be formulated for oral, parenteral or topical administration to a patient.

The invention further provides a pharmaceutical composition comprising an compound and a pharmaceutically acceptable excipient, the pharmaceutical composition being formulated for oral, parenteral or topical administration to a patient. A pharmaceutical composition may alternatively comprise one or a plurality of compounds and a pharmaceutically acceptable carrier or excipient. Treatment of individuals with an compound or pharmaceutical composition may include contacting with the compound in vitro culture, in an extracorporeal treatment, or by administering (oral, parenteral or topical) the compound or pharmaceutical composition to a subject whose cells are to be treated.

Synthesis of the Inventive Compounds

The invention includes a method for preparing the inventive compounds. An exemplary method for preparing the inventive compounds is discussed below and in the following examples. In a synthesis according to the invention, a compound containing a desired terminal group (intended as a "terminal moiety" in compounds of the invention) undergoes a reaction to produce an anion of the terminal moiety-containing compound. Subsequently, the resulting anion is reacted with a substituted olefin to displace a targeted functional group on the olefin, resulting in an intermediate product. A predetermined amount of a terminal moiety-containing compound is reacted with a suitable base, a solvent and a substituted olefin, the substituted olefin having at least one other functional group which may be substituted in a displacement reaction by the desired terminal moiety-containing compound.

Preferred bases include, but are not limited to, sodium hydride, sodium amide, sodium alkoxide, lithium hydride, potassium hydride, lithium amide, sodium amide and potassium amide. An especially preferred base is sodium hydride. Preferred solvents may be dimethylsulfoxide, dimethylformamide, or an alcohol. Exemplary preferred alcohols include, but are not limited to, methanol, ethanol or isopropanol. Any substituted olefin comprising a chain structure of the inventive compounds may be used in the reaction according to the invention. Preferred olefins may be ω-substituted olefins. Preferred substituted olefins include, but are not limited to halo-substituted olefins.

The intermediate product, having a composite structure of the terminal moiety-containing compound and substituted olefin, may subsequently be converted to a corresponding epoxide. In the method according to the invention, the intermediate product may be reacted with an organic peracid to obtain a desired epoxide. Preferred, exemplary organic peracids include 3-chloroperoxybenzoic acid, peracetic acid and trifluoroperacetic acid. An especially preferred peracid is 3-chloroperoxybenzoic acid.

Alternatively, the intermediate product may be converted first to a corresponding diol by reacting the intermediate product with a suitable oxidizing agent. Preferred oxidixing agents include, but are not limited to, osmium tetroxide. Preferred oxidizing agents, such as osmium tetroxide may require a catalytic amount of the oxidizing agent in the presence of a regenerating agent. Exemplary, regenerating agents may be 4-methylmorpholine-N-oxide and trimethylamine-N-oxide. An especially preferred regenerating agent is 4-methylmorpholine-N-oxide. In a subsequent halogenation reaction, the resulting diol is converted to a haloester using a halogenating agent in the presence of an organic acid. Exemplary halogenating agents include hydrogen bromide and hydrogen chloride. Preferred organic acids may be acetic acid and propionic acid. The resulting haloester is subsequently reacted with a basic ester-hydrolyzing reagent to obtain a desired epoxide product. Preferred ester-hydrolyzing agents include, but are not limited to metal alkoxides and metal hydroxides. Especially preferred metal alkoxides are sodium methoxide, ethoxide, isopropoxide and pentoxide. A preferred metal hydroxide is sodium hydroxide.

A final step in the inventive method is preparation of the desired inventive compound from a terminal moiety-containing epoxide, synthesized in the foregoing procedure. The final step may be accomplished by either of two preferred methods. In a first method, the terminal moiety-containing epoxide is heated in the presence of a substituted or unsubstituted amine having functional groups which are present in the final inventive compound. Preferred amine functional groups are disclosed above.

A second method comprises reacting the unsubstituted or substituted amine with the terminal moiety-containing epoxide and a reaction activator in a solvent. Exemplary reaction activators include lithium perchlorate. Preferred solvents include solvents for reactions previously discussed herein.

Preferred compounds of the invention include, but are not intended to be limited to, both R and S enantiomers and racemic mixtures of the following compounds:

| Compound No. | Compound Name | Chemical Structure |
|---|---|---|
| 1 | N-(9-Octylamino-8-hyroxynonyl)phthalimide | 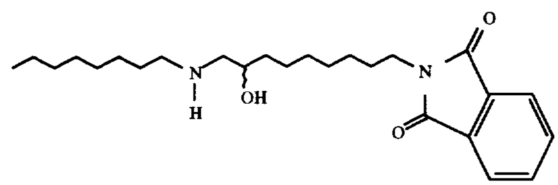 |
| 2 | N-(11-Octylamino-10-hydroxyundecyl)homophthalimide | 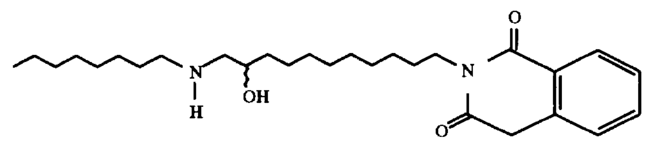 |
| 3 | 1-(5-hydroxy-6-(N-benzyl)aminohexyl)-3-methylbenzoyleneurea | 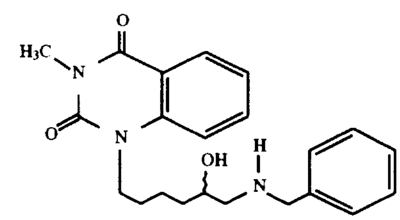 |
| 4 | 3-(11,10-Oxidoundecyl)quinazoline-4(3H)-one | 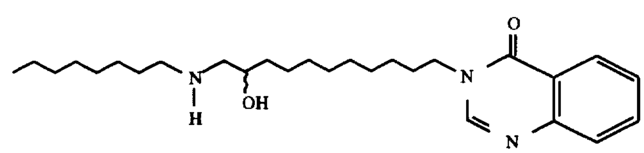 |
| 5 | $N^2$-(5-hydroxy-6-($N^3$-propyl)aminohexyl)-($N^1$-propyl)glutaric acid | 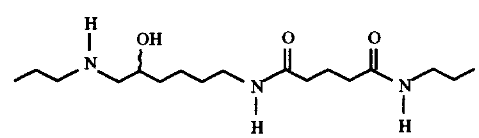 |
| 6 | 2-(11-Octylamino-10-hydroxyundecylcarboxamido)-octylcarboxamidobenzyl | 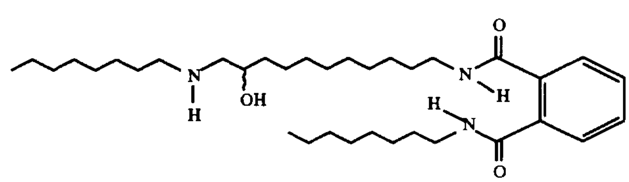 |
| 7 | 1-Octylamino-2,11-undecadiol | 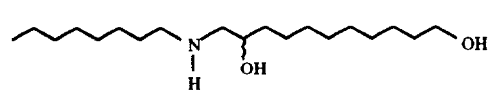 |

-continued

| Compound No. | Compound Name | Chemical Structure |
|---|---|---|
| 8 | 1-(9-Octylamino-8-hydroxynonyl)-3-methylxanthine | 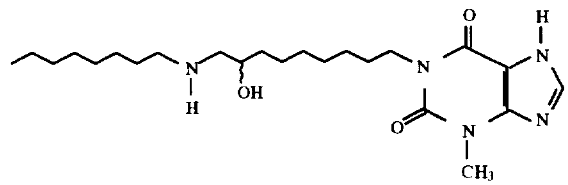 |
| 9 | 1-(9-Tetradecylamino-8-hydroxynonyl)-3-methylxanthine | 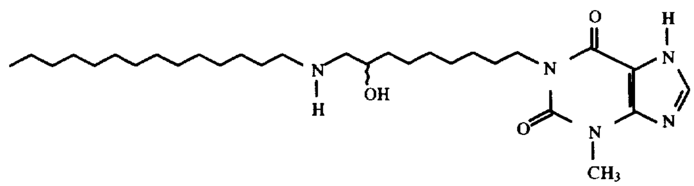 |
| 10 | 1-(11-Octylamino-10-hydroxyundecyl)-3-methylxanthine | 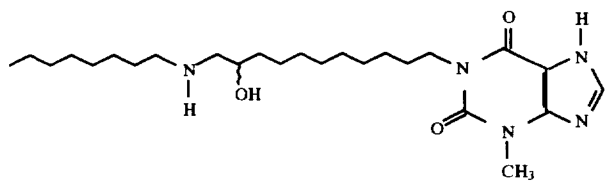 |
| 11 | 7-(11-Octylamino-10-hydroxyundecyl)-1,3-dimethylxanthine | 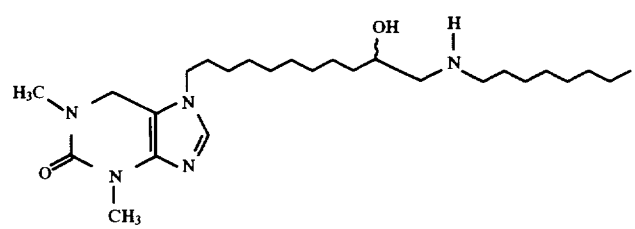 |
| 12 | 1-(11,10-Octylamino-10-hydroxyundecyl)-1-methyl-2,4-dioxotetrahydropteridine | 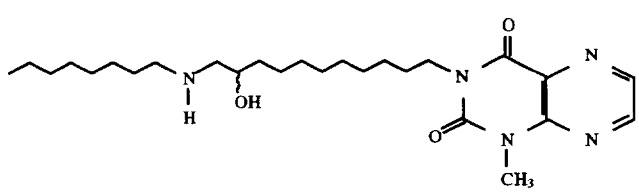 |
| 13 | 1-(5-hydroxy-6-(N-benzyl)aminohexyl)-3,7-dimethylxanthine | 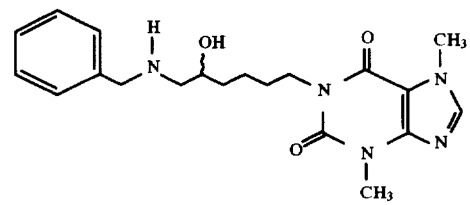 |

-continued

| Compound No. | Compound Name | Chemical Structure |
|---|---|---|
| 14 | 1-(5-hydroxy-6-(N-propyl)aminohexyl)-3,7-dimethylxanthine | 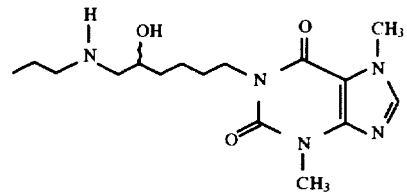 |
| 15 | N-(11-Ocytlamino-10-hydroxyundecyl)glutarimide | 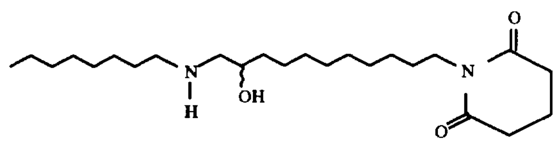 |
| 16 | N-(11-Octylamino-10-hydroxyundecyl)-2-piperidone | 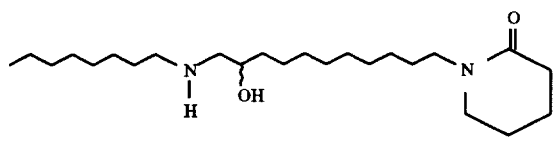 |
| 17 | N-(11-Octylamino-10-hydroxyundecyl)succinimide | 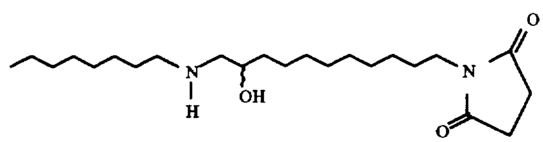 |
| 18 | 2-(11-Octylamino-10-hydroxyundecyl)-1,3-dimethoxybenzene | 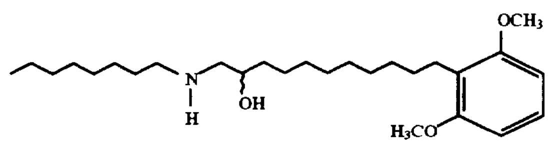 |
| 19 | 3-(5-hydroxy-6-(N-propyl)aminohexyl)-1-methyluracil | 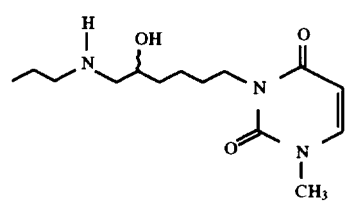 |
| 20 | 3-(9-Octylamino-8-hydroxynonyl)-1-methyluracil | 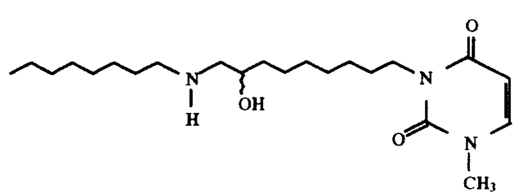 |

-continued

| Compound No. | Compound Name | Chemical Structure |
|---|---|---|
| 21 | 3-(11-Octylamino-10-hydroxyundecyl)-1-methyluracil | 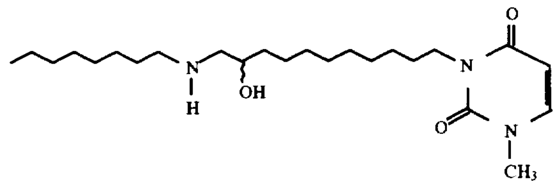 |
| 22 | 3-(11-Octylamino-10-hydroxyundecyl)-1-methyldihydrouracil | 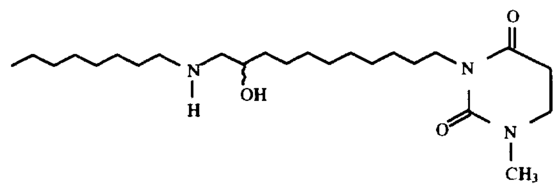 |
| 23 | 3-(9-Octylamino-8-hydroxynonyl)-1-methylthymine | 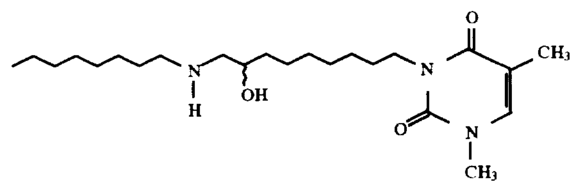 |
| 24 | 3-(5-hydroxy-6-(N-undecyl)aminohexyl)-1-methylthymine | 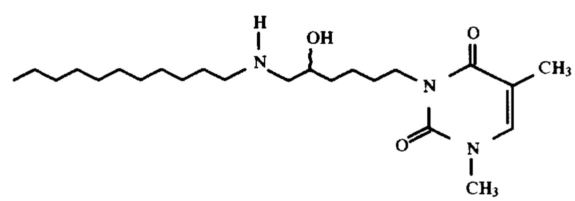 |
| 25 | 3-(11-Octylamino-10-hydroxyundecyl)-1-methylthymine | 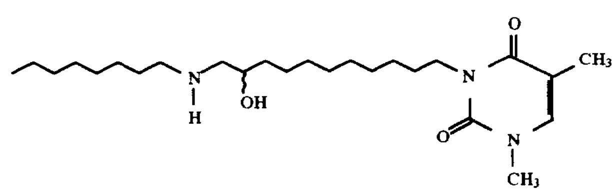 |
| 26 | 3-(6-Propylamino-5-hydroxyhexyl)-1-methylthymine | 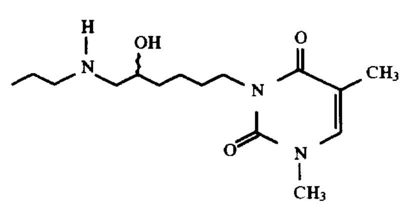 |

-continued

| Compound No. | Compound Name |
|---|---|
| 27 | 1-(8-hydroxy-9-(N-benzyl)aminononyl)-3,7-dimethylxanthine |
| 28 | 1-(5-hydroxy-6-(N-octyl)aminohexyl)-3,7-dimethylxanthine |
| 29 | 1-(5-hydroxy-6-(N-(4-phenyl)butyl)aminohexyl)-3,7-dimethylxanthine |
| 30 | 1-(6-Undecylamino-5-hydroxyhexyl)-3,7-dimethylxanthine |
| 31 | 1-(5-hydroxy-6-(N-cyclohexylmethyl)aminohexyl)-3,7-dimethylxanthine |
| 32 | 1-(5-hydroxy-6-(N-(6-hydroxy)hexyl)aminohexyl)-3,7-dimethylxanthine |

-continued

| Compound No. | Compound Name | Chemical Structure |
|---|---|---|
| 33 | 1-(5-hydroxy-6-(N,N-dihexyl)aminohexyl)-3,7-dimethylxanthine | 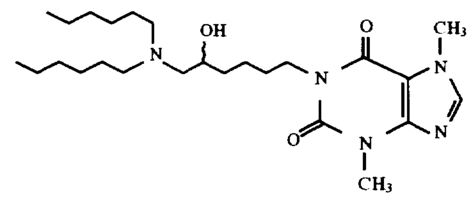 |
| 34 | 1-(5-hydroxy-6-(N-(4-methoxy)benzyl)aminohexyl)-3,7-dimethylxanthine | 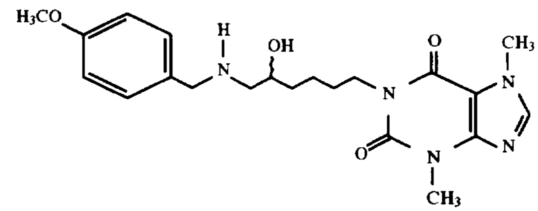 |
| 35 | 1-(8-hydroxy-9-(N-octyl)aminononyl)-3,7-dimethylxanthine | 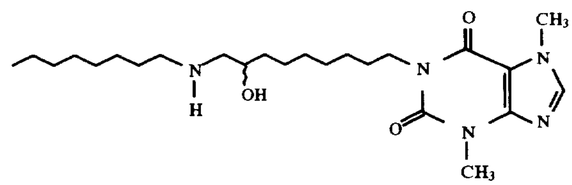 |
| 36 | 1-(5-hydroxy-6-(N-tetradecyl)aminohexyl)-3,7-dimethylxanthine | 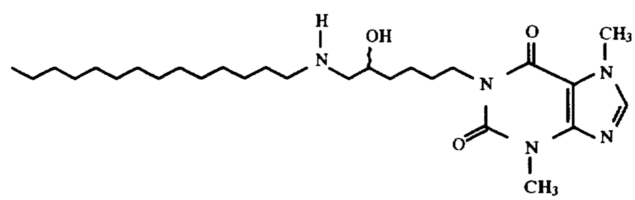 |
| 37 | 1[6-(Cyclopropylmethylamino)-5-hydroxyhexyl)]-3,7-dimethylxanthine | 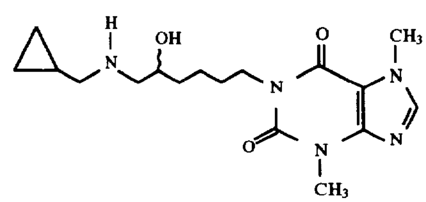 |
| 38 | 1-(6-Decylamino-5-hydroxyhexyl)-3,7-dimethylxanthine | 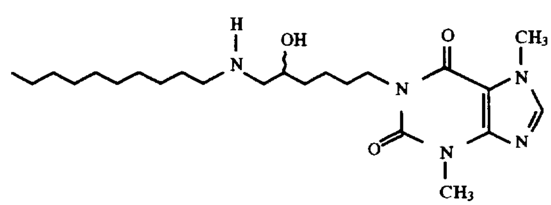 |

-continued

| Compound No. | Compound Name | Chemical Structure |
|---|---|---|
| 39 | 1-(6-Dodecylamino-5-hydroxyhexyl)-3,7-dimethylxanthine | 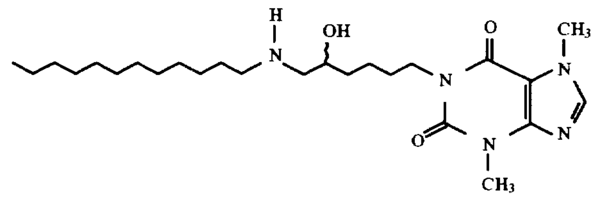 |
| 40 | 1-(11-Benzylamino-10-hydroxyundecyl)-3,7-dimethylxanthine | 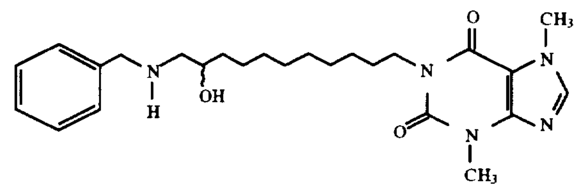 |
| 41 | 1-(9-Decylamino-8-hydroxynonyl)-3,7-dimethylxanthine | 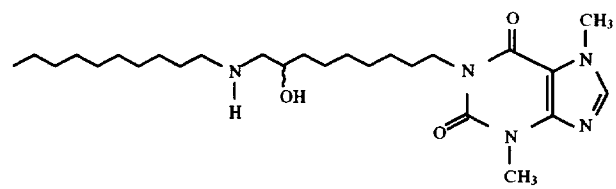 |
| 42 | 1-(9-Dodecylamino-8-hydrononyl)-3,7-dimethylxanthine | 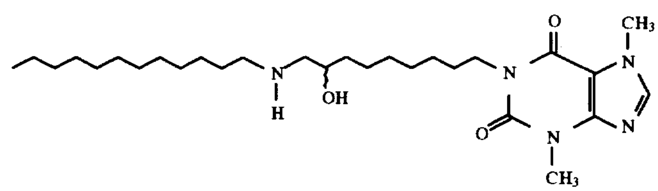 |
| 43 | 1-(9-Tetradecylamino-8-hydroxynonyl)-3,7-dimethylxanthine | 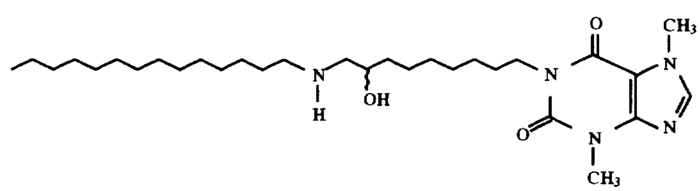 |
| 44 | 1-(11-Hexylamino-10-hydroxyundecyl)-3,7-dimethylxanthine | 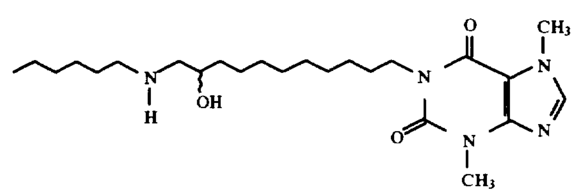 |
| 45 | 1-(11-Octylamino-10-hydroxyundecyl)-3,7-dimethylxanthine | 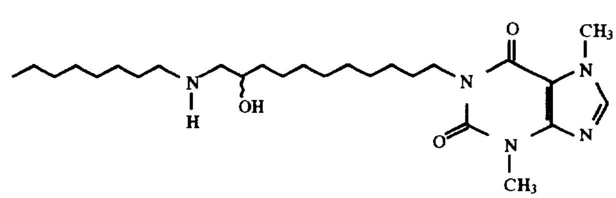 |

-continued

| Compound No. | Compound Name | Chemical Structure |
|---|---|---|
| 46 | 1-(6-Allylamino-5-hydroxyhexyl)-3,7-dimethylxanthine | 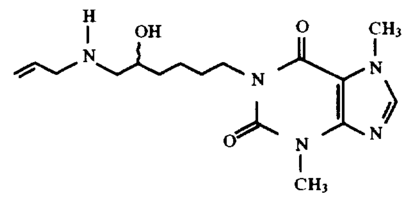 |
| 47 | 1-(11-Allylamino-10-hydroxyundecyl)-3,7-dimethylxanthine | 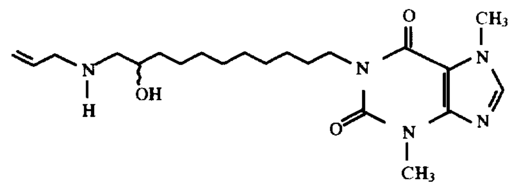 |
| 48 | 1-(6-N-Methyloctadecylamino-5-hydroxyhexyl)-3,7-dimethylxanthine | 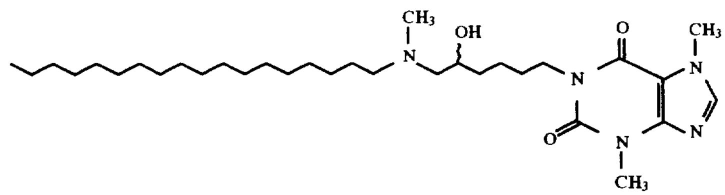 |
| 49 | 1-(11-Decylamino-10-hydroxyundecyl)-3,7-dimethylxanthine | 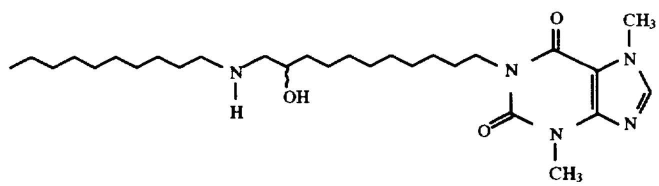 |
| 50 | 1-(11-Dodecylamino-10-hydroxyundecyl)-3,7-dimethylxanthine | 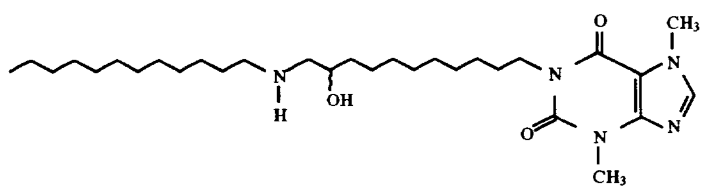 |
| 51 | 1-(11-Tetradecylamino-10-hydroxyundecyl)-3,7-dimethylxanthine | 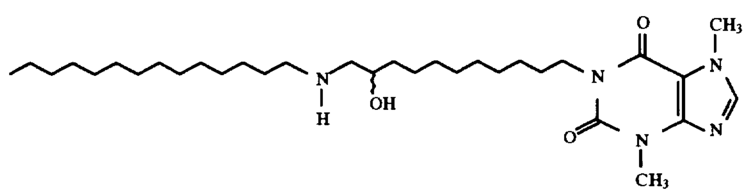 |

-continued

| Compound No. | Compound Name |
|---|---|
| 52 | 1-[11-(4-Fluorobenzylamino)-10-hydroxyundecyl]-3,7-dimethylxanthine |
| 53 | 1-[11-(4-Trifluoromethylbenzylamino)-10-hydroxyundecyl]3,7-dimethylxanthine |
| 54 | 1-[11-(3-Diethylaminopropylamino)-10-hydroxyundecyl]-3,7-dimethylxanthine |
| 55 | N,N'-bis[(10-yl-9-hydroxydecyl)-3,7-dimethylxanthine]diaminododecane |
| 56 | 1-(14-Bromo-13-hydroxytetradecyl)-3,7-dimethylxanthine |
| 57 | 1-[11-(4-Aminobenzylamino)-10-hydroxyundecyl]-3,7-dimethylxanthine |
| 58 | 1-[11-(3,4,5-Trimethoxybenzylamino)-10-hydroxyundecyl]-3,7-dimethylxanthine |

-continued

| Compound No. | Compound Name | Chemical Structure |
|---|---|---|
| 59 | 1-{11-(3-Butoxypropylamino)10-hydroxyundecyl}3,7-dimethylxanthine | 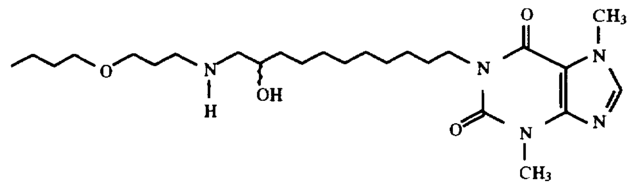 |
| 60 | 1-(14-Octylamino-13-hydroxytetradecyl)-3,7-dimethylxanthine | 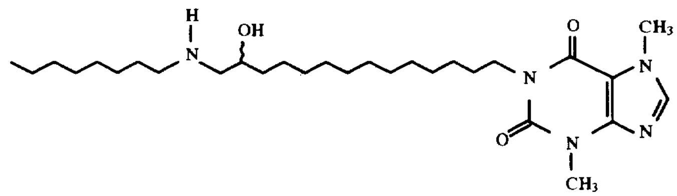 |
| 61 | 1-(11-Propylamino-10-hydroxyundecyl)-3,7-dimethylanthine | 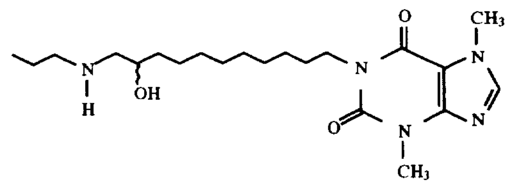 |
| 62 | 1-(11-Undecylamino-10-hydroxyundecyl-3,7-dimethylxanthine | 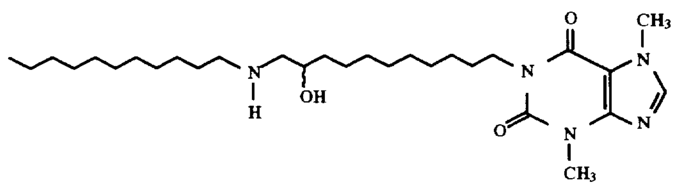 |
| 63 | 1-(11-Phenylamino-10-hydroxyundecyl)-3,7-dimethylxanthine | 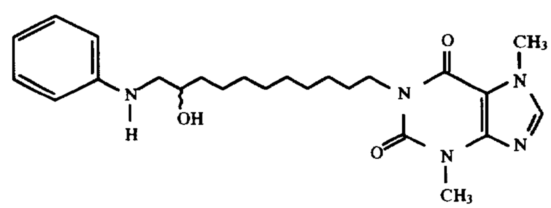 |
| 64 | N,N-bis{11-yl-10-hydroxyundecyl)-3,7-dimethylxanthine}undecylamine | 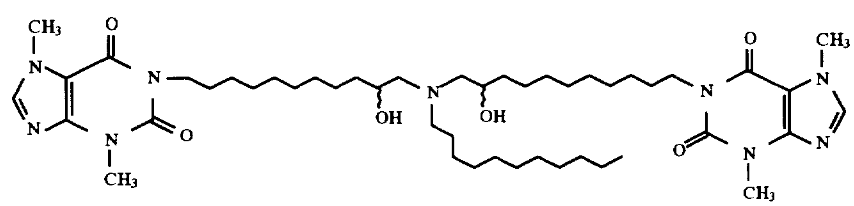 |

| Compound No. | Compound Name |
|---|---|
| 65 | 1-(11-Octadecylamino-10-hydroxyundecyl)-3,7-dimethylxanthine |
| 66 | 1-[9-(N-Methyloctylamino-8-hydroxynonyl)]-3,7-dimethylxanthine |
| 67 | 1-(4-Tetradecylamino-3-hydroxybutyl)-3,7-dimethylxanthine |
| 68 | 1-[9-(2-hydroxydecyl-1-amino)nonyl]-3,7-dimethylxanthine |
| 69 | 1-(6-Octadecylamino-5-hydroxyhexyl)-3,7-dimethylxanthine |
| 70 | 1-[11-(N-Octylacetamido)10-hydroxyundecyl]-3,7-dimethylxanthine |
| 71 | 2-(11-Octylamino-10-hydroxyundecyl)-N-methylbenzamide |

-continued

| Compound No. | Compound Name | Chemical Structure |
|---|---|---|
| 72 | 1-(11-(N-Methyl-N-octylamino)-10-hydroxyundecyl)-3,7-dimethylxanthine | 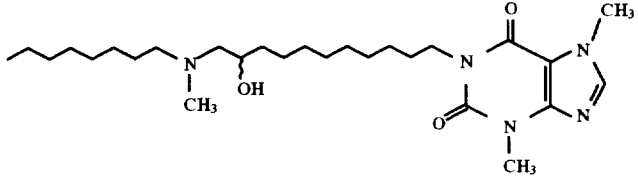 |
| 73 | N-(11-Octylamino-10-hydroxyundecyl)piperidine | 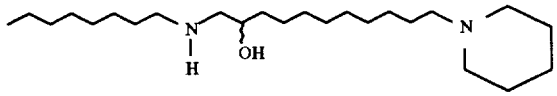 |
| 74 | 2-(11-Octylamino-10-hydroxyundecyl)-1,3-dihydroxybenzene | 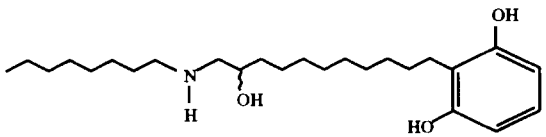 |
| 75 | 1-[11-Amino-10-hydroxyundecyl)-3,7-dimethylxanthine | 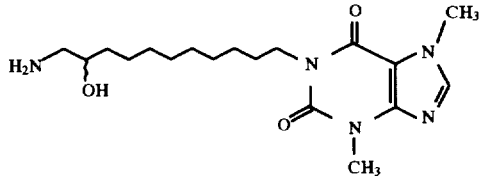 |
| 76 | 1-(11-Hexadecylamino-10-hydroxyundecyl)-3,7-dimethylxanthine | 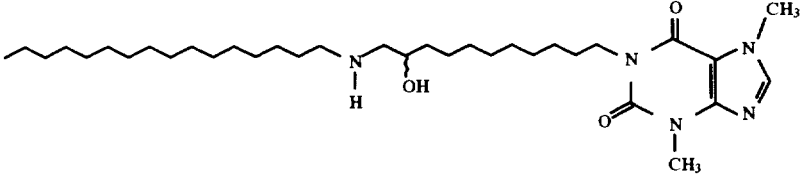 |
| 77 | 1-(11-Tridecylamino-10-hydroxyundecyl)-3,7-dimethylxanthine | 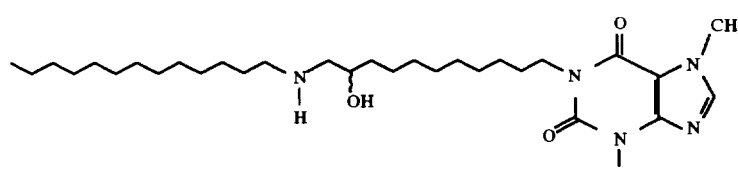 |
| 78 | 1-[11-Dihexylamino-10-hydroxyundecyl)-3,7-dimethylxanthine | 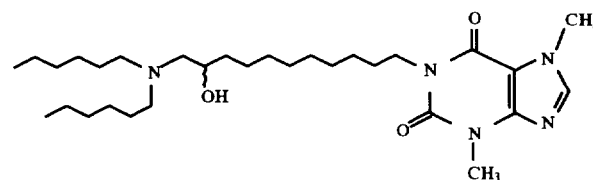 |

-continued

| Compound No. | Compound Name | Chemical Structure |
|---|---|---|
| 79 | 1-(11-Pentadecylamino-10-hydroxyundecyl)-3,7-dimethylxanthine | 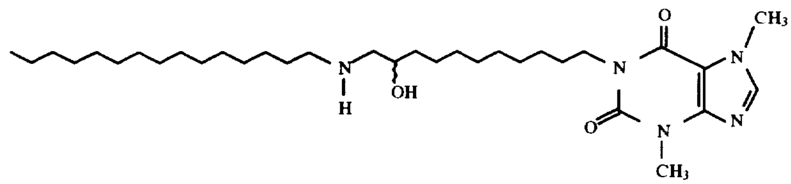 |
| 80 | 1-[11-(N,N-Diethanolamino)undecyl]-3,7-dimethylxanthine | 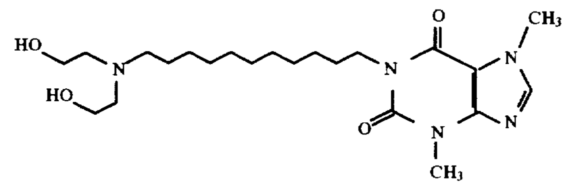 |
| 81 | 1-[11-(2-Piperidinoethylamino)-10-hydroxyundecyl]-3,7-dimethylxanthine | 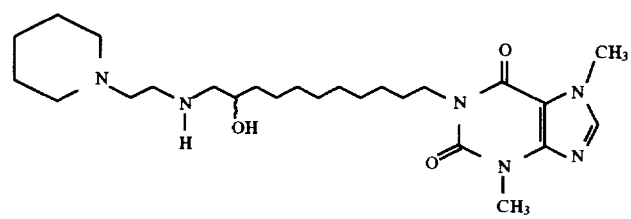 |
| 82 | 1-[11-(4-Methyl-1-yl-piperazino)-10-hydroxyundecyl]-3,7-dimethyxanthine | 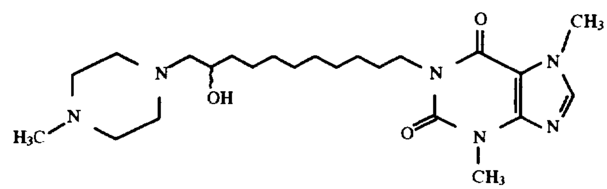 |
| 83 | 1-[11-Hydroxy-10-aminoundecyl]-3,7-dimethylxanthine | 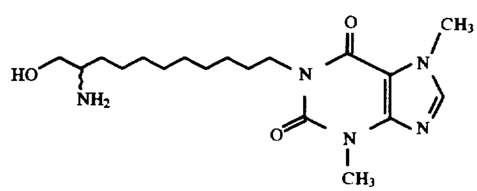 |
| 84 | 1-[11-(4-Chlorobenzyl)-10-hydroxyundecyl]-3,7-dimethylxanthine | 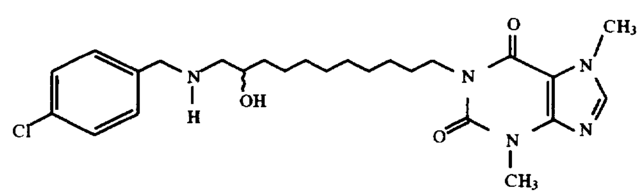 |

-continued

| Compound No. | Compound Name | Chemical Structure |
|---|---|---|
| 85 | 1-[11-(2,4,6-Trimethoxybenzylamino)-10-hydroxyundecyl]-3,7-dimethylxanthine | 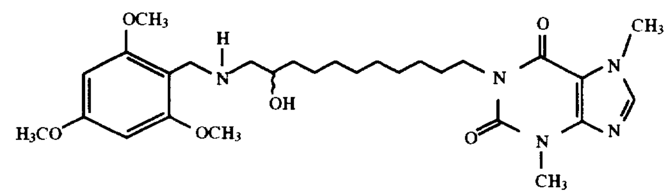 |
| 86 | 1-(11-tert-Butylamino-10-hydroxyundecyl)-3,7-dimethylxanthine | 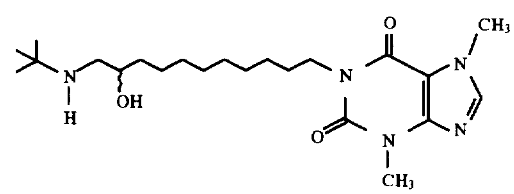 |
| 87 | 6-(11-dodecylamino-10-hydroxyundecoxy)-2-hydroxy-3,7-methylpurine | 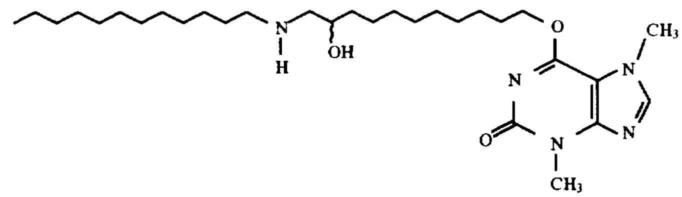 |
| 88 | N,N-bis-[(11-yl-10-hydroxyundecyl)-3,7-dimethylxanthine]dodecylamine | 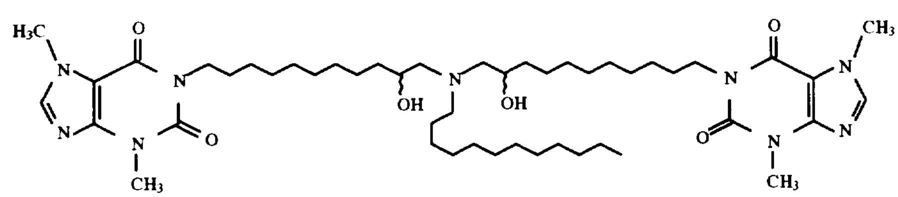 |
| 89 | 1-[11-(3,4,5-Trimethoxyphenylamino)-10-hydroxyundecyl]-3,7-dimethylxanthine | 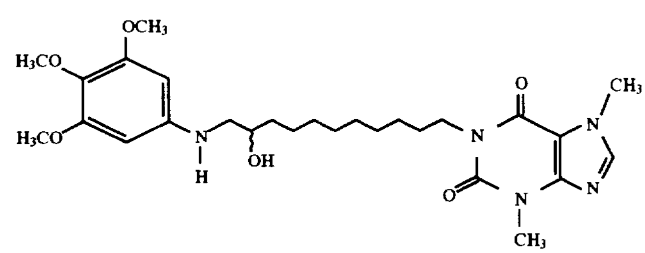 |
| 90 | 1-[11-(N-Methyl-N-dodecylamino)-10-hydroxyundecyl]-3,7-dimethylxanthine | 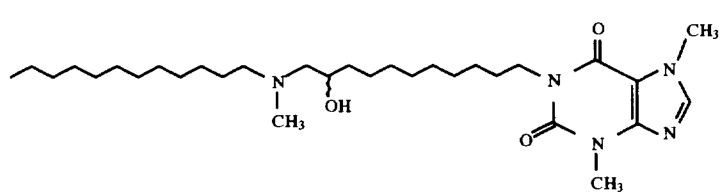 |

| Compound No. | Compound Name |
|---|---|
| 91 | 1-[11-(N-Dodecylacetamido)-10-hydroxyundecyl]-3,7-dimethylxanthine |
| 92 | 1-[11-(N-Tetradecylacetamido)-10-hydroxyundecyl]-3,7-dimethylxanthine |
| 93 | 1-[11-(3,4,5-Trimethoxybenzylacetamido)-10-hydroxyundecyl]-3,7-dimethylxanthine |
| 94 | 1-[11-(N-Dodecylacetamido)-10-acetoxyundecyl]-3,7-dimethylxanthine |
| 95 | 1-[11-(N-Methyl-N-dodecylamino)-10-acetoxyundecyl]-3,7-dimethylxanthine |
| 96 | 1-[11-(Morpholine-4-yl)-10-hydroxyundecyl]-3,7-dimethylxanthine |
| 97 | 1-[11-(Dodecyl benzamido)-10-hydroxyundecyl]-3,7-dimethylxanthine |

| Compound No. | Compound Name |
|---|---|
| 98 | 1-[11-(3,5-Dimethoxybenzylamino)-10-hydroxyundecyl]-3,7-dimethylxanthine |
| 99 | 1-[7-(3-Octyl-2-oxo-5-oxazolidinyl)heptyl]-3,7-dimethylxanthine |
| 100 | 1-[9-(N-Dodecyl-2-oxazolidin-5-yl)nonyl]-3,7-dimethylxanthine |

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier, optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration the dosage is suitably from about 0.001 mg/kg to about 40 mg/kg of the inventive compound or a pharmaceutically acceptable salt thereof, calculated as the free base. The active ingredient may be administered from 1 to 6 times a day, sufficient to exhibit activity.

The inventive compounds may be administered by inhalation (e.g., intranasal or oral). Appropriate dosage forms include an aerosol or a metered dose inhaler, as prepared by conventional techniques. The daily dosage is suitably from about 0.001 mg/kg to about 40 mg/kg of the inventive compound or a pharmaceutically acceptable salt thereof, calculated as the free base. Typical compounds for inhalation are in the form of a solution, suspension or emulsion that may be administered as a dry powder or in the form of an aerosol using a conventional propellant.

The following examples are illustrative of specific, preferred embodiments of the invention; however, these examples are not intended to be construed as limiting the scope of the invention as disclosed herein.

EXAMPLE 1

This example illustrates the synthesis of several compounds that are used as intermediates for the synthesis of other compounds.

1-(8,9-Oxidononyl)-3,7-dimethylxanthine was synthesized as follows: A mixture of theobromine (17.64 g, 98 mmol) and sodium hydride (2.35 g, 98 mmol) in dimethylsulfoxide (250 ml) was stirred for 15 minutes. 9-Bromo-1-nonene (20.0 g, 98 mmol) was added and stirring continued for 3 days. The reaction mixture was poured into water (300 ml) and extracted with dichloromethane (4×200 ml). The combined organic layers were washed with saturated aqueous sodium chloride solution (2×150 ml), dried over sodium sulfate, and the solvents evaporated under vacuum. The residue was crystallized (dichloromethane-ether) to give 1-(8-nonenyl)-3,7-dimethylxanthine (24.34 g, 99% yield) as white crystals.

A solution of 1-(8-nonenyl)-3,7-dimethylxanthine (810 mg, 2.7 mmol), 4-methylmorpholine-N-oxide (340 mg, 2.9 mmol) and 2.5% osmium tetroxide in t-butanol (3 drops) in acetone (20 ml) and water (20 ml) was stirred for 24 hours. Saturated aqueous sodium dithionite solution (5 ml) was added. After stirring for 15 minutes, the reaction was extracted with 25% ethanol-dichloromethane (4×50 ml). The combined organic phases were dried over sodium sulfate and the solvents evaporated under vacuum. The solid residue was recrystallized (ethanol-chloroform) to give 1-(8,9-dihydroxynonyl)-3,7-dimethylxanthine (490 mg, 54% yield).

A mixture of 1-(8,9-dihydroxynonyl)-3,7-dimethylxanthine (428 mg, 1.3 mmol) and 30% hydrogen bromide in acetic acid (0.8 ml, 3.9 mmol) was stirred for 90 minutes. The solution was poured into a mixture of water (10 ml), sodium bicarbonate (1.35 g), and dichloromethane (10 ml). After 10 minutes of vigorous stirring the layers were separated and the aqueous portion was extracted with dichloromethane (3×15 ml). The combined organic phases were dried over sodium sulfate and the solvent was evaporated under vacuum to give 1-(8-acetoxy-9-bromononyl)-3,7-dimethylxanthine (550 mg, 96% yield) as a yellow oil. Without further purification, the oil was dissolved in methanol (5 ml) and then a 1M solution of sodium methoxide in methanol (1.4 ml) was added. After 30 minutes the reaction mixture was poured into water (30 ml) and extracted with dichloromethane (3×40 ml). The combined organic phases were dried over sodium sulfate and the solvents evaporated under vacuum. The solid residue was recrystallized (dichloromethane-petroleum ether) to give 1-(8,9-oxidononyl)-3,7-dimethylxanthine (380 mg, 91% yield).

1-(5,6-Oxidohexyl)-3,7-dimethylxanthine was synthesized as follows: A mixture of 1-bromohexene (10.7 g, 66 mmol), sodium hydride (1.58 g, 66 mmol), and theobromine (11.9 g, 66 mmol) in dimethylsulfoxide (100 ml) was stirred for 43 hours. The solution was treated with water (200 ml) and then extracted with dichloromethane (3×80 ml). The combined extracts were washed with water (3×100 ml), dried over magnesium sulfate, and then the solvent was evaporated under vacuum to give 1-(5-hexenyl)-3,7-dimethylxanthine (17 g, 98% yield) as a white powder.

To 1-(5-hexenyl)-3,7-dimethylxanthine (1.07 g, 4.1 mmol) and 4-methylmorpholine-N-oxide (1.44 g, 12.3 mmol) in water (20 ml) and acetone (10 ml) was added 2.5% solution of osmium tetraoxide in t-butanol (6 drops). After stirring for 48 hours, the mixture was treated with 20% aqueous sodium dithionite solution (20 ml). After 2 minutes, the mixture was extracted with 25% ethanol-dichloromethane (3×30 ml). The combined extracts were dried over magnesium sulfate and the solvents were evaporated under vacuum to give 1-(5,6-dihydroxyhexyl)-3,7-dimethylxanthine (750 mg, 62% yield) as a white powder.

To 1-(5,6-dihydroxyhexyl)-3,7-dimethylxanthine (1.0 g, 3.38 mmol) was added 30% hydrogen bromide-acetic acid (3.4 ml) over 30 seconds and then stirred until all of the solid had dissolved (2.5 hours). The solution was poured carefully over a mixture of sodium bicarbonate (12 g) and ice water (50 ml). After carbon dioxide evolution had subsided, the mixture was extracted with dichloromethane (3×25 ml). The combined extracts were dried over magnesium sulfate and the solvent was evaporated under vacuum to give 1-(5-acetoxy-6-bromohexyl)-3,7-dimethylxanthine (1.3 g, 96% yield) as a viscous oil which was dissolved in methanol (5 mL). A 1M solution of sodium methoxide in methanol (3.9 ml) was added over 30 seconds. After stirring for 20 minutes, the solution was treated with water (20 ml) and then extracted with dichloromethane (3×15 ml). The combined extracts were dried over magnesium sulfate and the solvents were evaporated under vacuum to give 1-(5,6-oxidohexyl)-3,7-dimethylxanthine (900 mg, 100% yield) as white crystals.

3-(5,6-Oxidohexyl)-1-methyluracil was synthesized as follows: A mixture of sodium hydride (86 mg, 3.6 mmol) and 1-methyluracil (500 mg, 4 mmol) in dimethyl sulfoxide (25 ml) was stirred for 15 minutes, and then 6-bromo-1-hexene (647 mg, 4 mmol) was added. After stirring for 20 hours, the reaction mixture was poured into water (50 ml) and extracted with 20% ethanol-dichloromethane (3×50 ml). The combined organic layers were washed with saturated aqueous sodium chloride solution (20 ml) and dried over sodium sulfate. The solvent was evaporated under vacuum to give a residue which was purified by column chromatography (silica, ethyl acetate) to give 3-(5-hexenyl)-1-methyluracil (598 mg, 72% yield).

A solution of 3-(5-hexenyl)-1-methyluracil (598 mg, 2.9 mmol), 4-methylmorpholine-N oxide (408 mg, 3.5 mmol), and a 2.5% solution of osmium tetroxide in t-butanol (3 drops) in acetone (15 ml) and water (5 ml) was stirred for 3 days. Saturated aqueous sodium hydrosulfite solution (10 ml) was added and the mixture was stirred for 15 minutes. Water (50 ml) was added and the mixture was extracted with 20% ethanol-dichloromethane (4×40 ml). The combined organic layers were dried over sodium sulfate and the solvents were evaporated under vacuum to give 3-(5,6-dihydroxyhexyl)-1-methyluracil (461 mg, 66% yield) as a colorless oil.

3-(5,6-Dihydroxyhexyl)-1-methyluracil (350 mg, 1.4 mmol) was stirred with 30% hydrogen bromide in acetic acid (0.87 ml, 4.3 mmol) for 45 minutes. The solution was added to a mixture of sodium bicarbonate (1.6 g), water (10 ml) and dichloromethane (20 ml). After 15 minutes of vigorous stirring, the layers were separated and the aqueous layer was extracted with dichloromethane (3×40 ml). The combined organic layers were dried over sodium sulfate and the solvent was evaporated under vacuum to give 3-(5-acetoxy-6-bromohexyl)-1-methyluracil (500 mg, 100% yield). The bromoacetate thus obtained was used in the next step without further purification. 3-(5-Acetoxy-6-bromohexyl)-1-methyluracil (360 mg, 1.0 mmol) was dissolved in methanol (5 ml) and treated with a solution of 1M sodium methoxide in methanol (1 ml). After stirring for 15 minutes, the solution was poured into water (10 ml) and extracted with dichloromethane (3×30 ml). The combined organic layers were dried over sodium sulfate and the solvents were evaporated to give 3-(5,6-oxidohexyl)-1-methyluracil (150 mg, 67% yield) as a colorless oil.

3-(5,6-Oxidohexyl)-1-methylthymine was synthesized as follows: A mixture of sodium hydride (343 mg, 14 mmol) and 1-methylthymine (2.00 g, 14 mmol) in dimethylsulfoxide (30 ml) was stirred for 15 minutes, and then 6-bromo-1-hexene (2.30 g, 14 mmol) was added. After stirring for 69 hours, the reaction mixture was poured into water (100 ml) and extracted with dichloromethane (4×50 ml). The combined organic layers were washed with saturated aqueous sodium chloride solution (40 ml), dried over sodium sulfate, and then the solvent was evaporated under vacuum to give a residue which was recrystallized (dichloromethane-ethyl ether) to give 3-(5-hexenyl)-1-methylthymine (2.80 g, 88% yield).

A solution of 3-(5-hexenyl)-1-methylthymine (2.00 g, 9 mmol), 4-methylmorpholine-N-oxide (1.17 mg, 10 mmol), and osmium tetroxide (0.15 ml of a 2.5% solution in t-butanol) in acetone (15 ml) and water (10 ml) was stirred for 20 hours. Saturated aqueous sodium hydrosulfite solution (10 ml) was added and after 15 minutes of stirring, the mixture was extracted with 20% ethanol-dichloromethane (4×40 ml). The combined organic layers were dried over sodium sulfate and the solvents were evaporated under vacuum to give a solid residue. The solid was recrystallized (ethanol) to give 3-(5,6-dihydroxyhexyl)-1-methylthymine (2.00 g, 89% yield).

3-(5,6-Dihydroxyhexyl)-1-methylthymine (1.65 g, 6.4 mmol) was stirred with 30% hydrogen bromide in acetic acid (3.8 ml, 19.3 mmol) for 1.5 hours. The mixture was then added to a mixture of sodium bicarbonate (6.7 g), water (40 ml), and dichloromethane (50 ml). After 15 minutes of vigorous stirring, the layers were separated and the aqueous layer was extracted with dichloromethane (2×50 ml). The combined organic layers were dried over sodium sulfate and the solvent was evaporated under vacuum to give 3-(5-acetoxy-6-bromohexyl)-1-methylthymine (2.30 g, 100% yield). The bromoacetate was used in the next step without further purification. 3-(5-Acetoxy-6-bromohexyl)-1-methylthymine (2.30 g, 6.4mmol) was dissolved in methanol (10 ml) and a solution of 1M sodium methoxide in methanol (7 ml) was added. After stirring for 15 minutes, the solution was poured into water (60 ml) and extracted with 20% ethanol-dichloromethane (2×70 ml). The combined organic layers were dried over sodium sulfate and the solvents were evaporated under vacuum to give 3-(5,6-oxidohexyl)-1-methylthymine (1.30 g, 85% yield) as a white solid.

3-(5,6-Oxidohexyl)-1-methylbenzoyleneurea was synthesized as follows: A solution of sodium hydride (0.76 g, 30 mmol) and benzoyleneurea (4.86 g, 30 mmol) in dimethylsulfoxide (100 ml) was stirred for 10 minutes and then methyl iodide (1.87 ml, 30 mmol) was added. After stirring for 14 hours, water (100 ml) was added and the solution was extracted with dichloromethane (3×100 ml). The mixture was filtered and the dichloromethane phase was dried over sodium sulfate. After evaporation of the solvent under vacuum, the residue was recrystallized (dichloromethane) to give 1-methylbenzoyleneurea (1.3 g, 25% yield) as a white solid.

A solution of sodium hydride (0.17 g, 6.8 mmol) and 1-methylbenzoyleneurea (1.07 g, 6.1 mmol) in dimethyl sulfoxide (50 ml) was stirred for 10 minutes and then 1-bromohexene (0.82 ml, 6.8 mmol) was added. After 14 hours, water (50 ml) was added and the solution was extracted with dichloromethane (3×30 ml). The combined organic phases were washed with water (3×50 ml), dried over sodium sulfate, and the solvent was evaporated under vacuum to give 3-(5-hexenyl)-1-methylbenzoyleneurea (1.51 g, 96%) as a white solid.

A solution of 3-(5-hexenyl)-1-methylbenzoyleneurea (1.5 g, 5.8 mmol), 4-methylmorphline-N-oxide (0.87 g, 7.4 mmol), and potassium osmate(IV) dihydrate (0.021 g, 0.1 mmol) in acetone (12.5 ml) and water (4 ml) was stirred. After 18 hours, a 20% aqueous solution hydrosulfite (20 ml) was added and stirred for 30 minutes. The solution was extracted with dichloromethane (3×75 ml). The combined organic phases were dried over sodium sulfate and the solvent was evaporated under vacuum. The residue was purified by flash chromatography (silica, 5% methanol-dichloromethane) to give 3-(5,6-dihydroxyhexyl)-1-methylbenzoyleneurea (1.59 g, 94%) as a white solid.

A mixture of 3-(5,6-dihydroxyhexyl)-1-methylbenzoyleneurea (0.92 g, 3.1 mmol) in 30% hydrogen bromide in acetic acid (0.63 ml, 9.3 mmol) was stirred for 90 minutes. The reaction mixture was poured into a mixture of sodium bicarbonate (0.78 g, 9.3 mmol), water (20 ml), and dichloromethane (20 ml). The phases were separated and the aqueous phase was extracted with dichloromethane (2×20 ml). The combined organic phases were washed with brine (20 ml), dried over sodium sulfate, and the solvent was evaporated under vacuum to give 3-(5-acetoxy-6-bromohexyl)-1-methylbenzoyleneurea (1.2 g, 96%).

To a 1M solution of sodium methoxide in methanol (3.1 ml) was added 1-(5-acetoxy-6-bromohexyl)-3-methylbenzoyleneurea (1.17 g, 2.9 mmol) in methanol (25 ml) over 5 minutes. After stirring for 1 hour, water (50 ml) was added. The solution was extracted with dichloromethane (3×25 ml). The combined organic phases were dried over sodium sulfate and the solvents were evaporated under vacuum to give 3-(5,6-oxidohexyl)-1-methylbenzoyleneurea (0.77 g, 97%) as a white solid.

1-(5,6-Oxidohexyl)glutarimide was synthesized as follows: A mixture of glutarimide (2.00 g, 7.7 mmol) and sodium hydride (425 mg, 17.7 mmol) in dimethyl sulfoxide (40 ml) was stirred for 20 minutes and then 6-bromo-1-hexene (2.90 g, 17.7 mmol) was added. After 20 hours of stirring, the reaction was poured into water (100 ml) and extracted with dichloromethane (4×50 ml). The combined organic layers were washed with water (50 ml) and then with saturated aqueous sodium chloride solution (50 ml). After drying over sodium sulfate the solvent was evaporated under vacuum to give 1-(5-hexenyl)glutarimide (2.92 g, 85% yield).

To a solution of 1-(5-hexenyl)glutarimide (630 mg, 3.2 mmol) in dichloromethane (10 ml) was added sodium bicarbonate (2.20 g, 26 mmol) in water (10 ml) by 50% m-chloroperoxybenzoic acid (2.5 g, 7.2 mmol). After stirring for 17 hours, sodium metabisulfite (1.7 g, 9.0 mmol) was added and stirred for 30 minutes. The mixture was extracted with dichloromethane (3×10 ml) and then the combined organic layers were washed with saturated aqueous sodium bicarbonate solution (10 ml). After drying over sodium sulfate and evaporation of the solvent under vacuum, the residue was purified by column chromatography (silica, 10% ethanol-dichloromethane) to give 1-(5,6-oxidohexyl)glutarimide (180 mg, 27% yield).

EXAMPLE 2

This example illustrates a method for synthesis of 1-(8-hydroxy-9-(N-benzyl)aminononyl)-3,7-dimethylxanthine (compound no. 27). A mixture of 1-(8,9-oxidohexyl)-3,7-dimethylxanthine (500 mg, 1.6 mmol) from Example 1 and benzylamine (2.0 g, 19 mmol) was heated at 150° C. for 4 hours. After cooling to ambient temperature, ether (30 ml) was added. The precipitate was washed with cold ether to give (compound no. 27) (278 mg, 41% yield).

EXAMPLE 3

This example illustrates the synthesis of 1-(5-hydroxy-6-(N-octyl)aminohexyl)-3,7-dimethylxanthine (compound no. 28). A mixture of 1-(5,6-oxidohexyl)-3,7-dimethylxanthine (400 mg, 1.4 mmol) synthesized in example 1, and 1-octylamine (391 mg, 3 mmol) was heated at 135° C. for 4 hours. After cooling to ambient temperature, ether (15 ml) was added. The precipitate was washed several times with hexane to give compound no. 28 (537 mg, 94% yield).

EXAMPLE 4

This example illustrates the synthesis of 1-(5-hydroxy-6-(N-(4-phenyl)butyl)amino)hexyl)-3,7-dimethylxanthine (compound no. 29). A mixture of 1-(5,6-oxidohexyl)-3,7-dimethylxanthine (300 mg, 1.1 mmol) from example 1 and 4-phenyl-1-butylamine (322 mg, 2.2 mmol) was heated at 130° C. for 70 minutes. After cooling to ambient temperature, the residue was dissolved in dichloromethane (2 ml) and added to ether (20 ml). The precipitate was washed several times with hexane to give compound no. 29 (280 mg, 60% yield).

EXAMPLE 5

This example illustrates the synthesis of 1-(5-hydroxy-6-(N-undecyl)aminohexyl)-3,7-dimethylxanthine (compound no. 30). A mixture of 1-(5,6-oxidohexyl)-3,7-dimethylxanthine (300 mg, 1.1 mmol) from example 1 and 1-undecylamine (754 mg, 4.4 mmol) was heated at 100° C. for 4 hours and then at 130° C. for 1 hour. After cooling to ambient temperature, ether (10 ml) was added. The waxy precipitate was washed several times with hexane to give compound no. 30 (403 mg, 82% yield).

EXAMPLE 6

This example illustrates the synthesis of 1-(5-hydroxy-6-(N-cyclohexylmethyl)aminohexyl)-3,7-dimethylxanthine (compound no. 31). A mixture of 1-(5,6-oxidohexyl)-3,7-dimethylxanthine (300 mg, 1.1 mmol) from example 1 and cyclohexanemethylamine (249 mg, 2.2 mmol) was heated at 100° C. for 5 hours and then at 120° C. for 1 hour. After cooling to ambient temperature, ether (7 ml) and hexane (10 ml) were added. The precipitate was washed several times with hexane to give compound no. 31 (294 mg, 68% yield).

EXAMPLE 7

This example illustrates the synthesis of 1-(5-hydroxy-6-(N-(6-hydroxy)hexyl)aminohexyl)-3,7-dimethylxanthine (compound no. 32). A mixture of 1-(5,6-oxidohexyl)-3,7-dimethylxanthine (300 mg, 1.1 mmol) from example 1 and 6-amino-1-hexanol (754 mg, 2.6 mmol) was heated at 120° C. for 2 hours. After cooling to ambient temperature, ether (20 ml) was added. The precipitate was washed several times with hexane to give compound no. 32 (321 mg, 74% yield).

EXAMPLE 8

This example illustrates the synthesis of 1-(5-hydroxy-6-(N,N-dihexyl)aminohexyl)-3,7-dimethylxanthine (compound no. 33). A mixture of 1-(5,6-oxidohexyl) 3,7-dimethylxanthine (300 mg, 1.1 mmol) from example 1 and dihexylamine (556 mg, 3.0 mmol) was heated at 135° C. for 5 hours and then at 170° C. for 2 hours. After cooling to ambient temperature, petroleum ether (20 ml) was added. After cooling in a freezer, the precipitate was washed several times with petroleum ether to give compound no. 33 (263 mg, 52% yield).

EXAMPLE 9

This example illustrates the synthesis of 1-(5-hydroxy-6-(N-(4-methoxy)benzyl)aminohexyl)-3,7-dimethylxanthine (compound no. 34). A mixture of 1-(5,6-oxidohexyl)-3,7-dimethylxanthine (300 mg, 1.1 mmol) from example 1 and 4-methoxybenzylamine (0.7 g, 5 mmol) was heated at 100° C. for 4 hours. After cooling to ambient temperature, ether (10 ml) was added. The precipitate was washed several times with petroleum ether to give compound no. 34 (355 mg, 78% yield).

EXAMPLE 10

This example illustrates the synthesis of 3-(5-hydroxy-6-(N-propyl)aminohexyl)-1-methyuracil (compound no. 19). A mixture of 3-(5,6-oxidohexyl)-1-methyluracil (100 mg, 0.4 mmol) from example 1 and n-propylamine (10 ml) was heated in a sealed pressure bottle at 80°–90° C. for 69 hours. Evaporation of the unreacted n-propylamine gave a yellow oil which was crystallized (ether-dichloromethane) to give compound no. 19 (80 mg, 71%) as a white solid.

EXAMPLE 11

This example illustrates the synthesis of 3-(5-hydroxy-6-(N-benzyl)aminohexyl)-1-methylbenzoyleneurea (compound no.3). A mixture of 3-(5,6-oxidohexyl)-1-methylbenzoyleneurea (0.1 g, 0.4 mmol) from example 1 and benzylamine (0.13 g, 1.2 mmol) was stirred under argon at 115° C. After 3 hours, the unreacted benzylamine was evaporated under vacuum. The residue crystallized on standing to give (compound no. 3) (0.14 g, 93% yield) as a white solid.

EXAMPLE 12

This example illustrates the synthesis of 1-(5-hydroxy-6-(N-propyl)aminohexyl)-3,7-dimethylxanthine (compound no. 14). A solution of 1-(5,6-oxohexyl)-3,7-dimethylxanthine (238 mg, 0.86 mmol) from example 1 in n-propylamine (5 ml) was heated at 100° C. in a sealed pressure bottle for 23 hours. After cooling to 4° C., the bottle was unsealed and unreacted n-propylamine was evaporated under vacuum to give (compound no. 14) (190 mg, 64% yield) as a viscous oil.

EXAMPLE 13

This example illustrates the synthesis of 1-(5-hydroxy-6-(N-benzyl)aminohexyl)-3,7-dimethylxanthine (compound no. 13). A mixture of (5,6-oxidohexyl)-3,7-dimethylxanthine (500 mg, 1.8 mmol) from example I and benzylamine (1.7 g, 15.8 mmol) was heated at 150° C. for 4 hours. After cooling to ambient temperature, ether was added (20 ml). The precipitate was washed with cold ether to give compound no. 13 (470 mg, 70% yield).

EXAMPLE 14

This example illustrates the synthesis of $N^2$-(5-hydroxy-6-($N^3$-propyl)aminohexyl)-($N^1$-propyl)glutaric acid (compound no. 5). A solution of 1-(5,6-oxidohexyl) glutarimide (60 mg, 0.3 mmol) from example 1 in n-propylamine (5 ml) was heated in a sealed pressure bottle at 80°–90° C. for 30 hours. Unreacted n-propylamine was evaporated under vacuum to give a residue which was triturated with ether to give compound no. 5 (100 mg, 100% yield).

EXAMPLE 15

This example illustrates the synthesis of 3-(5-hydroxy-6-(N-undecyl)aminohexyl)-1-methylthymine (compound no. 24). A mixture of 3-(5,6-oxidohexyl)-1-methylthymine from example 1 (250 mg, 1.1 mmol) and 1-undecylamine (0.7 ml) were heated at 110° C. for 4 hours. After cooling to ambient temperature, ether (5 ml) and petroleum ether (10 ml) were added. After cooling to -10° C. for 2 hours, the precipitate was washed several times with petroleum ether to give compound no. 24 (361 mg, 80% yield).

EXAMPLE 16

This example illustrates the synthesis of 3-(6-propylamino-5-hydroxyhexyl)-1-methylthymine (compound no. 26). A solution of 3-(5,6-oxidohexyl)-1-methylthymine (200 mg, 0.8 mmol) from example 1 in n-propylamine (10 ml) was heated in a sealed pressure bottle at 100°–105° C. for 24 hours. After evaporation of unreacted n-propylamine, the residue was crystallized (ether) to give compound no. 26 (162 mg, 68% yield).

EXAMPLE 17

This example illustrates the synthesis of 1-(8-hydroxy-9-(N-octyl)aminononyl)-3,7-dimethylxanthine (compound no. 35). A mixture of 1-(8,9-oxidohexyl)-3,7-dimethylxanthine (300 mg, 0.9 mmol) from example 1 and octylamine (1 ml) were heated at 110° C. for 3 hours. After cooling to room temperature, ether (10 ml) was added. The precipitate was washed several times with petroleum ether to give compound no. 35 (342 mg, 85% yield).

EXAMPLE 18

This example illustrates the synthesis of 1-(5-hydroxy-6-(N-tetradecyl)aminohexyl)-3,7-dimethylxanthine (compound no. 36). A mixture of 1-(5,6-oxohexyl)-3,7-dimethylxanthine (300 mg, 1.1 mmol) from example 1 and 1-tetradecylamine (604 mg, 2.8 mmol) was heated at 110° C. for 3 hours. After cooling to ambient temperature, ether (6 ml) was added. The precipitate was washed several times with petroleum ether to give compound no. 36 (356 mg, 66% yield).

EXAMPLE 19

This example illustrates a method of synthesis for 1-(9-tetradecylamino-8-hydroxynonyl)-3,7-dimethylxanthine (compound no. 43). A mixture of 1-(8,9-oxidononyl)-3,7-dimethylxanthine (synthesized in example 1 above, 1.00 g, 3.1 mmol) and anhydrous lithium perchlorate (329 mg, 3.1 mmol) was stirred in anhydrous acetonitrile (30 ml). After addition of 1-tetradecylamine (Aldrich, 722 mg, 3.4 mmol), the mixture was stirred at 60° C. for 4 hours. After cooling, water (50 ml) was added and the mixture was extracted with dichloromethane (3×50 ml). The combined organic layers were washed with water (30 ml) and saturated aqueous salt solution (30 ml) and subsequently dried over sodium sulfate. The solvent was removed under vacuum to give a white residue. Chromatography (neutral activity II alumina, dichloromethan/5%methanol) of the white residue resulted in 860 mg of compound no. 43 (52% yield).

EXAMPLE 20

This example illustrates a method of synthesis for compound no. 63. Sodium hydride (95%) (1.26 g, 50 mmol) was added to a solution of theobromine (7.2 g, 40 mmol) in dimethylsulfoxide (300 ml). After 20 minutes of stirring, undecenylmesylate (7.95 g, 30 mmol) was added and stirred for 12 hours at room temperature. The reaction, warmed to 70°–80° C., was stirred for 4 hours. The reaction mixture was poured into a separatory funnel containing 1 L of water and extracted with dichloromethane (5×200 ml). The organic extracts were combined, washed with water (100 ml) and brine (100 ml), dried over anhydrous magnesium sulfate and concentrated under reduced pressure. A crude product obtained was further purified by flash chromatography over silica gel using an eluant of 20% hexane/dichloromethane to obtain 4.6 g of 1-10-undecenyl)-3,7-dimethylxanthine (yield, 46.3%).

A solution of 1-(10-undecenyl)-3,7-dimethylxanthine, prepared above (4.3 g, 13 mmol), 4-methylmorpholine-N-oxide (1.942 g, 16.6 mmol) and potassium osmate dihydrate (9.5 mg; 0.026 mmol) in acetone (45 ml) and water (10 ml) was stirred for 6 hours. A solution of 20% aqueous sodium sulphite (12 ml) was added and stirred for 30 minutes. The reaction mixture was extracted with 25% ethanol/dichloromethane (4×100 ml). The combined organic extracts were dried over anhydrous magnesium sulfate, concentrated under reduced pressure and purified by flash chromatography over silica gel using a methanol/5% dichloromethane eluent to obtain 3.6 g of 1-(10,11-dihydroxyundecanyl)-3,7-dimethylxanthine (yield, 76%).

1-(10,11-dihydroxyundecanyl)-3,7-dimethylxanthine, prepared above (3.6 g, 10 mmol), was stirred with hydrogen bromide (6.2 ml, 8.4 g of a 30% solution in acetic acid, 31.1 mmol) for 90 minutes. The mixture was then added to a flask containing 100 ml aqueous sodium bicarbonate solution and 75 ml dichloromethane. After 10 minutes of vigorous stirring, the layers were separated and an aqueous portion washed with dichloromethane (3×75 ml). The organic portions were combined, dried over magnesium sulfate, and evaporated to give 1-(10-acetoxy-11-bromoundecanyl)-3,7-dimethylxanthine (3.6 g). Without further purification, the bromoacetate was taken up in methanol (25 ml) and treated with a solution of sodium methoxide (prepared from 0.28 g, 12.2 mmol sodium, and 25 ml methanol). After 30 minutes, most of the solvent was removed under reduced pressure and the residue was extracted with dichloromethane (3×75 ml). The organic portions were combined, dried over magnesium sulfate and concentrated under reduced pressure to give an off-white solid, purified by column chromatography over silica gel using dichloromethane/3% methanol eluant to obtain 2.0 g of 1-(10,11-oxidoundecanyl)-3,7-dimethylxanthine (yield, 57.5%).

A mixture of 1-(10,11-oxidoundecyl)-3,7-dimethylxanthine, prepared above (500 mg, 1.4 mmol), and lithium perchlorate (from Aldrich, 149 mg, 1.4 mmol) was stirred in anhydrous acetonitrile (from Aldrich, 20 ml) until homogeneous. Aniline (from Aldrich, 670 mg, 7.2 mmol) was added, and the mixture stirred at ambient temperature for 16 hours, then at a reflux temperature for 3 hours. The residue was directly deposited on a silica column. Chromatography using a dichloromethane/10% methanol gradient produced 0.45 g of compound no. 63 (73% yield).

EXAMPLE 21

This example illustrates data of proliferative activity of various compounds for inducing CMV promoter activity. The CMV promoter assay measures gene transcription and translation activity wherein any active compounds will have cytotoxic activity for inhibiting cellular protein synthesis in transformed (adenovirus) cells. Each compound was tested and the data is listed in Table I below. Compound no. 30 was the most cytotoxic compound tested.

TABLE I

| Compound | $IC_{50}$ (μM) |
| --- | --- |
| 13 | >500 |
| 28 | 50 |
| 29 | >100 |
| 30 | 15 |
| 31 | >100 |
| 32 | >100 |
| 33 | 100 |
| 5 | >500 |
| 19 | >500 |
| 26 | >500 |

EXAMPLE 22

This example shows the effects of five compounds on inhibition of mast cell degranulation by a serotonin release assay. This assay provides an in vitro model for an allergy and asthma therapeutic product. Table II below shows the results of five compounds (see above

TABLE II

| Compound | % Inhibition | Concentration (μM) |
| --- | --- | --- |
| 13 | 28% | 100 |
| 27 | 29% | 50 |
| 30 | too toxic | 50 |
| 35 | too toxic | 50 |
| 19 | inactive | 50 |

EXAMPLE 23

Figure 1B:
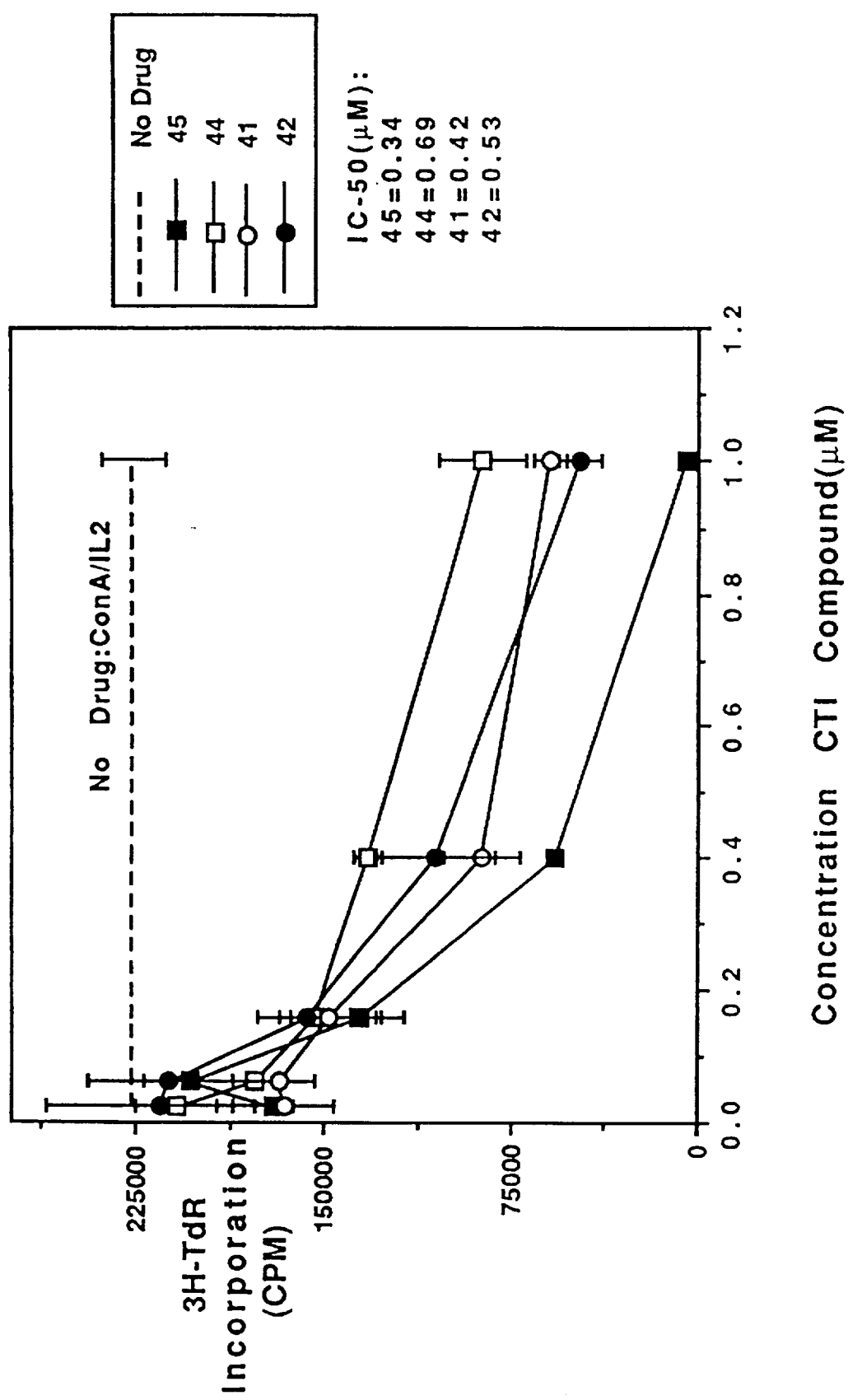

This example illustrates dose response curves used to generate 50% inhibition concentration ($IC_{50}$) of for both cyclosporin A (CsA, FIG. 1A) and various compounds (FIG. 1B) for murine thymocyte proliferation, co-stimulated by Concanavalin A (ConA) and interleukin-2 (IL-2). Con A, used to activate CD3, induces T-cell proliferation and differentiation. Thymuses, obtained from normal, female Balb/C mice, were dissociated and plated into 96-well plates at a density of $2 \times 10^5$ cells/well. ConA (0.25 mg/ml) and IL-2 (15 U/ml) were added to the wells. The cells were incubated for 4 days at 37° C. On day 4, the cells were pulsed with tritiated thymidine and incubated for an additional 4 hours. The amount of tritiated thymidine dye incorporated by the harvested cells was determined in a liquid scintillation counter. Drug doses (shown in FIGS. 1A and 1B) were added two hours prior to ConA and IL-2 activation. Background counts were less than 200 cpm. Both CsA and the compounds tested inhibit thymocyte proliferation and activation.

EXAMPLE 24

Figure 2A:
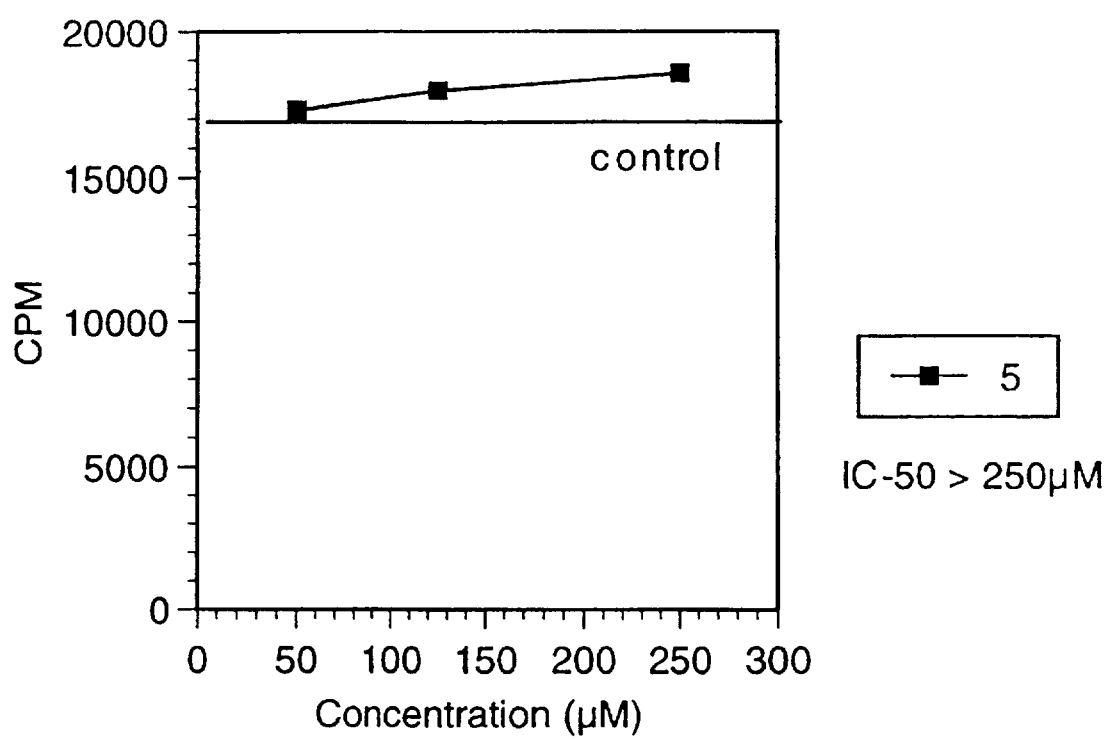
FIGS. 2A and 2B illustrate immune modulating activity of compounds nos. 5 and 26 (see corresponding names and structures below) in an assay determining proliferative PMBC response to allogeneic stimulation using a two-way mixed lymphocyte reaction.
Figure 2B:
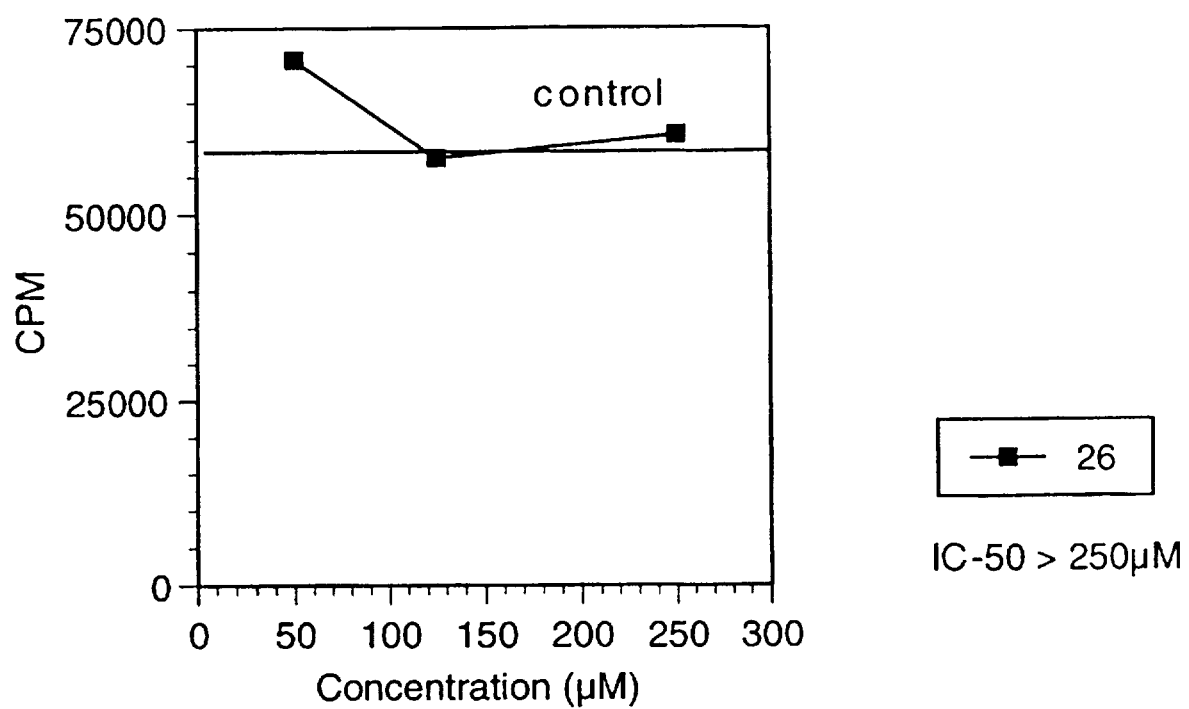
Figure 2C:
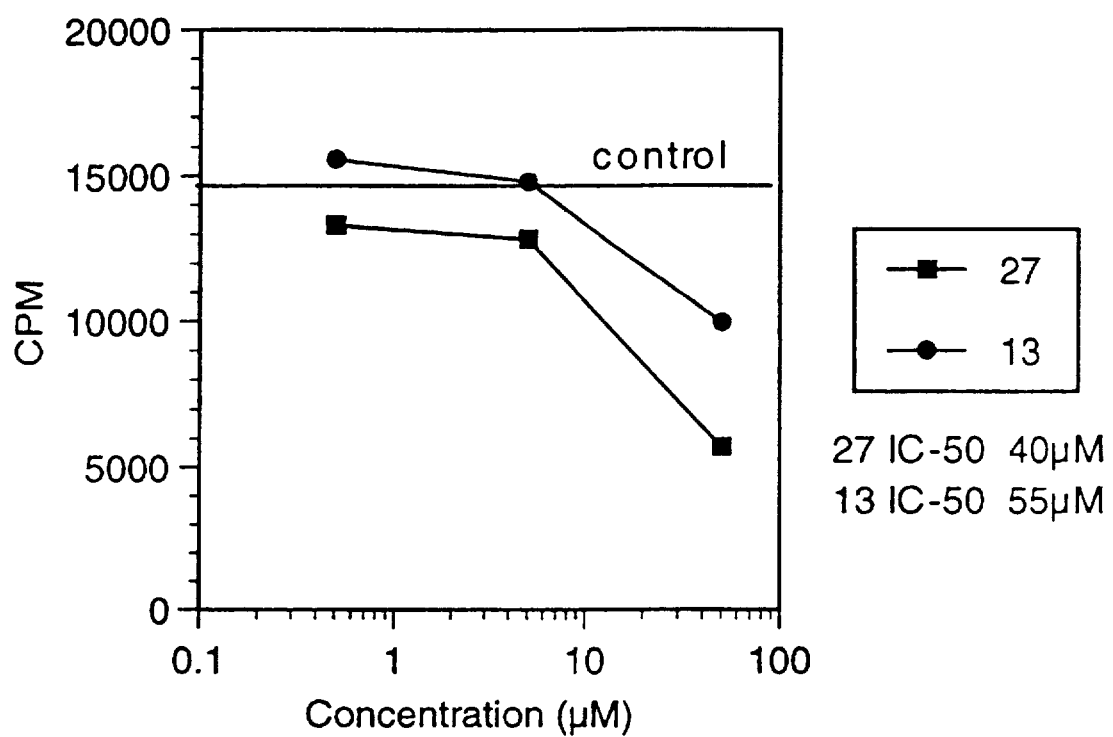
FIG. 2C and 2D report activity data for compounds nos. 27 and 13 and $IC_{50}$ data, respectively in a mixed lymphocyte reaction.

This example illustrates therapeutic potential for various autoimmune and inflammatory diseases of the compounds by comparing potency (inhibitive activity) with cytotoxicity data obtained using the following indicative assay procedures. In a mixed lymphocyte reaction assay of compounds nos. 5, 13, 26 and 27, a two-way mixed lymphocyte reaction shows a proliferative PMBC response to allogeneic stimulation. Compounds nos. 5 and 26 exhibit the least assay activity in this specific, immune-modulating activity assay, having $IC_{50}$ values exceeding 250 μM, as shown in FIGS. 2A and 2B. Both compounds nos. 27 and 13 exhibit dose-response activity in this assay, having $IC_{50}$'s of 40 and 55 μM, respectively, illustrated in FIG. 2C.

Figure 2D:
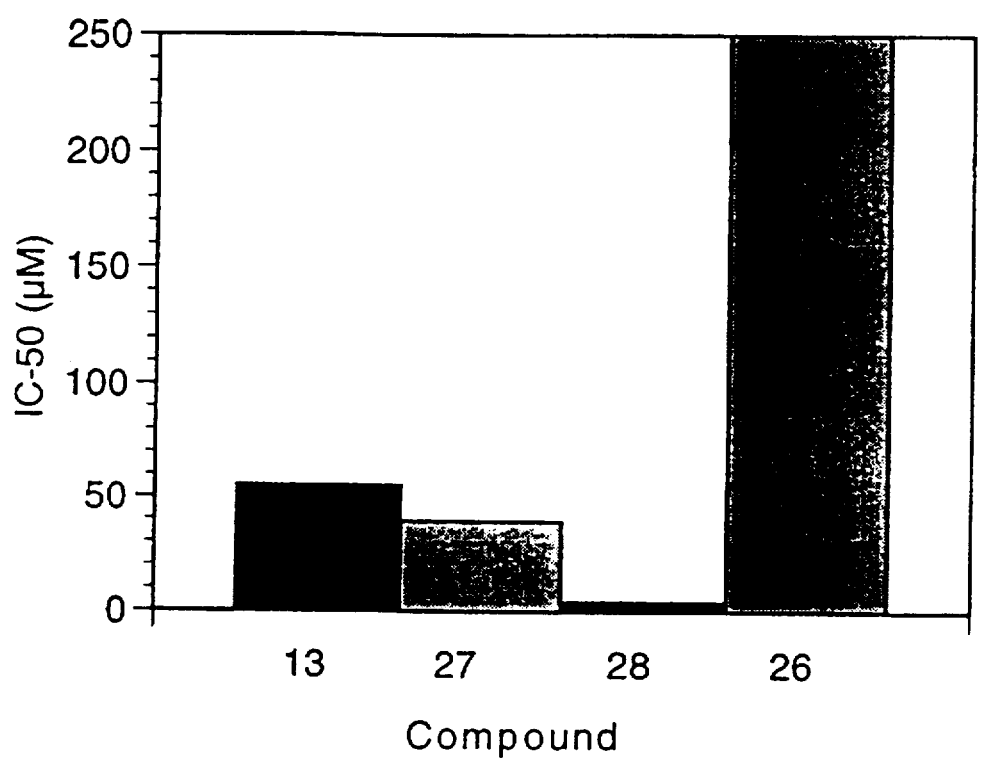

FIG. 2D shows a bar graph of $IC_{50}$ values for five compounds (see above for corresponding chemical names) in a mixed lymphocyte assay measuring immune suppression activity of the compounds. Compound no. 27 did not exhibit significant suppressive activity. Compound no. 28 proved the most potent compound of those assayed.

Figure 2E:
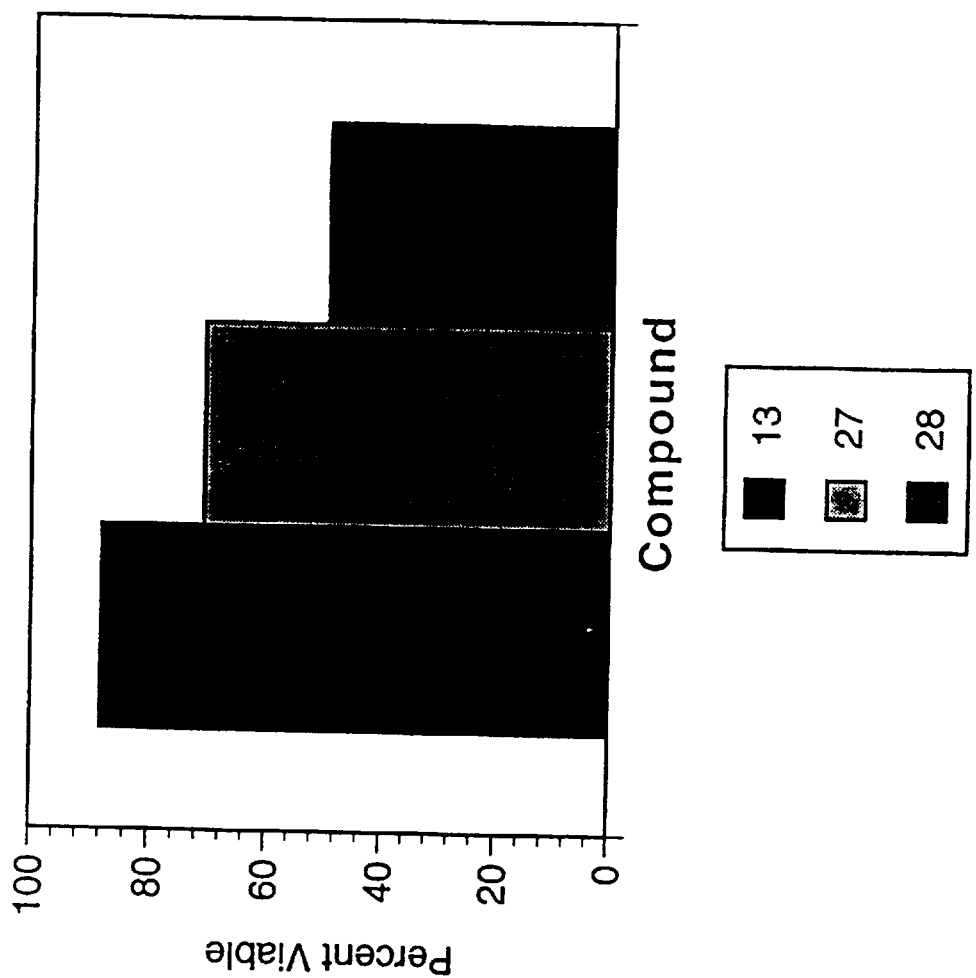
FIG. 2E shows percent viability for five compounds (corresponding chemical names below) in a mixed lymphocyte assay measuring immune suppression activity of the compounds tested.

Cell percent viability in mixed lymphocyte reaction assay culture was determined after six days of cell culture. FIG. 2E shows percent viability bar graph results. Control cells unexposed to drugs are generally 78 to 85% viable under these culture conditions. In this assay, all compounds were present at 100 μM concentrations, generally well above corresponding $IC_{50}$ values in this assay (see FIG. 2D). The most potent compound, compound no. 28, was also the most cytotoxic at 100 μM, but this concentration is well above its $IC_{50}$ value, suggesting a significant therapeutic window. Compounds nos. 13 and 27 exhibited little or no cytotoxicity at concentrations well above their respective $IC_{50}$ values.

Ten additional representative compounds were assayed, showing impressive biological activity results, in a procedure according to that used in Example 21. $IC_{50}$ values for tested compounds were obtained in the thymocyte ConA/IL-2, co-stimulation assay, as described above. Fifty percent (50%) lethal dose concentrations ($LD_{50}$) for these ten compounds were obtained using the following cytotoxicity assay.

Figure 2F:
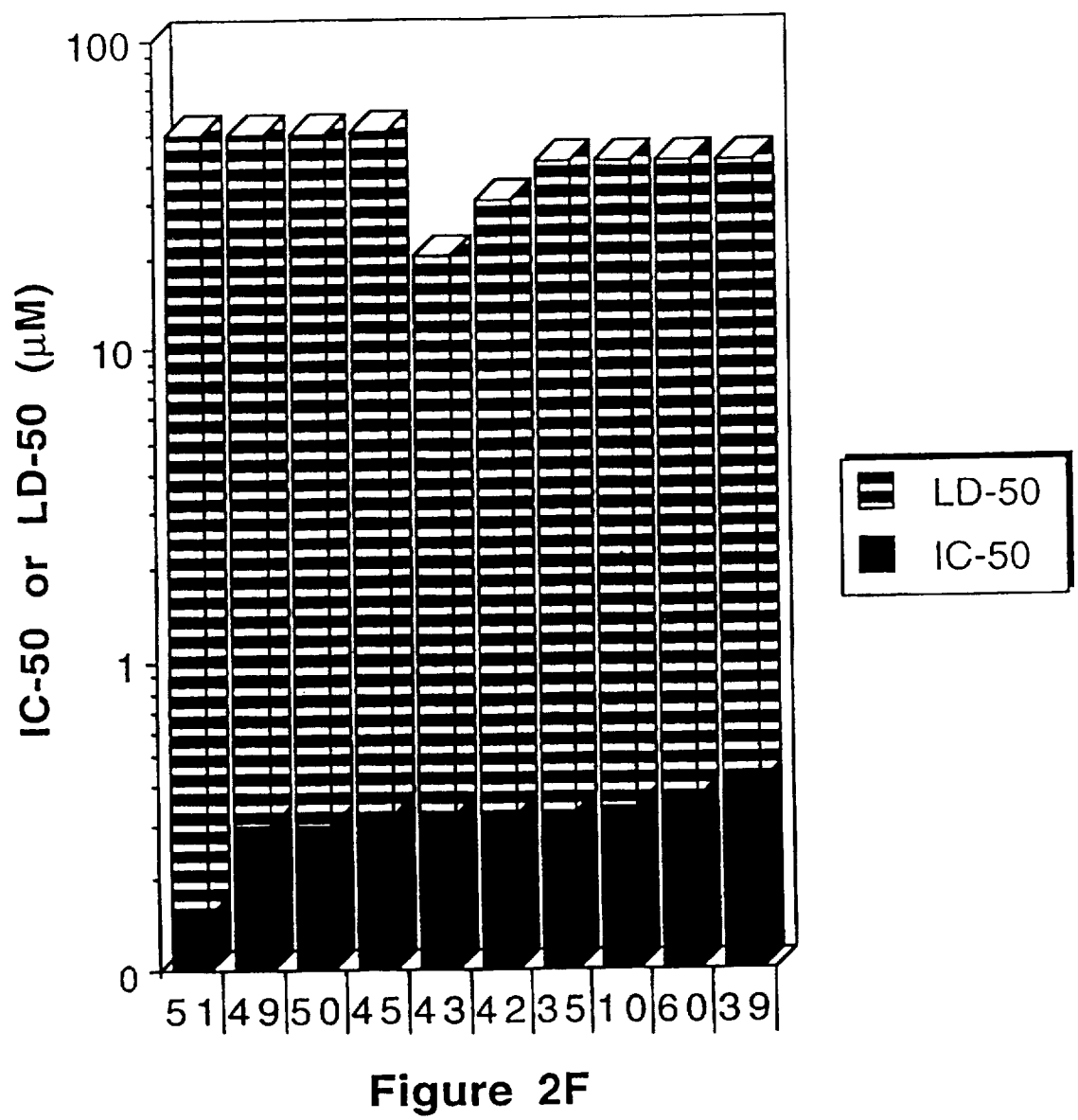
FIG. 2F shows percent viability results from a mixed lymphocyte reaction assay.

Human bone marrow-derived stromal cells (early passage) were plated at $10^4$ cells/well and allowed to reach confluency following 3 days of refeeding. The stromal cells were treated with compounds for 2 hours prior to washing, and using a viability dye, BCECF, analyzing fluorescence. The highest concentration used was 50 μM (hence, an $LD_{50}$ value greater than 50 μM would indicate no effect at 50 μM). FIG. 2F illustrates results obtained from both the thymocyte co-stimulation assay ($IC_{50}$ values) and the cytotoxicity assay ($ID_{50}$) for compounds nos.: 10, 35, 39, 42, 43, 45, 49, 50, 51 and 60. As shown, most of the compounds are non-cytotoxic to stromal cells, yet are very potent proliferation inhibitors in the thymocyte IL-2 co-stimulation assay.

EXAMPLE 25

This example illustrates the effects of several compounds exhibiting inhibitive effects on murine thymocyte proliferation. The data presented and discussed suggests that the compounds function by mechanisms previously unknown.

In a first part of this example, compounds nos. 30, 33, 28 and 27 (see above for chemical names and structures) show effective inhibition of murine thymocyte proliferation stimulated by Con A and interleukin 1 alpha (IL-1α). Compounds nos. 30, 33, 28 and 27 were added to cell cultures two hours prior to activation with Con A and IL-1α in a thymocyte co-stimulation procedure akin to that discussed in example 21. All compounds tested in the assay exhibited dose-response inhibitive properties and dose-response curves for each compound were obtained. $IC_{50}$ values determined for each compound tested are as follow: compound no. 30 has an $IC_{50}$ of 0.94 µM, compound no. 33 has an $IC_{50}$ of 8.6 µM, compound no. 28 has an $IC_{50}$ of 4.6 µM, and compound no. 27 has an $IC_{50}$ of less than 12.5 µM. Background counts in the assay were less than 200 cpm.

Figure 3A:
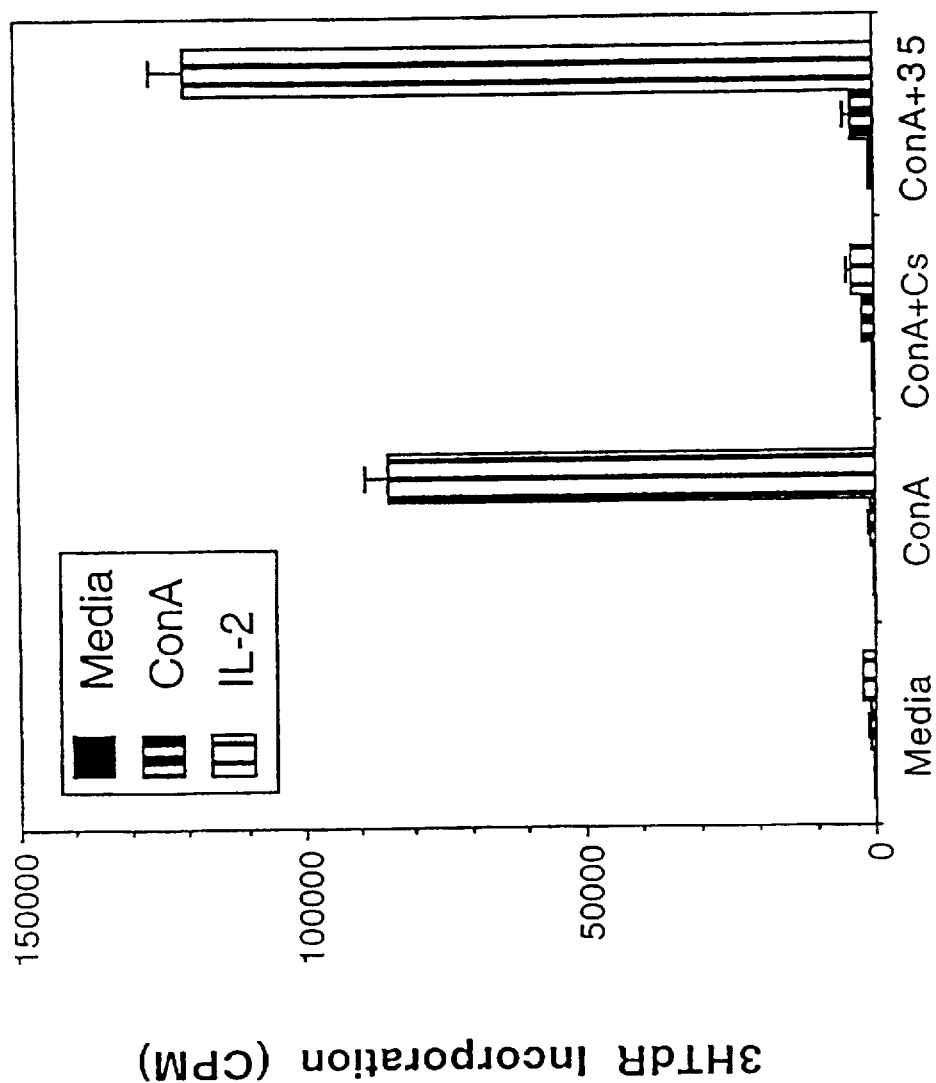
FIG. 3A reports results obtained for several compounds exhibiting inhibitive effects on murine thymocyte proliferation.

In supplemental investigations, results obtained illustrate that the compounds utilize different immunosuppressive mechanisms than known mechanisms of two widely-studied immunosuppressants, CsA and or FK506. In a proliferation assay, mouse thymocytes were pre-incubated overnight with Con A (a "priming step"), washed, and re-stimulated with IL-2 in the absence of compounds. On day 4, the-cells were pulsed with tritiated thymidine and allowed to incubate for an additional 4 hours. The cells were harvested and the amount of tritiated thymidine incorporated by the harvested cells was determined in a liquid scintillation counter. FIG. 3A reports results obtained. In control cells, pre-incubation with Con A "primes" thymocytes by stimulating the CD3 receptor in a manner similar to antigen recognition. Research has shown that CD3 antibody can be substituted for Con A. When IL-2 was subsequently added, the thymoctye cells proliferated. CsA added during Con A incubation, "priming," inhibited thymocyte proliferation in response to IL-2 stimulation. However, when thymocytes were pre-incubated with ConA and compound no. 35, "priming" occurred, shown by subsequently-observed, normal thymocyte proliferation in response to IL-2 stimulation, as shown in FIG. 3. The compounds do not inhibit proliferation by interfering with this "priming step," necessary for subsequent proliferation in response to IL-2 stimulation.

Figure 3B:
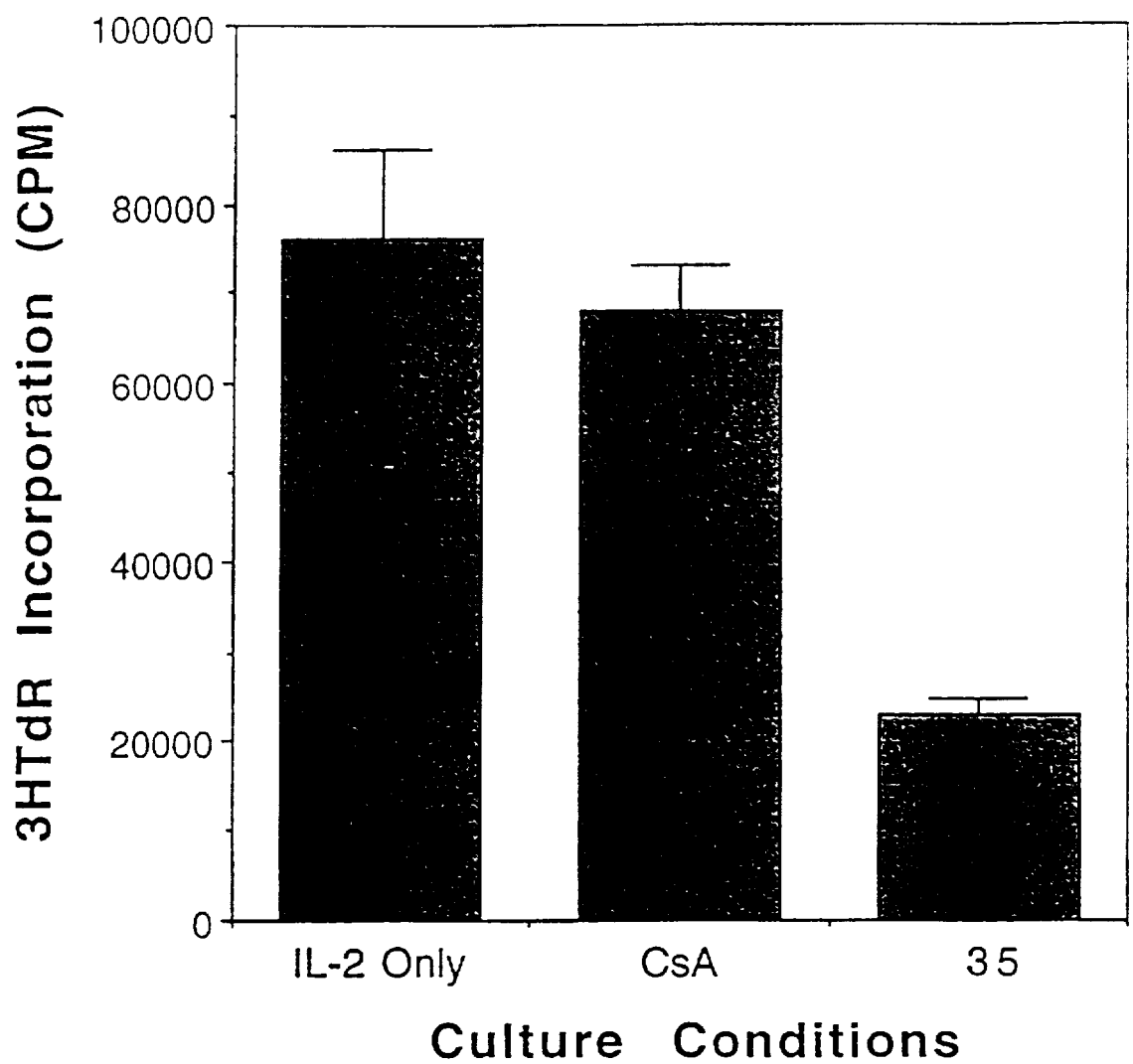
FIG. 3B shows comparative results from inhibition assays for co-stimulated thymocyte proliferation.

Additionally, the cells were pre-incubated with Con A overnight, washed and stimulated with IL-2 (with or without addition of CsA or compound). On day 4, the cells were pulsed with tritiated thymidine and allowed to incubate for an additional 4 hours. The cells were harvested and the amount of incorporated tritiated thymidine was determined in a liquid scintillation counter. Cells pre-treated with Con A proliferated in response to IL-2 addition. FIG. 3B shows results obtained in these assays. CsA (50 µM) exhibited very little inhibition of thymocyte proliferation (indicated by the amount of incorporated dye recorded). In sharp contrast however, compound no. 35 (at far less concentration, 1 µM) dramatically inhibited thymocyte proliferation.

These experiments conclusively indicate that CsA and FK506 (inhibiting CD3 in like manner) have a different action mechanism, as compared with the compounds. CsA inhibits ConA "priming." The compounds do not. The compounds inhibit IL-2 stimulation. CsA does not. The results shown indicate that the compounds would be useful for reducing or preventing side effects from conditions requiring cellular stimulants.

EXAMPLE 26

This example illustrates inhibitive effects of compounds nos. 27 and 28 on murine splenocyte proliferation stimulated by anti-mu (10 mg/ml) and interleukin-4 (IL-4, 12.5 ng/ml).

Figure 4:
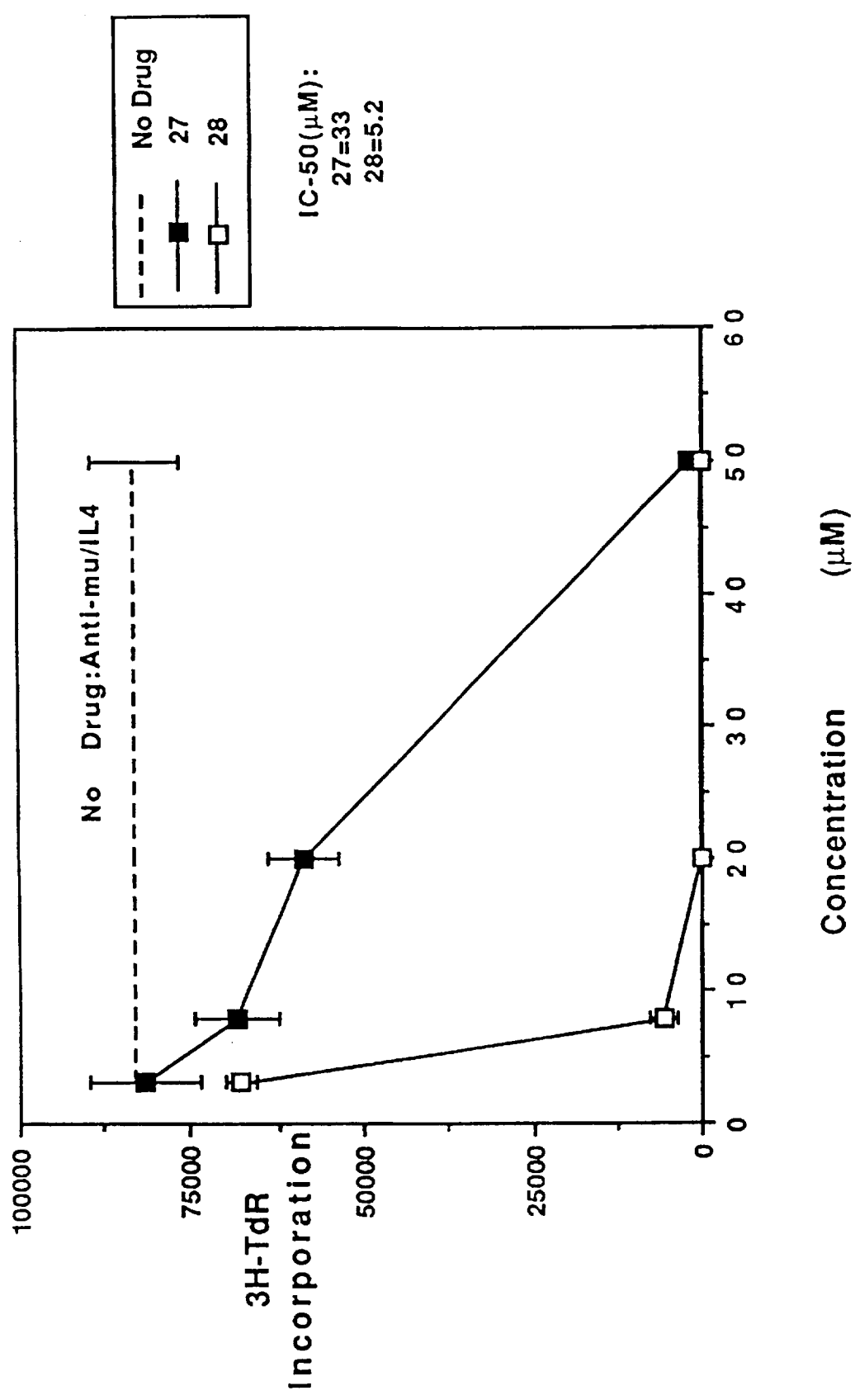
FIG. 4 reports $IC_{50}$ values for compounds nos. 27 and 28 in a murine splenocyte proliferation (anti-mu stimulated assay).

This in vitro assay, described above, is indicative of immune-suppressive/autoimmune treatment assay emphasizing humoral or B cell immune response. The compounds were added to the cells at the doses indicated two hours prior to activation with anti-mu and IL-4. Both compounds nos. 27 and 28 inhibited splenocyte proliferation in a dose-response manner. $IC_{50}$ values for compounds nos. 27 and 28 were 3.3 µM and 5.2 µM, respectively, as shown in FIG. 4. Background counts were less than 200 cpm.

EXAMPLE 27

Figure 5A:
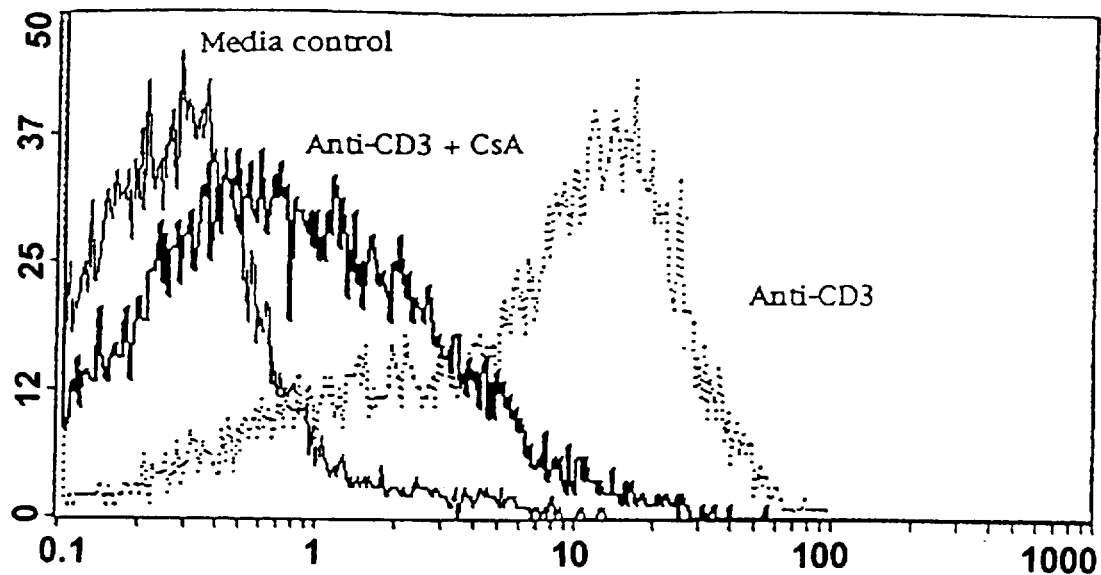
FIGS. 5A and 5B are frequency histograms of measurements for 20,000 cells in an assay illustrating IL-2 (alpha chain CD25) receptor expression.
Figure 5B:
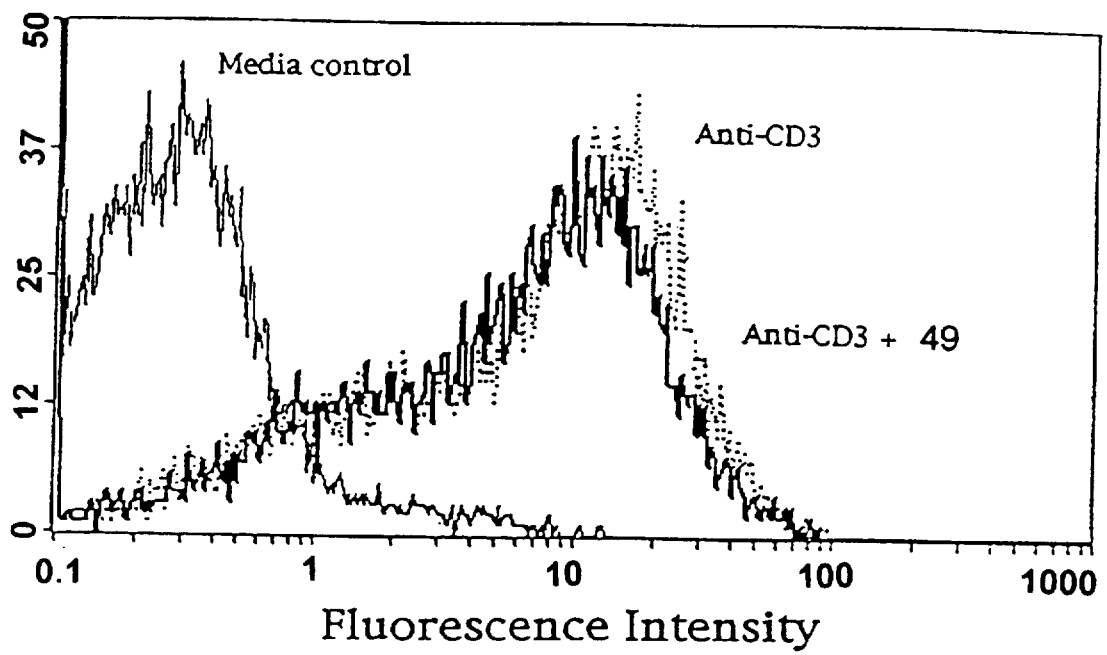

This investigation illustrates IL-2 (alpha chain CD25) receptor expression on mouse splenoyctes. The IL-2 receptor is not expressed on resting T-cells, but is rapidly-induced by certain stimulants, e.g. antigen recognition or treatment with ConA or antibodies to CD3 (anti-CD3). IL-2-dependent proliferation requires IL-2 receptor expression. Splenocytes were stimulated with anti-CD3 antibody (10 µg/ml) with or without the addition of CsA (20 µM) or compound no. 49 (1 µM). Following overnight incubation, the splenocytes were stained with a fluoresceinated anti-IL-2 receptor antibody and fluorescence measured by flow cytometry. FIGS. 5A and 5B are frequency histograms of measurements for 20,000 cells per sample. The media control has a low level of fluorescence, while stimulation with anti-CD3 stimulates large relative increases in IL-2 receptor expression (peak labeled anti-CD3 in FIGS. 5A and 5B). Co-incubation with CsA inhibits CD3-stimulated, IL-2 receptor expression, while incubation with compound no. 49, at a concentration that blocks 90% of splenocyte IL-2-stimulated proliferation, has no effect on receptor expression. These data confirm that CsA and compound no. 49 affect immune cells by different mechanisms.

EXAMPLE 28

Figure 6:
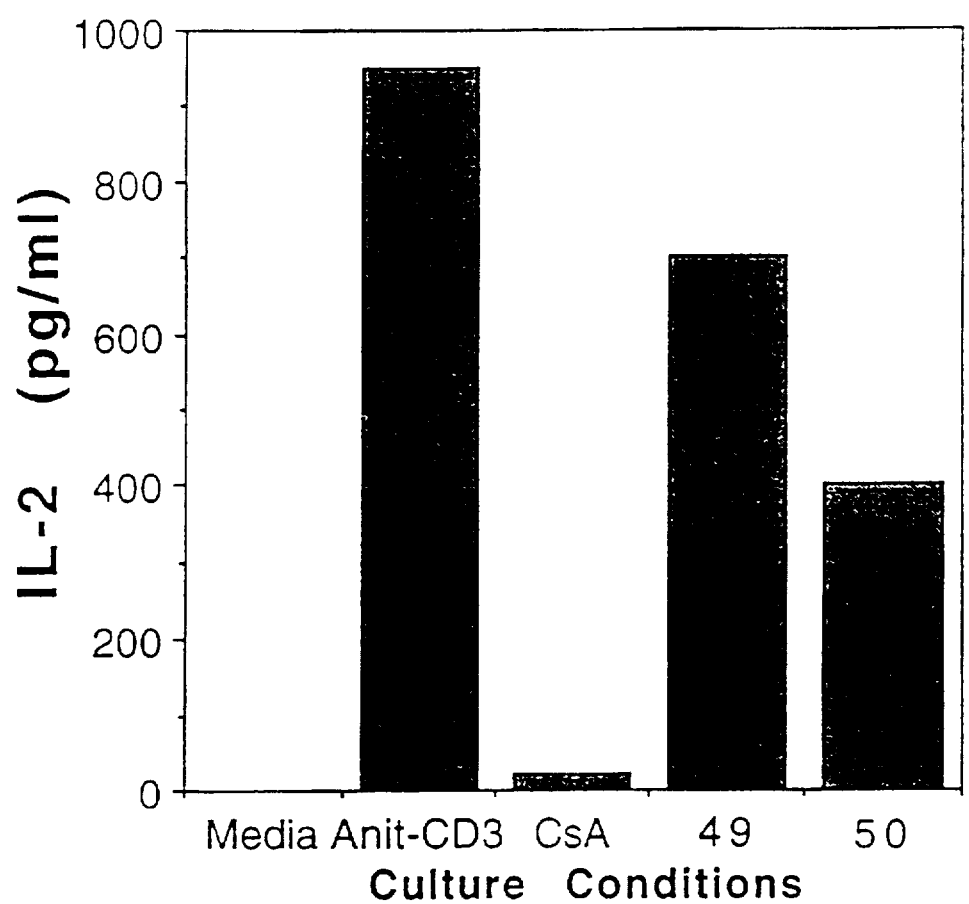
FIG. 6 shows results for compounds nos. 49 and 50 as compared with CsA in an inhibitive assay for production of IL-2 in murine thymocytes.

This example shows that compounds nos. 49 and 50 did not inhibit production of IL-2 in murine thymocytes, in contrast to the effects of CsA. Thymocytes were stimulated with ConA and IL-1β for 4 days with or without adding compounds to the culture media. The supernatants were removed and assayed by ELISA for IL-2 levels by a commercially available kit. The results, shown in FIG. 6, illustrate that CsA incubation at 20 nM inhibited IL-2 production and secretion. Also shown, these exemplary compounds tested did not inhibit IL-2. These data illustrate that CsA and the compounds tested interfere with immune cell function via different mechanisms.

EXAMPLE 29

Figure 7:
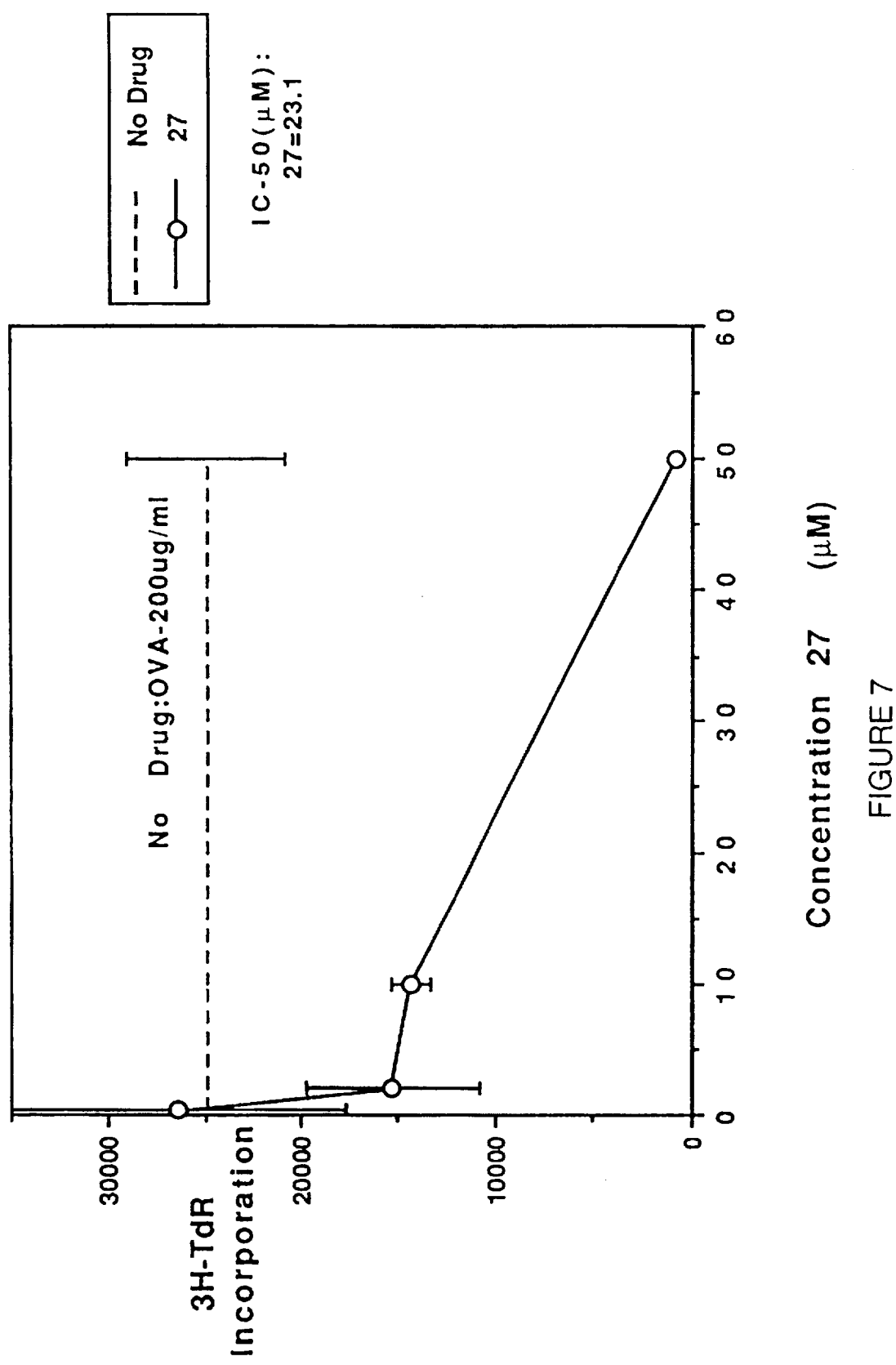

This example illustrates activity of representative compounds nos. 27, 49, 50, 45, 43 or 41 (above) in assays detecting activity in response to cell stimulus. One assay, murine lymph node cell proliferation (stimulated by antigen), was used to determine inhibitive activity of compound no. 27 on proliferation of the lymph node cells. This in vitro assay is an immune suppressive/autoimmune treatment predictive assay emphasizing cellular or T-cell immune response. The assay used murine T-cells that proliferate in vitro in response to a soluble protein antigen, used to prime the T-cells in vivo. Compound was added to the cells at doses indicated in FIGS. 7 and 8 (showing assay results) two hours prior to activation with alloantigen. Compound no. 27 inhibited T-cell proliferation in a dose-response manner. $IC_{50}$ values for compound no. 27 were 23.1 µM for a first experiment (results shown in FIG. 7) and 19 µM for a second experiment (results shown in FIG. 8).

Figure 9A:
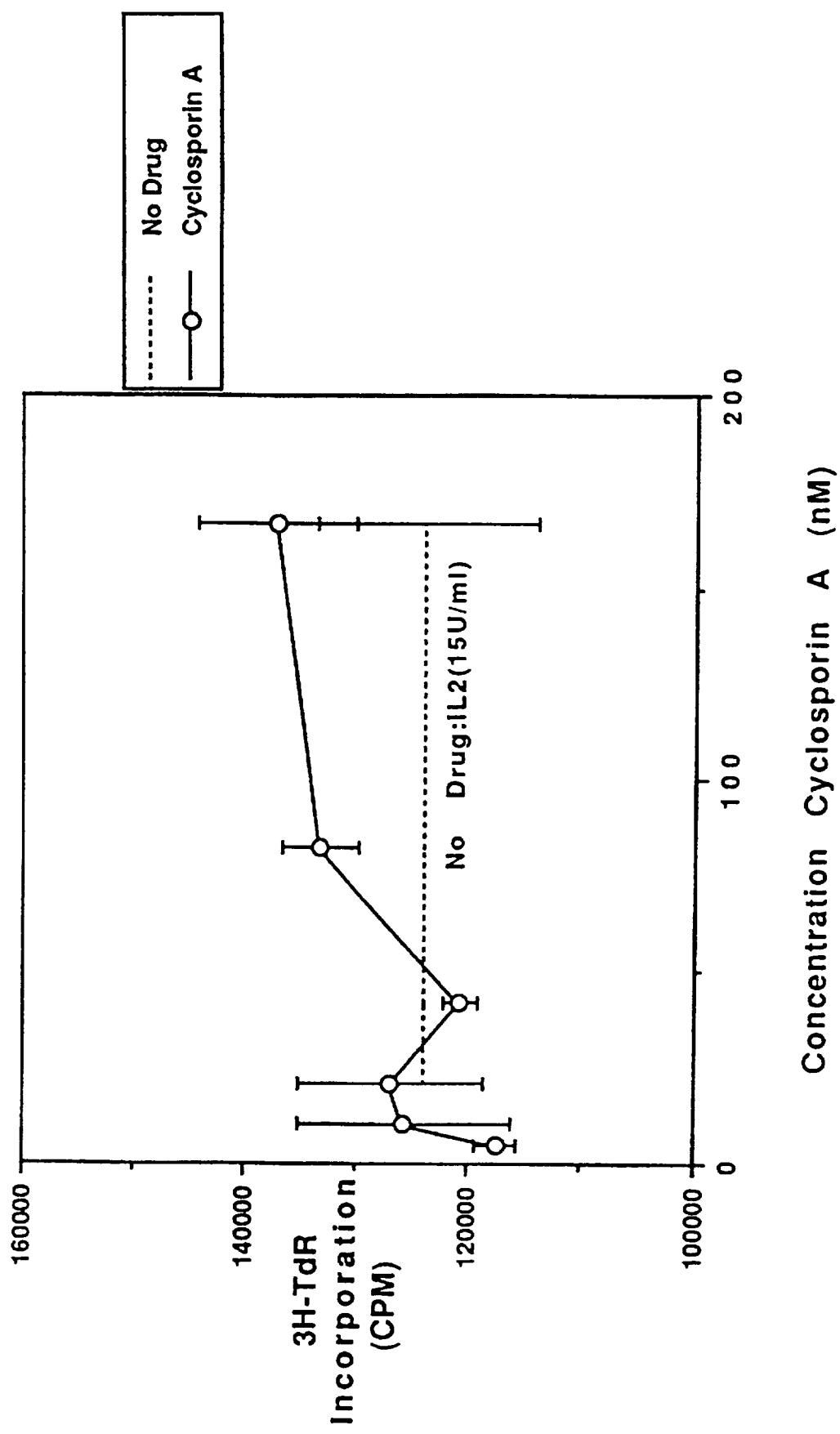
FIGS. 9A and 9B report inhibitive activity for the compounds, as compared with CsA on direct IL-2-induced proliferation in a murine cytotoxic T-cell line, CT6.
Figure 9B:
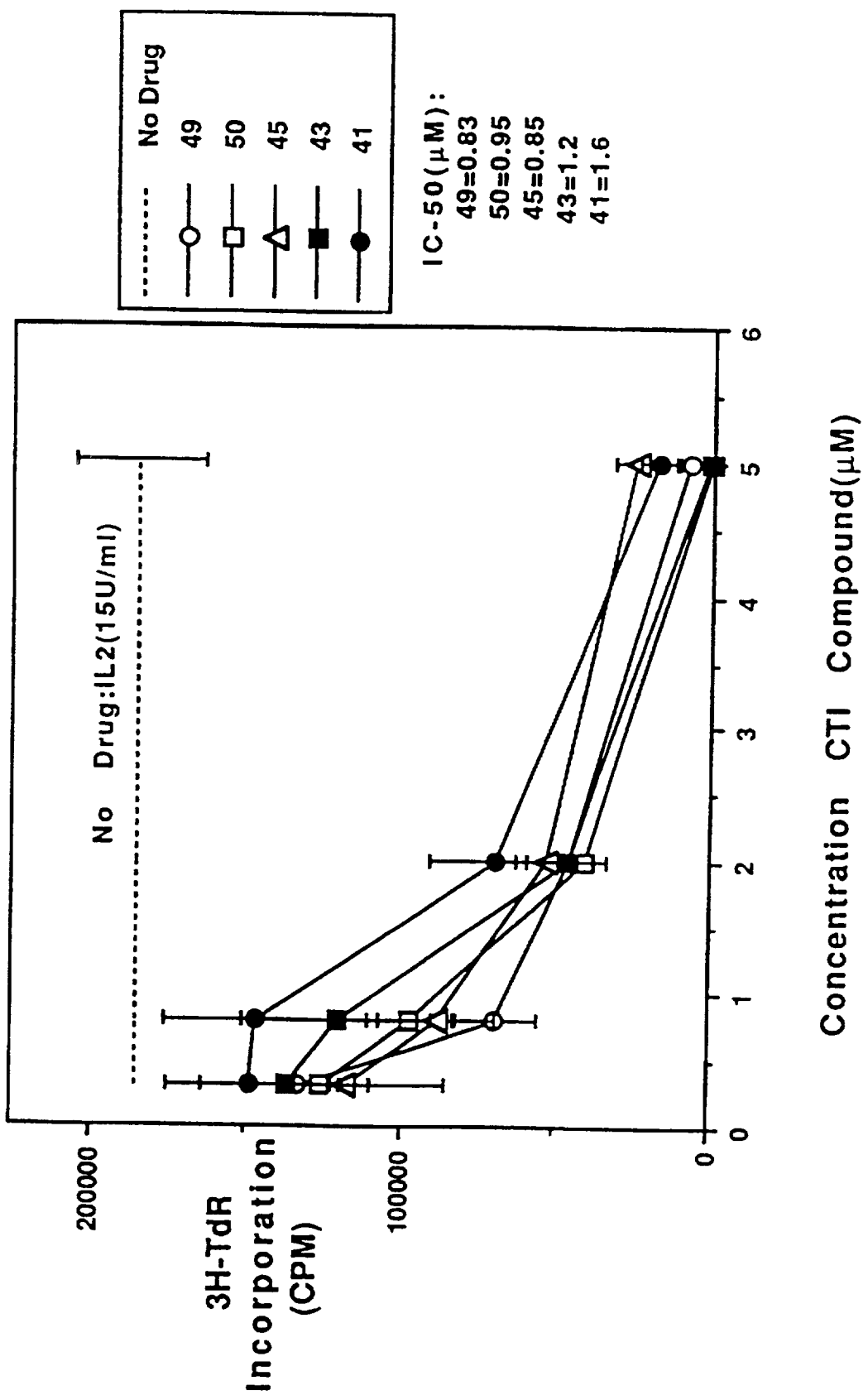

Another assay in this example was used to determine inhibitive activity of the compounds on direct IL-2-induced proliferation in a murine cytotoxic T-cell line, CT6. The CT6 cell line is an IL-2-dependent cell line. IL-2 was removed from the medium for 24 hours prior to stimulation. One hour prior to IL-2 stimulation, either CsA or compounds nos. 49, 50, 45, 43 or 41 were added at various concentrations. The cells were stimulated with IL-2 and amount of tritiated thymidine dye incorporated was measured 48 hours later. Background counts were less than 5000 cpm. Assay results are graphically represented in FIGS. 9A and 9B. The two graphs show that CsA and the compounds have divergent effects on IL-2-induced proliferation. CsA did not inhibit proliferation, even at very high concentrations. However, in distinct contrast, the compounds inhibited direct IL-2-induced CT6 proliferation.

EXAMPLE 30

Figure 10:
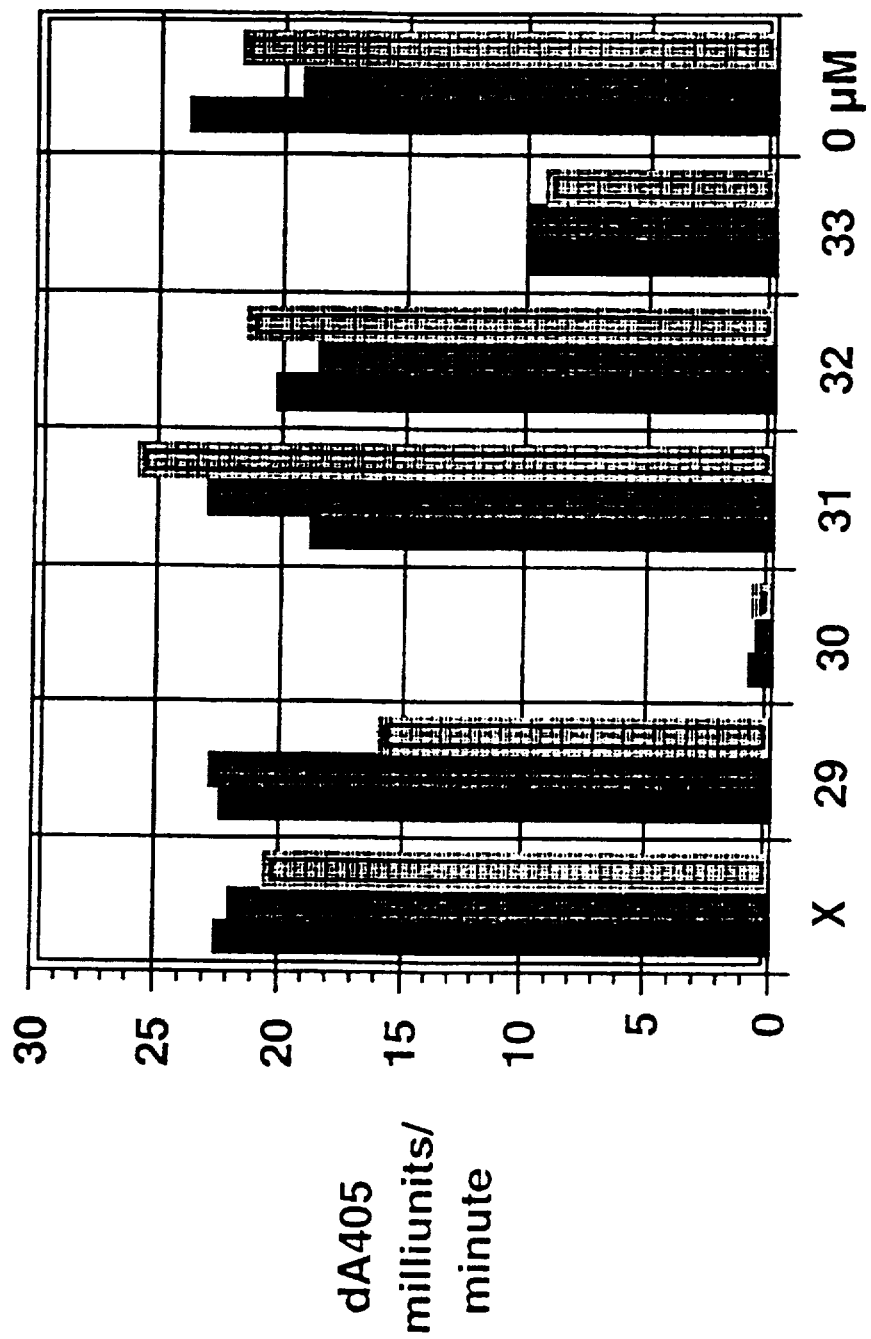
FIG. 10 illustrates activity of the compounds in anti-yeast and anti-fungal assays.

This example illustrates the effects of a reference compound "X", and compounds nos. 29, 30, 31, 32 and 33 (see above for names and structures) on yeast growth (Saccharomyces cervisiae)—using 100 μM concentrations—as compared with yeast activity in the absence of any compound additive (control). This assay measured anti-yeast and anti-fungal activity of the the compounds tested. As shown in FIG. 10, compounds no. 30 and 33 showed yeast-growth inhibitive activity, predicting that the compounds tested are topical and systemic anti-microbial compounds.

EXAMPLE 31

This example illustrates potential antigen specific anergy-induction of compounds. Anergy is a prolonged state of T-cell "unresponsiveness" due to T-cell antigen recognition (without co-stimulation) or induced proliferation blockage. This later T-cell anergy may occur when a T-cell's proliferation ability in response to IL-2 is blocked by some agent. Anergy is generally considered to be a type of tolerance to antigen activation. Thus, in vitro anergy is a means for predicting in vivo tolerance-enhancing agents. Tolerance is important in preventing organ rejection in transplant procedures, as well as other autoimmune diseases such as scleroderma, rheumatoid arthritis, lupus, and diabetes-related autoimmunity.

Figure 11:
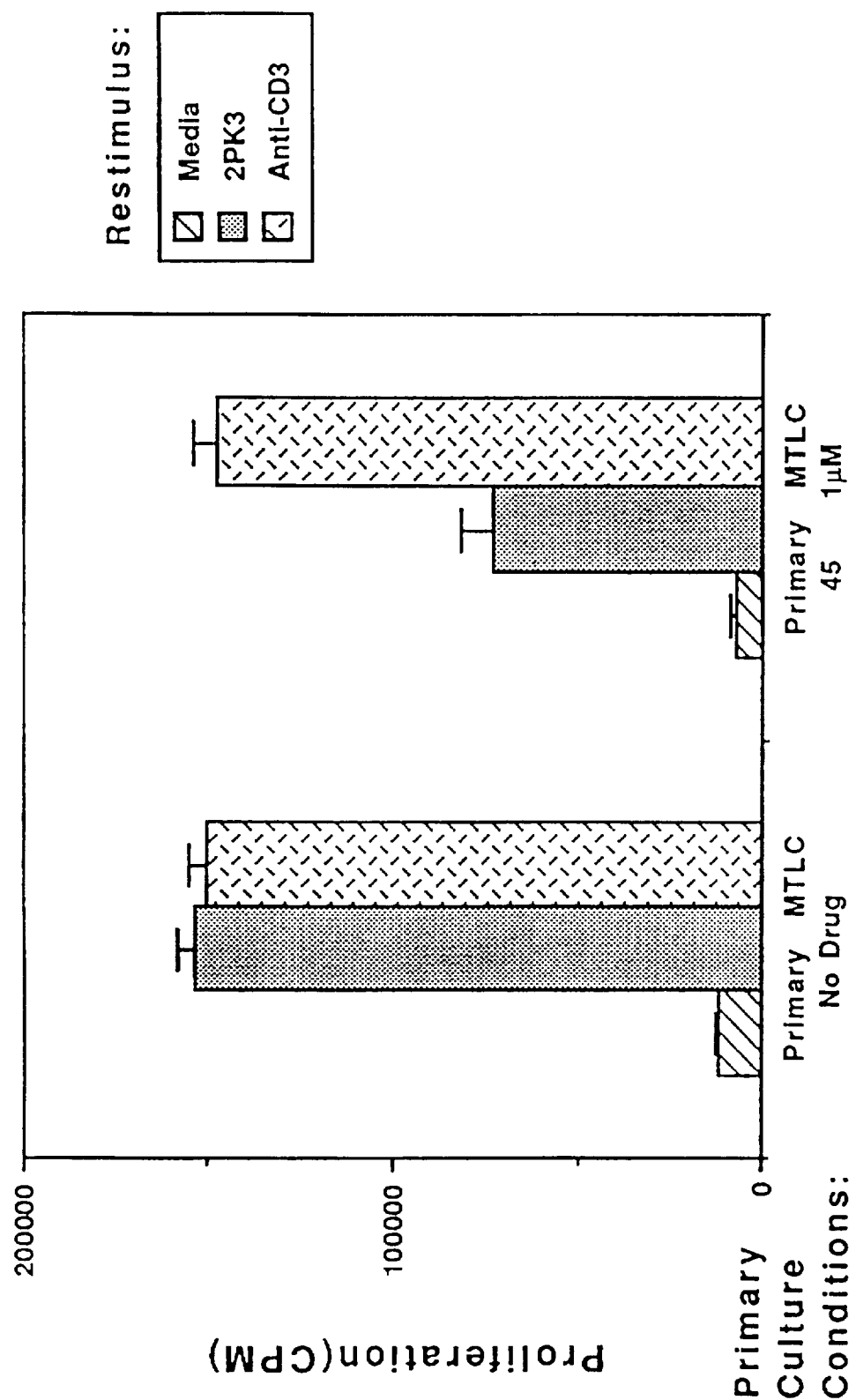
FIG. 11 reports activity data for compounds in an assay designed to detect potential antigen specific anergy induction.

A B-cell tumor, 2PK3 (H-2d) was used as a stimulating cell for C57BL/6 splenocytes (H-2b), a responding cell. Mixed cultures of B-cell tumor and splenocytes were incubated for 5 days with and without 1 μM of compound no. 45. After 5 days, the cells were washed and resuspended with either media, the original antigen (2PK3) or anti-CD3. Tritiated thymidine was added to the resulting suspensions and thymidine incorporation measured 24 hours later. Results are shown in FIG. 11. As illustrated, culture treated with compound no. 45 and untreated cultures responded equivilantly to anti-CD3. However, cultures incubated with compound no. 45 for 5 days exhibited a decreased response to primary antigen, 2PK3. Thus, C57BL/6 splenocytes were inhibited from responding to an original antigen by the compound used in the pre-incubation step. However, a normal culture response to anti-CD3 stimulation predicts the compounds exhibited antigen-specific anergy induction properties.

EXAMPLE 32

This example illustrates inhibitive effects of the compounds on human stromal and Balb/3T3 cell proliferation in response to PDGF stimulation.

Figure 12:
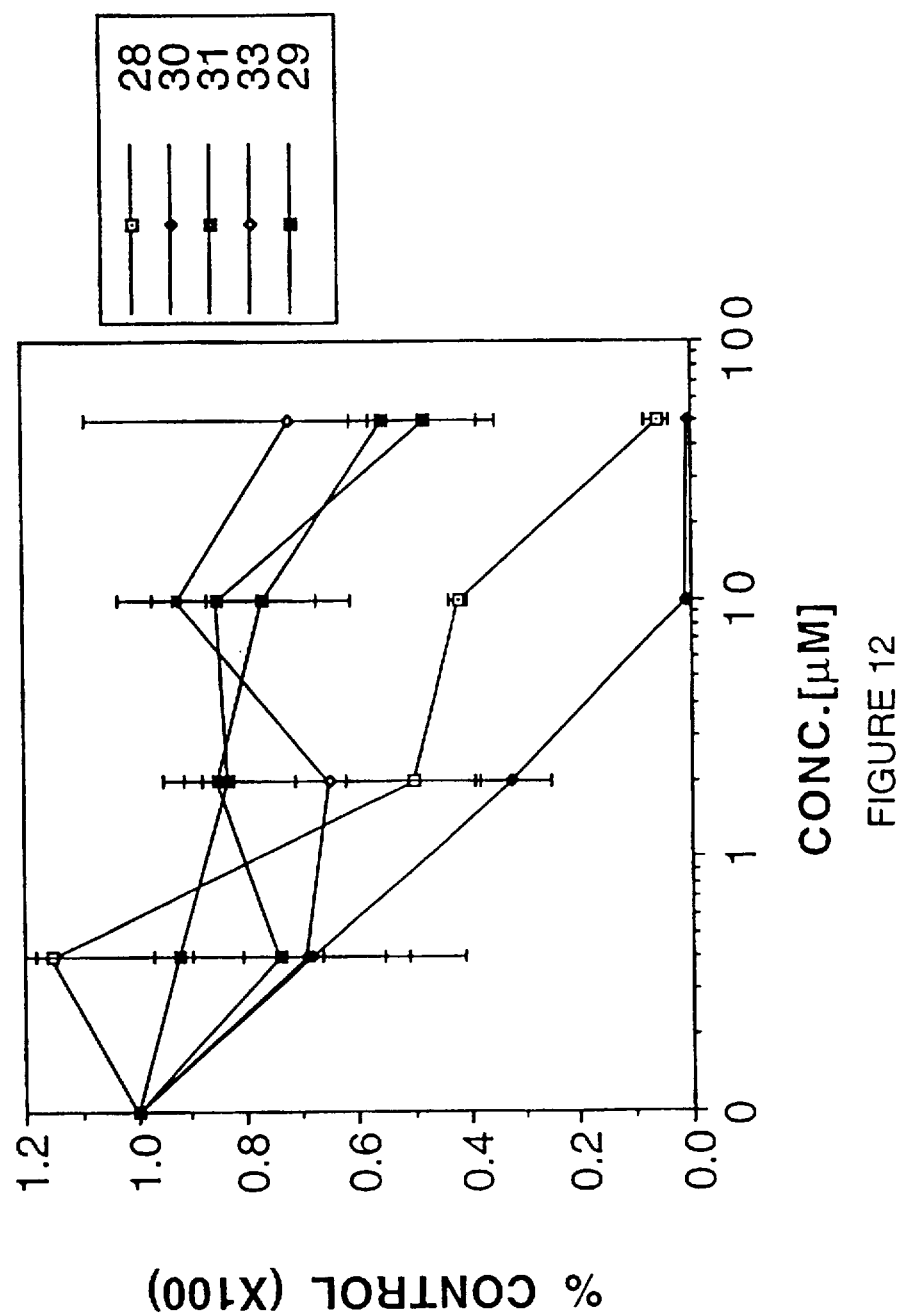
FIG. 12 shows activity results for compounds nos. 28, 30, 31, 33 and 29 in an assay useful in predicting therapeutic activity for preventing or treating restenosis, atherosclerosis and coronary artery disease.

This assay is useful for predicting therapeutic activity for preventing or treating restenosis, atherosclerosis and coronary artery disease. Human stromal cells were starved in serum-free media for one day and then stimulated with 50 ng/ml PDGF-BB. Compounds, at various concentrations, were added one hour prior to PDGF stimulation. PDGF and tritiated thymidine were added and the cells allowed to incubate for one day, following addition of the PDGF and thymidine. 24 Hours later, the cells were harvested and counted by liquid scintillation counting. Results for compounds nos. 28, 30, 31, 33 and 29 are shown in FIG. 12. Background counts (i.e., starved cells) were approximately 1% of control levels. The results illustrate that the drugs were active in this predictive in vitro model with $IC_{50}$ values (in μM) of 0.9, 3.2, 40, >50 and >50 for compounds nos. 30, 28, 29, 32 and 31, respectively.

Figure 13:
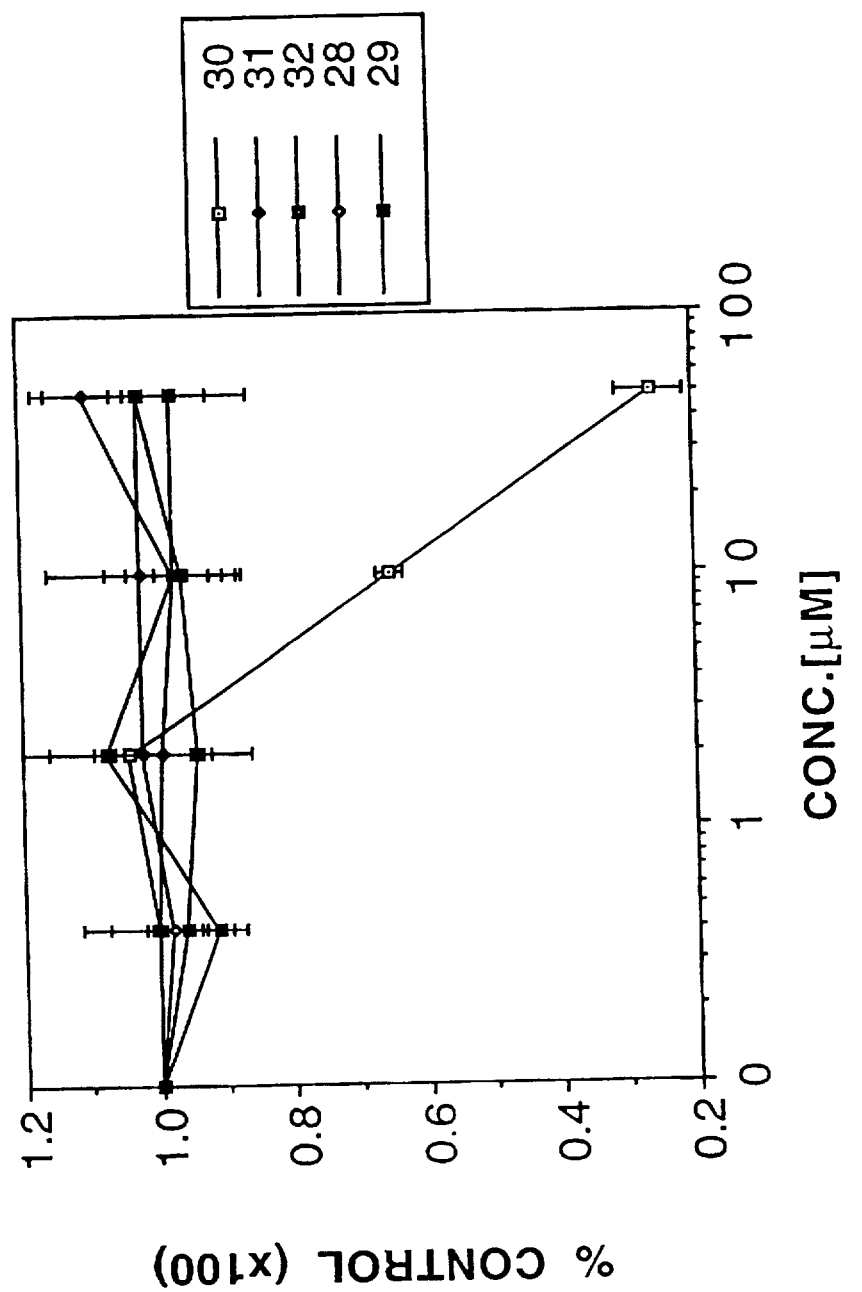
FIG. 13 shows cytotoxic results for compounds in a human stromal cell/PDGF stimulation assay.

In conjunction with the human stromal cell/PDGF stimulation assay, cytotoxicity of the compounds tested to stromal cells was also determined. FIG. 13 shows results for this cytotoxicity assay. Only compound no. 30, exhibiting the most pronounced inhibitive activity of the compounds tested, exhibited cytotoxic effects at concentrations above 0.9 μM, its $IC_{50}$ value.

Figure 14:
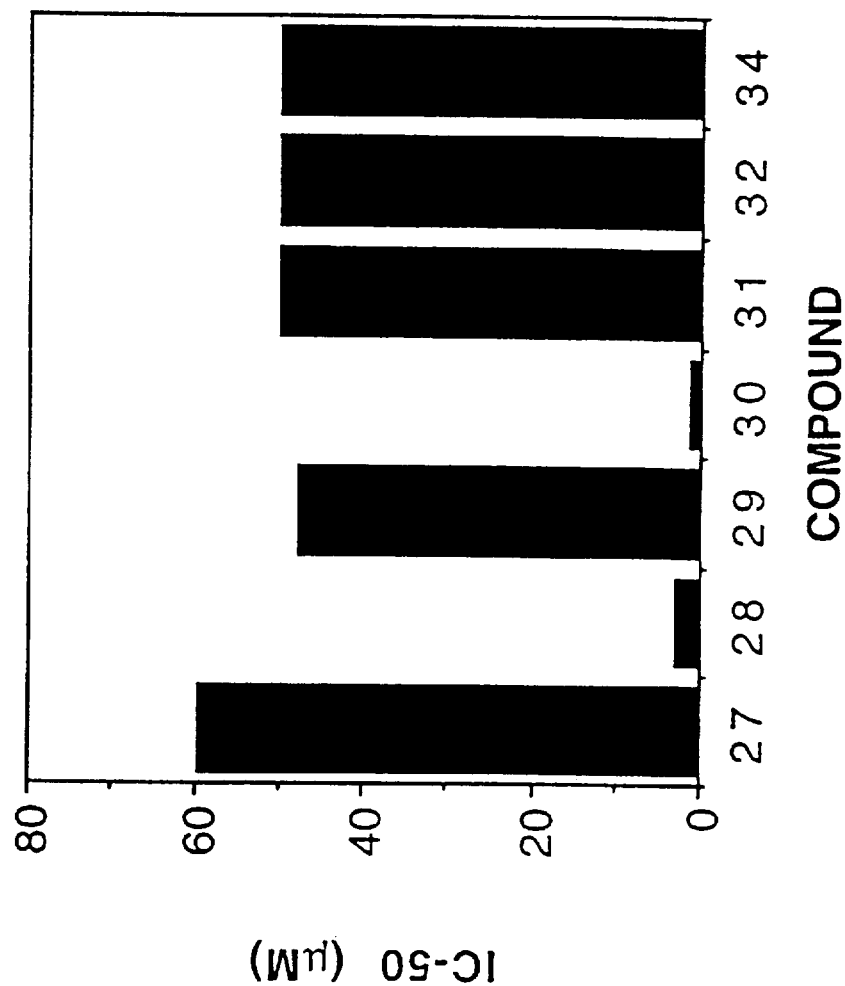
FIG. 14 reports inhibitive activity results for compounds nos. 27, 28, 29, 30, 31, 32 and 34 in an assay measuring inhibitive effects in a PDGF/IL-1β co-stimulation.

In an assay measuring inhibitive effects in a PDGF/IL-1β co-stimulation, proliferation assay, a group of compounds showed inhibitive properties. The PDGF/IL-1β assay is useful in measuring in vitro activity, indicative of therapeutic potential for treating or preventing restenosis and reperfusion. FIG. 14 reports $IC_{50}$ bar graph results for a group of compounds nos. 27, 28, 29, 30, 31, 32 and 34. In this predictive, in vitro model, compounds nos. 28 and 30 exhibited potent inhibitive activity, predicting therapeutic applications for restenosis and reperfusion.

Figure 15:
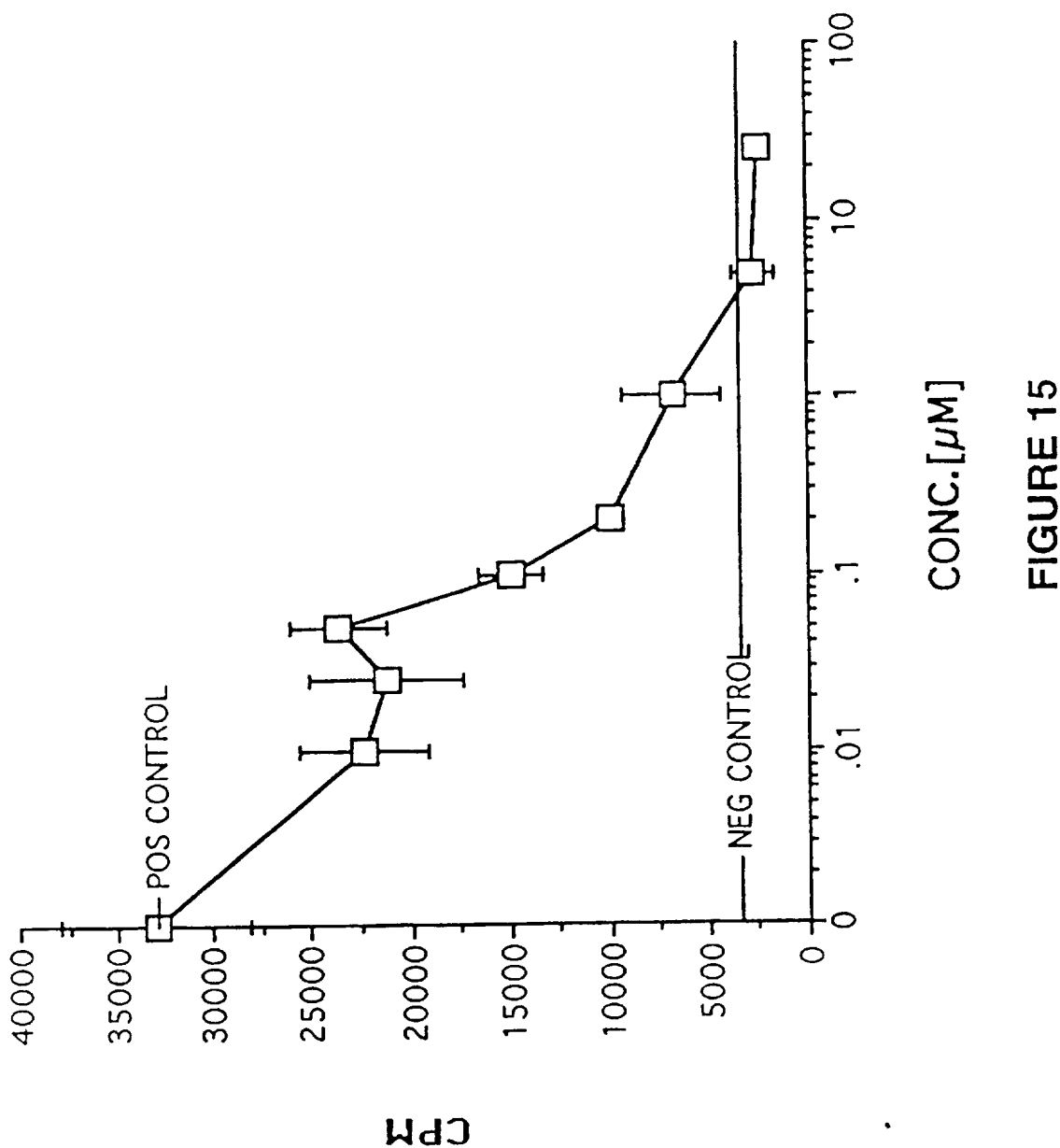
FIG. 15 illustrates a dose response curve for selected compounds in an assay measuring PDGF-induced proliferation of Balb/3T3 cells.

The compounds possess inhibitory effects on PDGF-induced proliferation of Balb/3T3 cells. Balb/3T3 cells respond vigorously to PDGF stimulation, and are useful in vitro models for further study of PDGF-induced proliferation. Disregulated PDGF-proliferative response has been linked to a variety of diseases, including, e.g., restenosis, atherosclerosis, fibrosis, and tumor cell angiogenesis. Cells were plated in low serum-containing medium for 24 hours prior to stimulation with various concentrations of compound no. 45. PDGF-BB was added at constant 10 μM concentrations. Tritiated thymidine was added and cells harvested for scintillation counting 24 hours later. FIG. 15 illustrates a dose response curve from this assay, including an $IC_{50}$ value of approximately 0.08 μM, exemplifying inhibitory activity of the tested compound.

EXAMPLE 33

Figure 16:
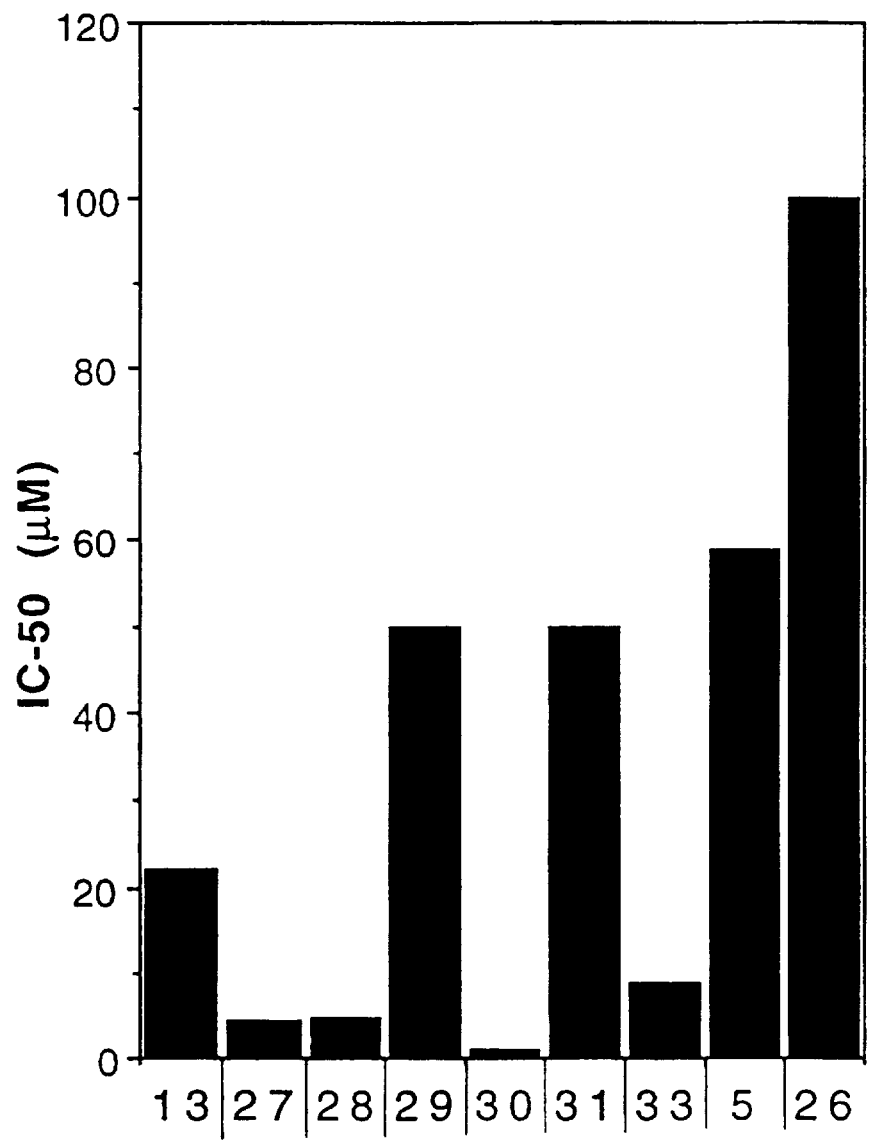
FIG. 16 reports suppressive results for selected compounds in a murine thymocyte ConA/IL-2 co-stimulation assay.

In assays described above and similar to those used in Example 32 and other examples, the ability of various compounds to suppress murine thymocyte and Balb/3T3 cell proliferation in response to selected stimuli was investigated. In a murine thymocyte ConA/IL-2 co-stimulation assay according to Example 23, $IC_{50}$ values were obtained for inventive compound nos. 13, 27, 28, 29, 30, 31, 33, 5 and 26. FIG. 16 reports comparative results for the different compounds tested in this in vitro model. Compounds nos. 28, 30, and 27 exhibited the most potent immune-suppressive effects in these in vitro models.

Figure 17:
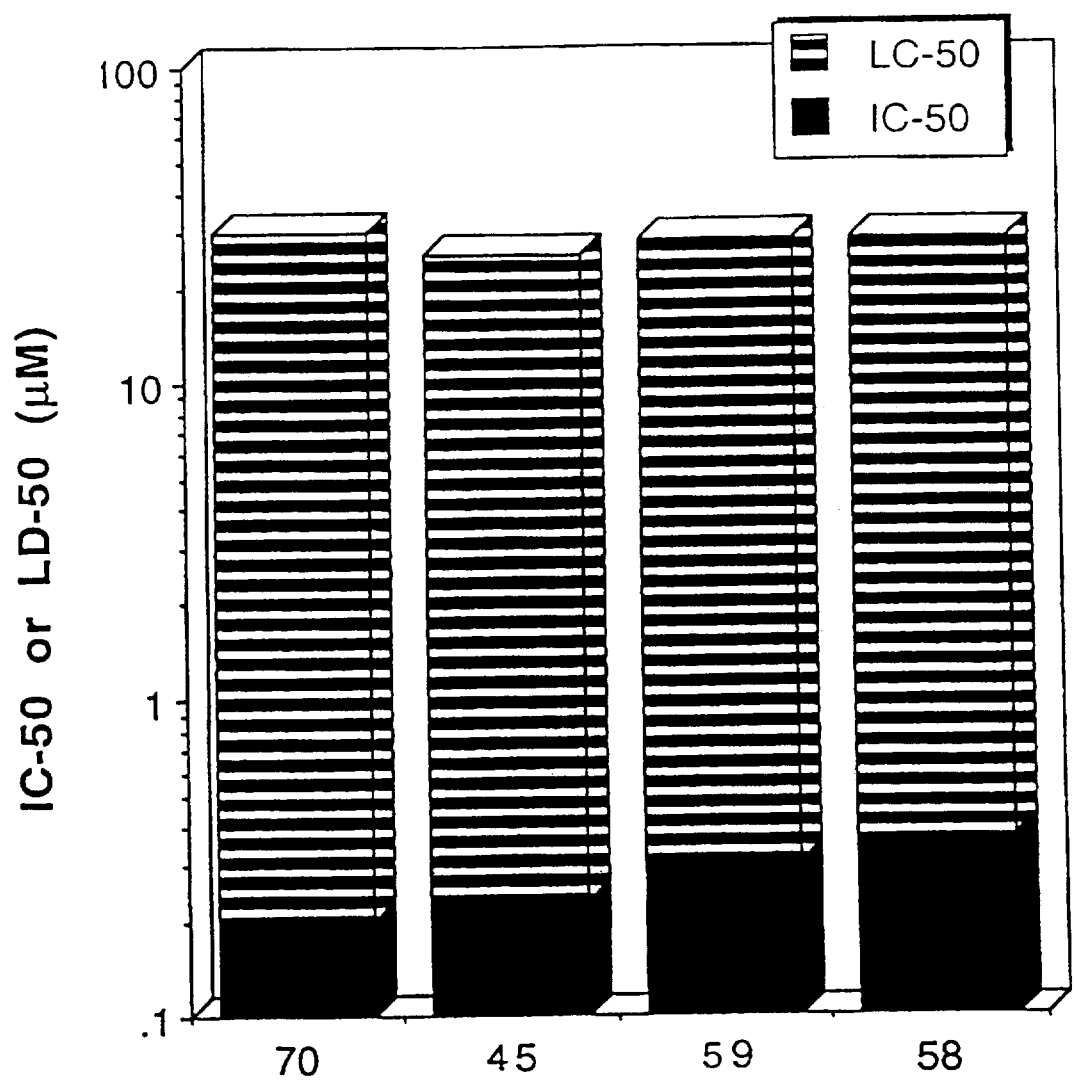
FIG. 17 compares $IC_{50}$ and $ID_{50}$ data for several compounds.

In another investigation similar to the Balb/3T3 proliferation assay of Example 32, $IC_{50}$ and $ID_{50}$ values for compounds nos. 70, 45, 59 and 58 were determined. $LD_{50}$ values were determined using a cytotoxicity assay, as in Example 32. In these assays, Balb/3T3 cells, stimulated with PDGF and treated with one of the above compounds in a manner identical to the tritiated thymidine procedure above, were incubated instead with a viable dye BCECF, a fluorescent dye. Fluorescence was measured using a fluorescent plate reader. The highest concentration used was 50 µM, therefore an $LD_{50}$ value greater than 50 µM indicates no effect at 50 µM. FIG. 17 illustrates assay results by comparing $LC_{50}$ value against $LD_{50}$ values for the compounds tested. Most compounds tested were non-cytotoxic yet were significant inhibitors of proliferation.

EXAMPLE 34

Figure 18:
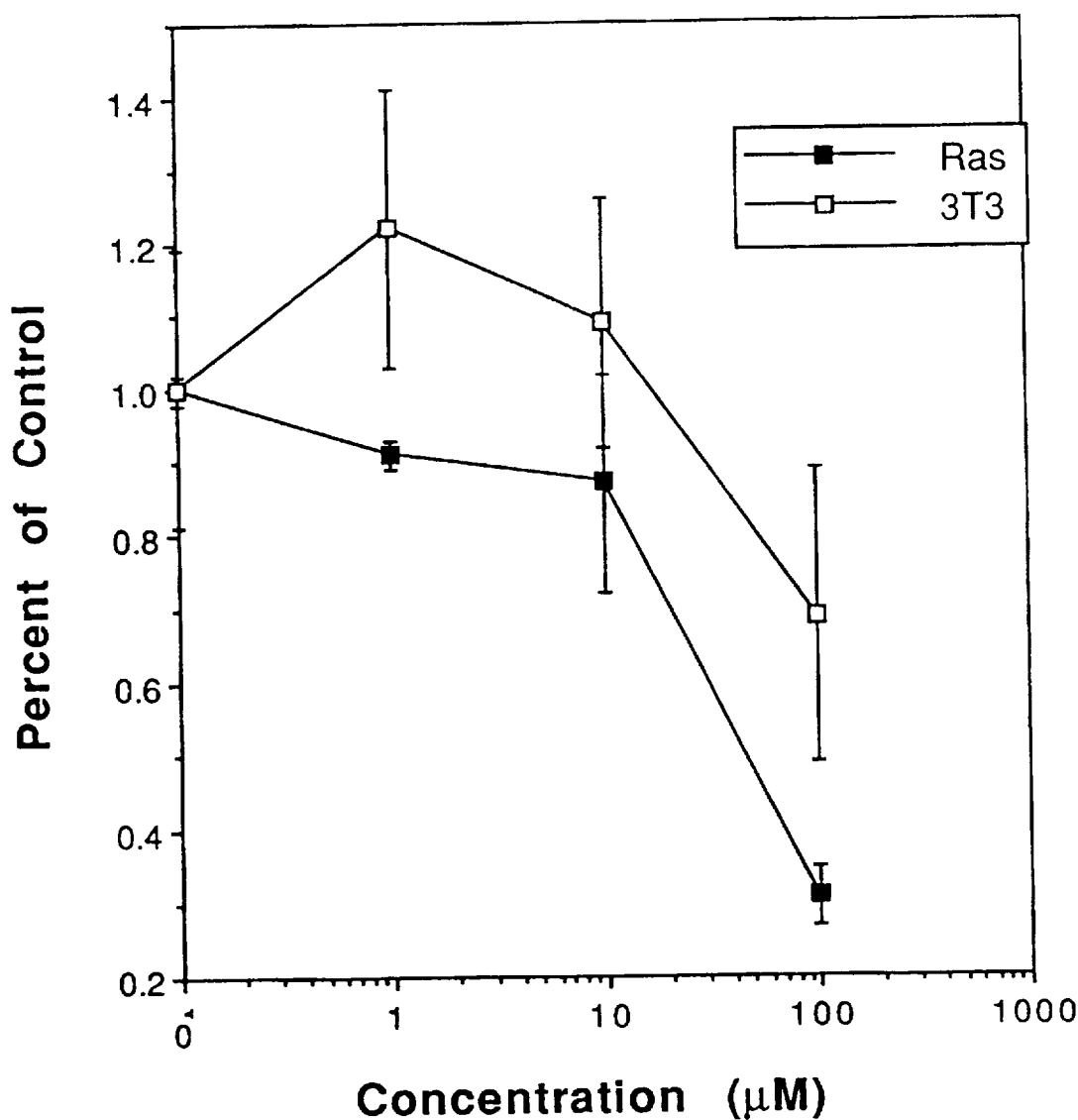
FIG. 18 reports cytotoxicity results for compound no. 27 for transformed (Ras 3T3) cells and non-transformed (normal) cells.

This example compares cytotoxicity results for compound no. 27 for transformed cells and non-transformed cells. In transformed cells (Ras 3T3) and in normal 3T3 cells, cytotoxicity of compound no. 27 at concentrations of 1, 10 and 100 µM was determined. FIG. 18 reports results obtained in this assay. At each of the above concentrations, compound no. 27 was more cytotoxic for the cancer cells than normal cells. These results indicate the compound tested has differential toxicity for tumor cells, predicting potential utility in chemotherapeutic cancer treatment.

EXAMPLE 35

Figure 19:
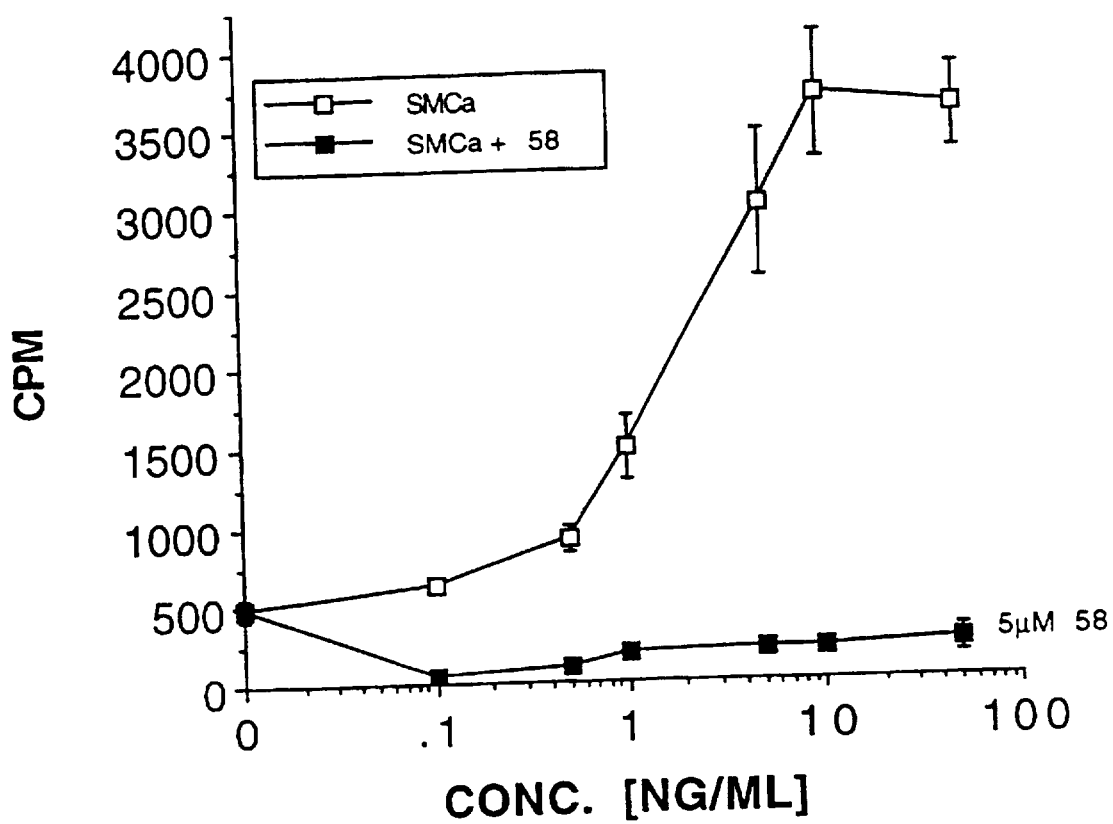
FIG. 19 shows data demonstrating inhibitory effects of compound no. 58 on PDGF-induced proliferation of human aortic smooth muscle cells (aortic SMC).

This example demonstrates an inhibitory effect on proliferation of compound no. 58. One assay was used for investigating effects on PDGF-induced proliferation of human aortic smooth muscle cells (aortic SMC). Cells, purchased from a commercial supplier (Cell Systems, Inc., Seattle, Wash.), were cultured with various concentrations of PDGF-BB with and without addition of compound no. 58 (5 µM). As illustrated in FIG. 19, compound no. 58 inhibited PDGF-induced proliferation even at high PDGF concentrations providing maximum proliferative stimulation. In addition, some cultures were treated 1 hour prior to PDGF stimulation with compound no. 58. As shown, PDGF stimulated proliferation in this cell line. Addition of 5 µM of compound no. 58 blocked PDGF-stimulated proliferation and no toxic effects of compound no. 58 were observed.

Figure 20A:
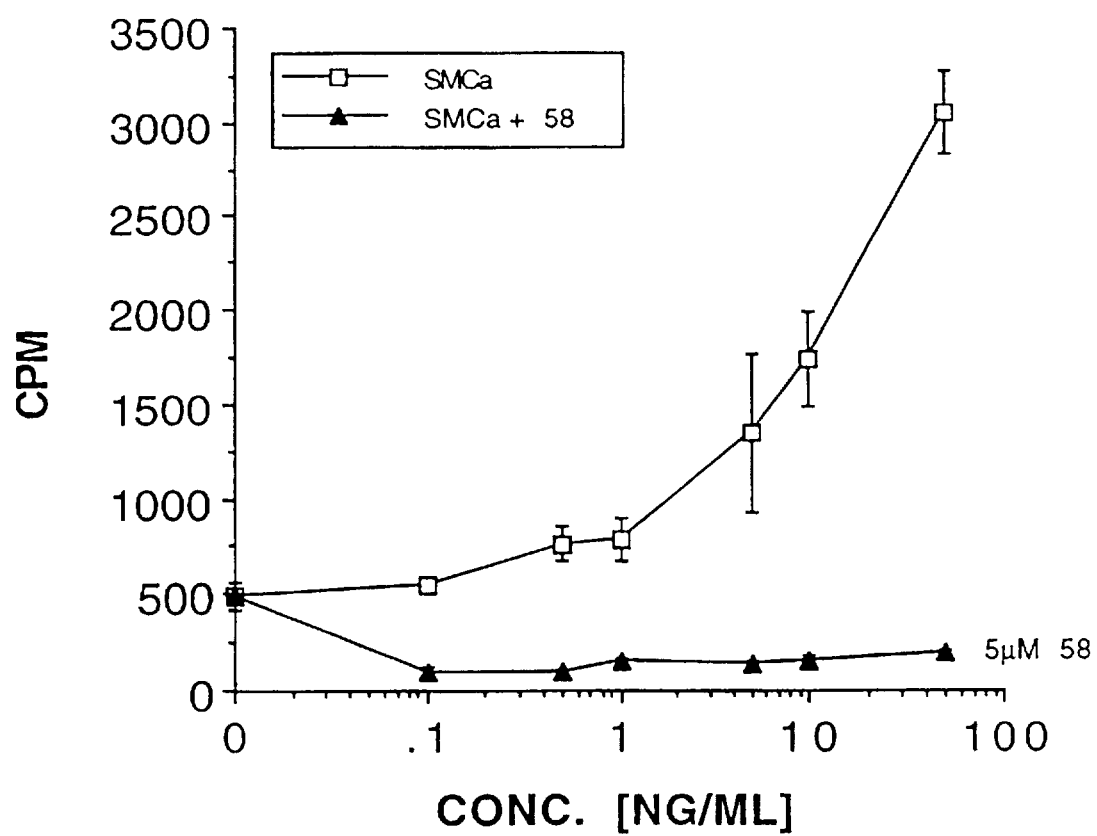
FIGS. 20A and 20B show the effects of compound no. 58 on aFGF and bFGF- induced proliferation in human aortic smooth muscle cells (aortic SMC).
Figure 20B:
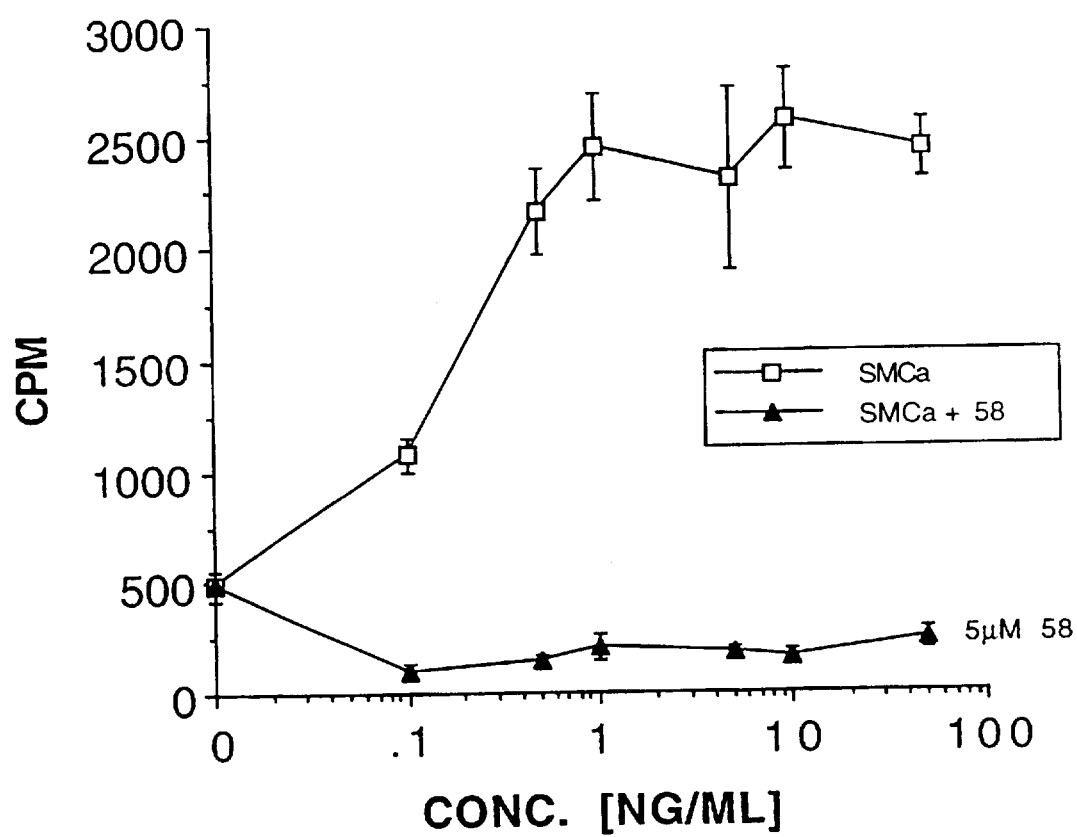

Another assay was used for investigating inhibitory effects of compound no. 58 on either basic or acidic FGF-induced proliferation in human aortic smooth muscle cells (aortic SMC). Disregulated bFGF- or aFGF-induced proliferation is linked to SMC proliferation and neointimal occlusion in atherogenesis and restenosis and plays a role in autocrine and paracrine stimulation of tumor cells and tumor cell-induced angiogenesis. In this assay, cells were grown in reduced serum (0.5% fetal calf serum) for 24 hours prior to stimulating with various concentrations of PDGF. Cells were stimulated with various concentrations overnight of either aFGF or bFGF, adding 5 µM of compound no. 58 in selected cultures. Compound no. 58 was a potent inhibitor of both aFGF- and bFGF-induced proliferation in this cell type, representative of other cell types examined. Results shown in FIG. 20A (aFGF) and FIG. 20B (bFGF) illustrate the degree of inhibition. No toxic effects of compound no. 58 were observed for this cell type in this assay.

EXAMPLE 36

Figure 21A:
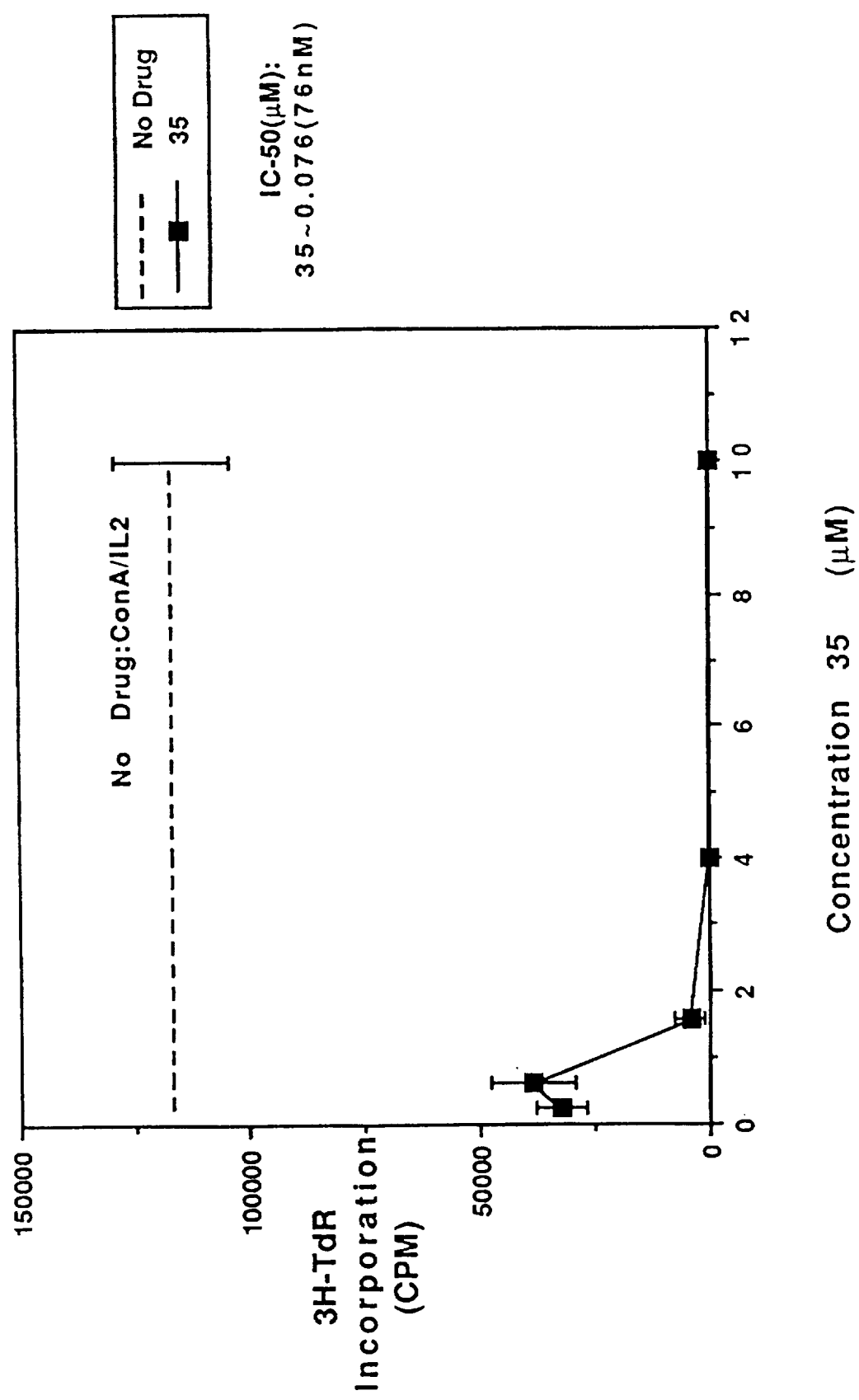
FIGS. 21A and 21B show inhibitory activity of compound no. 35 and CsA, respectively, on murine thymocytes, co-stimulated with ConA and IL-2.
Figure 21B:
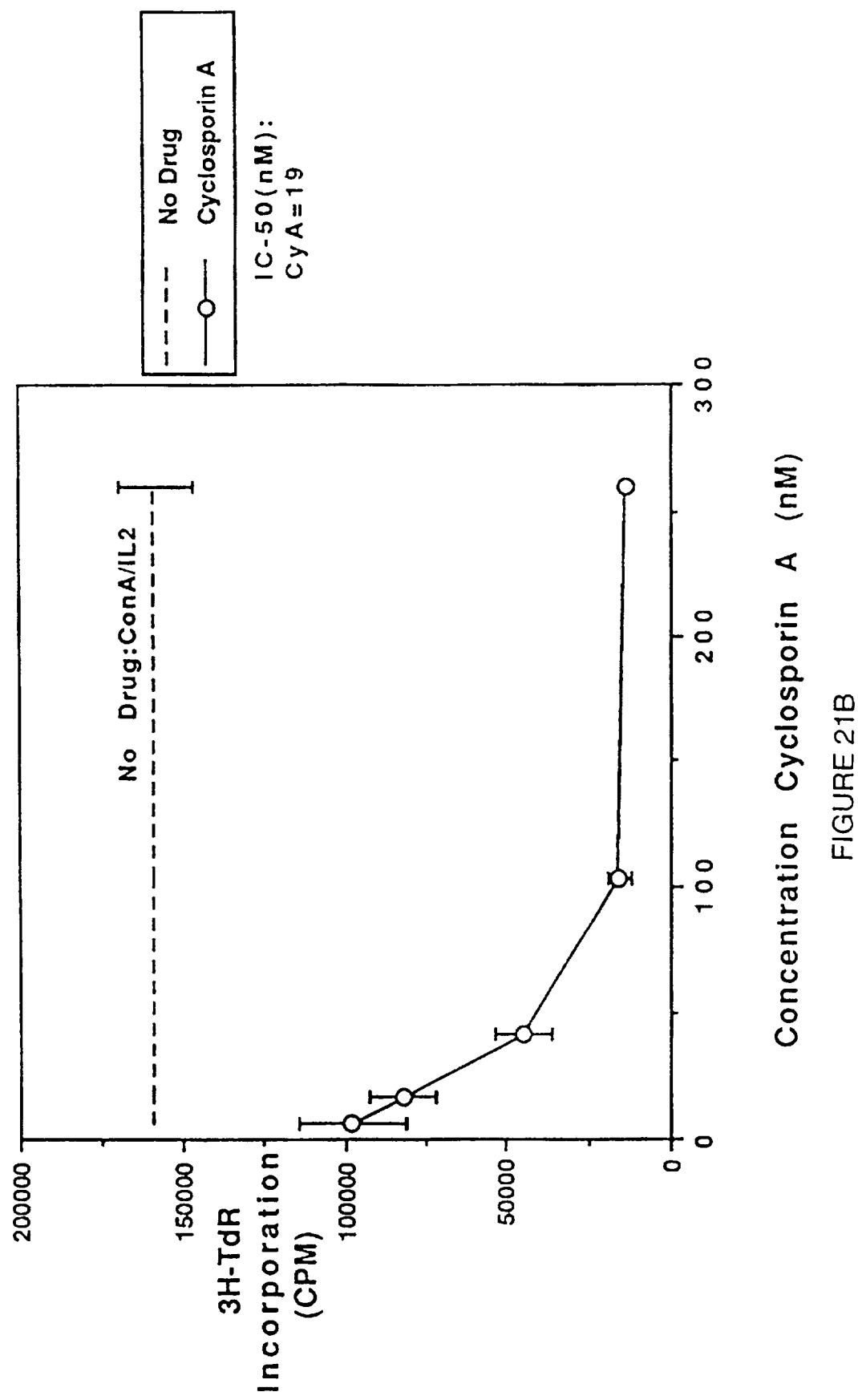
Figure 21C:
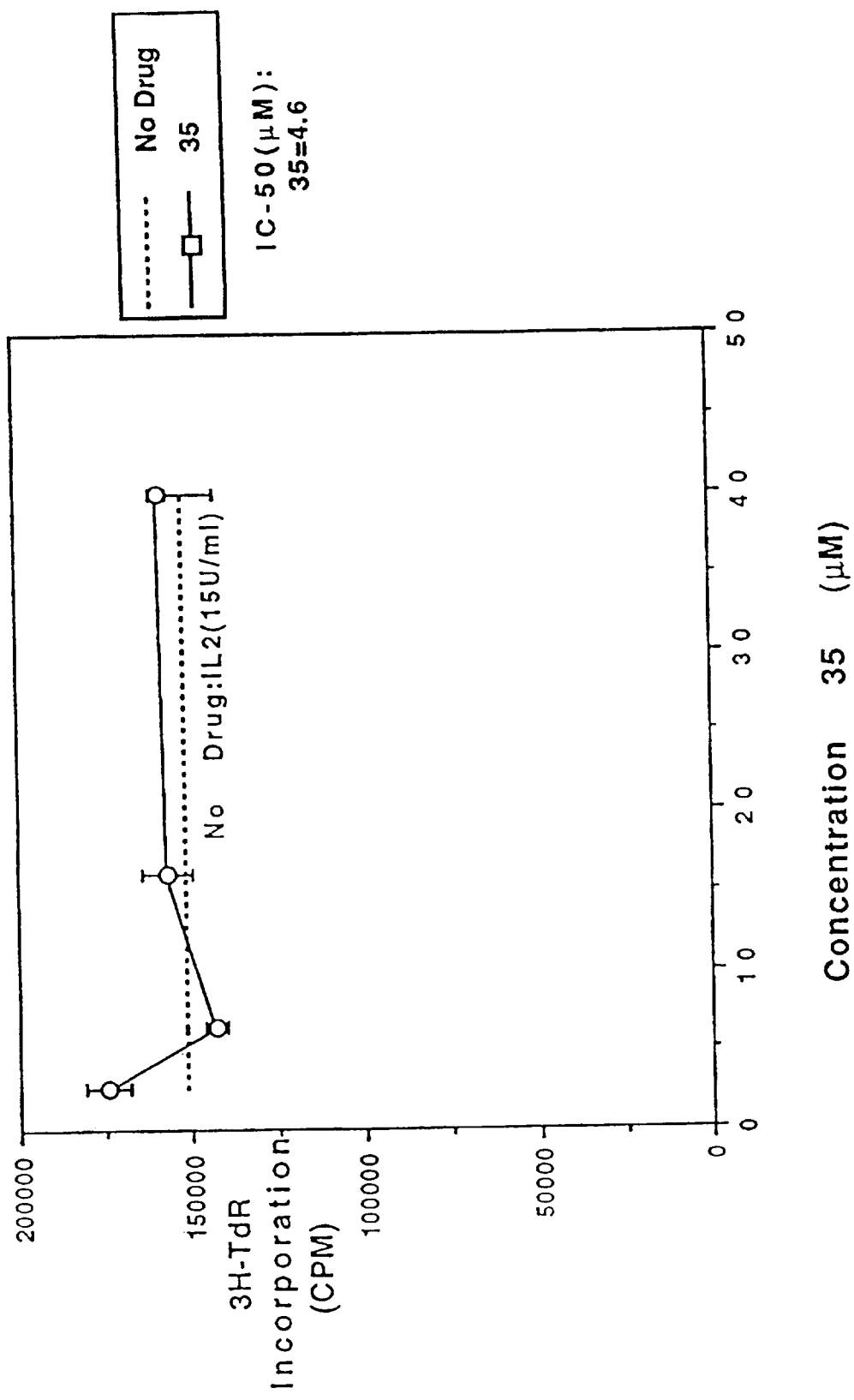
FIGS. 21C and 21D illustrate inhibitory effects of compound no. 35 and CsA, respectively, on IL-2-induced proliferation of cytotoxic CT-6 cells.
Figure 21D:
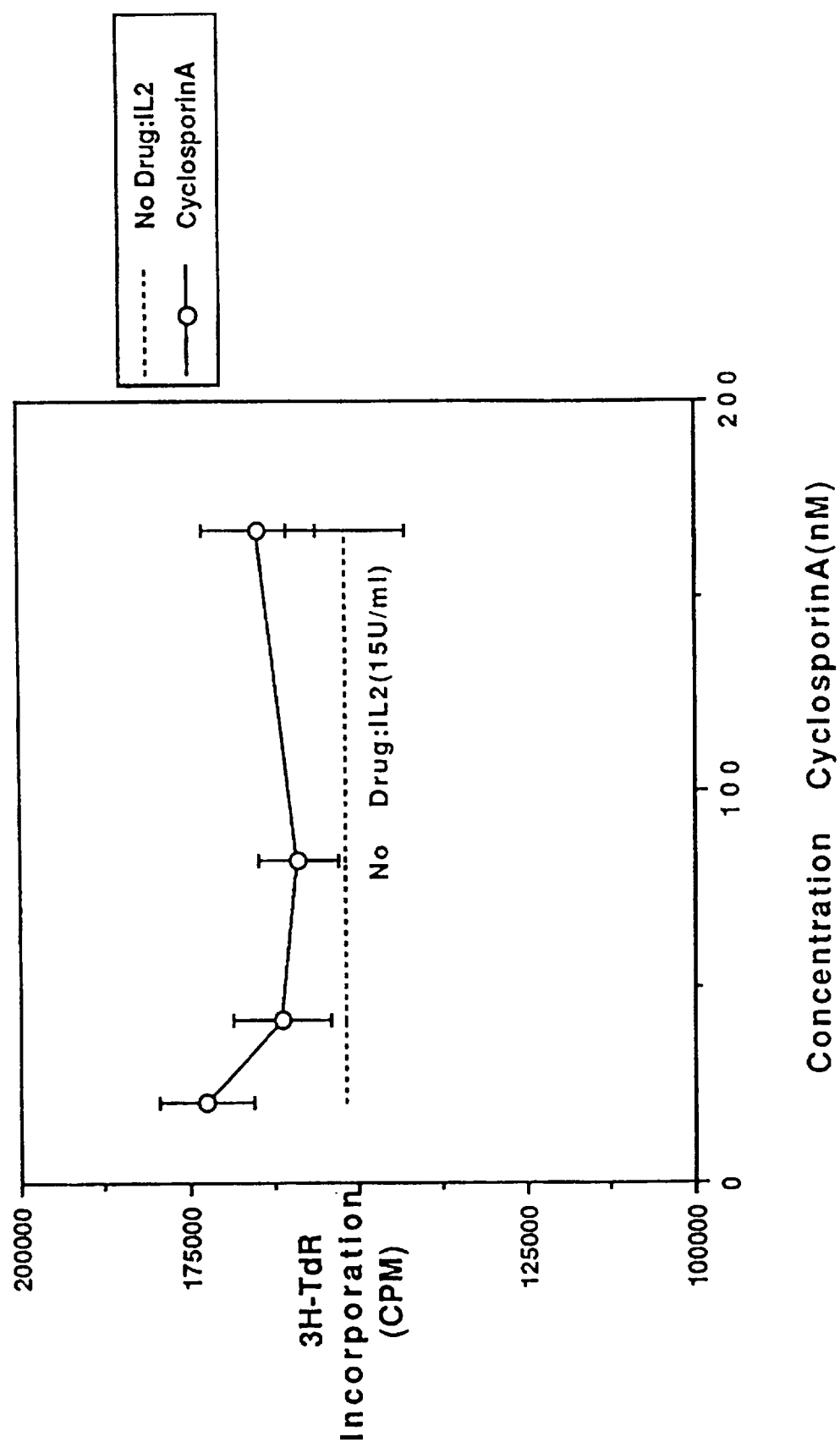

This example illustrates an investigation of proliferation of murine thymocytes co-stimulated with ConA and IL-2 using a procedure akin to the procedure in Example 23. In another related assay, inhibitory effects on CT6 cell proliferation is examined. CT6 cells are a murine IL-2 dependent, cytotoxic T cell line that proliferate in response to murine IL-2 (15 U/ml). FIGS. 21A, 21B, 21C and 21D illustrate experimental results of both compound no. 35 and CsA in each assay. FIG. 21A illustrates the extent of inhibitory activity of compound no. 35 on murine thymocyte co-stimulation and FIG. 21B shows comparative inhibitory activity of CsA. Both compound no. 35 and CsA exhibit significant inhibition of thymocyte proliferation with $IC_{50}$ values in the low micromolar and nanomolar ranges, respectively. FIGS. 21C and 21D illustrate inhibitory effects of compound no. 35 and CsA, respectively. Both compound no. 35 and CsA exhibited no activity in this assay, indicating neither inhibits IL-2-induced proliferation of cytotoxic CT6 cells.

EXAMPLE 37

Figure 22:
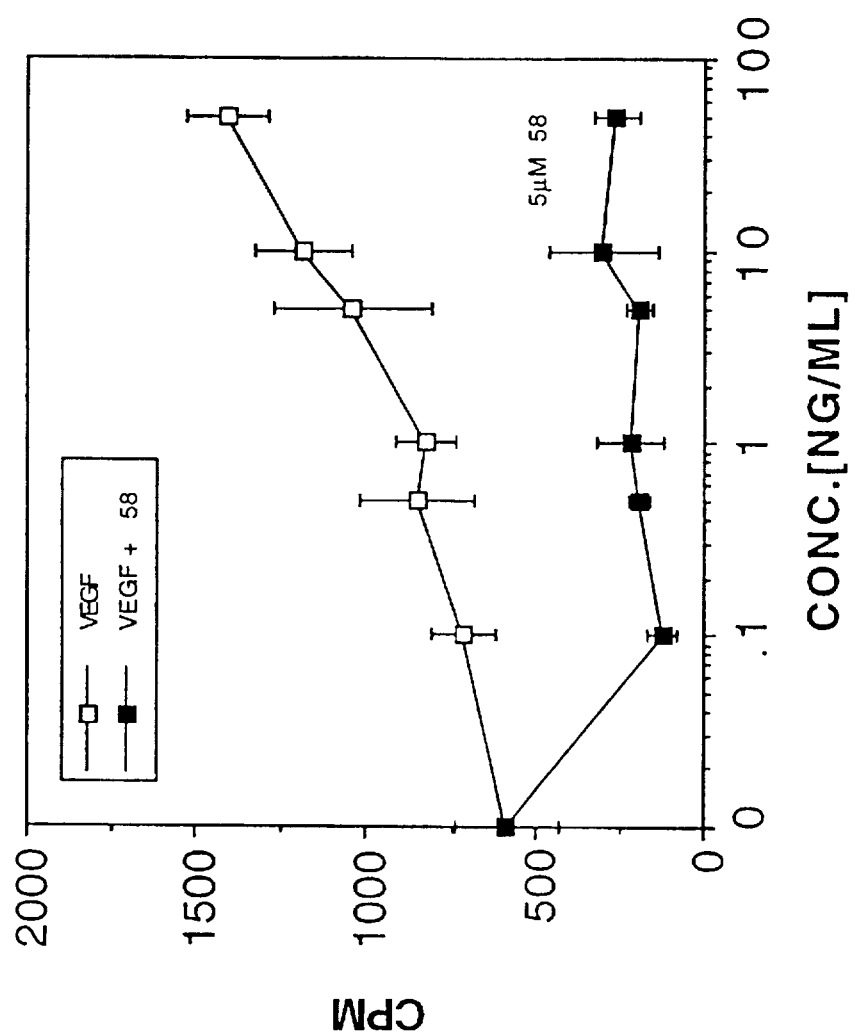
FIG. 22 reports activity results for compound no. 58 on vascular endothelial growth factor (VEGF)-induced proliferation in a human umbilical vein endothelial cell line (HUVEC).

This example illustrates an investigation of inhibitory effects of compound no. 58 on Vascular Endothelial Growth Factor (VEGF)-induced proliferation in a human umbilical vein endothelial cell line (HUVEC). In this assay procedure, cells were grown in reduced serum (0.5% fetal calf serum) for 24 hours prior to stimulating with various concentrations of VEGF. VEGF has been shown to be important in tumor cell-mediated angiogenesis. Compound no. 58, at 5 µM, inhibited VEGF-induced proliferation at all concentrations of VEGF tested, as shown in FIG. 22.

EXAMPLE 38

Figure 23:
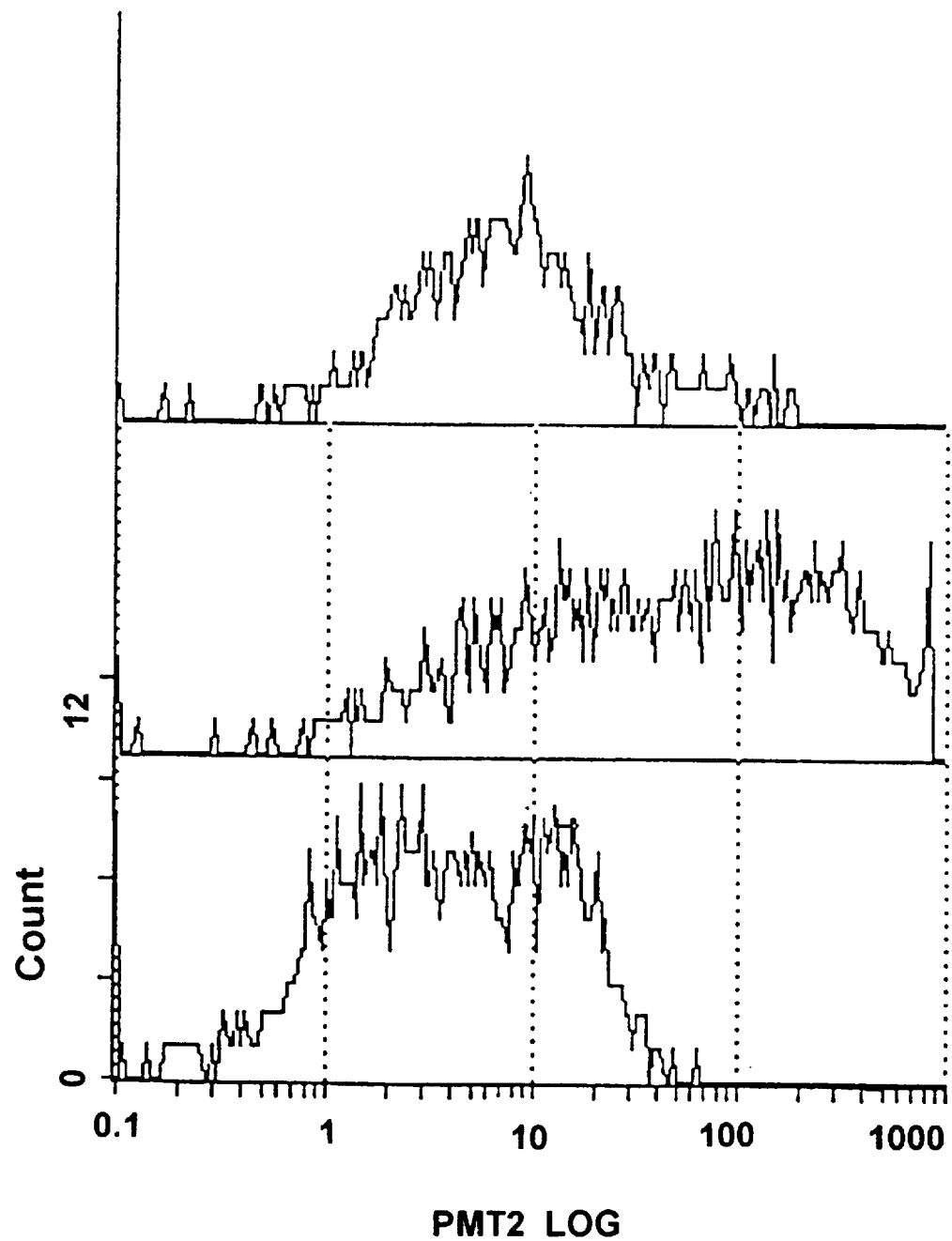
FIG. 23 is a series of frequency histograms obtained from flow cytometric analysis of HUVEC cells.

This example illustrates an investigation of inhibition of vascular cell adhesion molecule (VCAM) expression on HUVEC by compound no. 58. VCAM expression by endothelial cells is an early event in the pathogenesis of atherogenesis and multiple sclerosis, among other various autoimmune diseases. FIG. 23 is a series of frequency histograms obtained in this exemplary assay. The top panel shows a frequency histogram obtained from flow cytometric analysis of HUVEC cells stained with an antibody directed against VCAM and a second stem goat anti-mouse-FITC antibody. In the absence of TNFα, VCAM expression on HUVEC was at a very low level. The middle panel shows a frequency histogram of cells stimulated with TNFα for 6 hours prior to analyzing by flow cytometry. The average increase in cell fluorescence was approximately 10-fold. The bottom panel is a frequency histogram of TNFα -stimulated cells in the presence of compound no 58. Presence of compound reduced mean fluorescence by a factor of 8, compared with mean fluorescence from TNFα -stimulated cells in the absence of compound no. 58.

EXAMPLE 39

Figure 24:
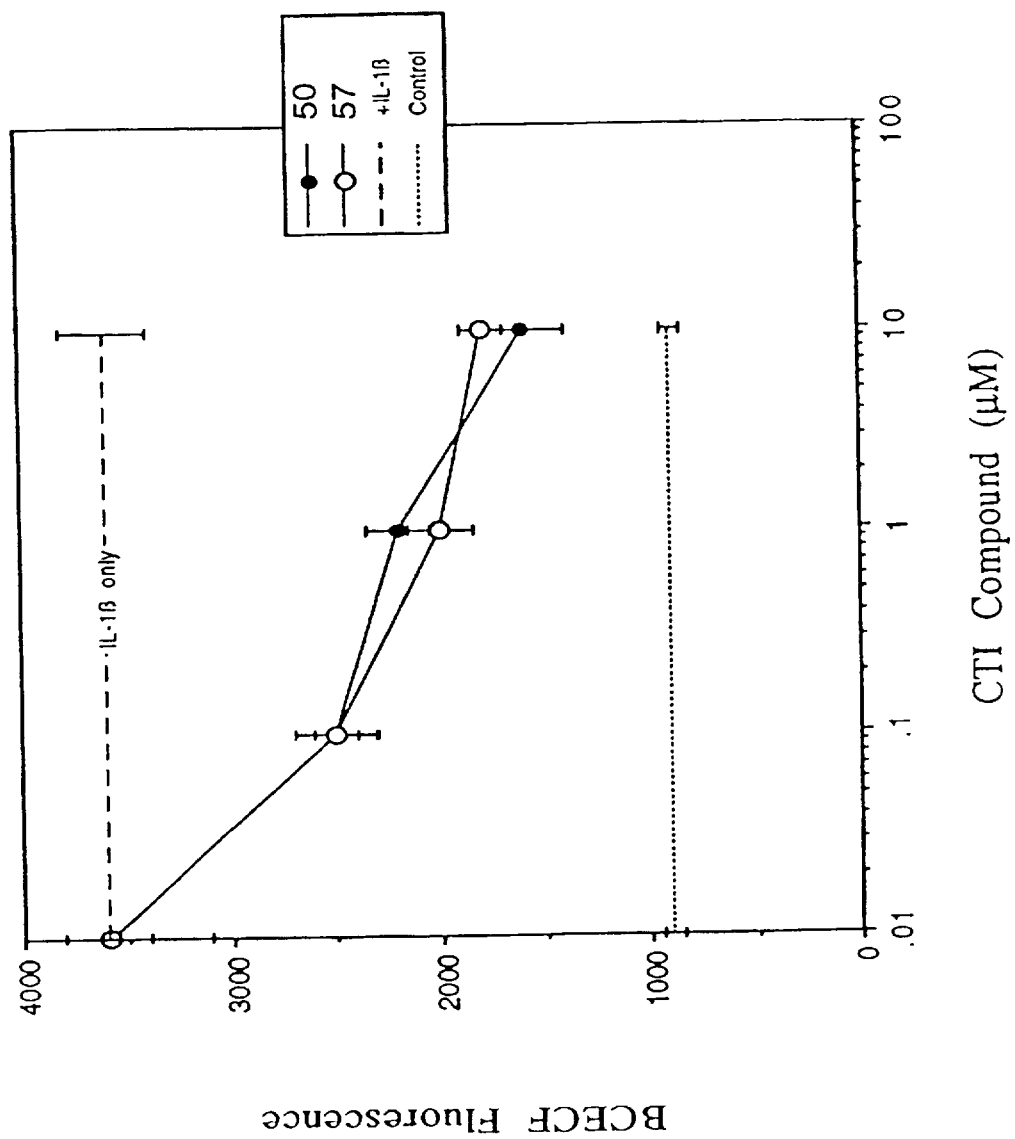
FIG. 24 illustrates inhibitive results obtained for compounds nos. 50 and 57 on THP-1 cell adhesion to IL-1β-activated HUVEC.

This example illustrates inhibitive activity of compounds nos. 50 and 57 on THP-1 cell adhesion to IL-1β-activated HUVEC. In an investigative assay, HUVEC were stimulated with IL-1β (10 ng/ml), both in the absence and presence of varying concentrations of drugs for 8 hours in a 96-well microtiter plate. In the wellplate, human monocytic leukemia cell line THP-1 cells were added at 50,000 cells per well. The THP-1 cells were pre-incubated with BCECF, a fluorescence dye that can be used to measure cell number using a fluorescence plate reader. After 10 minutes at 37° C., the microtiter plate was inverted and spun at 900 rpm. The remaining adhering THP-1 cells were then analyzed. As shown in FIG. 24, non-stimulated background adherence was approximately 1500 relative units, increasing to approximately 6500 under TNFα stimulation. The compounds tested significantly inhibited THP-1 adhesion, ever at low concentrations.

EXAMPLE 40

Figure 25A:
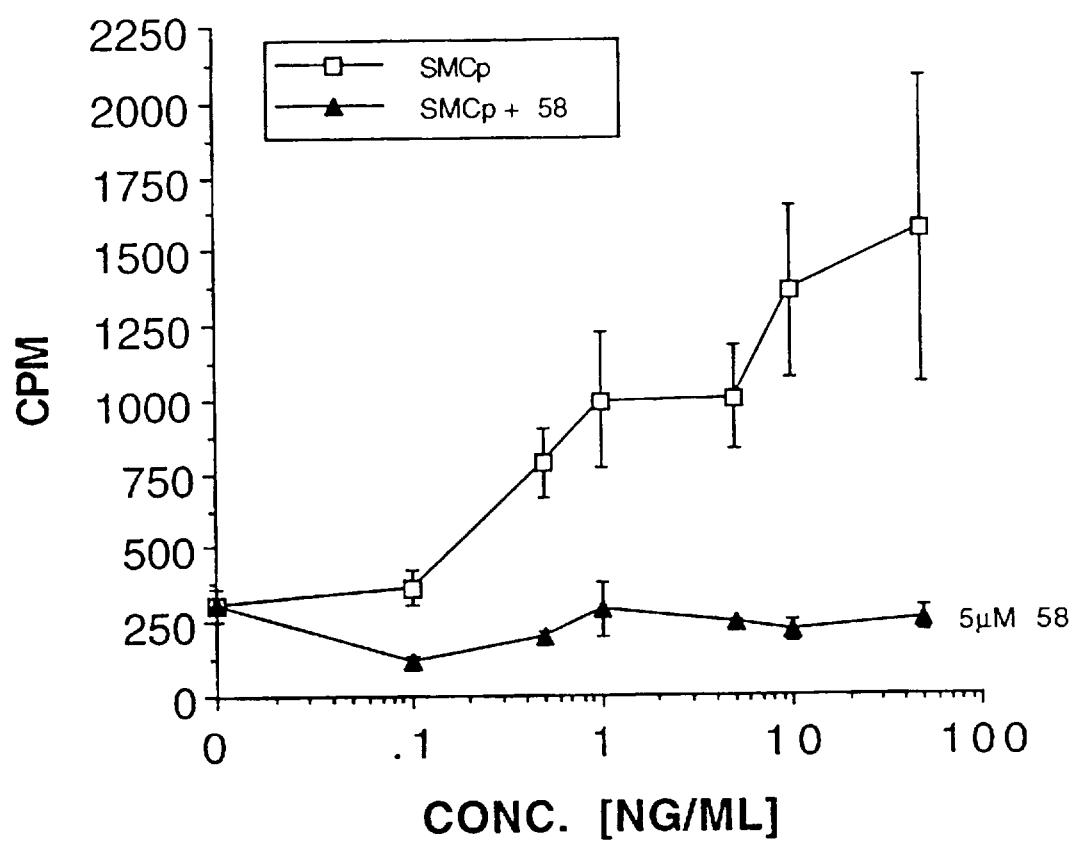
FIGS. 25A and 25B show the effects of compound no. 58 on aFGF and bFGF-induced proliferation in pulmonary smooth muscle cell.
Figure 25B:
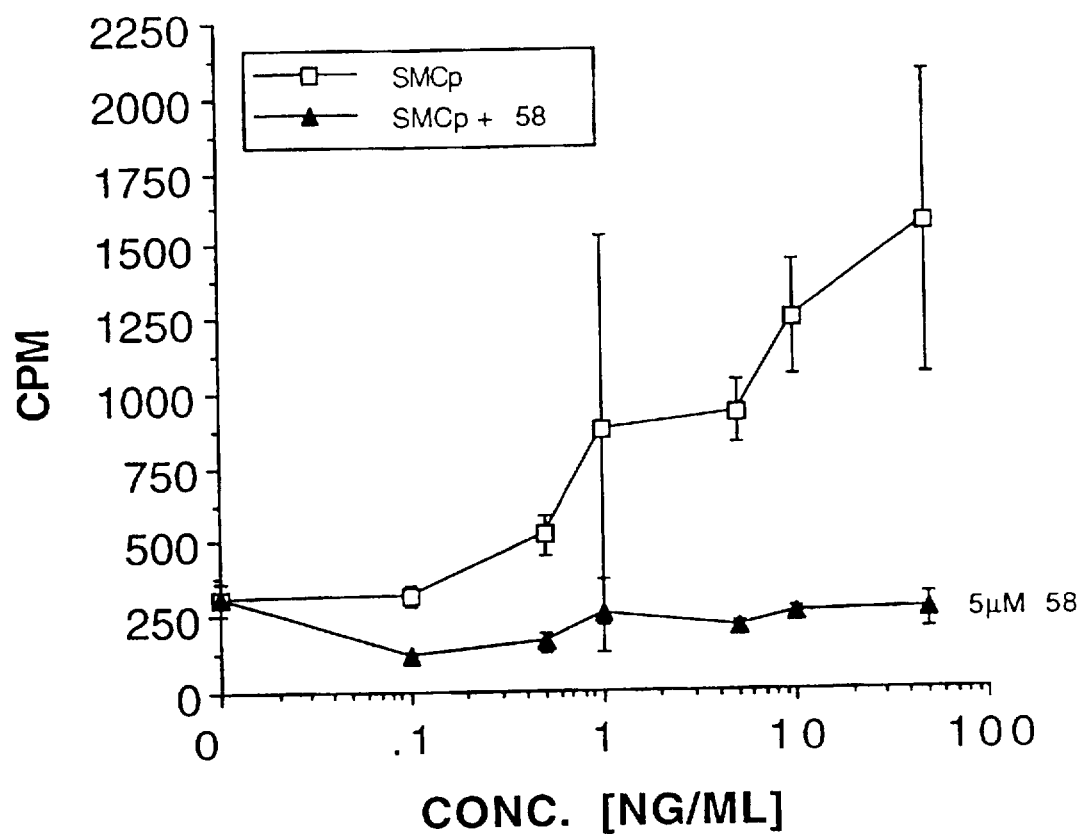

This example shows the inhibitory effect of compound no 58 on either aFGF or bFGF-induced proliferation in human pulmonary smooth muscle cells. Cells were grown in reduced serum (0.5% fetal calf serum) for 24 hours prior to stimulating with various concentrations of PDGF. Cells, stimulated with either aFGF or bFGF, were analyzed in the presence and absence of compound no. 58 (5 μM). Assay results are reported in FIGS. 25A and 25B (aFGF and bFGF, respectively). As shown in the results, compound no. 58 was a potent inhibitor of both aFGF and bFGF-induced proliferation in this cell type, this pulmonary smooth muscle cell being representative of other cell types examined. No toxic effect of compound no. 58 was observed in this assay.

EXAMPLE 41

Figure 26A:
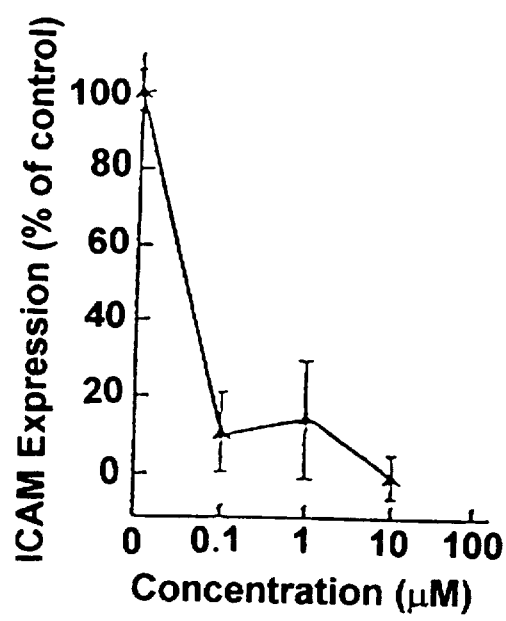
FIGS. 26A and 26B illustrate inhibition of VCAM-1 or ICAM-1 expression, respectively, in HUVEC activated by TNFα by compound no. 58.
Figure 26B:
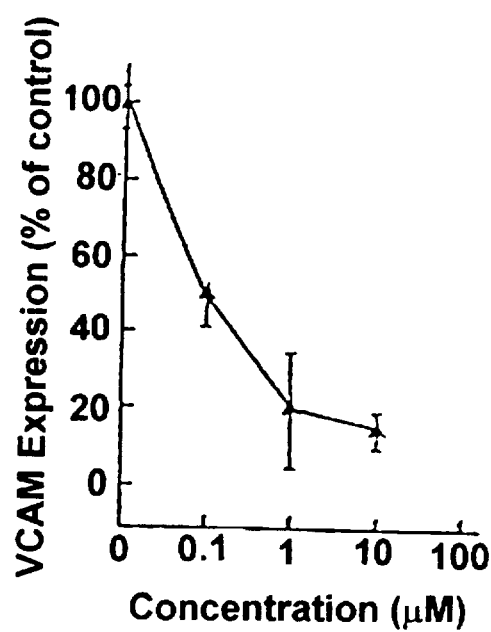

This example illustrates an ability of compound no. 58 to inhibit VCAM-1 or ICAM-1 expression in HUVEC stimulated by TNFα. FIGS. 26A and 26B report data obtained for compound no. 58 in this assay. These data show that at concentrations as little as 0.1 μM of compound no. 58, ICAM-1 expression is inhibited by more than 80% (i.e., ICAM-1 expression is 20% of a control value). Procedurally this assay is nearly identical to the assay procedure used in Example 38. In this assay, cells were stimulated for 8 hours in the presence or absence of compounds and stained with fluorescent antibodies to VCAM-1 or ICAM-1. The resulting ICAM-1 or VCAM-1 expression was analyzed by flow cytometry.

EXAMPLE 42

Figure 27:
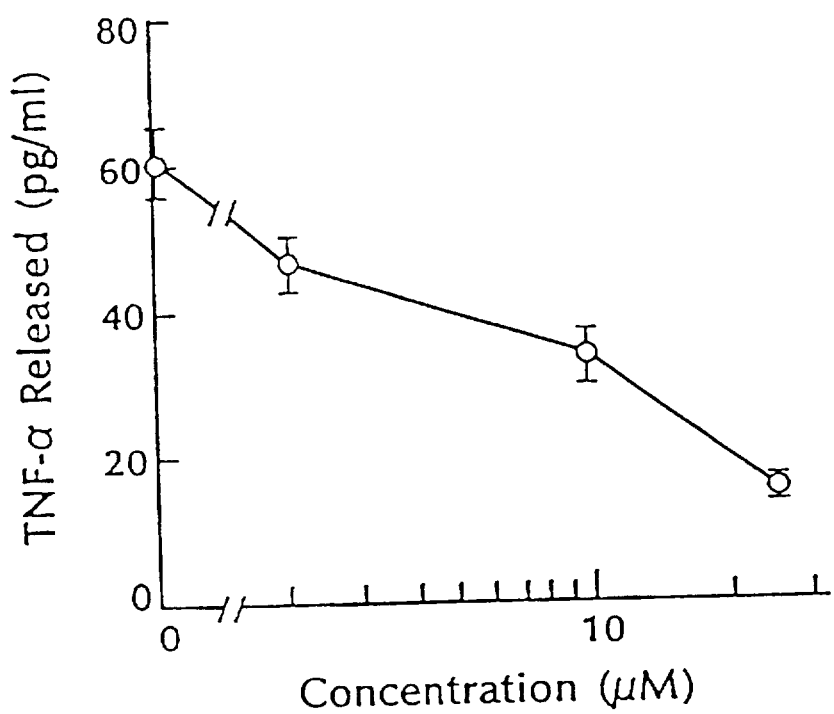
FIG. 27 illustrates that compound no. 58 inhibits TNFα release by compound no. 58 using a human whole blood ex vivo assay.

FIG. 27 illustrates that compound no. 58 inhibited TNFα release using a human whole blood ex vivo assay. Using a conventional screening procedure, human whole blood was stimulated with mouse TNFα and human IL-1α with or without various concentrations of compound no. 58. After 6 hours, the plasma was analyzed for human TNFα levels using a commercial ELISA. Results are reported in FIG. 27.

EXAMPLE 43

This example illustrates conclusive data, compiled from various in vitro and in vivo assay results that the compounds, as represented by a species of the disclosed genus (compound no. 50) are anti-cancer therapeutics.

Generally, growth and spread of malignant tumors (rapid cell growth, uncontrolled by normal regulatory mechanisms) characterize cancer diseases. Precise causes of cancer remain unknown. Preclinical and clinical trials with the compounds indicate that cancer cell growth may be regulated through the second messenger pathway. Oncogenic mutations result in abnormal continuous stimulation of the pathway, leading to unregulated and undifferentiated growth (i.e., malignant transformation). Cancer cells metastasize (i.e., break through blood vessels and travel to distant body sites) and secrete enzymes called metalloproteases, which "break down" blood vessel walls, allowing the cancer cells to enter the bloodstream and form remote tumors (proteolysis). One such metalloprotease is Type IV collagenase. In addition, tumor cell adhesion receptors (integrins) effect attachment—apparently necessary for tumor residence in organs—of tumor cells to blood vessel walls and normal organs. Cancer cells also secrete certain proteins, such as bFGF, that stimulate new blood vessel development (angiogenesis or neovascularization), these new blood vessels supplying nutrients fostering malignant tumor growth. Resent research results suggest that the second messenger pathway appears integral to Type IV collogenase production, adhesion receptors expression and bFGF secretion.

Unlike conventional anti-cancer therapies, the compounds, by inhibiting the second messenger pathway, decrease: tumor cell growth by blocking oncogene-induced events; metastatic potential by blocking metalloprotease production; tumor adhesion to normal organs by blocking adhesion receptor expression; and a tumor's ability to induce nutrient-carrying blood vessel formation by blocking bFGF or other tumor-dependent growth factor signaling.

Figure 28:
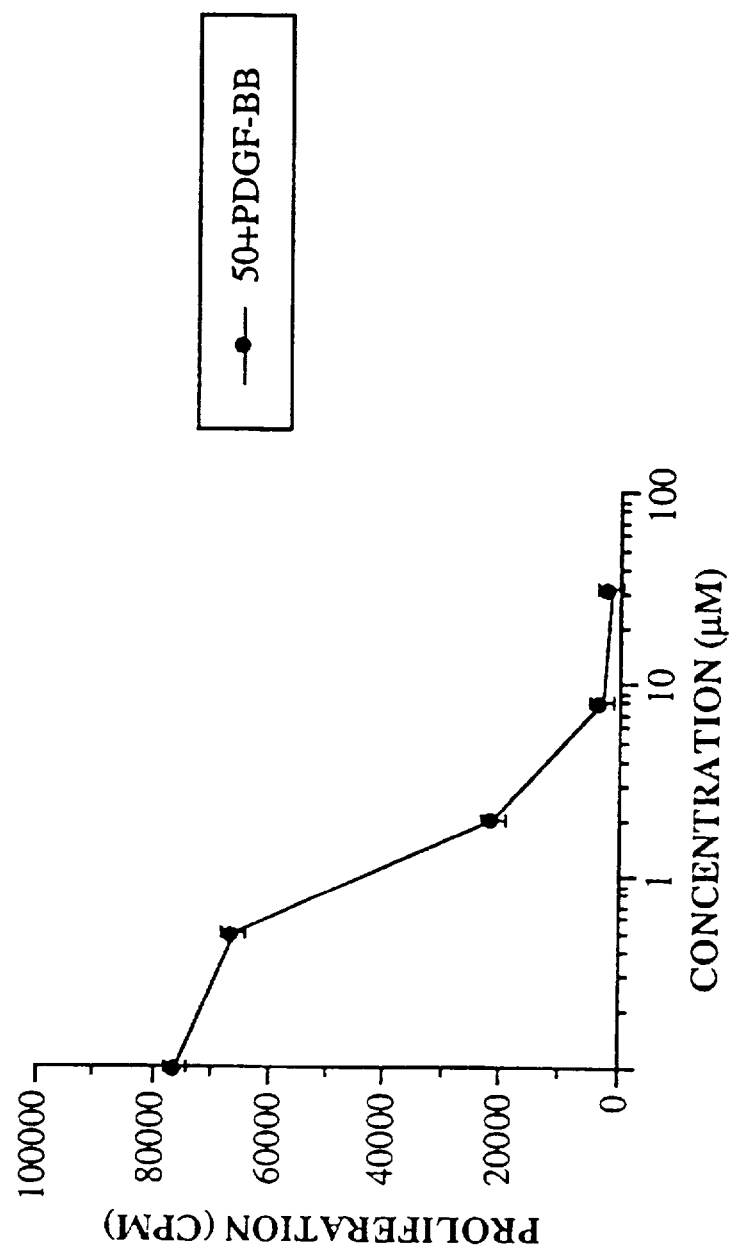
FIG. 28 reports results for compound no. 50 in the PDGF-induced proliferation of Balb/3T3 cells.

The compounds exhibit anti-cancer properties against several malignant conditions, including lung, breast and colon cancer, and unlike conventional cancer chemotherapy, in vitro, the compounds are non-toxic to normal cells at concentrations lethal to cancer cells. In vitro data obtained for representative compound no. 50 include the following:

Results obtained for compound no. 50 in the PDGF-induced proliferation of Balb/3T3 cells (Example 32), reported in FIG. 28, illustrate the inhibitive properties of this compound on proliferation induced by PDGF, representing significant inhibition at concentrations as low as 2 μM. This ability to block proliferation (representative of an oncogene-induced event in tumor-cell growth) suggests that the compounds, specifically compound no. 50, are capable of reducing tumor cell growth by blocking oncogene-induced events.

Figure 29:
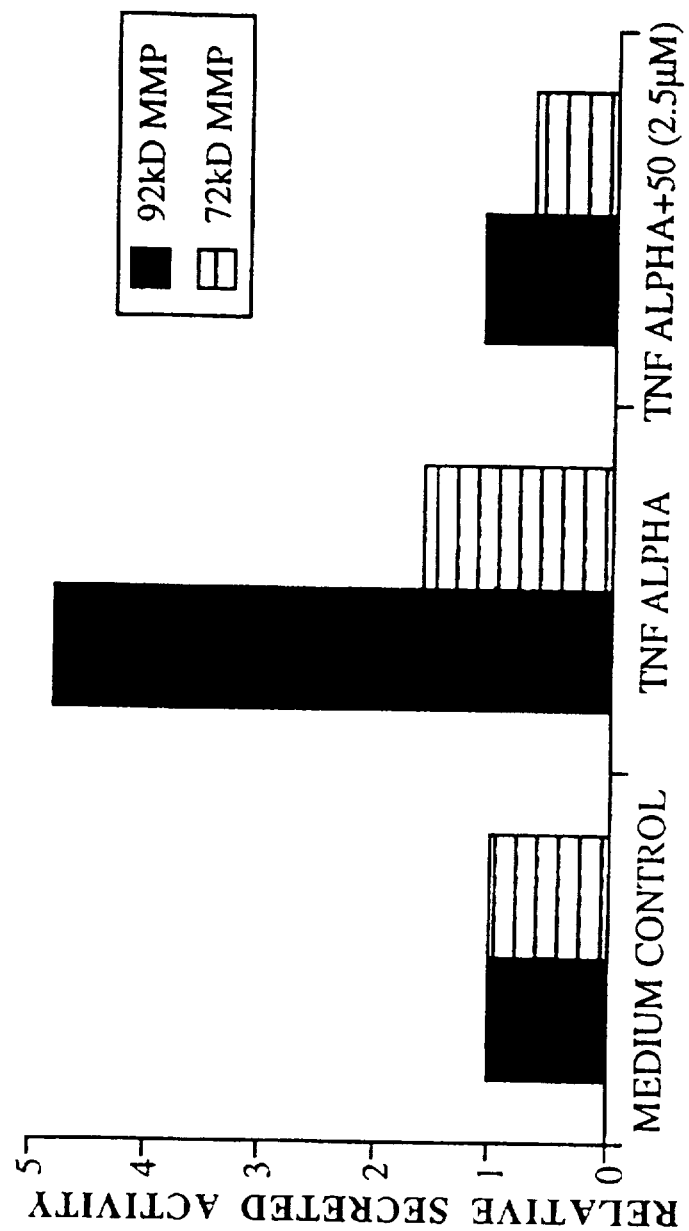
FIG. 29 shows that TNFα substantially increased expression of the 92 kD matrix metalloprotease (MMP) and moderately increased production of the 72 kD MMP and that the presence of compound no. 50 blocked the TNFα-stimulated expression of each MMP.

Another assay measures an ability of the compounds, as represented by compound no. 50, to inhibit metalloproteinase production in cancer cells. In the assay protocol, THP-1 human leukemia cells ($1-2 \times 10^6/35$ mm dish) were plated in RPMI medium with 0.5% serum. Compound no. 50 was added at 2.5 μM. Following incubation for 1 hour, TNFα was added and incubated for 18 hours. The supernatants from control and treated plates were collected and protease activity was determined in gelatin gels (zymogram) after electrophoretic protein separation. As shown in FIG. 29, TNFα substantially increased expression of the 92 kD matrix metalloprotease (MMP) and moderately increased production of the 72 kD MMP. The presence of compound no. 50 blocked the TNFα -stimulated expression of both the 92 and 72 kD MMPs. Compound no. 50, representative of compounds of the invention, is capable of substantially reducing metastatic potential of cancer cells by blocking metalloprotease production.

Other in vitro and in vivo evidence of this potent activity of the compounds is represented in the following experimental results.

Figure 30:
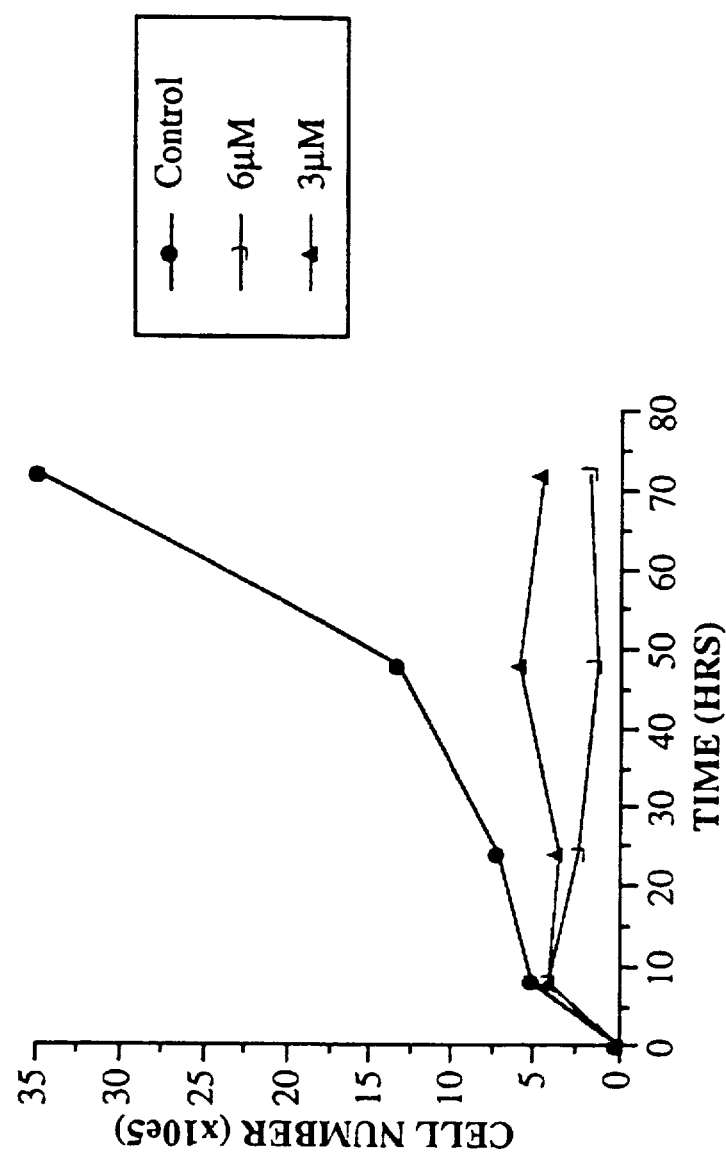
FIG. 30 shows anti-proliferative activity and FIG. 31 reports anti-clonogenicity activity of compound no. 50 with HT-29 cells.
Figure 31:
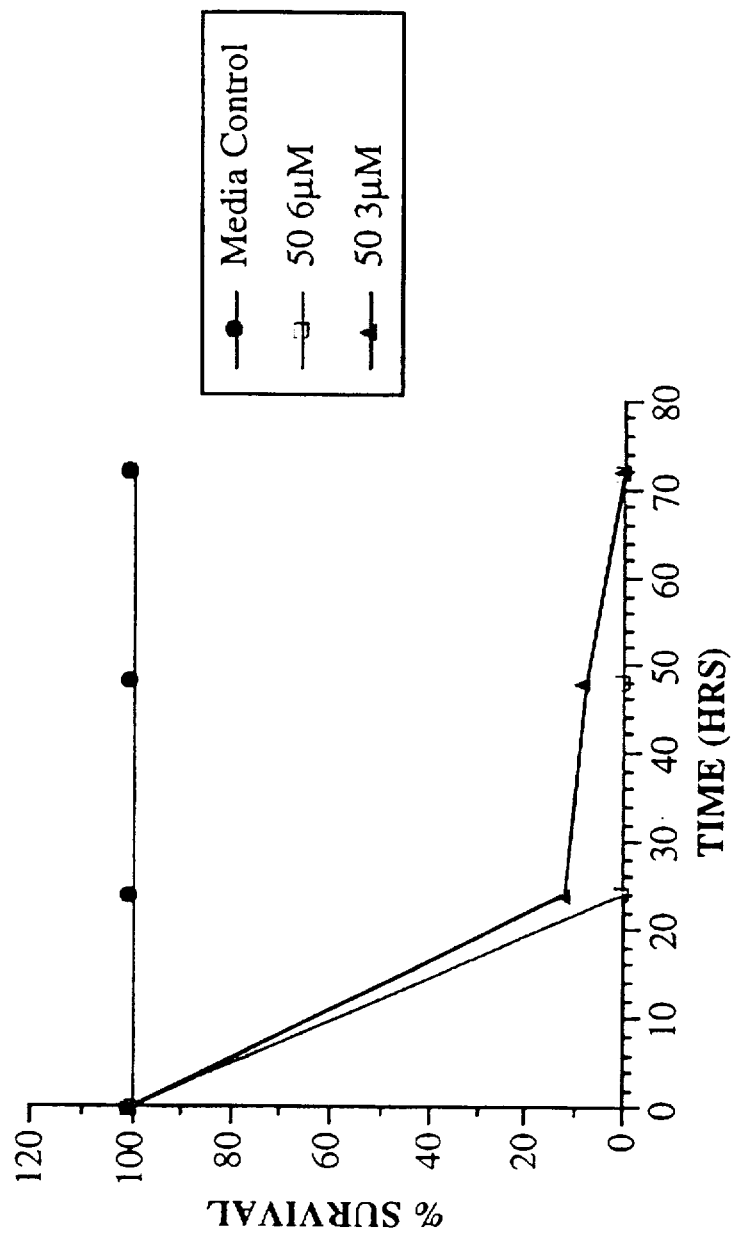

FIGS. 30 shows anti-proliferative activity and FIG. 31 reports anti-clonogenicity activity of compound no. 50 with HT-29 cells. HT-29 cells ($1 \times 10^5$ cells/35 mm dish) were plated in McCoy's medium with 10% serum and incubated overnight. Concentrations of 3 and 6 μM of compound no. 50 were added and viable cell counts made at the times shown. For clonogenic assays, treated and control cells (300/plate) were plated and allowed to grow colonies. After 7 days the colonies were fixed and counted. The values in FIG. 31 are the means of 3 plates.

Figure 32:
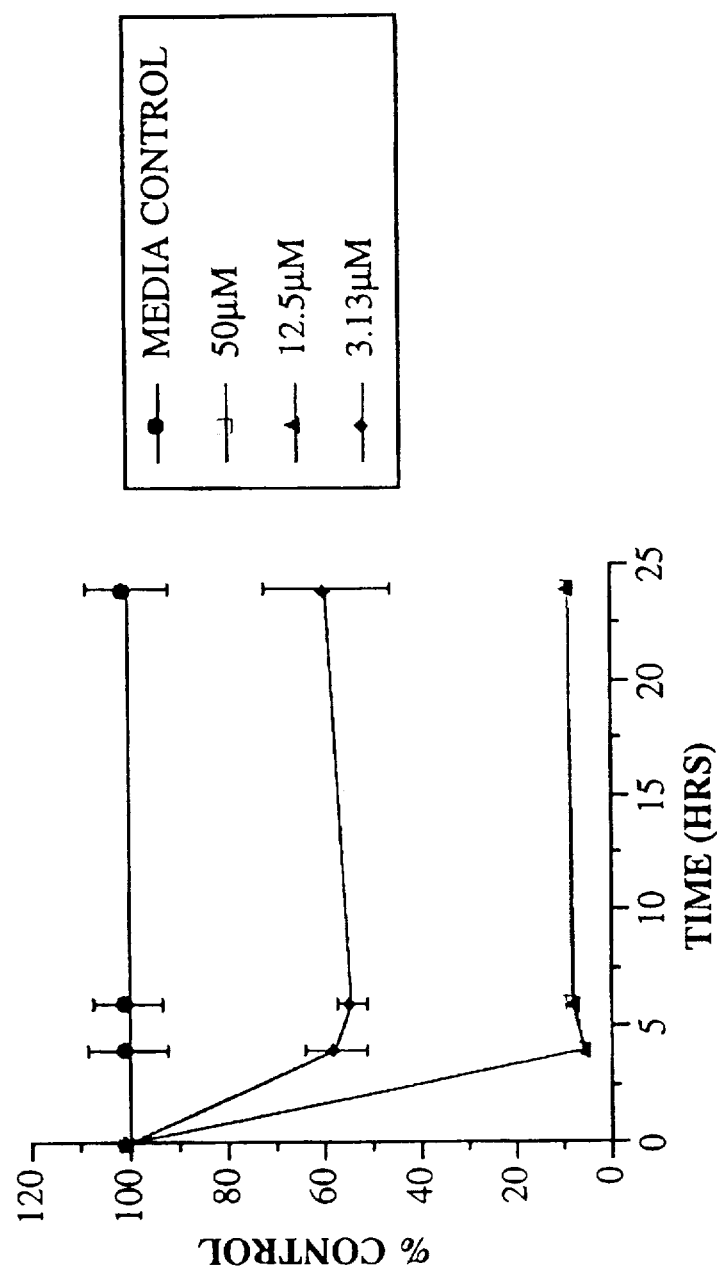
FIGS. 32 and 33 illustrate cytotoxicity and concentration dependence of compound no. 50 against 3LL cells (Lewis lung carcinoma).
Figure 33:
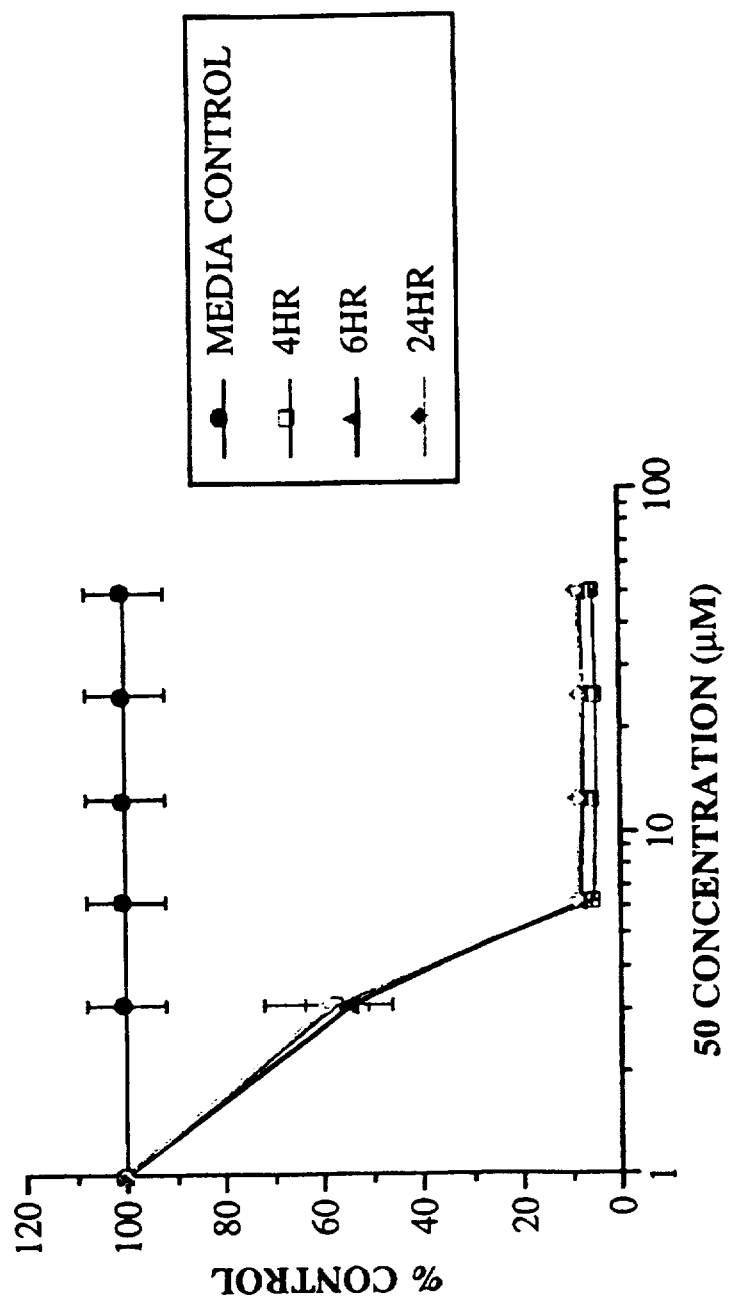

FIGS. 32 and 33 illustrate cytotoxicity and concentration dependence of compound no. 50 against 3LL cells. 3LL cells ($3 \times 10^3$ cells/well) were plated and incubated overnight in RPMI medium containing 10% serum. Compound no. 50 was added at different concentrations and cell number determined at various time points by a vital dye uptake method. The values shown are triplicate of wells.

Figure 34:
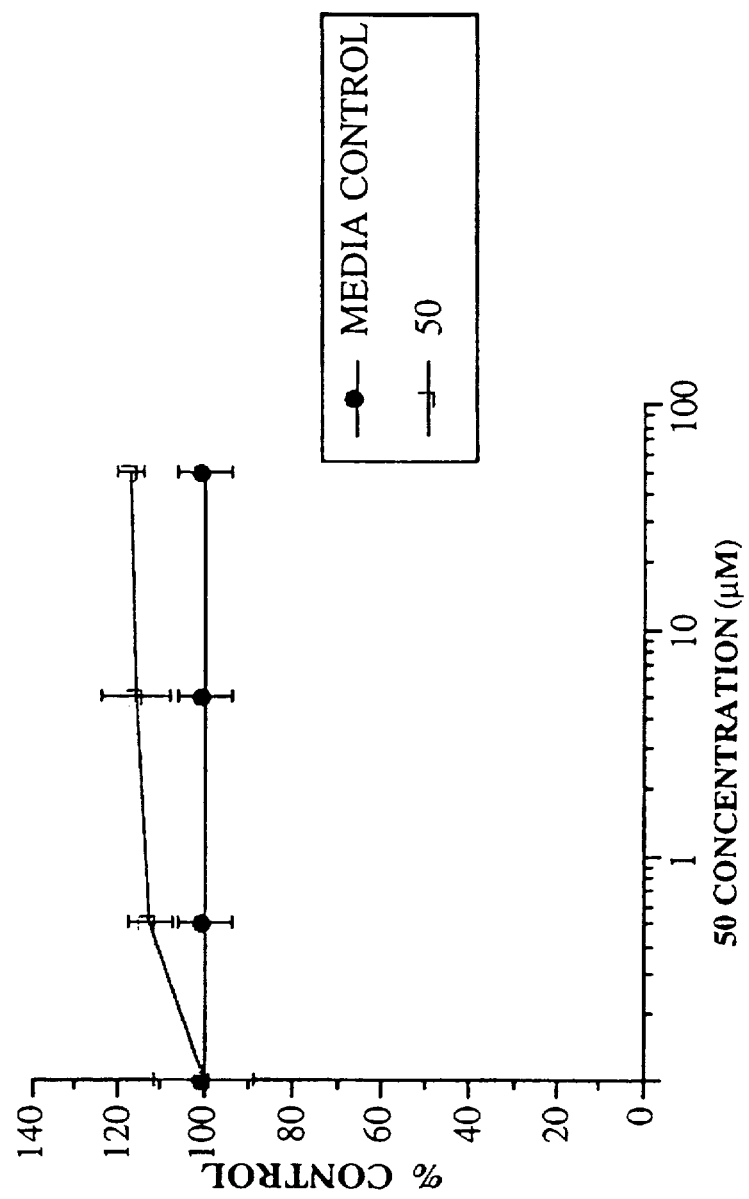
FIG. 34 shows that compound no. 50 lacks cytotoxic activity in normal human bone marrow stromal cells.

FIG. 34 shows that compound no. 50, even at much higher concentrations than shown having cytotoxicity to tumor cells, lacks cytotoxic activity in normal human bone marrow stromal cells. Human bone marrow stromal cells ($1 \times 10^4$ cells/well) were plated in 96 well plates in McCoy's medium with serum and incubated overnight. Different dilutions of compound no. 50 were added and viable cell counts made by vital dye uptake.

Figure 35:
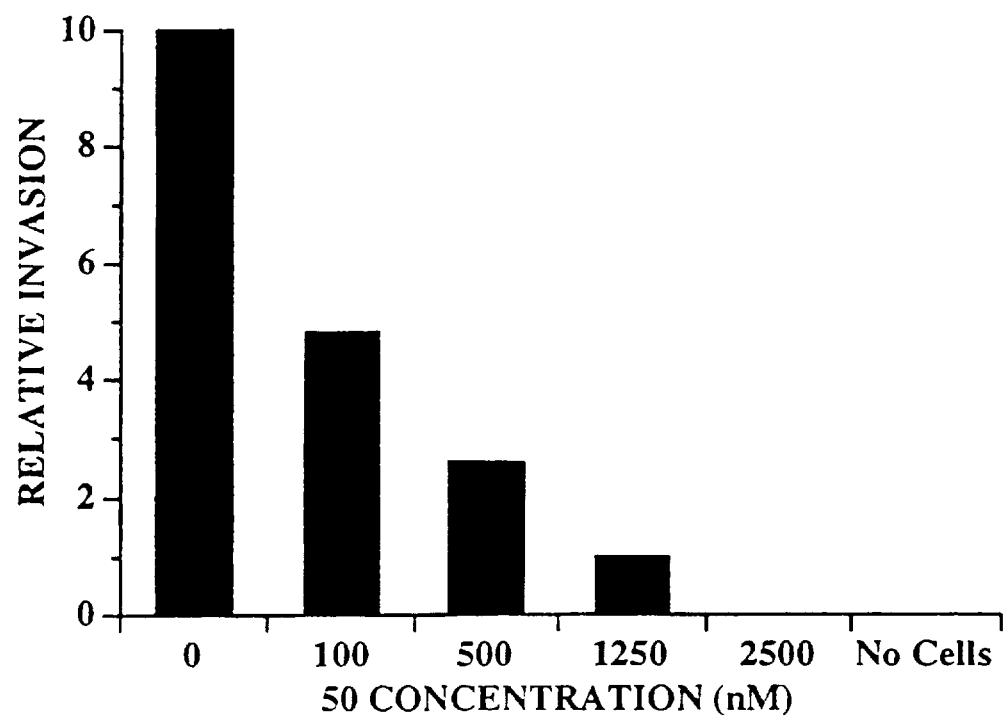
FIGS. 35 and 36 show the effects of compound no. 50 on matrigel invasion and viability in 3LL cells.
Figure 36:
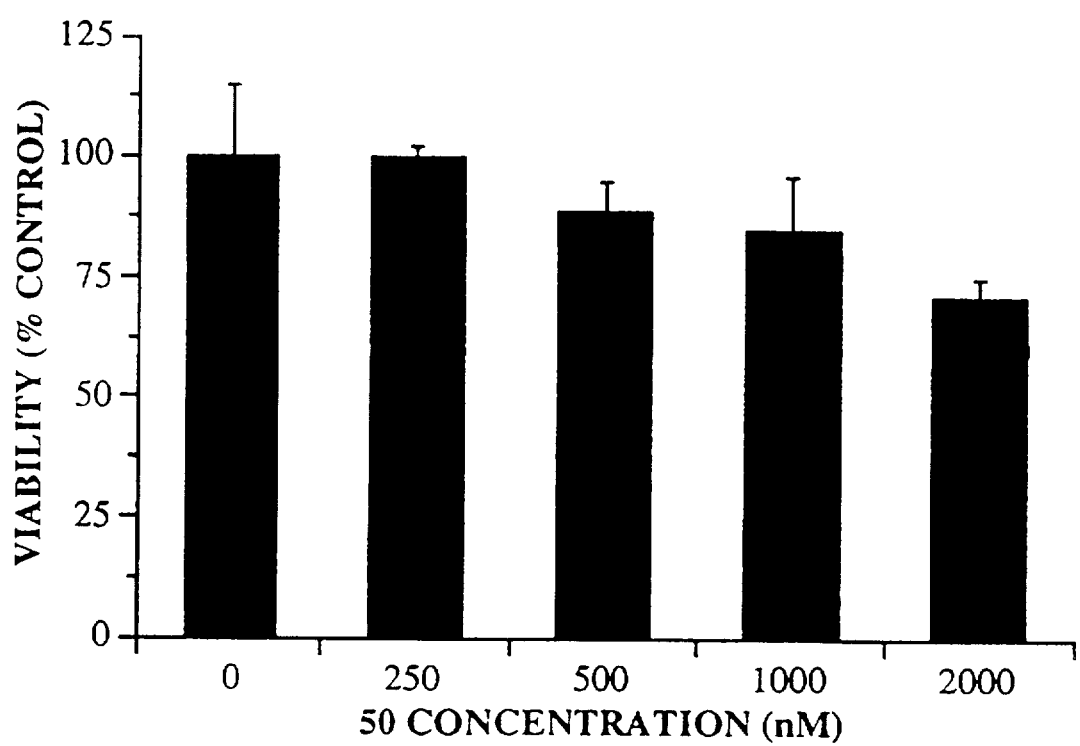

FIGS. 35 and 36 show the effects of compound no. 50 on matrigel invasion and viability in 3LL cells. 3LL cells ($4.5 \times 10^5$ cells/well) were plated into the inner membrane of matrigel chambers. Different concentrations of compound no. 50 were added to the chamber and incubated for 48 hours at 37° C. The cells on top of the membrane were removed and cells that migrated to the bottom were stained with Diff Quick Solutions and scored for relative invasion. The effect of compound no. 50 on viability of 3LL cells at different concentrations was determined separately.

Figure 37:
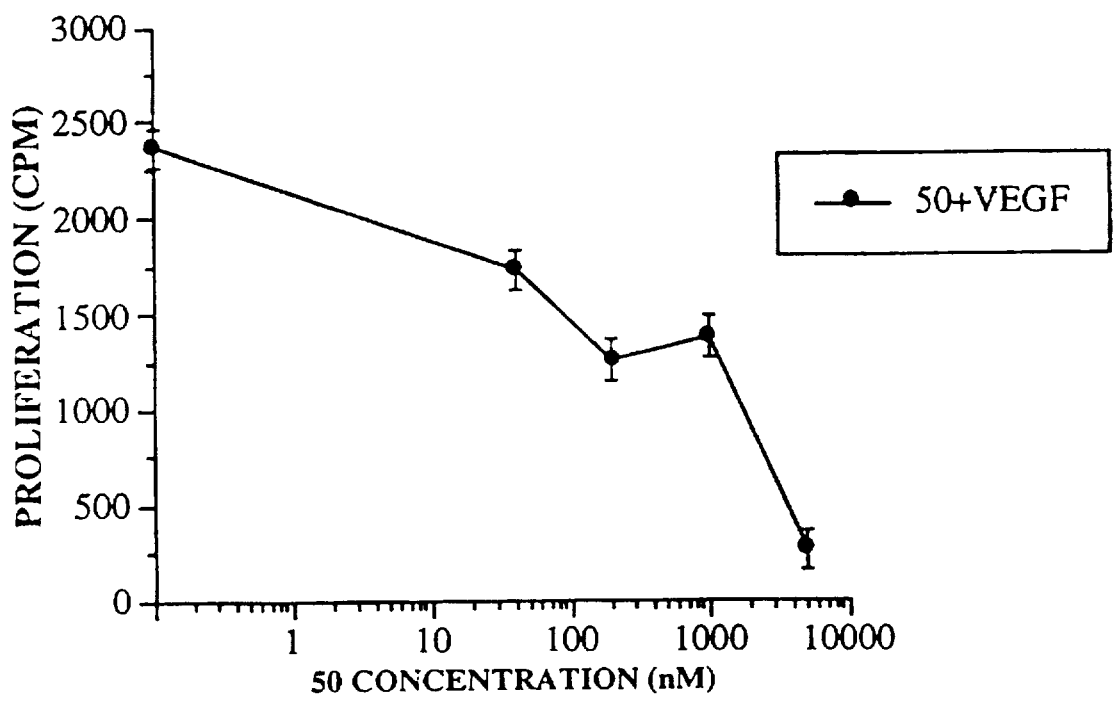
FIG. 37 illustrates VEGF-induced proliferation of HUVEC as a predictive adhesion assay.

FIG. 37 illustrates VEGF induced proliferation of HUVEC as a predictive adhesion assay. HUVEC were plated in EBM medium with serum and allowed to grow for 4 days. Different dilutions of compound no. 50 were added to the plates, followed by VEGF (50 ng/ml) along with tritiated thymidine (1 mCi/mi). Proliferation was measured in quadruplicate and these data show the effect of compound no. 50 to inhibit adhesion.

Figure 38:
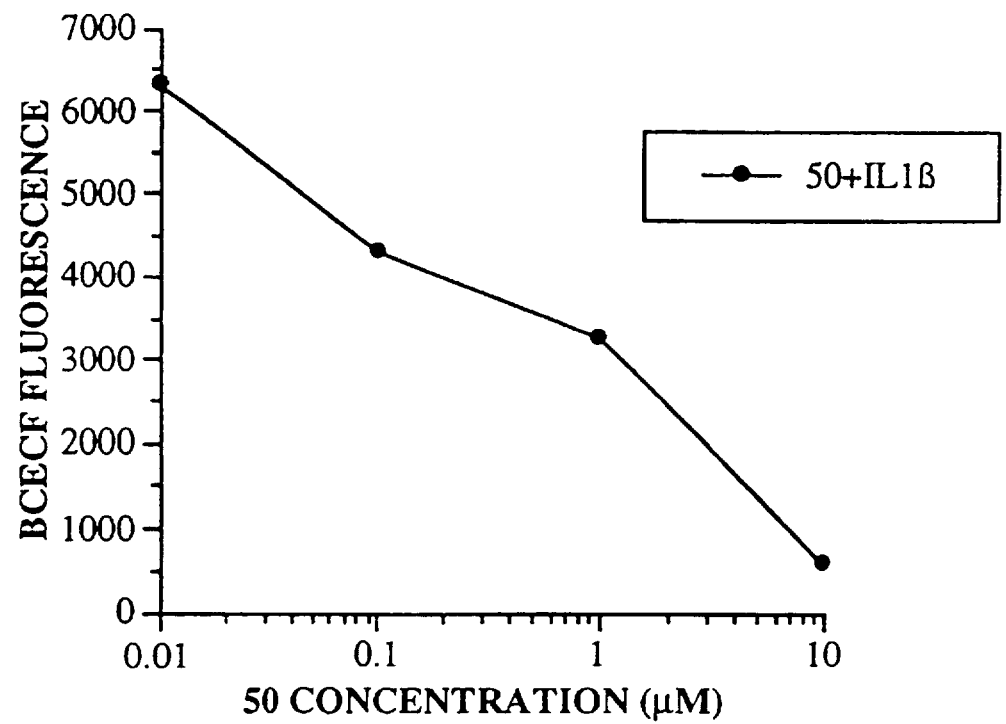
FIG. 38 shows the effect of compound no. 50 on THP-1 adherence to IL-1β-stimulated HUVEC.

FIG. 38 shows the effect of compound no. 50 on THP-1 adherence to IL-1β-stimulated HUVEC. HUVEC ($4 \times 10^3$ cells/well) were plated in RPMI medium with 10% serum and incubated for 48 hours. Different concentrations of compound no. 50 were added and incubated for 1 hour. IL-1β (15 ng/ml) was added and incubated for 6 hours. Exponential growth THP-1 tumor cells, prestained with dye BCECF, were added ($1.5 \times 10^5$ cells/well) and allowed to adhere for 20 minutes. The number of adhering tumor cells was determined after washing to remove non-adherent cells.

Figure 39:
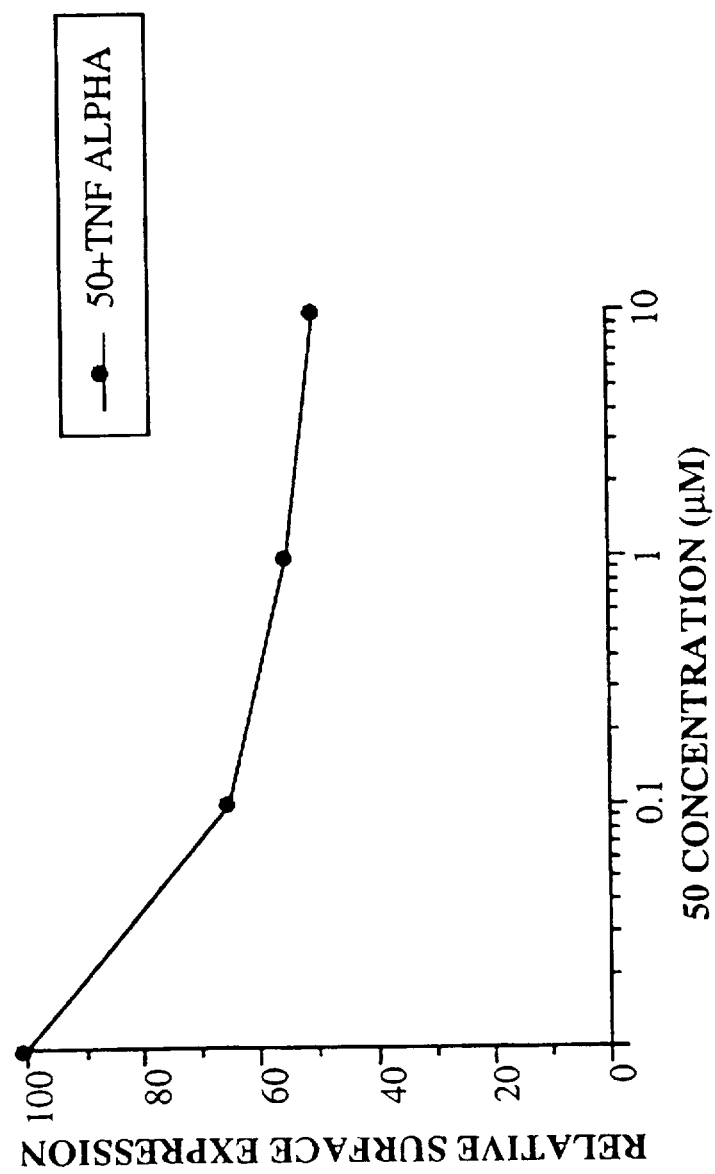
FIG. 39 illustrates the effect of compound no. 50 on VCAM-1 surface expression of TNFα-stimulated HUVEC.

FIG. 39 illustrates the effect of compound no. 50 on VCAM-1 surface expression of TNFα -stimulated HUVEC. This assay is a predictive model of adhesion. HUVECs grew to 90% confluence in 6 well plates in RPMI medium with 10% serum. Compound no. 50 was added at different concentrations and incubated for 30 minutes. TNFα (20 ng/mi) was added and the cells were incubated for 5 hours. The cells were collected and the amount of VCAM-1 determined by indirect immunostaining followed by fluorescence activated cell sorter (FACS) analysis. Mean fluorescent intensity of TNFα-stimulated cells was normalized to 100% with drug-treated samples expressed as a percent of control.

Figure 40:
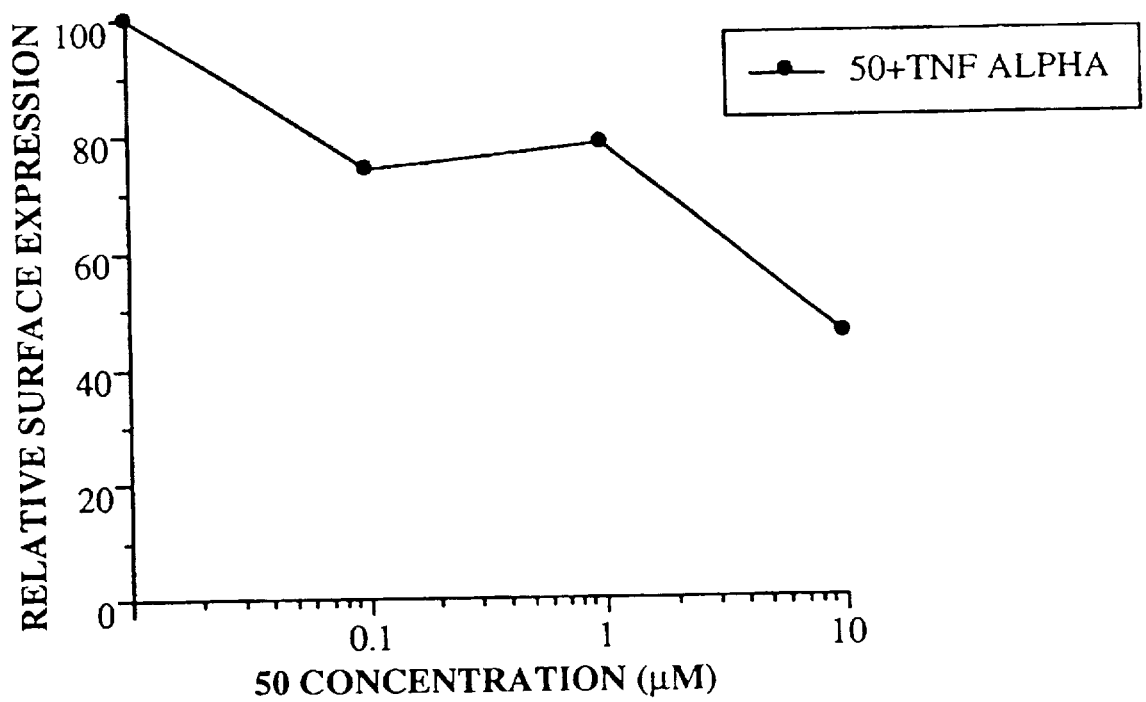
FIG. 40 illustrates the effect of compound no. 50 on ICAM-1 surface expression of TNFα-stimulated HUVEC.

FIG. 40 illustrates the effect of compound no. 50 on ICAM-1 surface expression of TNFα-stimulated HUVEC. This assay is a predictive model of adhesion. The procedures followed were the same as used in the immediately preceding assay, except that the cells were stained with an ICAM-1 antibody.

Figure 41C:
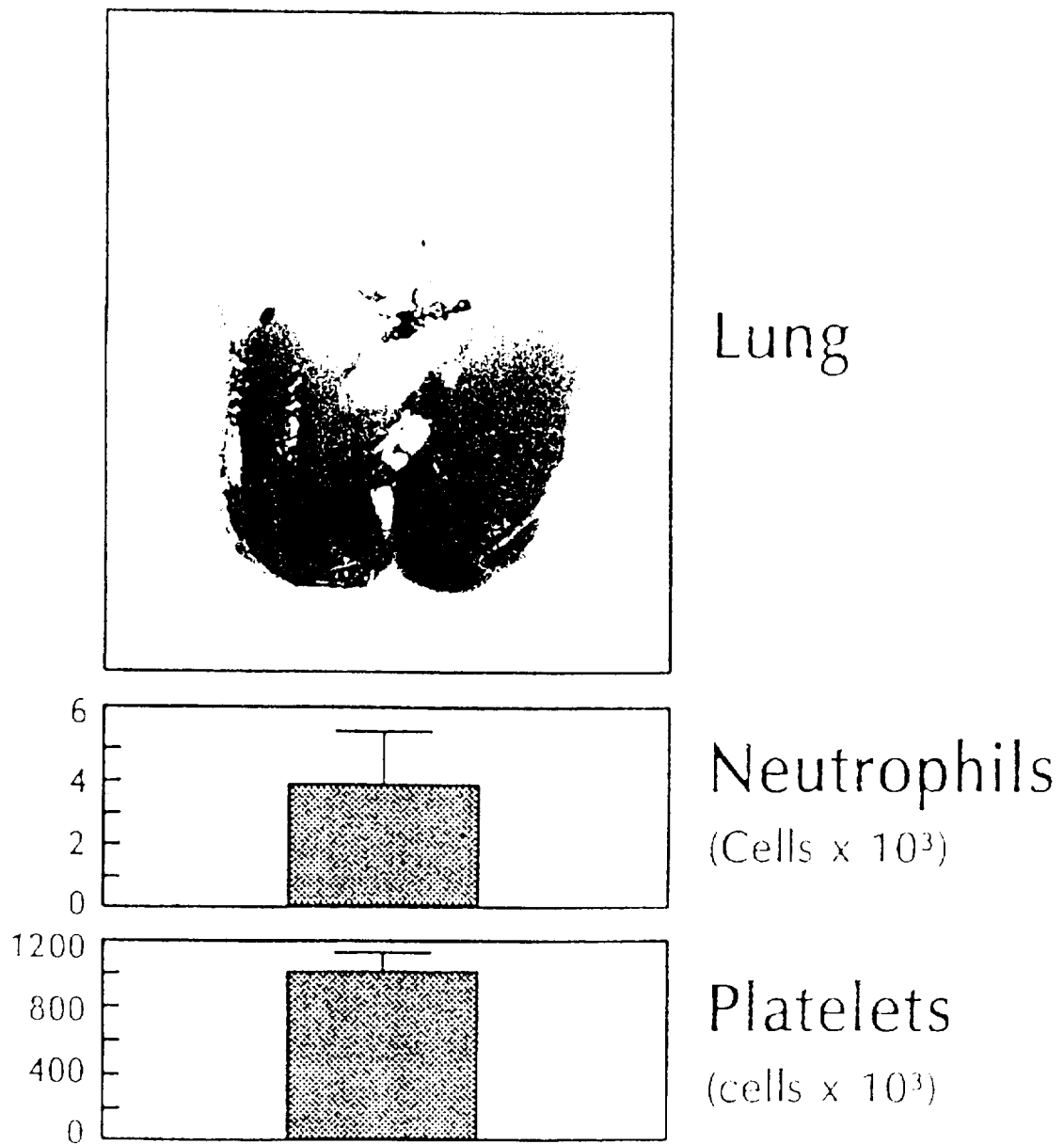

FIGS. 41A, 41B and 41C illustrates the results from an in vivo study in mice where B16 melanoma cells were injected intravenously through a tail vein on day 0 and compound no. 50 was administered inter parenterally at 10 mg/kg QD or 20 mg/kg QOC, starting days 1–14. The mice were sacrificed on day 15 and the lungs were dissected and fixed in formalin. The number of black metastatic foci were scored and are illustrated in the three lungs shown in FIGS. 41A, 41B and 41C. In addition bone marrow toxicity was evaluated by measuring neutrophil and platelet counts in the mice on day 15. These data are shown graphically below the lung photographs in each respective figure. These data show that at either dose administered compound no. 50 was not toxic to the bone marrow (in contrast to every known cancer chemotherapy regimen), and in fact, increased counts over non-treated control animals.

Figure 42A:
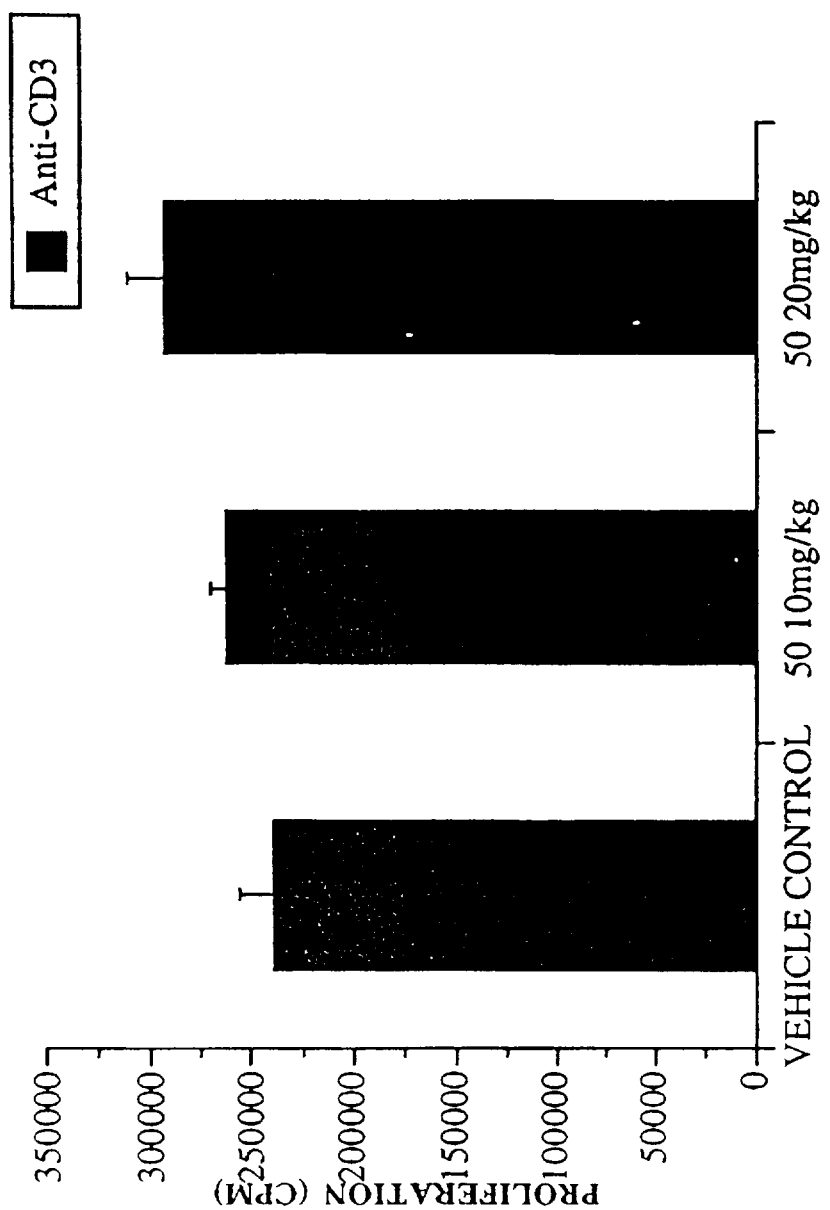
FIGS. 42A and 42B illustrate T- and B-cell response assays of mice treated with compound no. 50 in a B16 melanoma cell assay.
Figure 42B:
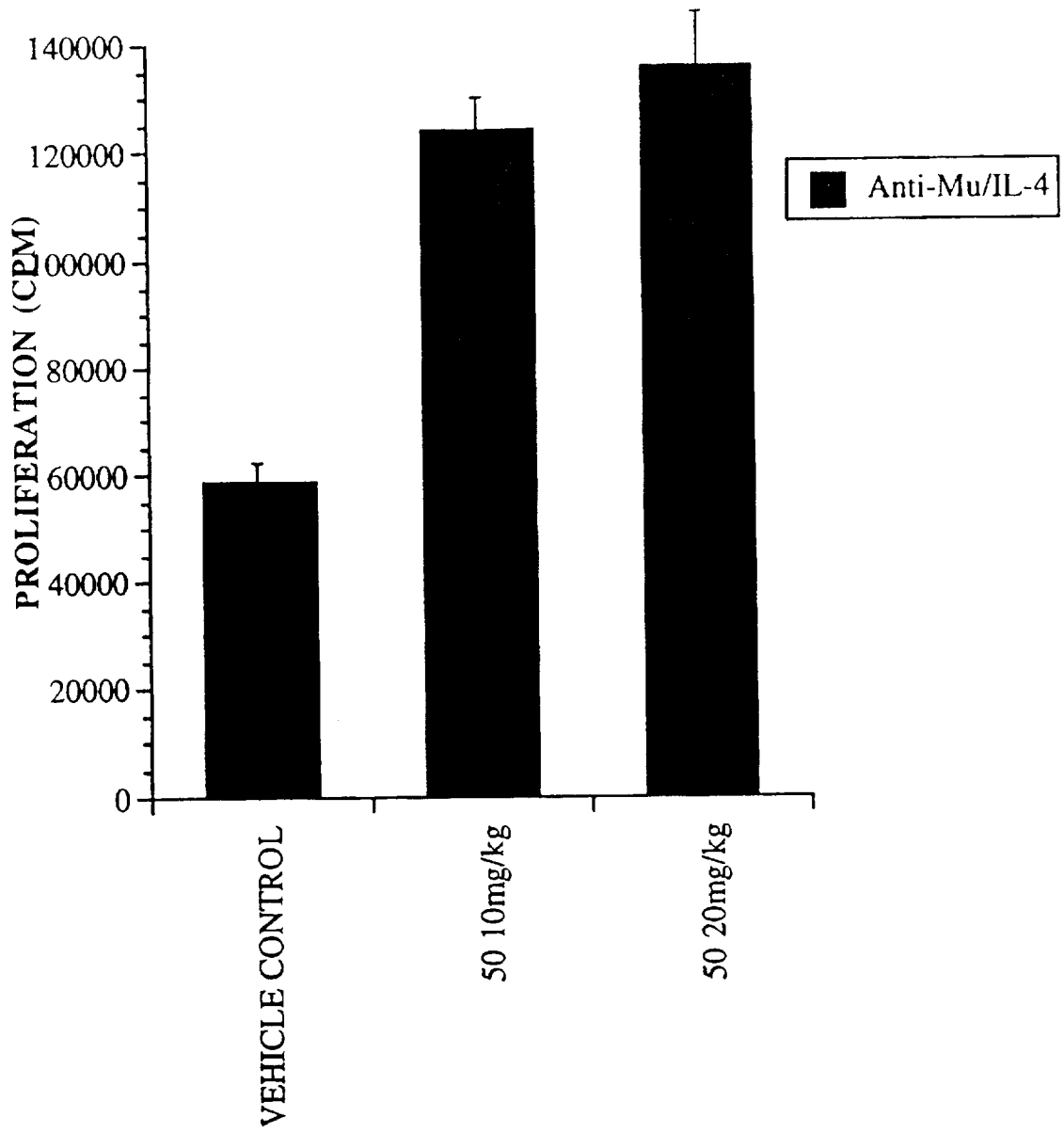

FIGS. 42A and 42B illustrate T and B cell response assays of mice treated with compound no. 50 in the immediately preceding assay protocol. Spleens from these treated mice were made into single cell suspensions in RPMI medium, supplemented with 10% serum, and placed (200.000 cells/well) in flat-bottomed 96 well plates. Anti-CD3 (FIG. 42A) or a mixture of an anti-mu/IL-4 (FIG. 42B) were added to the wells at final concentrations of 1 mg/ml and 1 mg/ml/ 12.5 ng/ml, respectively. Appropriate positive and negative controls were set up on each plate and all samples were assayed in quadruplicate. The plates were incubated for 2 days and proliferation was measured by tritiated thymidine incorporation.

Figure 43:
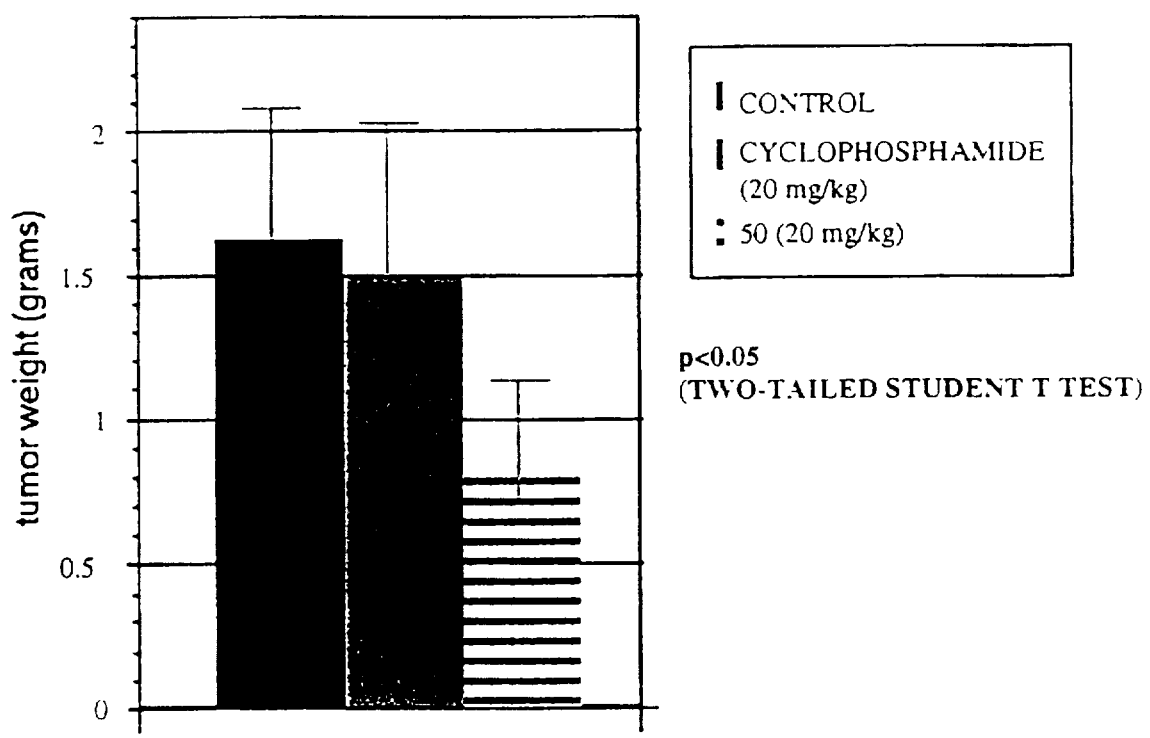
FIG. 43 reports results in an in vivo experiment showing that compound no. 50 can arrest growth of 3LL cells in mice.

FIG. 43 reports results in an in vivo experiment showing that compound no. 50 can arrest growth of Lewis Lung Carcinoma in mice. BDFI mice were injected subcutaneously with $1 \times 10^6$ 3 LL cells on day 0 and then treated with compound no. (20 mg/kg i.p.), cyclophosphamide (20 mg/kg) or vehicle on alternate days beginning on day 7. The animals were sacrificed on day 20 and the lung tumors dissected and weighed. FIG. 43 illustrates that compound no. 50 showed superior results over an existing cancer chemotherapeutic agent.

Figure 44A:
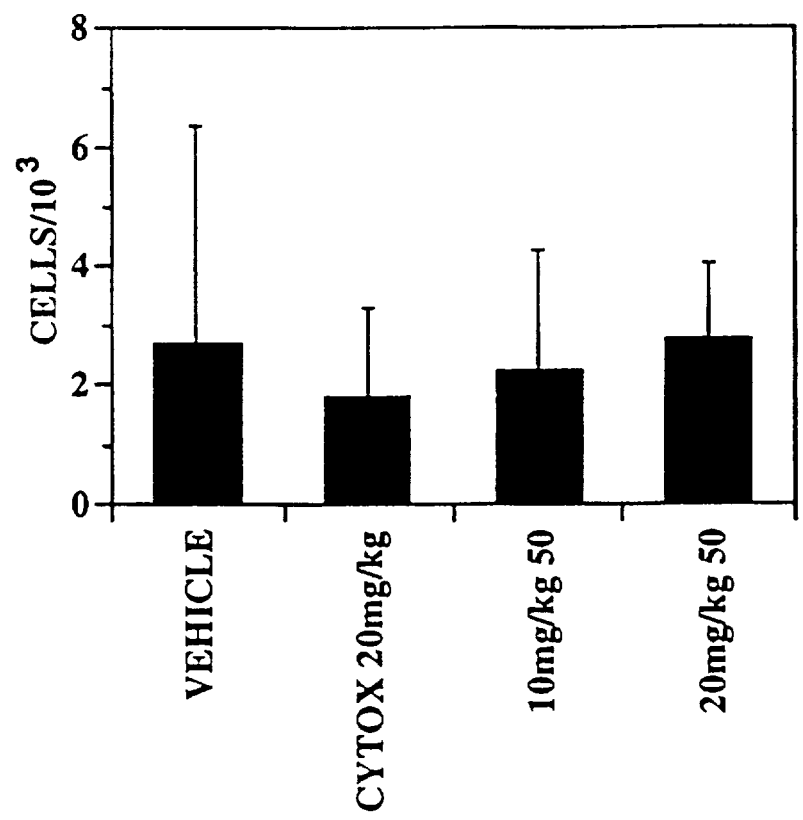
FIG. 44A and 44B illustrate platelet and neutrophil counts, respectively, of sacrificed mice in a Lewis Lung carcinoma assay.
Figure 44B:
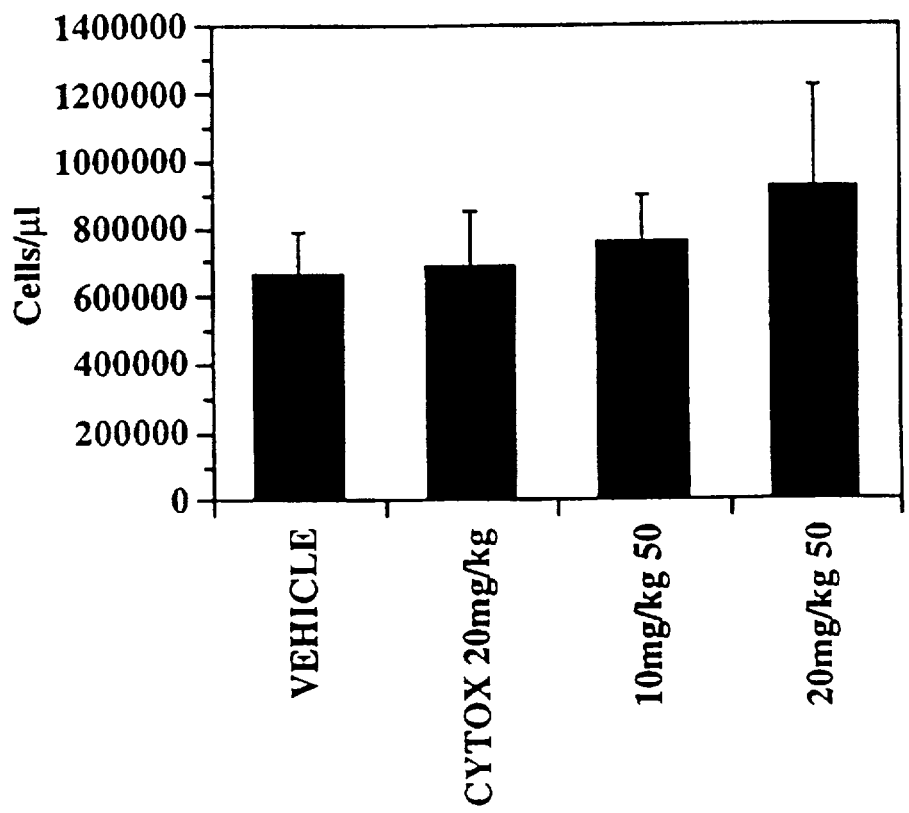

FIG. 44A and 44B illustrates platelet and neutrophil counts, respectively, of the sacrificed mice in the immediately preceding assay. In addition, platelet and neutrophil counts in the mice were not altered from vehicle, indicating that bone marrow was not a target of toxicity for compound no. 50.

Figure 45A:
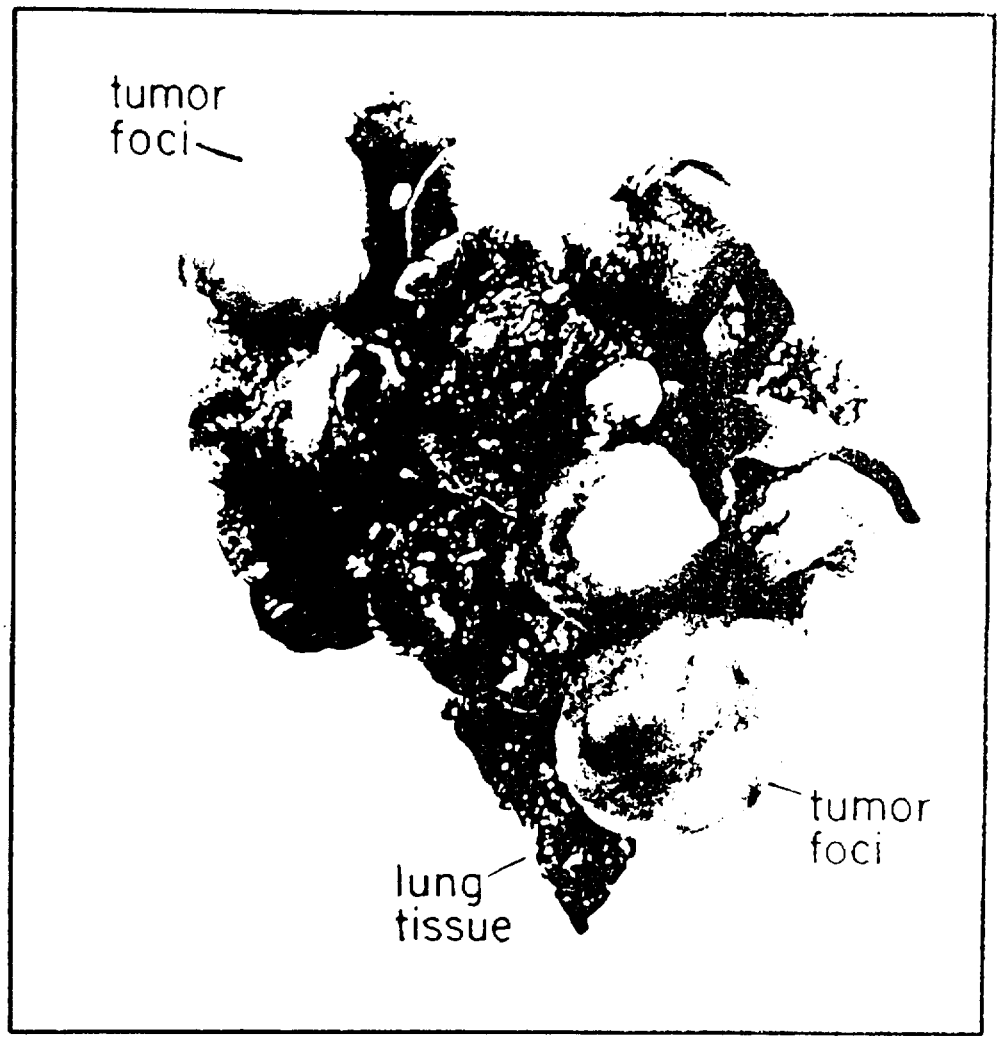
FIGS. 45A, 45B and 45C illustrate a photographic comparison of lungs from 3LL exposed mice with or without treatment using compound no. 50.
Figure 45B:
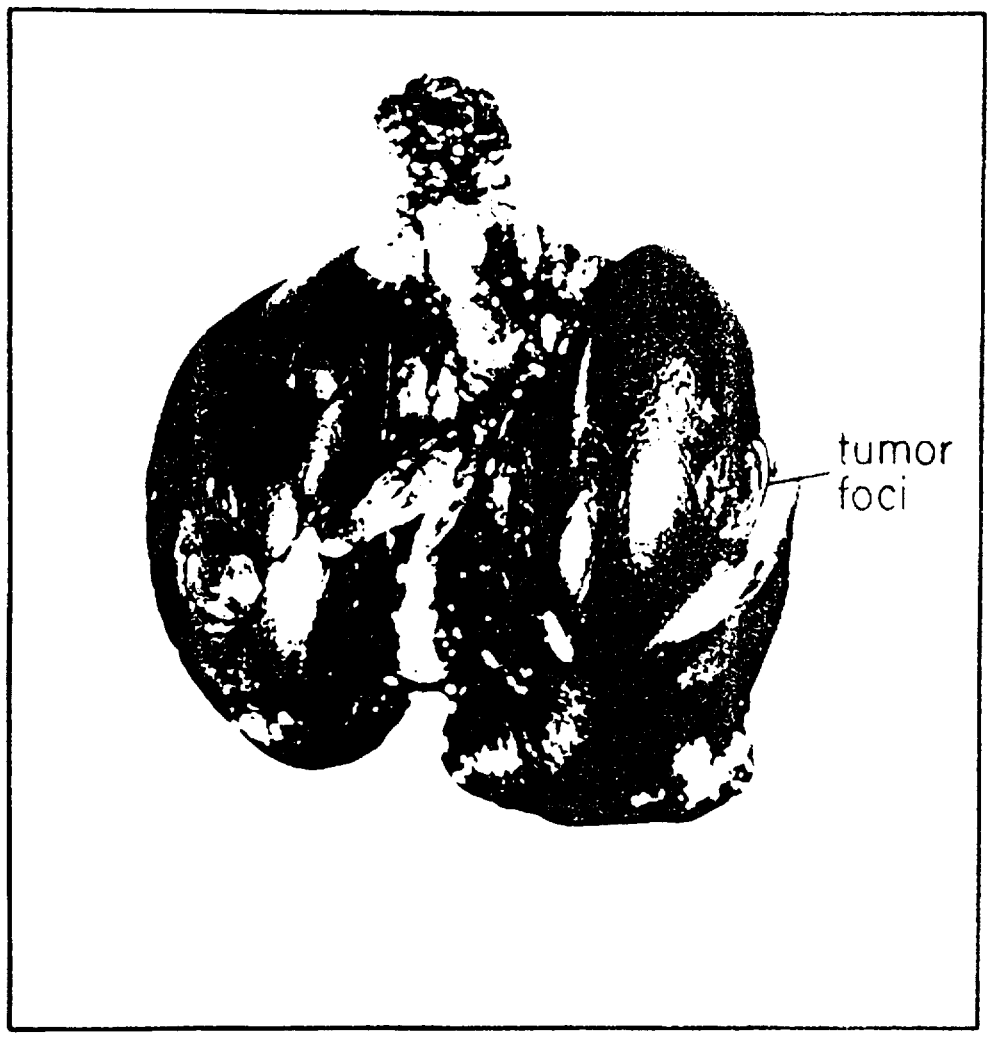
Figure 45C:
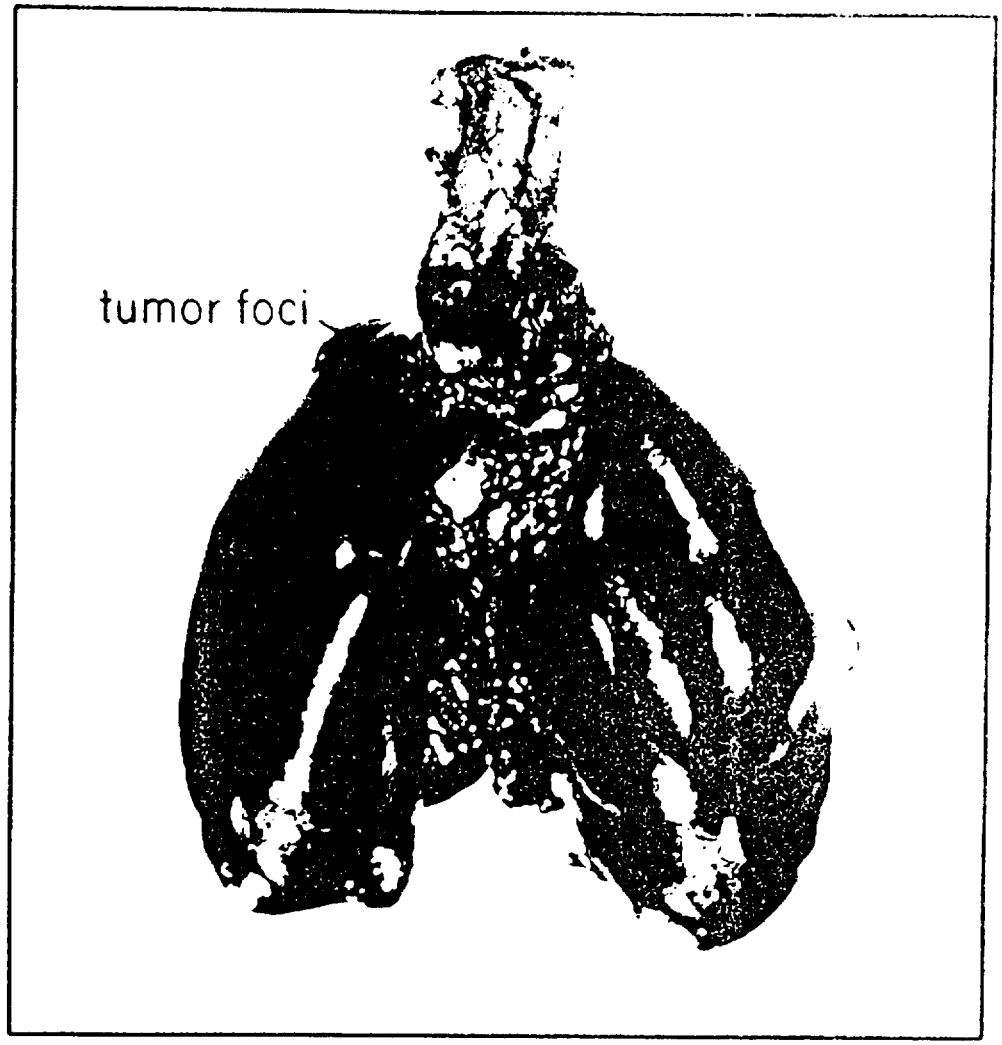

FIGS. 45A, 45B and 45C illustrate a photographic comparison of lungs from the 3LL exposed mice with or without treatment using compound no. 50. The lungs were injected with india ink such that normal lung tissue stains black and tumors appear white. The difference in lungs treated seven days after tumor cell administration was visually apparent. These in vivo data are highly predictive of significant clinical activity and reduced bone marrow toxicity of the compounds.

EXAMPLE 44

This example illustrates conclusive, in vitro and in vivo evidence predicting that the compounds, as represented by a species of the disclosed genus (compound no. 45), are effective therapies for treating autoimmune diseases and suppressing an immune response.

One such autoimmune disease, rheumatoid arthritis, is triggered by unknown environmental or endogenous events in a genetically susceptible individual. Dysregulation of B lymphocytes leads to the production of immune complexes. Activated T cells in involved joints (predominantly of the CD4 helper type) promote autoantibody production. Macrophages and dendritic cells produce large numbers of inflammatory cytokines, further stimulating lymphocytes. In addition, both lymphocytes and macrophages produce other cytokines which stimulate proliferation of synovial cells leading to "pannus" formation and joint deformity. Degradative enzymes such as type IV collagenase are released into the joint space and destroy connective tissue including the cartilage on articular surfaces. Lymphocyte- and macrophage-released cytokines play various roles in the pathogenesis of joint destruction and systemic symptoms in rheumatoid arthritis. Compounds that affect only a single component of this complex process are unlikely to be effective or disease-modifying unless these compounds target a process that is both proximal in the cascade of and fundamental to the inflammatory process itself. Because biologic systems appear invariably redundant, conventional treatments target a single aspect of a complex reaction and are thus only partially effective.

The compounds interrupt many key components of the cascade of events that lead to both joint destruction and the systemic complications of rheumatoid arthritis. Specifically in the following in vitro and in vivo assays, compound no. 45 (as a representative compound of the invention) inhibited: T and B cell proliferation, thus inhibiting abnormal autoantibody production; macrophage activation, cytokine production, and most importantly, signaling by multiple cytokines (for example, T and B cell driven proliferation in response to IL-2, IL-4, IL-7, TNFα and T cell receptor activation by antigen); proliferative signals to synovial cells in response to PDGF, FGF, EGF, and insulin-like growth factors (IGF); adhesion molecule expression (including VCAM and ICAM), stimulated by local inflammation, a suppression of these adhesion molecules likely leading to a decrease in lymphocyte and macrophage trafficking to the inflammation site, thus decreasing amplification of the inflammatory process. Therefore, the compounds, represented by compound no. 45, inhibit, from multiple points, the inflammatory and dysregulated immune response resulting in acute and chronic symptomatology of diseases such as rheumatoid arthritis.

In vitro and in vivo data confirm activity of the compounds as an immunosuppressive therapeutic, as represented in the following results.

Figure 46:
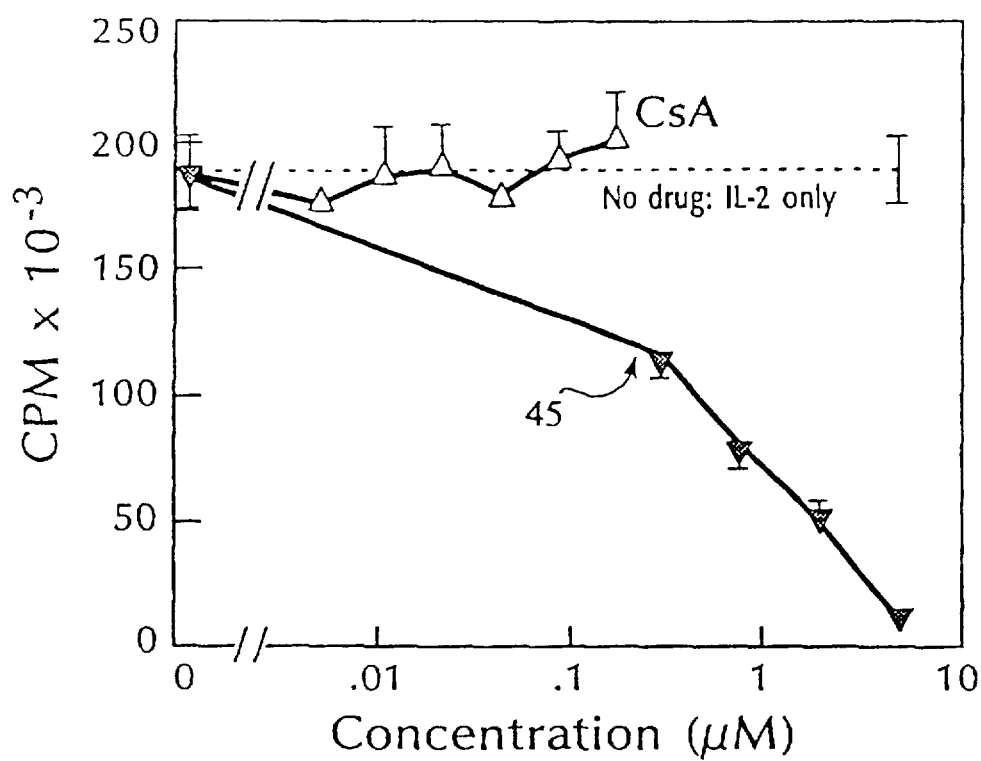
FIG. 46 reports results obtained in an assay investigating compound no.'s 45 effect on IL-2-mediated proliferation

CT-6.1 cells were starved overnight and stimulated with IL-2 (20 ng/ml). Twenty hours later, cells were labeled for 4 hours with $^3$H-TdR and counted by liquid scintillation. Background counts were approximately 2000 CPM. The IC50 for inhibition in this cell line was approximately 0.8 µM. CsA, used as a negative control, had no effect on IL-2-mediated proliferation. FIG. 46 reports results obtained in this assay, illustrating inhibition of proliferation by compound no. 45, as measured by $^3$H-TdR incorporation using cell counts.

Figure 47:
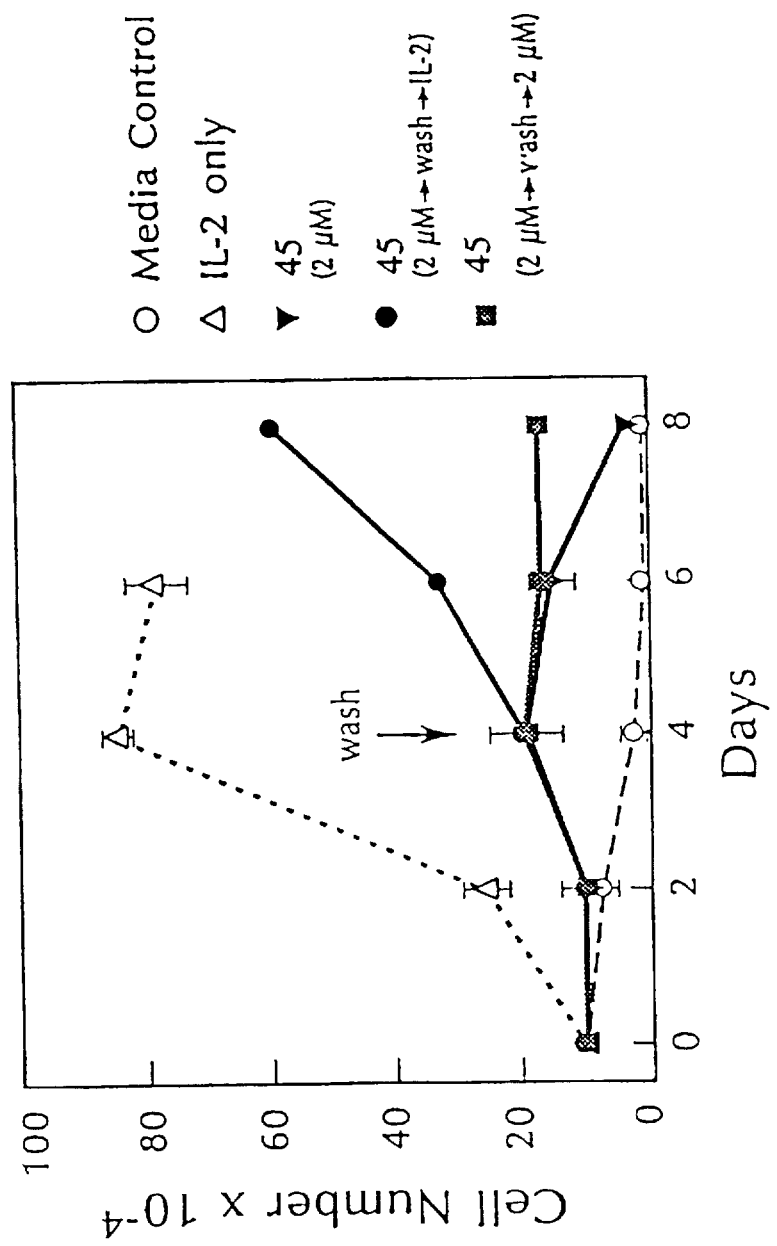
FIG. 47 illustrates that compound no. 45 inhibits CT-6.1 proliferation as measured by cell number.

CT6.1 cells were cultured with IL-2 with or without the addition of compound no. 45 (2 µM) and viable cells counted for up to 8 days. On day 4, two cultures previously incubated with compound no. 45, were washed and recultured with fresh IL-2 with or without compound no. 45 (2 µM). Results reported in FIG. 47 illustrate that compound no. 45 inhibits proliferation as measured by cell number, its effect being reversible even after 4 days in culture.

Figures 48A, 48B, 48C:
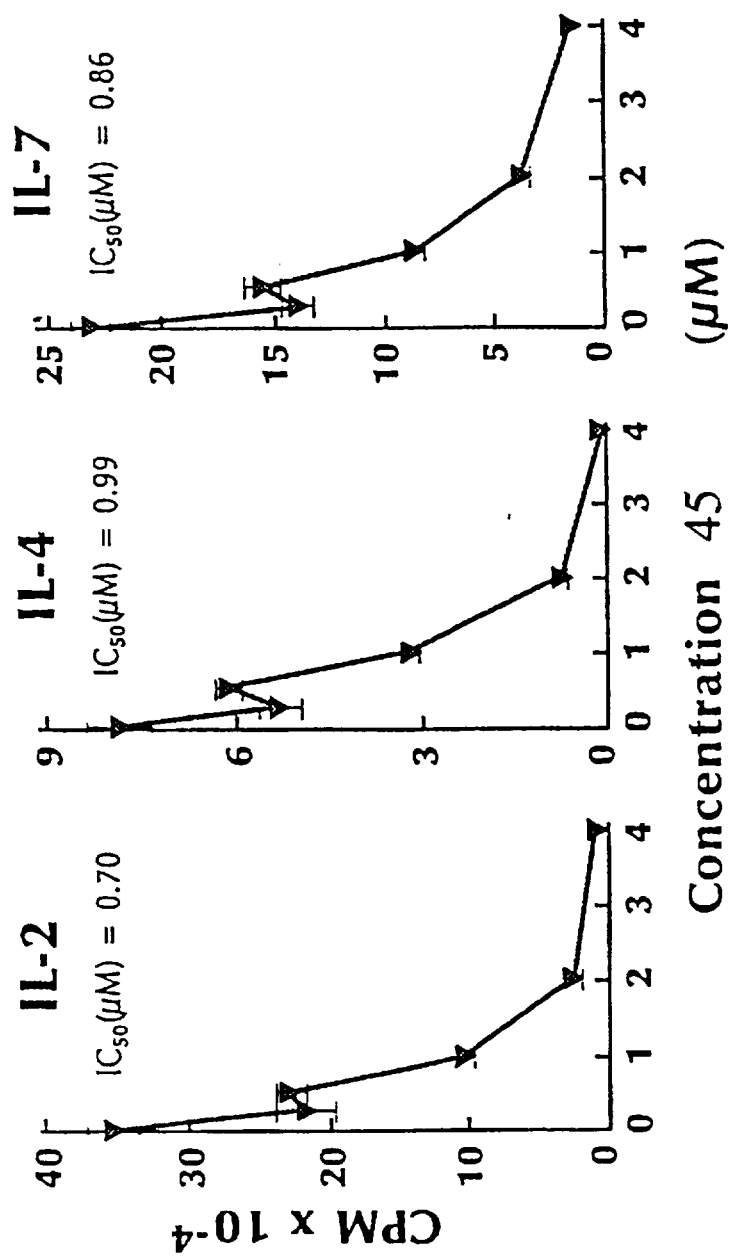
FIGS. 48A, 48B, and 48C illustrate that compound no. 45 also inhibits mitogenic responses to IL-2, IL-4 and IL-7.

The results shown in FIGS. 48A, 48B, and 48C illustrate that compound no. 45 also inhibited mitogenic responses to IL-2, IL-4 and IL-7. Procedurally, CT-6.1 cells were starved overnight and stimulated with either IL-2 (20 ng/ml), IL-4 (50 ng/ml ) or IL-7 (25 ng/ml). $^3$H-TdR was added at 20 hours, cells were harvested 4 hours later, and the incorporation of $^3$H-TdR was determined. Compound no. 45 illustrated IC50's<1.0 µM for IL-2, IL-4 or IL-7-stimulated proliferation of CT6.1 cells. All of the incorporation studies were confirmed with parallel cell counting experiments (data not shown). These data predict that the compounds induce immunosuppression similar to an X-linked SCID-like condition.

Figure 49:
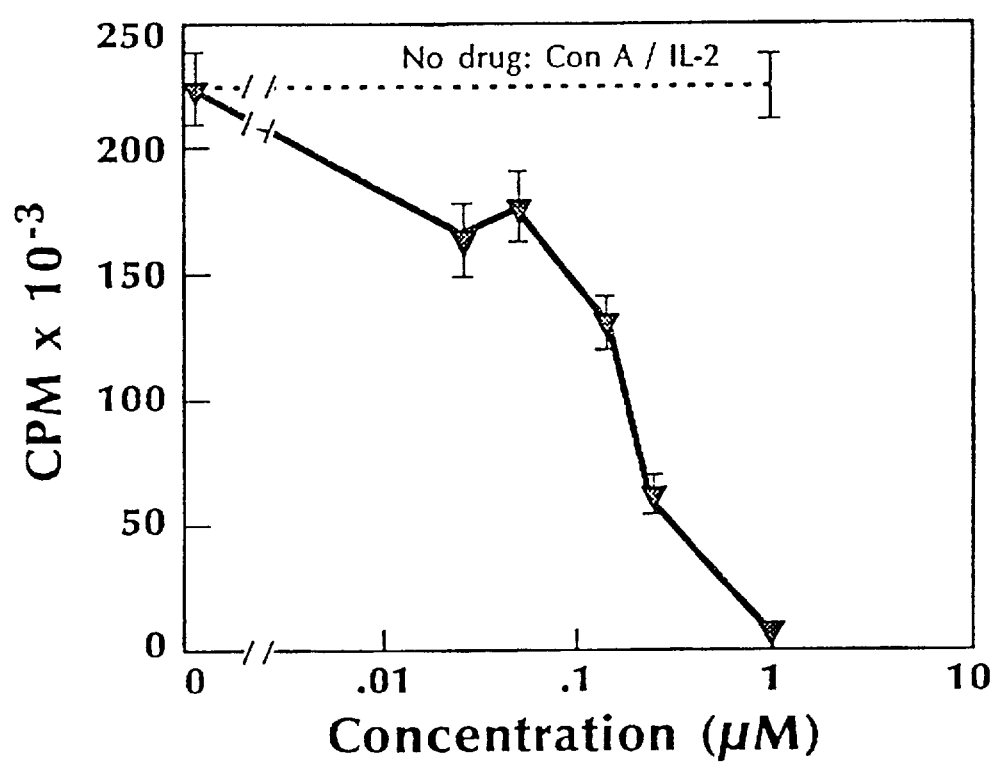
FIG. 49 shows that compound no. 45 also inhibited murine thymocyte proliferation in response to ConA and IL-2.

In another in vitro protocol, thymocyte proliferation was induced by sub-mitogenic doses of Con A (0.25 µg/ml) and IL-2 (20 ng/ml). Cells were stimulated for 96 hours, prior to addition of $^3$H-TdR for 4 hours. The cells were harvested and incorporation of $^3$H-TdR was determined. Background counts were approximately 2000 cpm. In the results reported in FIG. 49, compound no. 45 also inhibited murine thymocyte proliferation in response to ConA and IL-2, with an IC$_{50}$ of approximately 0.35 µM.

Figures 50A, 50B:
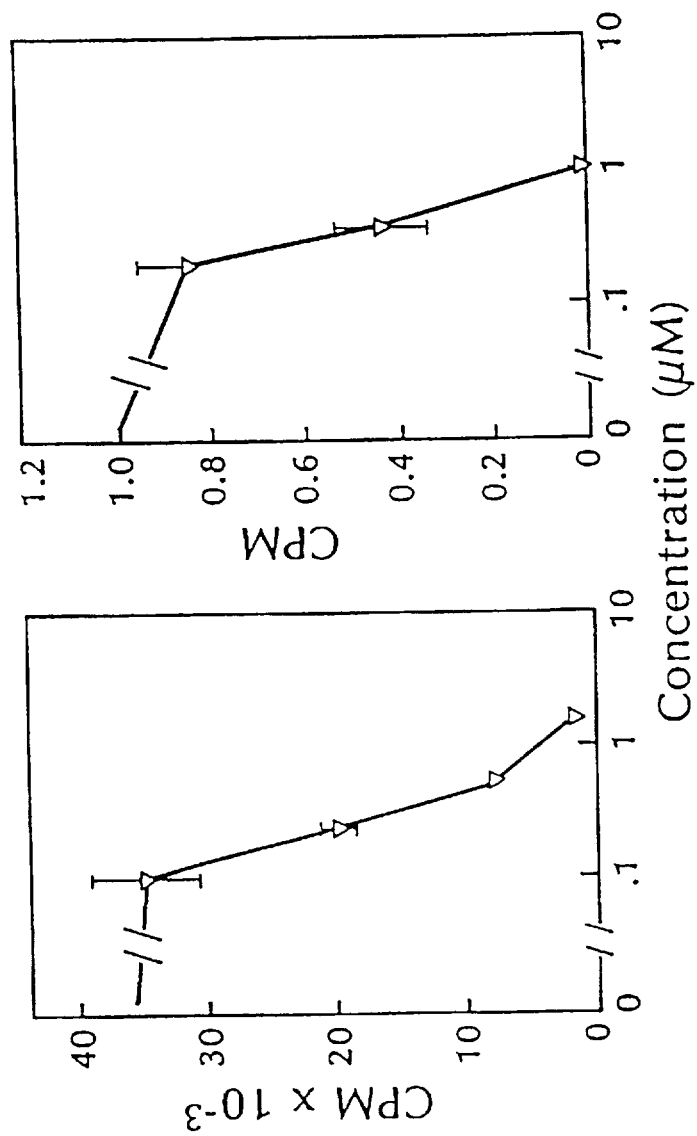
FIGS. 50A and 50B illustrate that compound no. 45 inhibits a murine mixed tumor lymophocyte culture (MTLC) and a human mixed leukocyte reaction (MLR), respectively.

FIGS. 50A and 50B illustrate that compound no. 45 inhibits a murine mixed tumor lymophocyte culture (MTLC) and a human mixed leukocyte reaction (MLR). In the MTLC, splenocytes were stimulated (co-culture) with an alloantigen, B cell tumor target cell line (2PK3) in the presence or absence of compound no. 45. Cells were stimulated for 3 days, $^3$H-TdR was added and the cells were harvested 4 hours later. Incorporation of $^3$H-TdR was determined by liquid scintillation. Background counts were 1000–1200 CPM. For the human MLR, purified peripheral lymphocytes from two HLA disparate individuals were co-cultured for 6 days with or without compound no. 45. On the 7th day the cultures were pulsed with $^3$HTdR for 24 hours and counted by scintillation. As reported in FIGS. 52A and 52B, an IC$_{50}$ for the MTLC and MLR were both approximately 0.5 µM.

Figure 51:
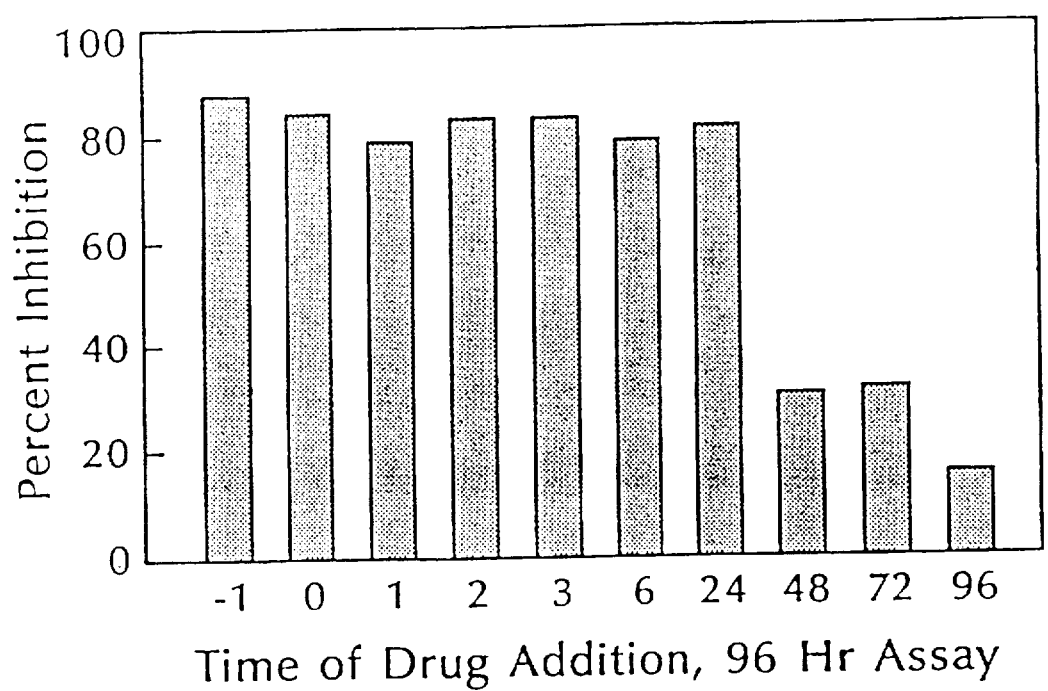
FIG. 51 illustrates an effect of the delayed addition of compound no. 45 on co-stimulated thymocyte proliferation.

FIG. 51 illustrates an effect of the delayed addition of compound no. 45 on co-stimulated thymocyte proliferation. In an assay procedure, murine thymocytes were stimulated with ConA and IL-2 with 1 µM compound no. 45 added either 1 hour prior to IL-2 (-1), simultaneous with IL-2 (0) or at various times following IL-2 addition (1–92 hour). At 92 hours the thymocytes were pulsed with $^3$H-TdR, harvested and counted by scintillation 4 hours later. The results reported in FIG. 53 illustrate that compound no. 45 maximally inhibited thymocyte proliferation even when added 24 hours following the IL-2 stimulation. Furthermore, significant inhibition remained even at 72 and 92 hours following addition of IL-2.

Figure 52:
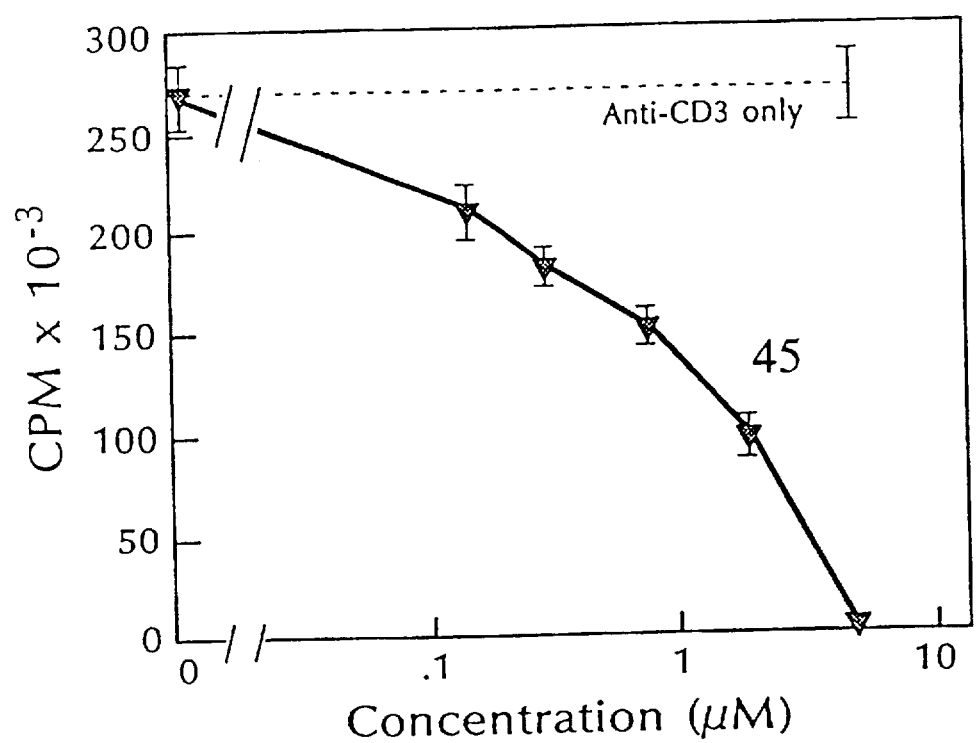
FIG. 52 illustrates that compound no. 45 inhibits anti-CD3 stimulated splenocyte proliferation.

FIG. 52 illustrates that compound no. 45 inhibited anti-CD3 stimulated splenocyte proliferation. In the assay, murine splenocytes were activated with a monoclonal antibody directed against CD3 (1 µg/ml), resulting in an IL-2 mediated proliferative response. Background was approximately 2000 cpm. As reported in FIG. 52, the IC50 for inhibition in splenocytes was approximately 0.85 µM.

Figures 53A, 53B:
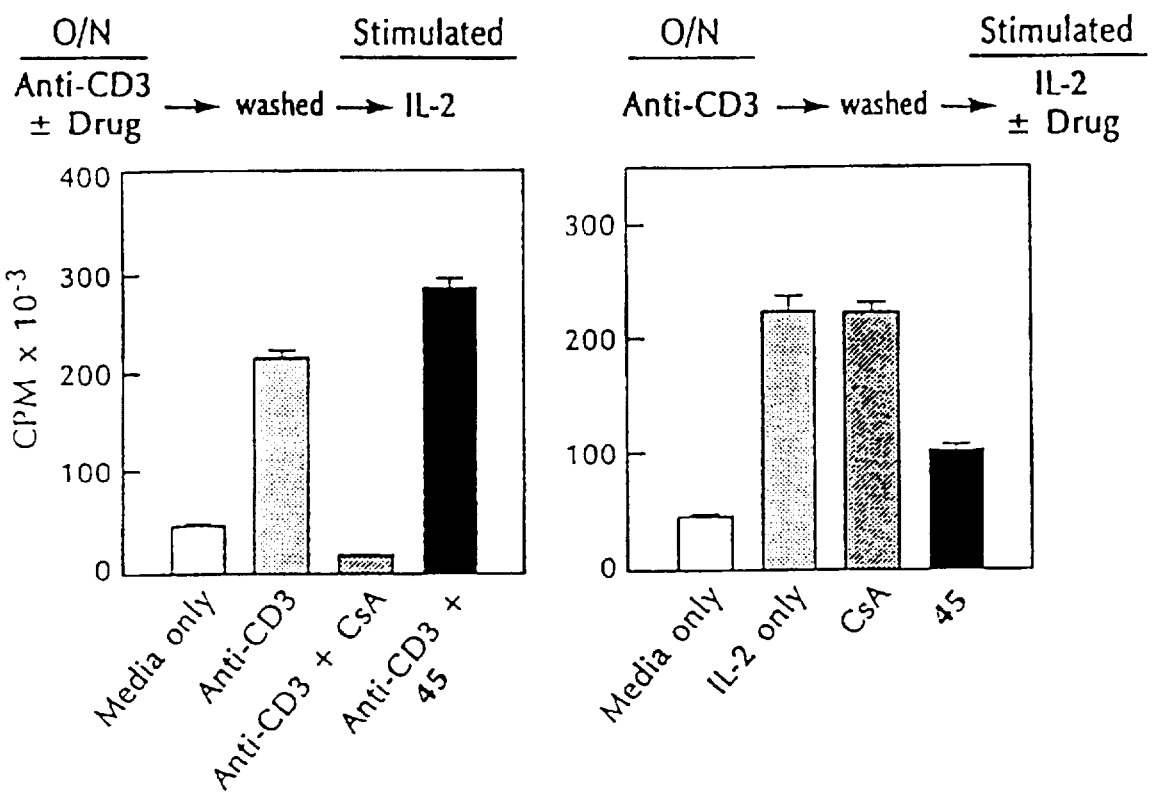
FIGS. 53A and 53B illustrate that compound no. 45 does not inhibit T-cell receptor (CD3) mediated signaling.

FIGS. 53A and 53B illustrate that compound no. 45 did not inhibit T cell receptor (CD3) mediated signaling. Procedurally, murine splenocytes were incubated overnight with anti-CD3 in the presence or absence of CsA (0.1 µM) or compound no. 45 (1 µM)—FIG. 53A. Following overnight incubation, cells were washed and restimulated with IL-2 for 20 hours without addition of CsA or compound. The cells were pulsed with $^3$H-TdR for 4 hours and harvested and incorporation of $^3$H-TdR determined. Preincubation of splenocytes with CsA together with anti-CD3 blocks the ability of the cells to respond to IL-2. This is due to the fact that CsA inhibited TCR mediated up-regulation of the IL-2 alpha chain receptor (CD25). In contrast, preincubation of the splenocytes with the compound and anti-CD3 did not block the splenocyte's ability to respond to IL-2.

If the cells were first treated with anti-CD3 overnight, washed and recultured using IL-2 with CsA (0.1 µM), proliferation was not inhibited compared to the IL-2 only control—FIG. 53B. CsA did not block IL-2 mediated signaling events. However if the anti-CD3 "primed" splenocytes were stimulated with IL-2 in the presence of compound no. 45 (1 µM), proliferation was inhibited. These data demonstrate that compound no. 45 specifically inhibited IL-2 induced proliferation of anti-CD3 activated splenocytes, without blocking TCR-mediated activation, therefore predicting a distinctly different mechanism of action than CsA.

Figures 54A, 54B:
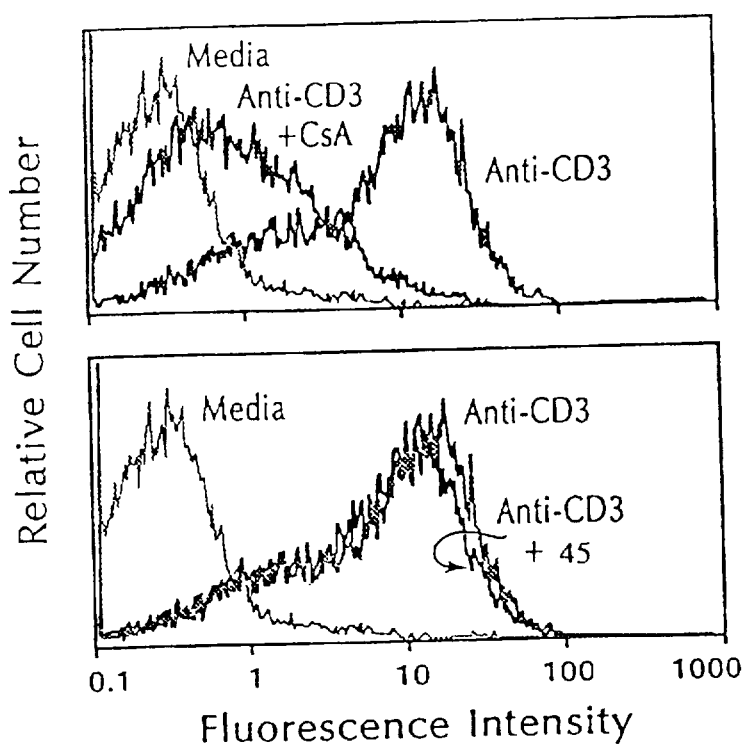
FIGS. 54A and 54B illustrate that compound no. 45 does not inhibit anti-CD3 mediated upregulation of the IL-2 receptor alpha subunit.

In another assay, compound no. 45 did not inhibit anti-CD3 mediated upregulation of the IL-2 receptor alpha subunit. These data are presented in the histograms in FIGS. 54A and 54B. Murine splenocytes were activated for 24 hours with anti-CD3 (1µ/ml), stained with a fluorescent antibody to CD25 and analyzed by flow cytometry. FIG. 54A is a histogram for cells treated with or without 100 nM CsA or the media control. CsA inhibits CD-25 receptor upregulation by inhibiting TCR signaling. However, in FIG. 54B, a similar experiment is shown, except that the cells were treated with compound no. 45 (1 µM) rather than CsA. Results reported confirm that compound no. 45 did not inhibit CD-25 (p55) receptor upregulation by anti-CD3.

Figure 55:
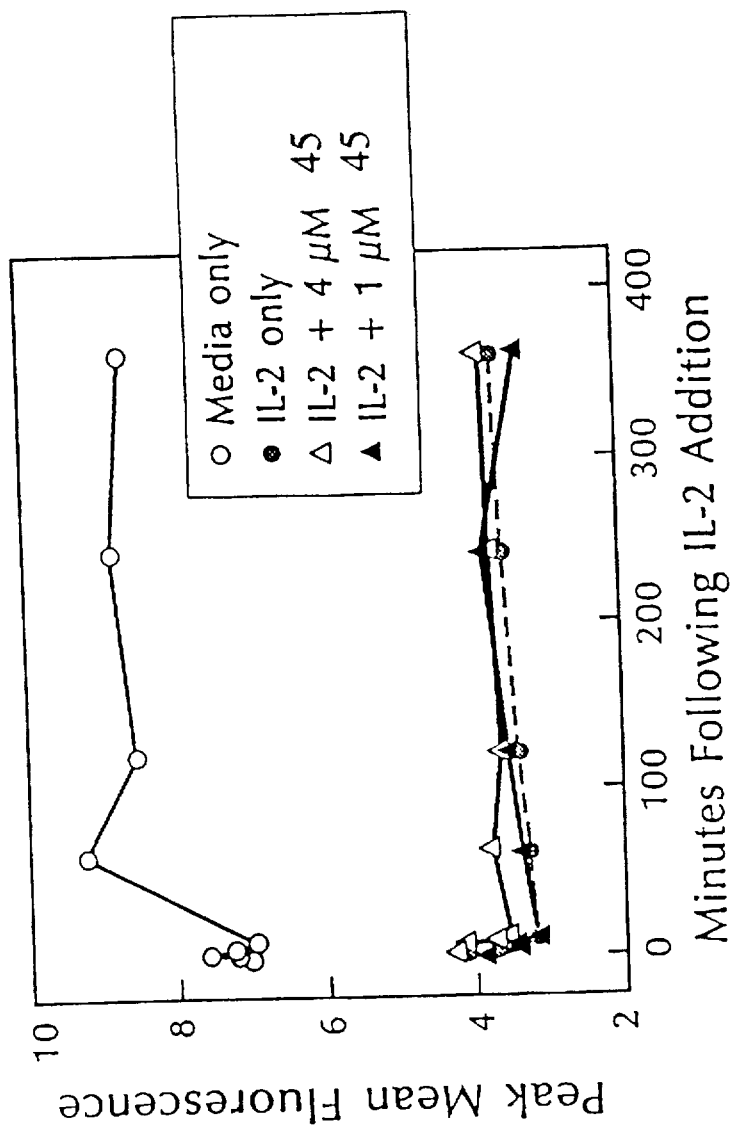
FIG. 55 illustrates that compound no. 45 does not inhibit IL-2 receptor beta (p70) subunit internalization.

In FIG. 55, compound no. 45 did not inhibit IL-2 receptor beta (p70) subunit internalization and cell surface downregulation following IL-2 stimulation. In this assay protocol, CT-6.1 cells were starved overnight and stimulated with 20 ng/ml IL-2. At various times following IL-2 stimulation, cells were rapidly suspended in ice cold PBS and stained using a fluoresceinated monoclonal recognizing the beta subunit of the IL-2 receptor and cell surface expression analyzed by flow cytometry. FIG. 55 is a plot of mean fluorescence versus time (in minutes) following IL-2 addition, illustrating that IL-2r beta subunit was rapidly internalized following IL-2 addition with cell surface expression remaining low for 6 hours. Compound no. 45 did not inhibit this receptor internalization activity.

Figure 56:
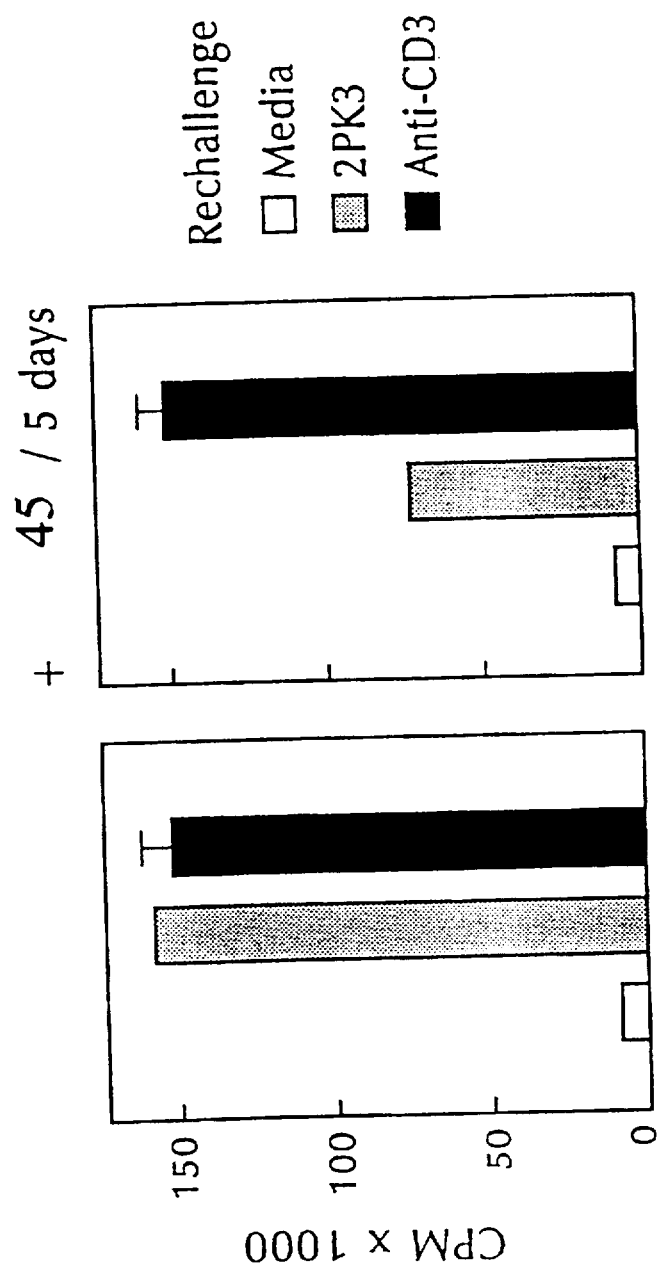
FIGS. 56A and 56B illustrate that the compound no. 45 also induces antigen specific T-cell anergy.

As shown in FIGS. 56A and 56B, compound no. 45 also induces antigen specific T-cell anergy. Procedurally, murine splenocytes were stimulated with an alloantigen target cell line 2PK3 in the presence or absence of compound no. 45 (1 µM; approximate $IC_{50}$). Following 5 days in culture, the cells were washed, re-cultured and re-stimulated with the original priming antigen and anti-CD3 monoclonal antibody. The secondary response to the priming antigen was inhibited if the cells were cultured with compound no. 45 during the five day primary culture. The polyclonal T-cell response to anti-CD3 was not affected, indicating that the compound was not cytotoxic during the 5 day priming period. Although cells pretreated with compound no. 45 could respond normally to polyclonal stimulation, those that were challenged with the alloantigen could not. Therefore, compound no. 45 induced a specific state of unresponsiveness or anergy to the alloantigen.

Figure 57:
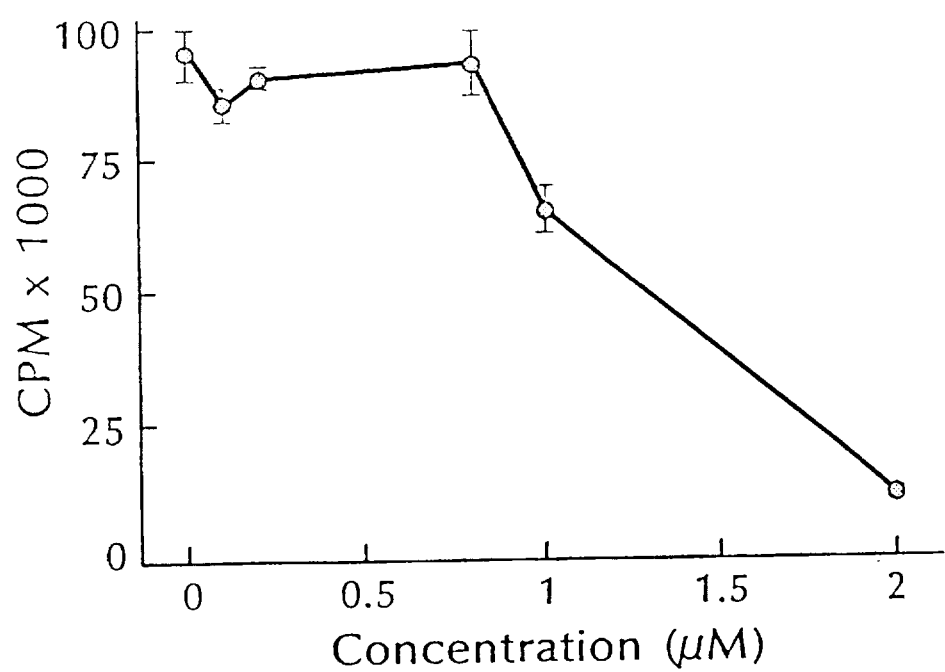
FIG. 57 illustrates that compound no. 45 inhibits B cell proliferation.

In FIG. 57, results shown illustrate that compound no. 45 inhibits B cell proliferation. Murine splenocytes were stimulated with anti-IgM antibodies (10 µg/ml) and murine IL-4 (12.5 ng/ml). Cells were pulsed with $^3$HTdR at 44 hours, harvested 4 hours later, and the incorporation of $^3$H-TdR was determined by liquid scintillation. As shown in FIG. 59, the compound inhibited proliferation, with an $IC_{50}$ of 1.2 µM.

Figure 58A:
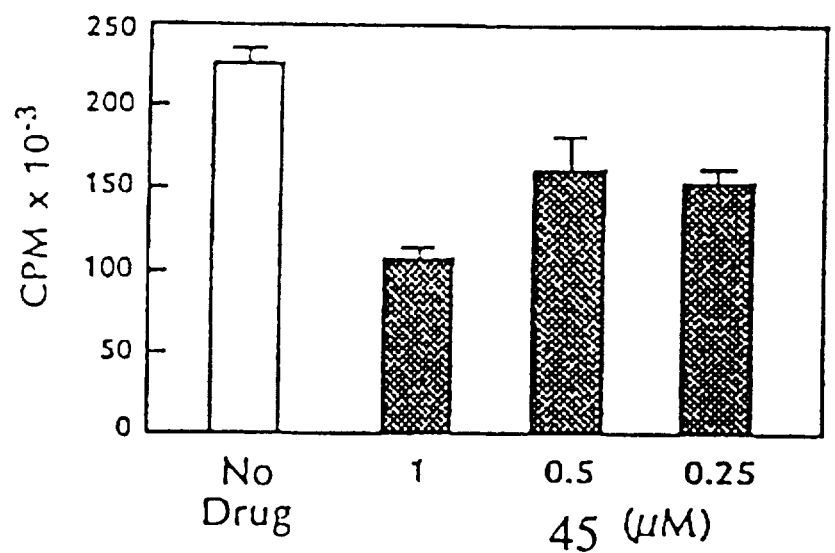
FIGS. 58A and 58B illustrate that compound no. 45 does not inhibit CD28-mediated IL-2 release.
Figure 58B:
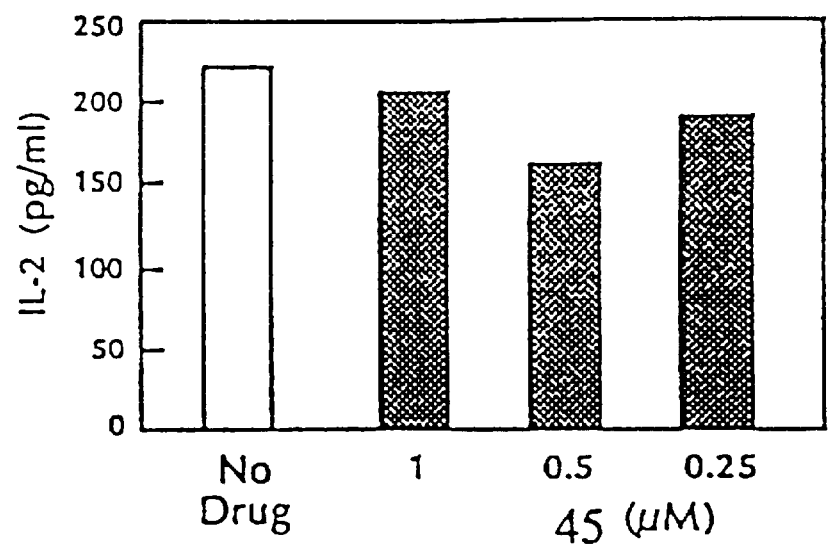
Figures 60A, 60B, 60C, 60D:
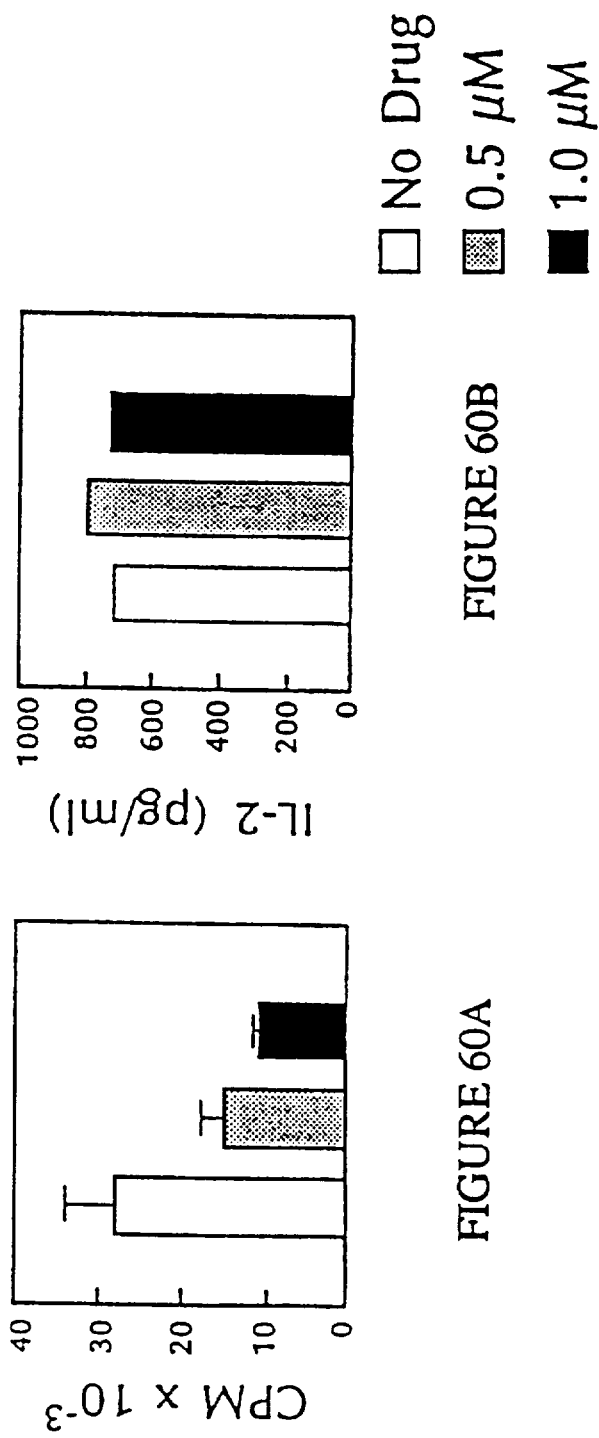
FIG. 60A shows inhibition of proliferation in an MTLC assay with compound no. 45.
FIG. 60B and 60C illustrate that compound no. 45 does not inhibit either IL-2 or TNFα release from the MTLC.
FIG. 60D shows that compound no. 45 inhibits IFN-γ release.

FIGS. 58A and 58B illustrate that compound no. 45 did not inhibit CD28-mediated IL-2 release. Murine splenocytes were stimulated with a mixture of anti-CD3 and anti-CD28 monoclonal antibodies. Compound no. 45 inhibited T-cell proliferation in this system (FIG. 60A) but did not inhibit the CD28-mediated release of IL-2 (FIG. 60B).

FIGS. 58C, 58D, and 58E illustrate that compound no. 45 inhibited IFN-γ release by blocking IL-2 signaling. Procedurally, murine splenocytes were stimulated with a mixture of anti-CD3/CD28 antibodies. Compound no. 45 inhibited release of IFN-γ (FIG. 60C). Addition of an anti-IL-2 receptor alpha subunit antibody and an anti-IL-2 receptor beta subunit antibody to the cultures inhibited both proliferation and the release of IFN-γ (FIG. 60D). This demonstrates that the inhibition of IFN-γ release after stimulation with anti-CD28/CD3 was due to blocking an IL-2 signal.

Figures 59A, 59B, 59C:
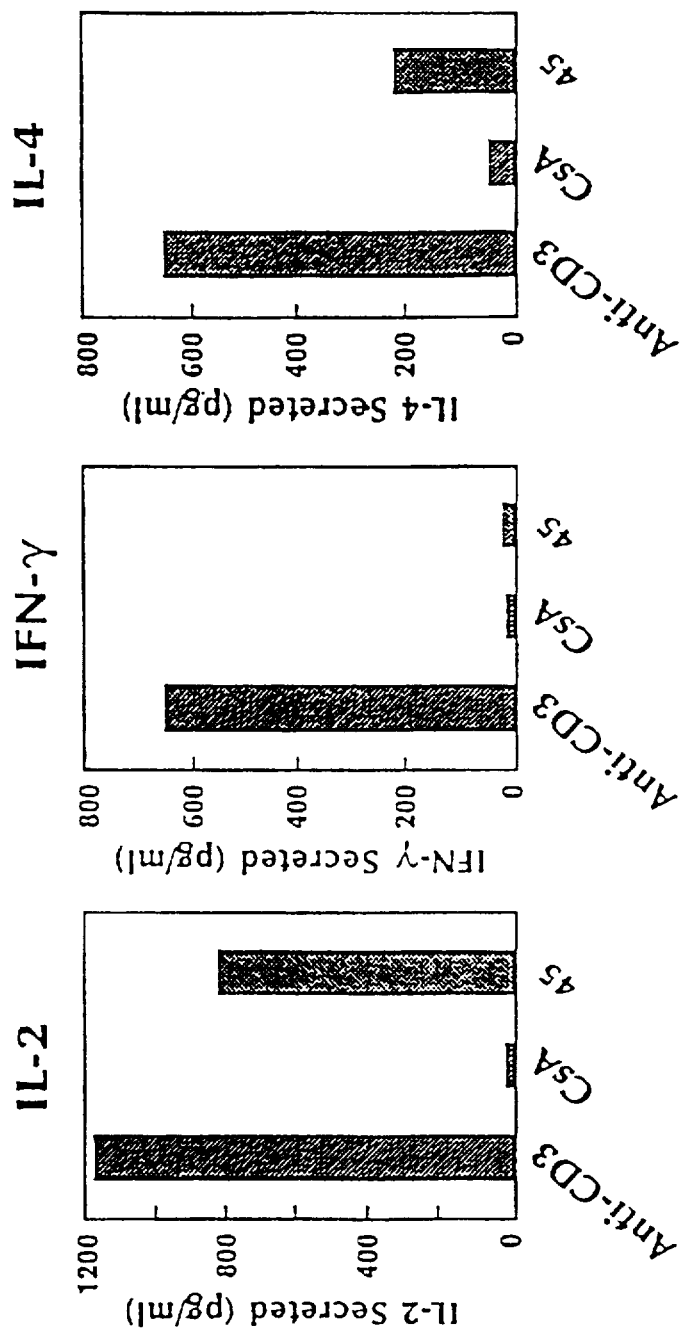
FIGS. 59A, 59B and 59C report assay results investigating the effect of compound no. 45 on cytokine release from anti-CD3-stimulated mouse splenocytes.

FIGS. 59A, 59B and 59C report assay results investigating the effect of compound no. 45 on cytokine release from anti-CD3-stimulated mouse splenocytes. Cells were stimulated with anti-CD3 overnight with or without either CsA (50 nM) or compound no. 45 (1 µM). Concentrations chosen were approximately equal to $IC_{50}$ values. The supernatants were harvested and assayed for cytokine levels using commercial ELISAs for proliferation. Anti-CD3 stimulated release of IL-2, IFN-γ and IL-4 (background levels for media control were negligible). As shown in FIG. 59A, compound no. 45 did not significantly inhibit IL-2 release, in contrast to CsA. However, compound no. 45 drastically inhibited IFN-γ release similar to CsA (FIG. 59B), predicting that the compound had a differential effect on Th-2 cell cytokine release, which secrete both IL-2 and IFN-γ. Compound no. 45 only partially inhibits IL-4 release, which is produced by Th-2 cells (FIG. 59C).

In an assay related to the MTLC assay, cytokine levels were measured by ELISA from the supernatants of an MTLC culture. FIG. 60A shows inhibition of overall proliferation with compound no. 45. FIGS. 60B and 60C illustrate that compound no. 45 did not inhibit either IL-2 or TNFα release from the MTLC. In contrast, FIG. 60D shows that compound no. 45 inhibited IFN-γ release.

Figure 61:
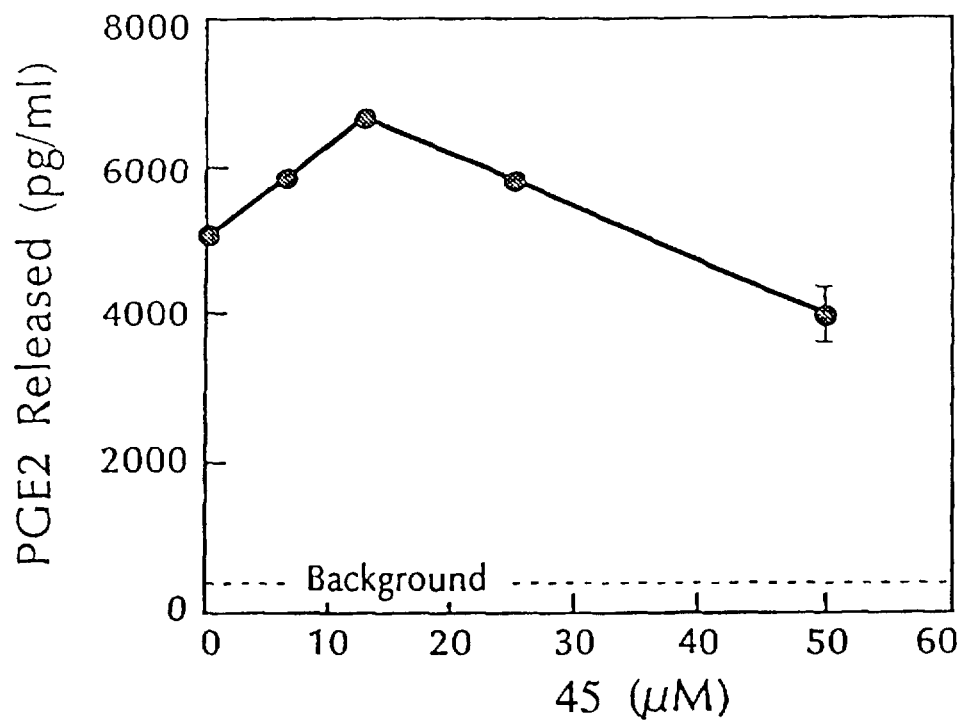
FIG. 61 illustrates that compound no. 45 does not have an effect on prostaglandin E2 release from IL-1α-stimulated human foreskin fibroblasts, HS68.

FIG. 61 illustrates that compound no. 45 did not have an effect on prostaglandin E2 release from IL-1α-stimulated human foreskin fibroblasts, HS68. Cells were stimulated with 100 pg/ml IL-1α. Compound no. 45 was added 1 hour prior to stimulation. Supernatants were harvested 24 hours later and levels of PGE2 were analyzed by commercial immunoassay. The results are reported in FIG. 61 and confirm no effect on $PGE_2$ release.

Figures 62A, 62B:
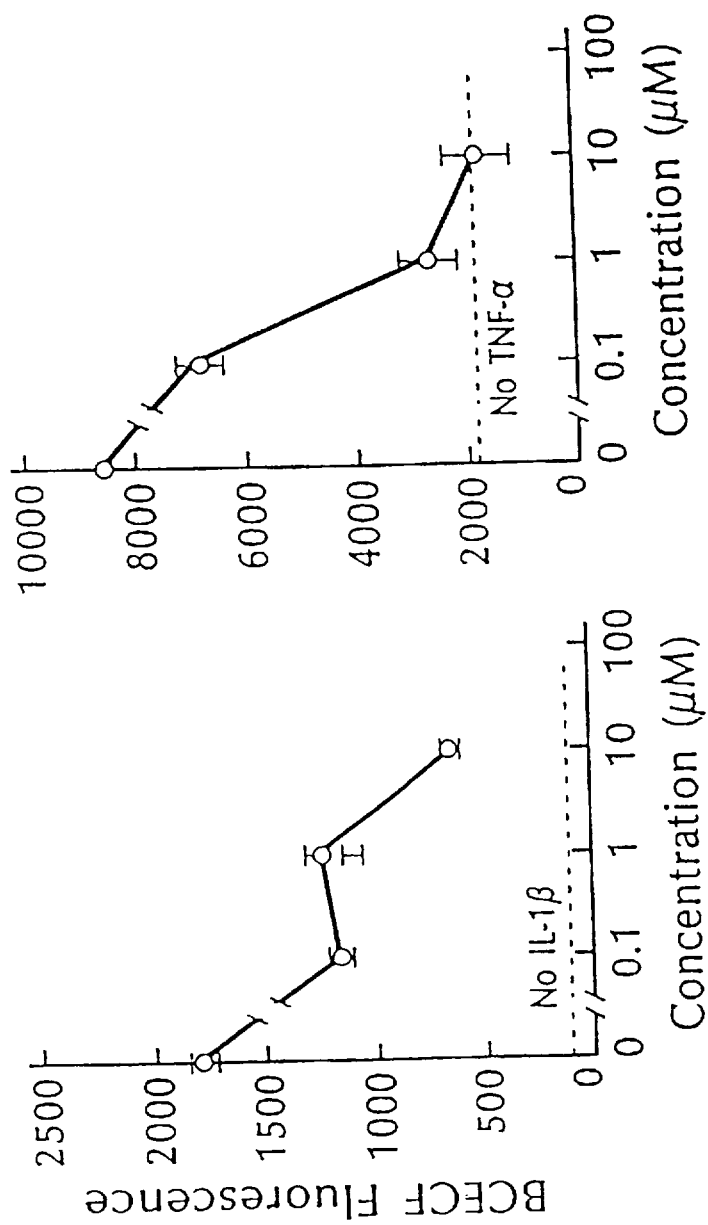
FIGS. 62A and 62B report inhibition of THP-1 adhesion to TNFα or IL-1β-stimulated HUVEC.

Compound no. 45 inhibited adhesion of monocytic leukemia cells (THP-1) to IL-1β or TNFα-activated HUVEC. HUVEC were stimulated with 20 ng/ml IL-1β or 15 ng/ml TNFα for 6 hours. Fluorescence labeled (BCECF-AM) THP-1 cells were allowed to adhere to the HUVEC for 20 minutes, washed once and the amount of fluorescence remaining analyzed on a fluorescence plate reader. The results, reported in FIGS. 62A and 62B (TNFα or IL-1β, respectively), show inhibition of THP-1 adhesion to HUVEC.

Figure 63A:
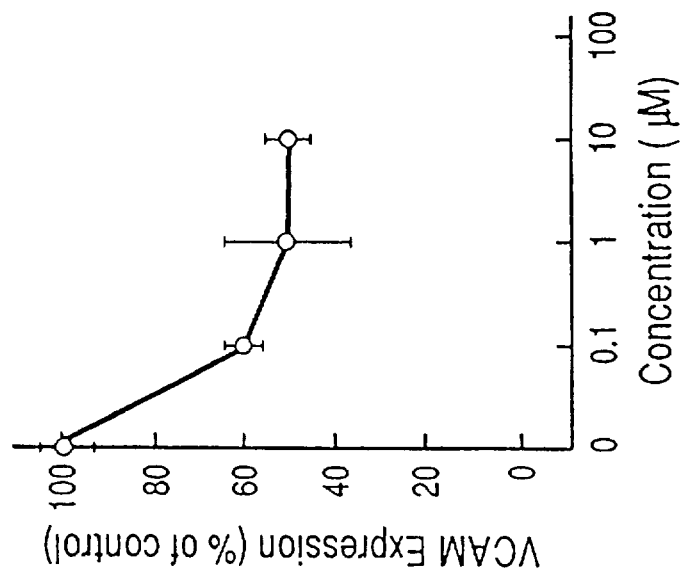
FIGS. 63A and 63B illustrate that compound no. 45 inhibits adhesion receptor expression on HUVEC.
Figure 63B:
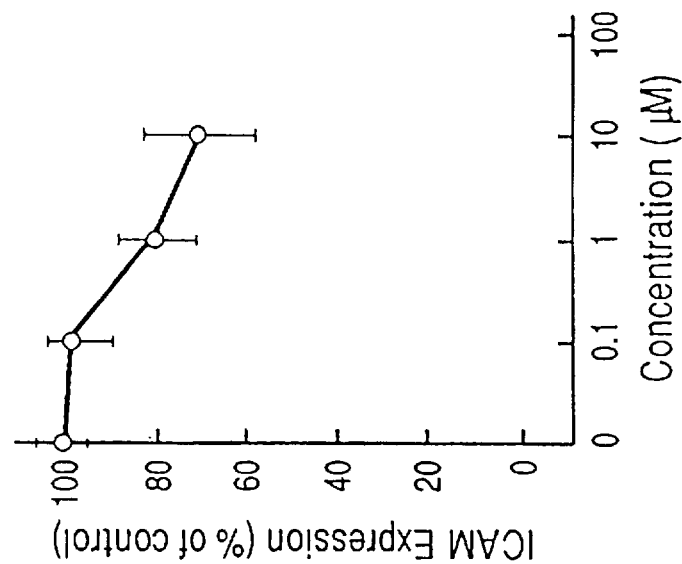

Assay results reported in FIGS. 63A and 63B, illustrate that compound no. 45 inhibited adhesion receptor expression on HUVEC. HUVEC were stimulated with TNFα (20 ng/ml) for 5 hours and stained using fluorescent antibodies to ICAM-1 or VCAM-1. Cell surface expression was analyzed by flow cytometry. All values were normalized to the peak mean fluorescence of the positive control (=100%). Average levels of induction using TNFα-stimulation were 20-fold higher for ICAM-1 and over 50-fold higher for VCAM-1 from that of nonstimulated controls, as shown in FIGS. 63 and 63B.

Figure 64:
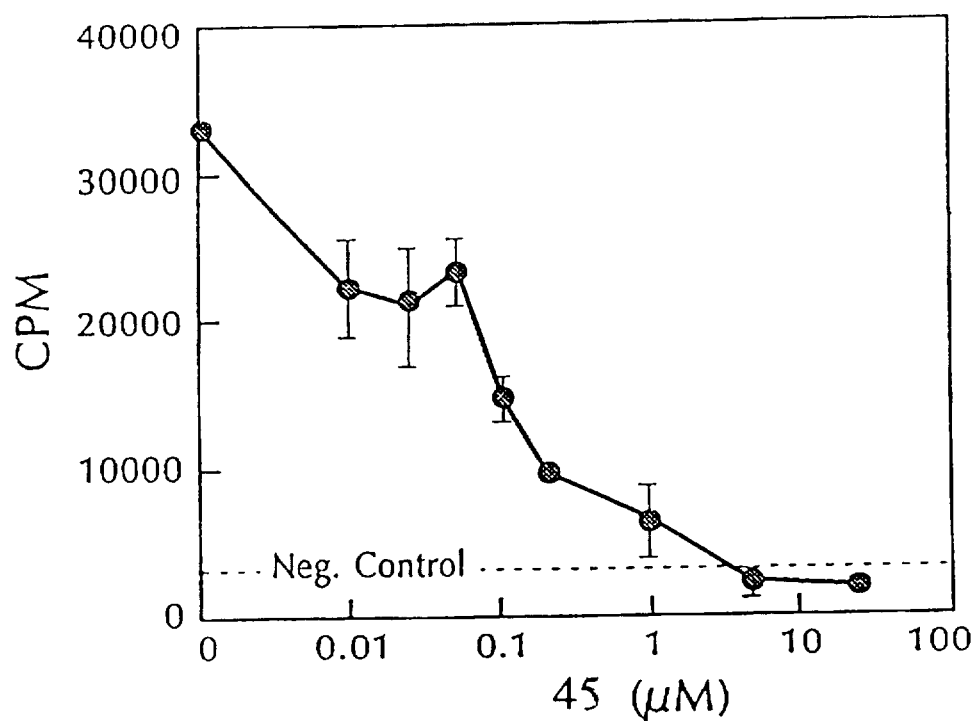
FIG. 64 reports that compound no. 45 inhibits PDGF-BB-induced murine BALB/3T3 proliferation.

FIG. 66 reports that compound no. 45 inhibited PDGF-induced murine BALB/3T3 proliferation. Procedurally, cells were rested overnight in 0.2% serum and stimulated with 25 ng/ml PDGF. Compound no. 45 was added 1 hour prior to stimulation. Cells were pulsed with $^3$H-TdR 24 hours later and harvested for scintillation counting 4 hours later. As shown in FIG. 64, compound no 45 inhibited proliferation in this assay at concentrations less than 30 µM.

Collectively, the foregoing data substantially support the conclusion that compound no. 45, representative of the compounds disclosed herein, is a good immunosuppressive and anti-inflammatory therapeutic, effecting many of the cascading events characteristic of diseases such as rheumatoid arthritis.

EXAMPLE 45

This example illustrates in vitro evidence predicting that the compounds, as represented by a specie of the disclosed genus (compound no. 58), are effective therapies for atherosclerosis and restinosis.

The pathologic mechanisms leading to restenosis mimmic processes observed in atherosclerosis, yet at an accelerated pace. Arterial narrowing resulting from atherosclerosis is the end result of a complex process involving injury to blood vessels, initiated by subintimal accumulation of lipids triggering a cascade of cellular and cytokine mediated events. Such events include accumulation of platelets and inflammatory cells at the site of injury. Cytokines are released which stimulate smooth muscle cell proliferation. The arterial narrowing observed is predominantly due to the localized accumulation of macrophages and proliferation of smooth muscle cells within the arterial wall. Unlike the slow chronic narrowing seen in atherosclerosis, the disease process is greatly accelerated after arterial injury caused by angioplasty or vascular surgery. In the assay data which follows, the cumulative reported results illustrate that compound no. 58, representative of the compounds, inhibits many of the cellular and cytokine-mediated events that lead to atherosclerosis and restenosis.

FIGS. 65A–65F illustrate inhibition of proliferation in either human aortic or pulmonary smooth muscle cells (SMC) by compound no. 58. Procedurally, cells were cultured in 0.5% serum containing medium 24 hours prior to stimulation with various concentrations of either PDGF (FIGS. 65A and 65B), acidic FGF (FIGS. 65C and 65D) or basic FGF (FIGS. 65E and 65F). Cells were stimulated for 24 hours prior to labeling with $^3$H-TdR for 4 hours and harvested and counted by scintillation. Compound no. 58 was added 1 hour prior to stimulation at a concentration of 5 µM. Even at points of maximum stimulation of the growth factors, compound no. 58 completely inhibited cellular proliferation in both aortic and pulmonary SMC. In addition cell number was assessed and those treated with compound no. 58 showed no increase in cell number following growth factor stimulation.

Figures 66A, 66B:
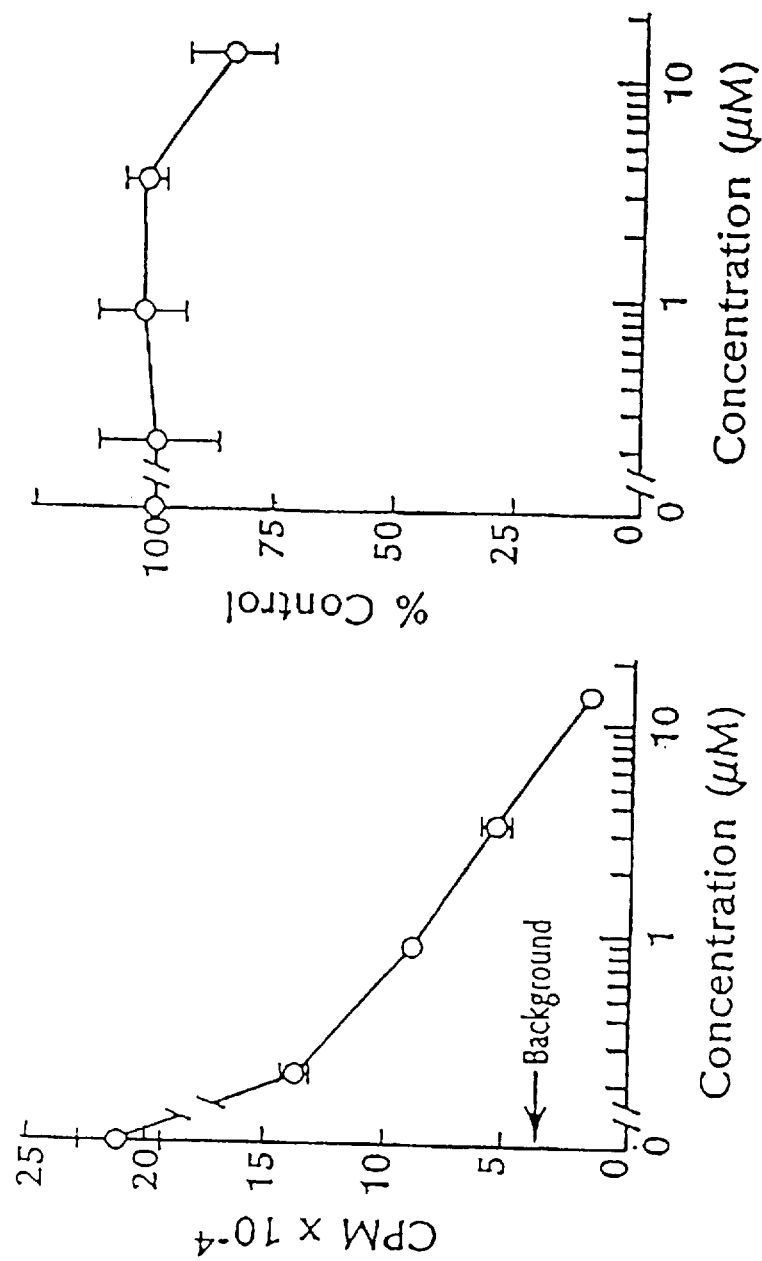
FIGS. 66A and 66B are a dose response and cytoxicity curves, respectively, for inhibition of proliferation in Balb/3T3 cells by compound no. 58.

FIGS. 66A and 66B are a dose response and cytoxicity curves, respectively, for inhibition of proliferation in Balb/3T3 cells by compound no. 58. In the assay protocol, cells were starved overnight in 0.5% serum containing medium, followed by stimulation with 20 ng/ml PDGF for 24 hours. The cells were labeled with $^3$H-TdR for 4 hours and harvested and counted by scintillation. The IC$_{50}$ for inhibition in this cell line was approximately 200–500 nM, the results being reported in FIG. 66A. FIG. 66B illustrates that compound no. 58 was not cytotoxic to Balb/3T3 cells.

Figure 67A:
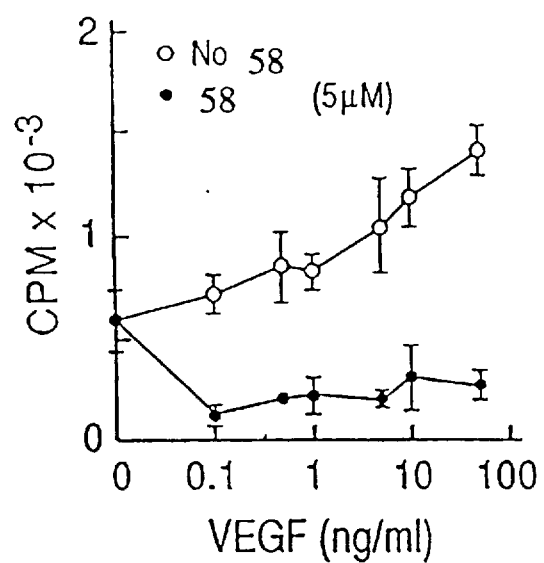
FIGS. 67A and 67B illustrate that compound no. 58 inhibits VEGF-induced proliferation in HUVEC and EGF-induced proliferation in Swiss/3T3 cells, respectively.
Figure 67B:
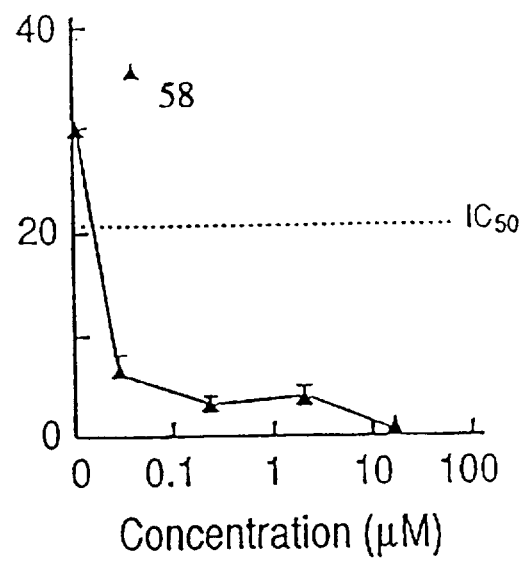

As illustrated in FIGS. 67A and 67B, compound no. 58 inhibited VEGF-induced proliferation in HUVEC and EGF-induced proliferation in Swiss/3T3 cells, respectively. Procedurally, HUVEC were placed in 0.5% serum containing medium prior to stimulation with various concentrations of VEGF, with or without compound no. 58 (5 µM). Twenty four hours later the cells were pulsed with $^3$H-TdR and 4 hours later harvested and counted by scintillation. The IC$_{50}$ for inhibition was approximately 50–100 nM. Swiss 3T3 cells were stimulated with 20 ng/ml EGF and 24 hours later harvested and counted by scintillation. The IC$_{50}$ for inhibition was approximately 20 nM.

Figure 68:
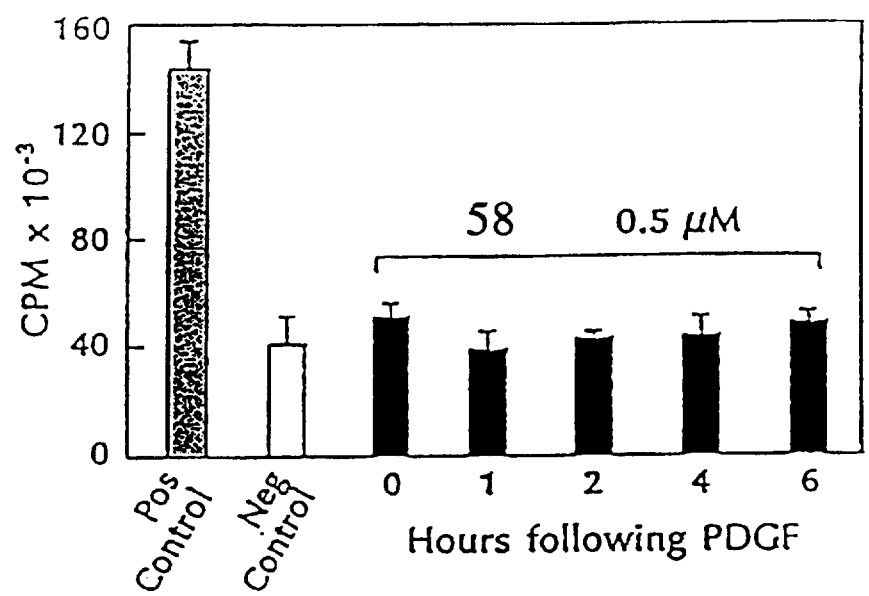
FIG. 68 illustrates an effect of the delayed addition of compound no. 58 to Balb/3T3 proliferation in response to PDGF-BB.

FIG. 68 illustrates an effect of the delayed addition of compound no. 58 to Balb/3T3 proliferation in response to PDGF-BB. Cells were stimulated with PDGF (20 ng/ml) and compound no. 58 added either simultaneous with PDGF (0) or at various times after addition of PDGF, up to 6 hours later. At 24 hours, the cells were pulsed with $^3$H-TdR and counted by scintillation four hours later. Further experimentation has shown nearly complete inhibition in proliferation, even if compound no. 58 was added as late as 20 hours after PDGF.

Figure 69:
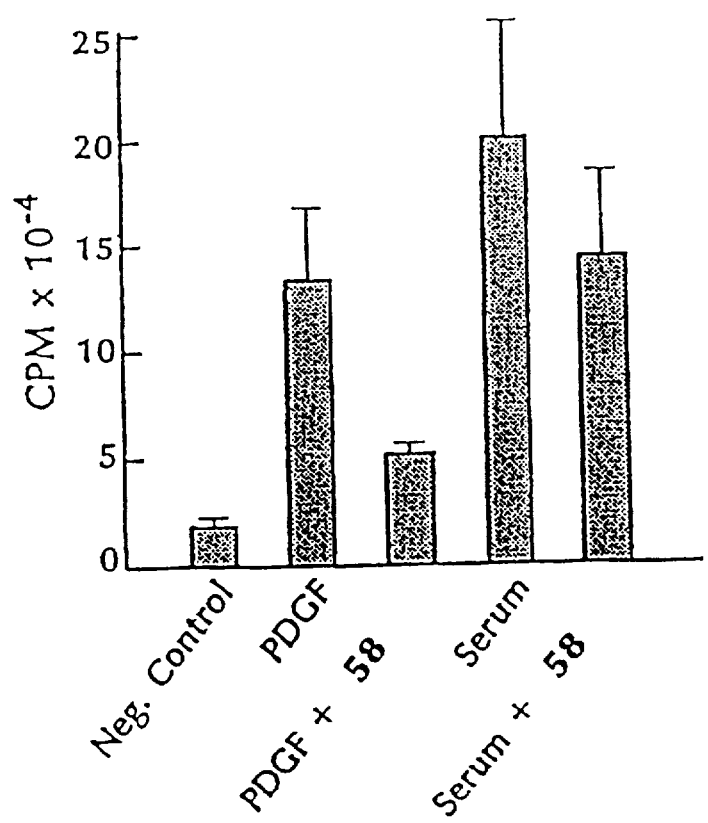
FIG. 69 illustrates that compound no. 58 inhibits PDGF-induced proliferation in Balb/3T3 cells to a greater extent than serum-induced proliferation.

FIG. 69 illustrates that compound no. 58 inhibited PDGF-induced proliferation in Balb/3T3 cells to a greater extent than serum-induced proliferation. In the assay protocol, cells were serum starved for 24 hours before adding either 20 ng/ml PDGF or 10% serum. The cells were pulsed with $^3$HTdR 24 hours later. Compound no. 58 did not have a significant effect on serum-induced Balb/3T3 proliferation.

Figure 70:
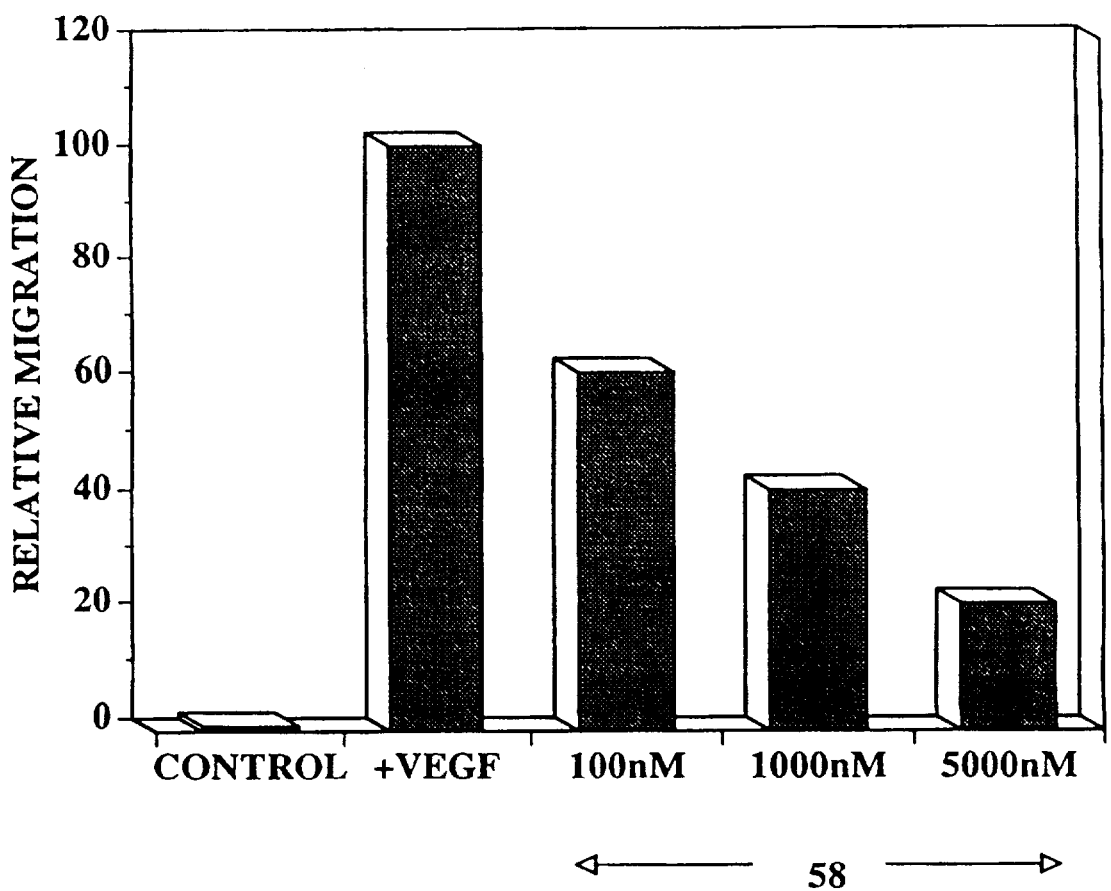
FIG. 70 illustrates that endothelial cell migration is inhibited by compound no. 58.

As shown in FIG. 70, endothelial cell migration is inhibited by compound no. 58. HUVEC were placed in a Matrigel invasion assay system (Becton Dickinson) and VEGF-induced migration assessed with or without varying concentrations of compound no. 58. Matrigel migration of HUVEC to 50 ng/ml VEGF was inhibited in a dose dependent manner, with an IC$_{50}$ of approximately 100–200 nM.

Figure 71:
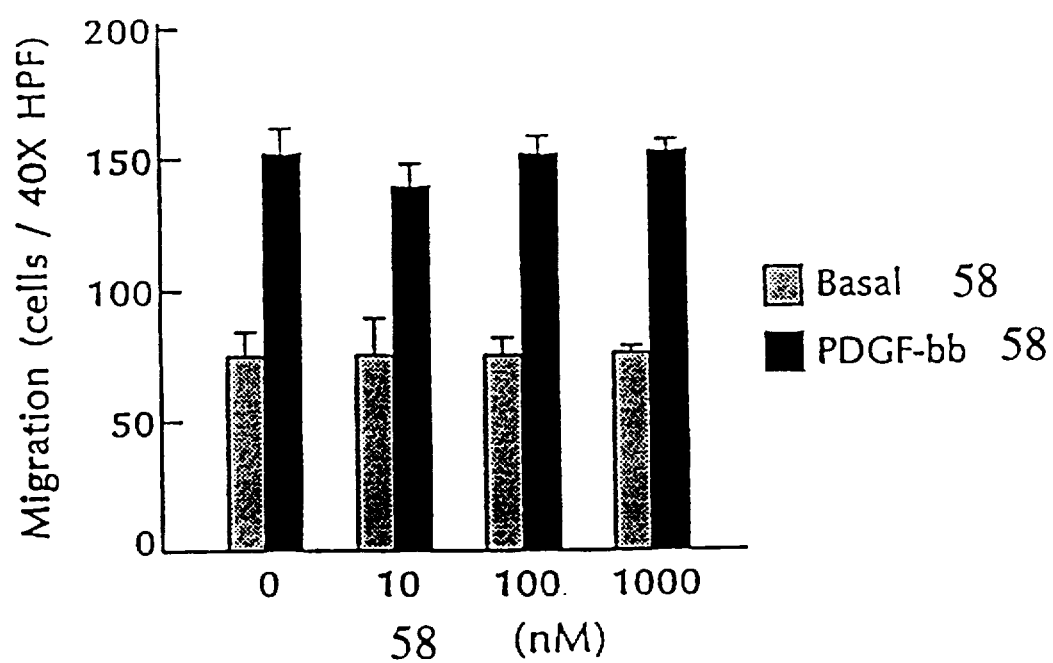
FIG. 71 illustrates that compound no. 58 does not inhibit chemotaxis of human smooth muscle cells (SMC) to PDGF.

FIG. 71 illustrates that compound no. 58 did not inhibit chemotaxis of human smooth muscle cells (SMC) to PDGF. In the assay, cells were seeded in a Boyden chamber with or without various concentrations of compound no. 58. Eight hours later, the number of cells that had migrated were scored visually. Compound no. 58 had no effect on PDGF-directed SMC chemotaxis.

Figures 72A, 72B:
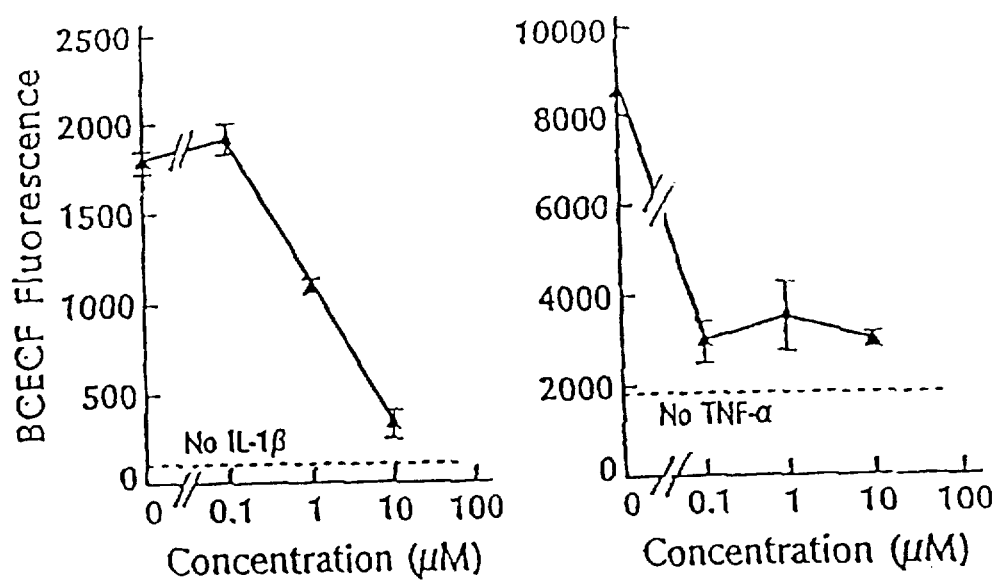
FIGS. 72A and 72B illustrate that compound no. 58 inhibits THP-1 cell adhesion to either TNFα or IL-1β-stimulated HUVEC (respectively).

FIGS. 72A and 72B illustrate that compound no. 58 inhibited THP-1 cell adhesion to either TNFα or IL-1β-stimulated HUVEC, respectively. Procedurally, HUVEC were stimulated with TNFα or IL-1β for 8 hours and THP-1 cells added for 20 minutes. The HUVEC were then washed and analyzed for adherence. Compound no. 58 inhibited adhesion of THP-1 cells to HUVEC with an IC$_{50}$ of approximately 1 µM for both TNFα and IL-1β.

EXAMPLE 46

This example illustrates an ability of the compounds to inhibit IL-12-mediated interferon gamma (IFNγ) production. The following assays are predictive of activity of the compounds nos. 45 and 76 as immunosuppresive agents. C57BL/6 splenocytes were induced to secrete IFNγ by addition of exogenous IL-12. Compounds nos. 45 and 76 were titrated into the cultures over a 0.01 to 10 µM range. The amount of IFNγ in the culture supernatants after 48 hours was quantitated by a commercially available ELISA. Techniques employed for culture preparation, compound addition, washing, supernatant isolation and concentration conform with procedures normally employed by skilled artisans in screening compounds for immunosuppressive activity. DMSO was used as a solvent for delivery of the compounds to cell cultures. Results obtained in the assay are provided in Table III below.

TABLE III

| Compound/ | IFNγ(ng/ml) | |
|---|---|---|
| (Concentration, µM)* | Exp 1 | Exp 2 |
| control/50 U IL-12 | 6.0 | 19.1 |
| Vehicle | — | 13.1 |
| 45/(10) | <0.2 | <0.2 |
| 45/(1.0) | 5.5 | 6.8 |
| 45/(0.1) | 5.8 | 15.1 |
| 45/(0.01) | — | 14.9 |
| 76/(10) | <0.2 | <0.2 |
| 76/(1.0) | — | 0.2 |
| 76/(0.1) | — | 15.0 |
| 76/(0.01) | 5.5 | 13.7 |

*All cultures contained 50 U IL-12

As shown in the above table, the IC$_{50}$ value for compounds nos. 45 and 76 are between 10 µM and 1.0 µM (no. 45) and 1.0 µM and 0.1 µM, respectively. These values are within concentrations which may be attained in vivo.

EXAMPLE 47

This example illustrates an ability of the compounds to inhibit both IL-1α or IL-6-stimulated proliferation of D10

(N4)M or B9 cells, respectively. Using procedures similar to those discussed in the foregoing examples, cultures of D10(N4)M and B9 cells were incubated with 10 pg/ml (approximately 5 U/ml) of IL-1α or 10 pg/ml (approximately 3 U/ml) of IL-6, respectively. DMSO was used as a solvent for delivery of the compounds to cell cultures. Compounds nos. 45, 58 and 76 were added at concentrations of 10, 1.0, 0.1 and 0.01 to each series of cultures, set up with appropriate, corresponding controls. Results obtained in the assays are provided in Tables IV |D10(N4)M| and V |B9| below:

TABLE IV

D10(N4)M

| Compound/ (Concentration, | Inhibition of Proliferation (%) | | |
|---|---|---|---|
| μM)* | Compound no. 45 | Compound no. 58 | Compound no. 76 |
| 10 μM | 100 | 100 | 100 |
| 1.0 μM | 100 | 0 | 72 |
| 0.1 μM | 0 | 0 | 0 |
| 0.01 μM | 0 | 0 | 0 |

TABLE V

B9

| Compound/ (Concentration, | Inhibition of Proliferation (%) | | |
|---|---|---|---|
| μM)* | Compound no. 45 | Compound no. 58 | Compound no. 76 |
| 10 μM | 100 | 100 | 100 |
| 1.0 μM | 100 | 0 | 100 |
| 0.1 μM | 73 | 0 | 0 |
| 0.01 μM | 0 | 0 | 0 |

These data indicate that compounds 45, 58 and 76 can block an IL-1α-mediated proliferative response in D10 (N4)M with $IC_{50}$'s between 0.1–1.0 μM for compound no. 45 and 76 and between 1.0–10 μM for compound 50. Similarly, compound nos. 45 and 76 inhibit IL-6-mediated growth of B9 cells with $IC_{50}$'s between 0.1–1.0 μM, and for compound no. 58, between 1.0–10 μM. All these concentrations are achievable in vivo.

EXAMPLE 48

This example is illustrates in vivo activity of the compounds in a predictive mouse hemolytic plaque assay (a model of B-cell activation). Compounds nos. 58 and 76 were evaluated for their ability to inhibit in vivo antibody formation to SRBC shown using a plaque-forming assay.

Procedurally, CD-1 (ICR) female mice (Charles River), 10–14 weeks of age were sensitized intraperitoneally with $1.25 \times 10^8$ sheep red blood cells (SRBC) in 0.2 ml saline. The mice were divided into groups of 508. Compound administration commenced on the day of sensitization and continued daily through day 3. Control mice received a coequal volume of vehicle. On the fourth day after sensitization, the mice were sacrificed, each spleen excised, a splenocyte suspension prepared by homogenization in 4 ml Hank's Buffered salt solution (HBSS), and a nucleated cell count (WBC) determined by Coulter counter. A splenic suspension with SRBC absorbed guinea pig complement was blended in a 0.5% agar solution. Two 0.1 ml aliquots were dispersed onto a petri dish and a monolayer formed by dispersion of each aliquot beneath a 22 mm cover slip. The dishes were incubated at 37° C. in 5% $CO_2$ for 2–2.5 hours. Plaques were counted with a dissecting microscope.

Data obtained in the assay are reported below in Table VI. Propylene glycol is the vehicle for all groups treated, with the exception of group #1, which was left untreated. Group #1 was immunized with SRBC like all other treated groups, but was not treated with propylene glycol or compounds. Group #2, the vehicle test group (in the absence of any compound) was used to verify any inhibitive or exacerbative plaques. From the data shown, it appears that the propylene glycol vehicle has an inhibitory effect on the subjects in group #2. All compounds were given twice daily at 7:30a.m. and 5:30p.m. For example, the subjects in group #3 were dosed 25 mg/0.1 ml/mouse in the morning dose and received the same dose in the evening for a total of 50 mg/ml daily.

TABLE VI

| Grp | Treatment | #/Grp | Dose mg/kg | PFC/ Spl × $10^3$ | Percent Inhibition | WBC/ Spl × $10^3$ | Percent Chg WBC |
|---|---|---|---|---|---|---|---|
| 1 | Untreated | 10 | — | 372 | — | 183 | — |
| 2 | RS-VEH | 5 | 0.0 | 321 | — | 174 | — |
| 3 | Comp. no. 58 | 5 | 50.0 | 190 | 41 | 161 | −7 |
| 5 | Comp. no. 58 | 6 | 12.5 | 283 | 12 | 207 | 19 |
| 9 | Comp. no. 76 | 7 | 50.0 | 29 | 91 | 171 | −2 |
| 11 | Comp. no. 76 | 3 | 12.5 | 221 | 31 | 155 | −11 |

As the above data report, compound no. 58 inhibits the immune response by about 41 percent at a concentration of 50.0 mg/kg and about 12 percent at a concentration of 12.5 mg/kg. Compound no. 76 inhibits the immune response by 91 percent at a concentration of 50.0 mg/kg and 31 percent at a concentration of 12.5 mg/kg.

EXAMPLE 49

This example illustrates an ability of the compounds to inhibit 6TIras bladder carcinoma cell-induced angiogenesis in chorio-allantoic membrane (CAM) of developing chick embryos. Tumor growth is dependent on neovascularization of angiogenesis mediated by several growth factors, including basic fibroblast growth factor (bFGF), vascular endothelial growth factor (VEGF), and epidermal growth factor (EGF), which are secreted by tumors. Inhibitors of angiogenesis, such as fumigalin and suramin, possess antitumor activity in animal tumor models. Angiogenesis induced by tumors in the chorioallantoic membrane (CAM) of developing chick embryos is one established in vivo model system effective in studying the effects of agents that inhibit neovascularization. This example tests the ability of the compounds to inhibit angiogenesis in vivo.

Procedurally, the surface of 6 day-old postertilization chicken eggs (white leghorn, NCSU poultry science) was sterilized with wescodyne, and the CAM was exposed by cutting a window (1 $cm^2$) on one side of the egg using a false airsac technique as described in Ausprunk et al., "Vascularization of Normal Neoplastic Tissues Grafted to Chicken Chorioallantois," Am. J. Path., Vol. 79, pp.597–618 (1975). After 24–48 hours, the 6TIras, bladder carcinoma cells without compound (i.e., positive controls) and with compounds nos. 50 and 58 were placed on the exposed CAM, the windows were sealed with a transparent tape, and the eggs were incubated in a humid incubator at 35° C. Eggs were examined at intervals for a period up to 6 days postinoculation. using a stereoscopic dissection microscope. Positive angiogenesis was scored based on the development of more than 5 loops of blood vessels delineating the added cells or bFGF. The respective compounds. dissolved in appropriate solvent, were absorbed on to 1×1×2 mm pieces of gelfoam sponges and placed on the CAM along with tumor cells and observed for surrounding inhibition zones (avascular areas). The results are expressed as the number of angiogenes in positive eggs/total number of eggs and the percentage of eggs showing inhibition of angiogenesis (percentage of positive).

Data obtained in this in vivo assay are presented Table VII below. The media control group (DMEM media only) were 0/6 positive for angiogenesis. The control group (6TIras cells alone) were 6/6 positive for angiogenesis with 0% inhibition. The positive control group (Suramin) were 2/8 positive for angiogenesis at 1 mM with 75% inhibition. In the treatment group using compound no. 50. there appeared a dose-dependent inhibition of angiogenesis. An $IC_{50}$ of 800 nM yielded 4/8 positive for angiogenesis with a corresponding 50% inhibition. In the treatment group using compound no. 58, a dose-dependent inhibition of angiogenesis was also observed. An $IC_{50}$ of 100 nM resulted in a 3/6 positive for angiogenesis with a corresponding 50% inhibition. These data confirm that the compounds tested, representative of compounds of the invention inhibit angiogenesis in this predictive in vivo model have therapeutic potential as growth inhibitors of cancerous tumors.

TABLE VII

| Group | Treatment | # Positive Angiogenesis | Percent Inhibition |
|---|---|---|---|
| 1 | Control (DMEM) | 0/6 | 0 |
| 2 | GTIras (cells) | 6/6 | 0 |
| 3 | Suramin (1 mM) | 2/8 | 75 |
| 4 | Compound no. 50/100 nM | 6/7 | 14.3 |
| 6 | Compound no. 50/800 nM | 4/8 | 50 |
| 7 | Compound no. 50/2000 nM | 3/7 | 67 |
| 8 | Compound no. 58/100 nM | 3/6 | 50 |
| 9 | Compound no. 58/500 nM | 3/7 | 57 |
| 10 | Compound no. 58/1000 nM | 2/5 | 60 |
| 11 | Compound no. 58/5000 nM | 1/6 | 83.4 |

What is claimed is:

1. A method for preparing a compound, including resolved enantiomers and/or diastereomers. hydrates, salts, solvates and mixtures thereof, the compound having a straight or branched aliphatic hydrocarbon structure of formula I:

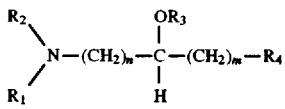

wherein:

n is an integer from one to four;

m is an integer from four to twenty;

independently, $R_1$ and $R_2$ are hydrogen, a straight or branched chain alkyl, alkenyl or alkynyl of up to twenty carbon atoms in length or —$(CH_2)_wR_5$, w being an integer from one to twenty and $R_5$ being an hydroxyl, halo, $C_{1-8}$ alkoxyl group or a substituted or unsubstituted carbocycle or heterocycle; or jointly $R_1$ and $R_2$ form a substituted or unsubstituted, saturated or unsaturated heterocycle having from four to eight carbon atoms, N being a hetero atom;

$R_3$ is hydrogen or $C_{1-3}$; or jointly one of $R_1$ or $R_2$ and $R_3$ form a substituted or unsubstituted linking carbon chain, having from one to four carbon atoms, joining the O and N in a cyclic structure, an integer sum equal to n+a number of carbon atoms in the linking carbon chain being less than six; a total sum of carbon atoms comprising $R_1$ or $R_2$, $(CH_2)_n$ and $(CH_2)_m$ does not exceed forty; and $R_4$ is a terminal moiety comprising a carbocycle or heterocycle having one ring or two-fused rings, each ring having five or six ring atoms, wherein a ring atom of the terminal moiety is attached to a terminal carbon atom of $(CH_2)_m$, the method comprising:

reacting a terminal moiety-containing compound with a suitable base, solvent and substituted olefin to obtain an intermediate product, the intermediate product having a composite structure of the terminal moiety-containing compound and substituted olefin; either:

A) converting the intermediate product to a terminal moiety-containing epoxide in a reaction with organic peracid; or B) first, converting the intermediate product to a corresponding diol in a reaction with a suitable oxidizing agent; second, reacting the corresponding diol using a halogenating agent in the presence of an organic acid to obtain a haloester; and third, converting the haloester to a terminal moiety-containing epoxide by reaction of the haloester and a basic ester-hydrolyzing reagent; and reacting the terminal moiety-containing epoxide with a substituted or unsubstituted amine to obtain the compound.

2. The method of claim 1, wherein the substituted olefin has at least one additional functional moiety which may be displaced in a chemical reaction with the terminal moiety-containing compound.

3. The method of claim 2, wherein the first reacting step further comprises:

chemically converting the terminal moiety-containing compound to a terminal moiety-containing anion.

4. The method of claim 3, wherein the terminal moiety-containing anion is reacted with the substituted olefin, displacing the at least one functional moiety to obtain the intermediate product.

5. The method of claim 1, wherein the suitable base is selected from the group consisting of sodium hydride, sodium amide, sodium alkoxide, lithium hydride, potassium hydride, lithium amide, sodium amide and potassium amide.

6. The method of claim 1, wherein the solvent is selected from the group consisting of dimethylsulfoxide, dimethylformamide, or an alcohol.

7. The method of claim 1, wherein the substituted olefin comprises a chain structure corresponding to $(CH_2)_m$.

8. The method of claim 7, wherein the substituted olefin is an ω-substituted olefin.

9. The method of claim 1, wherein the substituted olefin is a halo-substituted olefin.

10. The method of claim 1, wherein the organic peracid is selected from the group consisting of 3-chloroperoxybenzoic acid, peracetic acid and trifluoroperacetic acid.

11. The method of claim 1, wherein the oxidizing agent is osmium tetroxide.

12. The method of claim 1, wherein converting the intermediate product to a corresponding diol further comprises reacting the intermediate product with a catalytic amount of the oxidizing agent in the presence of a regenerating agent.

13. The method of claim 12, wherein the regenerating agent is 4-methylmorpholine-N-oxide or trimethylamine-N-oxide.

14. The method of claim 1, wherein the halogenating agent is selected from the group consisting of hydrogen bromide and hydrogen chloride.

15. The method of claim 1, wherein the organic acid is selected from the group consisting of acetic acid and propionic acid.

16. The method of claim 1, wherein the ester-hydrolyzing agent is selected from the group consisting of a metal alkoxide and metal hydroxide.

17. The method of claim 16, wherein the metal alkoxide is selected from the group consisting of sodium methoxide, ethoxide, isopropoxide and pentoxide.

18. The method of claim 16, wherein the metal hydroxide is sodium hydroxide.

19. The method of claim 1, wherein reacting the terminal moiety-containing epoxide with a substituted or unsubstituted amine comprises either:

A) heating the terminal moiety-containing epoxide in the presence of an amine, having amine substituents present in the compound; or B) reacting the terminal moiety-containing epoxide with an amine, having substituents present in the compound, with a reaction activator in a solvent.

20. The method of claim 19, wherein the reaction activator is lithium perchlorate.

21. The method of claim 19, wherein the solvent is selected from the group consisting of dimethylsulfoxide, dimethylformamide, or an alcohol.

22. The method of claim 19, wherein the substituted or unsubstituted amine has a molecular structure corresponding to

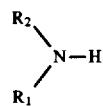

* * * * *